US010487337B2

(12) United States Patent
Roberts et al.

(10) Patent No.: US 10,487,337 B2
(45) Date of Patent: *Nov. 26, 2019

(54) METHODS FOR MONOCOT PLANT IMPROVEMENT

(71) Applicant: Agresearch Limited, Hamilton (NZ)

(72) Inventors: Nicholas John Roberts, Feilding (NZ); Kim Archer Richardson, Palmerston North (NZ); Derek William Richard White, Palmerston North (NZ)

(73) Assignee: AgResearch Limited, Hamilton (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/524,033

(22) PCT Filed: Nov. 3, 2015

(86) PCT No.: PCT/IB2015/058477
§ 371 (c)(1),
(2) Date: May 3, 2017

(87) PCT Pub. No.: WO2016/071829
PCT Pub. Date: May 12, 2016

(65) Prior Publication Data
US 2017/0314036 A1  Nov. 2, 2017

(30) Foreign Application Priority Data
Nov. 4, 2014  (NZ) ...................................... 701641

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8227* (2013.01)

(58) Field of Classification Search
None
See application file for complete search history.

(56) References Cited

U.S. PATENT DOCUMENTS

| | | |
|---|---|---|
| 4,795,855 A | 1/1989 | Fillatti et al. |
| 5,004,863 A | 4/1991 | Umbeck |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,416,011 A | 5/1995 | Hinchee et al. |
| 5,463,174 A | 10/1995 | Moloney et al. |
| 5,563,055 A | 10/1996 | Townsend et al. |
| 5,569,834 A | 10/1996 | Hinchee et al. |
| 5,591,616 A | 1/1997 | Hiei et al. |
| 5,639,952 A | 6/1997 | Quail et al. |
| 5,656,496 A | 8/1997 | Quail et al. |
| 5,750,385 A | 5/1998 | Shewmaker et al. |
| 5,750,871 A | 5/1998 | Moloney et al. |
| 5,792,935 A | 8/1998 | Arntzen et al. |
| 5,824,877 A | 10/1998 | Hinchee et al. |
| 5,837,848 A | 11/1998 | Ely et al. |
| 5,846,797 A | 12/1998 | Strickland |
| 5,952,543 A | 9/1999 | Firoozabady et al. |
| 5,968,830 A | 10/1999 | Dan et al. |
| 5,981,840 A | 11/1999 | Zhao et al. |
| 6,020,539 A | 2/2000 | Goldman et al. |
| 6,037,522 A | 3/2000 | Dong et al. |
| 6,074,877 A | 6/2000 | D'halluin et al. |
| 6,921,848 B2 | 7/2005 | Chory et al. |
| 8,426,683 B2 * | 4/2013 | Frankard ............ C12N 15/8261 435/320.1 |
| 2001/0047525 A1 | 11/2001 | Bruce et al. |
| 2004/0067506 A1 | 4/2004 | Scheres et al. |
| 2007/0039067 A1 | 2/2007 | Feldmann et al. |

FOREIGN PATENT DOCUMENTS

| | | |
|---|---|---|
| CN | 102260679 A | 11/2011 |
| WO | WO 2002/000894 A2 | 1/2002 |
| WO | WO 2007/105967 A1 | 9/2007 |
| WO | WO 2007/124312 A2 | 11/2007 |
| WO | WO 2007/105967 A8 | 7/2009 |

OTHER PUBLICATIONS

White. PEAPOD regulates lamina size and curvature in *Arabidopsis*. Proc Natl Acad Sci U S A. Aug. 29, 2006;103(35):13238-43. Epub Aug. 17, 2006.*
White. PEAPOD regulates lamina size and curvature in *Arabidopsis*. Proc Natl Acad Sci U S A. Aug. 29, 2006;103(35):13238-43. Epub Aug. 17, 2006. (Year: 2006).*
Bai et al. Origin and evolutionary analysis of the plant-specific TIFY transcription factor family. Genomics. Aug. 2011;98(2):128-36. 2011.05.002. Epub (Year: 2011).*
Zhou et al. The plant cyclin-dependent kinase inhibitor ICK1 has distinct functional domains for in vivo kinase inhibition, protein instability and nuclear localization. Plant J. Aug. 2003;35(4):476-89. (Year: 2003).*
Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.
Achard et al. (2009) "Releasing the brakes of plant growth: how Gas shutdown DELLA proteins," J. Exp. Bot. 60:1085-1092.
Alam et al. (1999) "Transgenic insect-resistant maintainer line (IR68899B) for improvement of hybrid rice," Plant Cell Rep. 18:572-575.
Altpeter et al. (2000) "Generation of large numbers of independently transformed fertile perennial ryegrass (*Lolium perenne* L.) plants of forage- and turf-type cultivars," Molecular Breeding. 6:519-528.

(Continued)

*Primary Examiner* — Cynthia E Collins
(74) *Attorney, Agent, or Firm* — Leydig, Voit & Mayer, Ltd.

(57) ABSTRACT

The invention provides methods and materials for increasing at least one of root biomass and above-ground biomass and in a Poaceae plant by expressing a PEAPOD protein, or fragment thereof, in the Poaceae plant. The invention also provides methods and materials producing a Poaceae plant with at least one of increased root biomass and increased above-ground biomass, by expressing a PEAPOD protein, or fragment thereof, in the Poaceae plant.

23 Claims, 14 Drawing Sheets

Specification includes a Sequence Listing.

(56) References Cited

OTHER PUBLICATIONS

Altschul et al. (1990) "Basic local alignment search tool," J. Mol. Biol. 215:403-410.
Altschul et al. (1997) "Gapped BLAST and PSI-BLAST: a new generation of protein database search programs," Nucleic Acids Res. 25:3389-3402.
Anjum et al. (2011) "Brassinolide application improves the drought tolerance in maize through modulation of enzymatic antioxidants and leaf gas exchange," J. Agronomy and Crop Sci. 197:177-185.
Bairoch et al. (1994) "PROSITE: recent developments," Nucleic Acids Res. 22:3583-3589.
Baxevanis (2001) "The Molecular Biology Database Collection: an updated compilation of biological database resources," Nucleic Acids Res. 29:1-10.
Bilang et al. (1991) "The 3'-terminal region of the hygromycin-B-resistance gene is important for its activity in *Escherichia coli* and *Nicotiana tabacum*," Gene. 100:247-250.
Birch (1997) "Plant Transformations: Problems and Strategies for Practical Applications," Ann. Rev. Plant Phys. Plant Mol. Biol. 48:297-326.
Bolton et al. (1962) "A General Method for The Isolation of RNA Complementary to DNA," Proc. Natl. Acad. Sci. USA. 48:1390-1397.
Bowie et al. (1990) "Deciphering the message in protein sequences: tolerance to amino acid substitutions," Science. 247:1306-1310.
Chen et al. (Jul. 4, 2013) "Transcriptome Analysis in Sheepgrass (*Leymus chinensis*): A Dominant Perennial Grass of the Eurasian Steppe," PLoS One. 8(7):e67974. pp. 1-15.
Clough et al. (1998) "Floral dip: a simplified method for Agrobacterium-mediated transformation of *Arabidopsis thaliana*," Plant J. 16(6):735-743.
Clouse (2011) "Brassinosteroid signal transduction: from receptor kinase activation to transcriptional networks regulating plant development," Plant Cell. 23:1219-1230.
Clouse et al. (1998) "Brassinosteroids: Essential regulators of plant growth and development," Annu. Rev. Plant Physiol. Plant Mol. Biol. 16:427-451.
Dan et al. (2006) "MicroTom—a high-throughput model transformation system for functional genomics," Plant Cell Reports. 25:432-441.
De Carvalho Niebel et al. (1995) "Post-transcriptional cosuppression of beta-1,3-glucanase genes does not affect accumulation of transgene nuclear mRNA," Plant Cell. 7:347-358.
Falquet et al. (2002) "The PROSITE database, its status in 2002," Nucleic Acids Res. 30:235-238.
Febregas et al. (Sep. 2013) "The brassinosteroid insensitive1-like3 signalosome complex regulates *Arabidopsis* root development," The Plant Cell. 25:3377-3388.
Feng et al. (1987) "Progressive sequence alignment as a prerequisite to correct phylogenetic trees," J. Mol. Evol. 25:351-360.
Folta et al. (2006) "Characterization of LF9, an octoploid strawberry genotype selected for rapid regeneration and transformation," Planta. 224(5):1058-1067.
Frohman (1993) "Rapid amplification of complementary DNA ends for generation of full-length complementary DNAs: thermal RACE," Methods Enzymol. 218:340-356.
Gallego-Bartolome et al. (2012) "Molecular mechanism for the interaction between gibberellin and brassionosteroid signalling pathways in *Arabidopsis*," Proc. Natl. Acad. Sci. 109:13446-13451.
Garcia et al. (2008) "A small plant-specific protein family of ABI five binding proteins (AFPs) regulates stress response in germinating *Arabidopsis* seeds and seedlings," Plant Mol. Biol. 67:643-658.
Giesen et al. (1998) "A formula for thermal stability (Tm) prediction of PNA/DNA duplexes," Nucleic Acids Res. 26(21):5004-5006.
Gonzalez Padilla et al. (2003) "Early antibiotic selection and efficient rooting and acclimatization improve the production of transgenic plum plants (*Prunus domestica* L.)," Plant Cell Rep. 22(1):38-45.

Graham et al. (1995) "Agrobacterium-mediated transformation of soft fruit Rubus, Ribes, and Fragaria," Methods Mol. Biol. 44:129-133.
Guo et al. (Aug. 27, 2013) "Mechanisms and networks for brassinosteroid regulated gene expression," Current Opinion in Plant Biology. 16:545-553.
He et al. (2005) "BZR1 is a transcriptional repressor with dual roles in brassinosteroid homeostasis and growth responses," Science. 307:1634-1638.
Hellens et al. (2000) "pGreen: a versatile and flexible binary Ti vector for Agrobacterium-mediated plant transformation," Plant Mol. Biol. 42:819-832.
Hellens et al. (2005) "Transient expression vectors for functional genomics, quantification of promoter activity and RNA silencing in plants," Plant Methods. 1:13 pp. 1-14.
Henikoff et al. (1992) "Amino acid substitution matrices from protein blocks," Proc. Natl. Acad. Sci. USA. 89:10915-10919.
Herrera-Estrella et al. (1993) "Expression of chimaeric genes transferred into plant cells using a Ti-plasmid-derived vector," Nature. 303:209-213.
Hofmann et al. (1999) "The PROSITE database, its status in 1999," Nucleic Acids Res. 27:215-219.
Horsch et al. (1985) "A simple and general method for transferring genes into plants," Science. 227:1229-1231.
Hothorn et al. (2011) "Structural basis of steroid hormone perception by the receptor kinase BRI1," Nature. 474:467-471.
Hou et al. (2010) "DELLAs modulate jasmonate signalling via competitive binding to JAZs," Devel. Cell. 19:884-894.
Huang (1994) "On Global Sequence Alignment," Computer Applications in the Biosciences. 10:227-235.
International Search Report with Written Opinion corresponding to International Patent Application No. PCT/IB2015/058477, dated Dec. 21, 2015.
Jeanmougin et al. (1998) "Multiple sequence alignment with Clustal X," Trends Biochem. Sci. 23:403-405.
Jiang et al. (Dec. 19, 2013) "DWARF 53 acts as a repressor of strigolactone signalling in rice," Nature. 504:401-405.
Jiang et al. (Oct. 2013) "Brassinosteroid functions in *Arabidopsis* seed development," Plant Signaling & Behavior. 8(10):e25928.
Jobling et al. (2003) "Immunomodulation of enzyme function in plants by single-domain antibody fragments," Nat. Biotechnol. 21(1):77-80.
Jones et al. (1998) "The effect of chimeric transgene architecture on co-ordinated gene silencing," Planta. 204:499-505.
Joshi (1987) "An inspection of the domain between putative TATA box and translation start site in 79 plant genes," Nucleic Acid Research. 15:6643-6653.
Jouvenot et al. (2003) "Targeted regulation of imprinted genes by synthetic zinc-finger transcription factors," Gene Therapy. 10:513-522.
Karimi et al. (2002) "Gateway vectors for Agrobacterium-mediated plant transformation," Trends Plant Sci. 7:193-195.
Keinonen-Mettala et al. (1998) "Comparisons of the efficiency of some promoters in silver birch (*Betula pendula*)," Plant Cell Rep. 17:356-361.
Khripach et al. (2000) "Twenty years of brassinosteroids: Steroidal plant hormones warrant better crops for the XXI century," Ann. Bot. 86:441-447.
Kinoshita et al. (2005) "Binding of brassinosteroids to the extracellular domain of plant receptor kinase BRI1," Nature. 433:167-171.
Krens et al. (1997) "Transgenic caraway, *Carum carvi* L.: a model species for metabolic engineering," Plant Cell Rep. 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Lawit et al. (2010) "Maize DELLA Proteins dwarf plant8 and dwarf plant9 as Modulators of Plant Development," Plant Cell Physiol. 51:1854-1868.
Li et al. (1996) "Genetic transformation of cassava (*Manihot esculenta* Crantz)," Nat. Biotechnol. 14:736-740.
Li et al. (1999) "Brassinosteroid actions in plants," J. Exp. Bot. 50(332):275-282.

(56) References Cited

OTHER PUBLICATIONS

Li et al. (2001) "A fast neutron deletion mutagenesis-based reverse genetics system for plants," Plant Journal. 27(3):235-242.
Li et al. (2003) "Transgenic rose lines harboring an antimicrobial protein gene, Ace-AMP1, demonstrate enhanced resistance to powdery mildew (*Sphaerotheca pannosa*)," Planta, 218:226-232.
Li et al. (Jul. 2013) "Mechanisms of signalling crosstalk between brassinosteroids and gibberellins," Plant Signaling & Behavior. 8(7):e24686.
Llave et al. (2002) "Cleavage of Scarecrow-like mRNA targets directed by a class of *Arabidopsis* miRNA," Science. 297:2053-2056.
Matsuda et al. (2005) "Development of an Agrobacterium-mediated transformation method for pear (*Pyrus communis* L.) with leaf-section and axillary shoot-meristem explants," Plant Cell Rep. 24(1):45-51.
Matthew et al. (2009) "Pasture response to gibberellins: A review and recommendations," NZ. J. Agric. Res. 52:213-225.
McIntyre (1996) "Strategies for the suppression of peroxidase gene expression in tobacco. I. Designing efficient ribozymes," Transgenic Res. 5:257-262.
Michelmore et al. (1987) "Transformation of lettuce (*Lactuca sativa*) mediated by Agrobacterium tumefaciens," Plant Cell Rep. 6:439-442.
Murashige et al. (1962) "A Revised Medium for Rapid Growth and Bio Assays with Tobacco Tissue Cultures," Physiol Plant. 15:473-497.
Napoli et al. (1990) "Introduction of a Chimeric Chalcone Synthase Gene into Petunia Results in Reversible Co-Suppression of Homologous Genes in trans," Plant Cell. 2:279-289.
Needleman et al. (1970) "A general method applicable to the search for similarities in the amino acid sequence of two proteins," J. Mol. Biol. 48:443-453.
Nielsen et al. (1991) "Sequence-selective recognition of DNA by strand displacement with a thymine-substituted polyamide," Science. 254(5037):1497-1500.
Nilsson et al. (1992) "Spatial pattern of cauliflower mosaic virus 35S promoter-luciferase expression in transgenic hybrid aspen trees monitored by enzymatic assay and non-destructive imaging," Transgenic Research. 1:209-220.
Niu et al. (1998) "Transgenic peppermint (*Mentha x piperita* L.) plants obtained by cocultivation with Agrobacterium tumefaciens," Plant Cell Rep. 17:165-171.
Notredame et al. (2000) "A novel method for fast and accurate multiple sequence alignment," J. Mol. Biol. 302:205-217.
Oosumi et al. (2006) "High-efficiency transformation of the diploid strawberry (*Fragaria vesca*) for functional genomics," Planta. 223(6):1219-1230.
Ortiz et al. (1996) "Hygromycin resistance as an efficient selectable marker for wheat stable transformation," Plant Cell Rep. 15:877-881.
Pauwels et al. (2010) "NINJA connects the co-repressor TOPLESS to jasmonate signaling," Nature. 464:788-791.
Pena et al. (1995) "High efficiency Agrobacterium-mediated transformation and regeneration of citrus," Plant Sci.104:183-191.
Perez et al. (Jan. 8, 2014) "The non-JAZ TIFY protein TIFY8 from *Arabidopsis thaliana* is a transcriptional repressor," PLoS One. 9(1):e84891.
Prusakova et al. (1999) "[The use of emistim, epibrassinolide and uniconazole to overcome quality difference of buckwheat grains]," Agrarian Russia. 1999:41-44. —with English machine translation.
Ramesh et al. (2006) "Improved methods in Agrobacterium-mediated transformation of almond using positive (mannose/pmi) or negative (kanamycin resistance) selection-based protocols," Plant Cell Rep. 25(8):821-828.
Reeves et al. (2011) "Direct targets of the transcription factors ABA-Insensitive(ABI)4 and ABI5 reveal synergistic action by ABI4 and several bZIP ABA response factors," Plant Mol. Biol. 75:347-363.

Rice et al. (2000) "EMBOSS: The European Molecular Biology Open Software Suite," Trends in Genetics. 16(6):276-277.
Robatzek et al. (2001) "A new member of the *Arabidopsis* WRKY transcription factor family, AtWRKY6, is associated with both senescence- and defence-related processes," The Plant Journal, 28:123-133.
Rodriguez-Ciria et al. (2003) "Synthesis and cytotoxic activity of N,N-bis-(3-[N-(4-chlorobenzo[g]-phthalazin-1-yl)]aminopropyl)-N-methylamine: a new potential DNA bisintercalator," Bioorg. Med. Chem. 11:2143-2148.
Sanford et al. (1993) "Optimizing the biolistic process for different biological applications," Meth. Enzymol. 217:483-509.
Schrott (1995) "Selectable Marker and Reporter Genes," Ch. 31 In; Potrykus et al.: Eds. Gene Transfer to Plants. Springer-Verlag. Berlin, Germany. pp. 325-336.
She et al. (2011) "Structural insight into brassinosteroid perception by BRI1," Nature. 474:472-476.
Song et al. (2005) "Transformation of Montmorency sour cherry (*Prunus cerasus* L.) and Gisela 6 (P. *cerasus* x P. *canescens*) cherry rootstock mediated by Agrobacterium tumefaciens," Plant Cell Rep. 25(2):117-123.
Sun (2011) "The molecular mechanism and evolution of the GA-GID1-DELLA signalling module in plants," Reviews in Current Biology. 21:R338-R345.
Szemenyei et al. (2008) "TOPLESS mediates auxin-dependent transcriptional repression during *Arabidopsis* embryogenesis," Science. 319:1384-1386.
Tatusova et al. (1999) "Blast 2 sequences—a new tool for comparing protein and nucleotide sequences," FEMS Microbiol. Lett. 174:247-250.
Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.
Thompson et al. (1994) "Clustal W: improving the sensitivity of progressive multiple sequence alignment through sequence weighting, position-specific gap penalties and weight matrix choice," Nucleic Acids Res. 22:4673-4680.
Thummel et al. (2002) "Steroid signalling in plants and insects—common themes, different pathways," Genes Dev. 16:3113-3129.
Till et al. (2003) "High-throughput TILLING for functional genomics," Methods Mol. Biol. 236:205-220.
Towbin et al. (1994) "Immunoblotting and dot immunobinding—current status and outlook," J. Immunol. Methods. 72:313-340.
Triglia et al. (1988) "A procedure for in vitro amplification of DNA segments that lie outside the boundaries of known sequences," Nucleic Acids Res. 16:8186.
Tuberosa et al. (2006) "Genomics-based approaches to improve drought tolerance of crops," Trends in Plant Science. 11:405-412.
Vanhaeren et al. (Apr. 29, 2014) "Combining growth-promoting genes leads to positive epistasis in *Arabidopsis thaliana*," eLife. 3:e02252. pp. 1-19.
Vanholme et al. (2007) "The tify family previously known as ZIM," Trends in Plant Science. 12:239-244.
Vardhini (2012) "Application of brassinolide mitigates saline stress of certain metabolites of sorghum grown in Karaikal," J. Phytology. 4:1-3.
Wang et al. (2002) "Nuclear-localised BZR1 mediates brassinosteroid-induced growth and feedback suppression of brassinosteroid biosynthesis," Developmental Cell. 2:505-513.
Wang et al. (2006) "Transformation of *Actinidia eriantha*: a potential species for functional genomics studies in Actinidia," Plant Cell Rep. 25(5):425-431.
Wang et al. (Sep. 9, 2013) "Identification of BZR1-interacting proteins as potential components of the brassinosteroid signalling pathway in *Arabidopsis* through tandem affinity purification," Mol. Cell. Proteomics. 12:3653-3665.
Werner et al. (2010) "Root-specific reduction of cytokinin causes enhanced root growth, drought tolerance, and leaf mineral enrichment in *Arabidopsis* and tobacco,"Plant Cell. 22:3905-3920.
Wheeler et al. (2001) "Database resources of the National Center for Biotechnology Information," Nucleic Acids Res. 29:11-16.
White (2006) "PEAPOD regulates lamina size and curvature in *Arabidopsis*," Proc. Natl. Acad. Sci. USA. 103(35):13238-43.

(56) References Cited

OTHER PUBLICATIONS

White et al. (2009) "PEAPOD limits and coordinates vascular procambium activity and stomatal density in *Arabidopsis*," In; The Abstracts of Plant Biology 2009. Abstract No. P67003. p. 409.

Winichayakul et al. (2009) "Head-to-tail fusions of camelid antibodies can be expressed in planta and bind in rumen fluid," Biotechnol. Appl. Biochem. 53:111-122.

Yamamoto et al. (1991) "Characterization of cis-acting sequences regulating root-specific gene expression in tobacco," Plant Cell. 3:371-382.

Yao et al. (1995) "Regeneration of transgenic plants from the commercial apple cultivar Royal Gala," Plant Cell Reports. 14:407-412.

Yu et al. (2008) "Activated expression of an *Arabidopsis* HD-START protein confers drought tolerance with improved root system and reduced stomatal density," Plant Cell. 20:1134-1151.

Zhu et al. (Apr. 2013) "Brassinosteroid signaling," Development. 140:1615-1620.

European Search Report, dated Jul. 6, 2018, corresponding to International Application No. PCT/IB2015058477 (filed Nov. 3, 2015), parent of the present application, 10 pp.

Rojas et al. (2010) "Genetically modified crops for biomass increase. Genes and strategies," GM Crops 1:3, 137-142.

\* cited by examiner

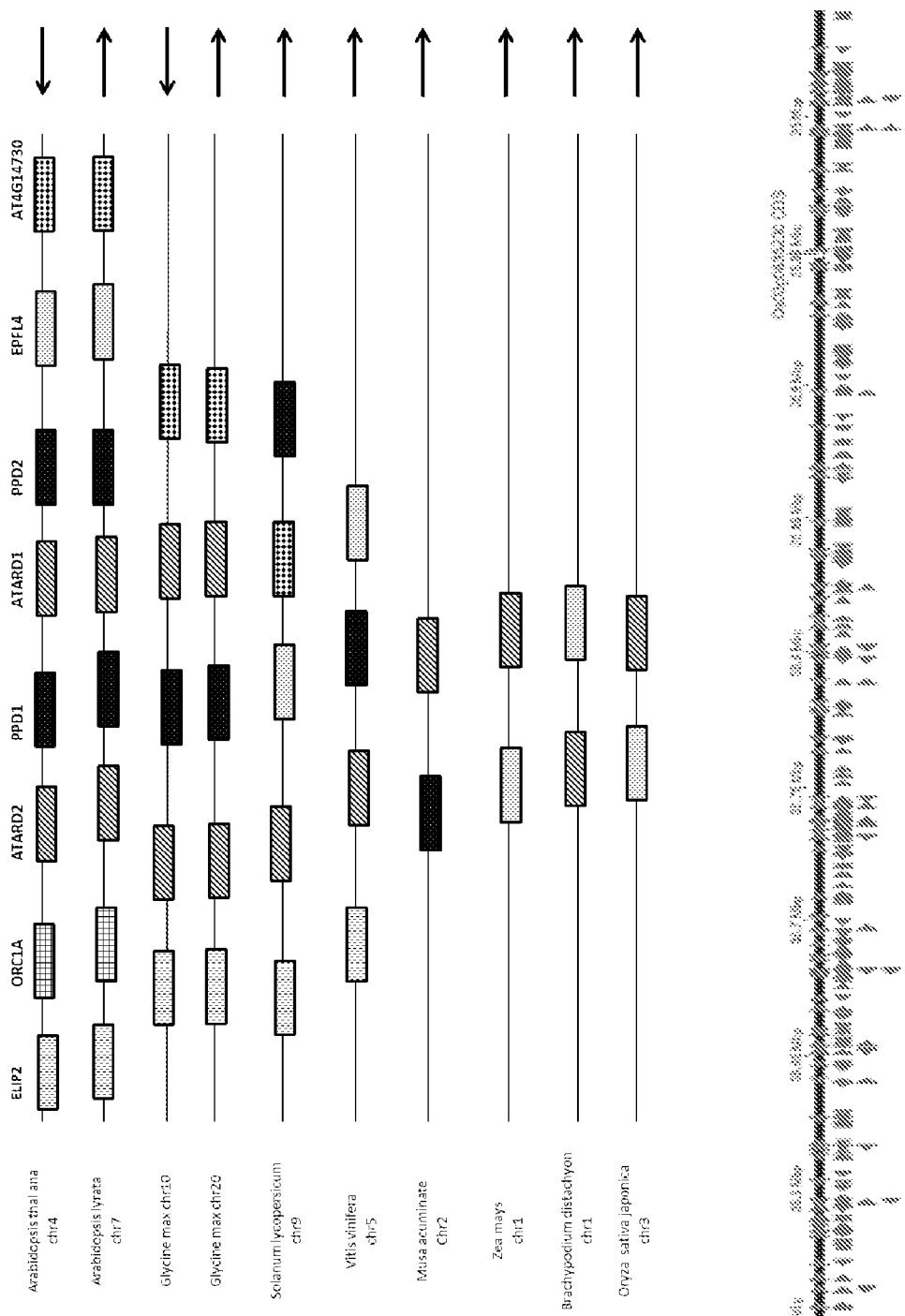
Figure 1A
Figure 1B

| Species | Sequence | SEQ ID NO |
|---|---|---|
| Amborella trichopoda | LEELITEEDISQLTREDCRRYLKEKGMRRPSWNRYLQAIQQVLSLKAL | (SEQ ID NO: 143) |
| Picea sitchensis | LEELITEEDIFQLTREDCRRYLKEKGMRRPSWNRYLQAIQQVLSLKSL | (SEQ ID NO: 144) |
| Spirodela polyrhiza | LSELITEEDIAQVTREDCRRFLKEKGMRRPSWNRPSWNRSQAVQQVISLKAL | (SEQ ID NO: 145) |
| Selaginella moellendorffii PPD1 | LEELITELDIRQLTREDCRRYLKERGMRRPSWNRPSWNRSQAIQQVLSLRSL | (SEQ ID NO: 146) |
| Selaginella moellendorffii PPD2 | LEELITEEDVMQLTREDCRRYLKEKGMERPSWNRGAVQQLLSLKSL | (SEQ ID NO: 147) |
| Musa species | LAELITEEDIAQITREDCREFLKAKGMERRPSWNRKSQAIQQVISLKAL | (SEQ ID NO: 148) |
| Elaeis guineensis | LSELITEEDIAQLTREDCRRFLKEKGMERRPSWNRKSQAIQQVISLKAL | (SEQ ID NO: 149) |
| Phalaenopsis aphrodite | LNLLITEDDIAQITREECSRFLKDRGMRRFSWNRKSQAIQQVISLKAL | (SEQ ID NO: 150) |
| Nicotiana tabacum | LHLITDDDISQITREDCRRYLKEKGMRRPSWNRKSQAIQQVISLKAL | (SEQ ID NO: 151) |
| Solanum lycopersicum | LXLLTDDDISQITREDCRRFLKAKGMAKPSWNRKSQAIQQVISLKAL | (SEQ ID NO: 152) |
| Solanum tuberosum | LMQLITEDDISQITREDCRRYLKQGMRRPSWNRKSQAIQQVISLKAL | (SEQ ID NO: 153) |
| Aquilegia coerulea | LRQLITEEDISQITREDCRRFLKDKGMERPSWNRKSQAIEQVISLKTL | (SEQ ID NO: 154) |
| Populus trichocarpa | LRQLITEEDISQVTREDCRRYLKEKGMRPSWNRKSQAIQQVISLKAL | (SEQ ID NO: 155) |
| Glycine max | LMQLITEEDISQLITREDCRRFLKEKGMRRPSWNRKSQAIQQVISLKAL | (SEQ ID NO: 156) |
| Medicago truncatula | LMQLITEDDISQLITREDCRRFLKDQGMRRPSWNRKSQAIQQVISLKAL | (SEQ ID NO: 157) |
| Trifolium repens | LNQLITEEDISQLITREDCRRFLKDGMERPSWNRKSQAIQQVISLKAL | (SEQ ID NO: 158) |
| Arabidopsis thaliana PPD1 | LAQLITEEDISQLITREDCRTLKGMERPSWNRKSQAIQQVISLKAL | (SEQ ID NO: 159) |
| Arabidopsis thaliana PPD2 | LMLITEEDISQLITREDCSRTLKGMERPSWNRKSQAIQQVISLKAL | (SEQ ID NO: 160) |
| Gossypium raimondii | LSQLITEEDISQITREDCRRTLKEKGMERPSWNRKSQAIQQVISMAL | (SEQ ID NO: 161) |
| Theobroma cacao | LSQLITEEDISQLTREDCRRTLKEKGMERPSWNRKSQAIQQVISLKAL | (SEQ ID NO: 162) |
| Citrus clementine | LSQLITEEDITQLITREDCRRTLKEKGMRRPSWNRKSQAIQQVISLKAL | (SEQ ID NO: 163) |
| Morus notabilis | LNQLITEEDISQLITREDCRRYLKEKGMRPSWNRKSQAIQQVISLKAL | (SEQ ID NO: 164) |
| Ricinus communis | LIQLITEEDISQLITREDCRYLKEKGMERPSWNRKSQAIQQVISLKAL | (SEQ ID NO: 165) |
| Vitis vinifera | LRELITEEDISQLITREDCRYLKEKGMRRPSWNRKSQAIQQVISLKSL | (SEQ ID NO: 166) |
| Identical amino acids | :.:** . * .**** ** * *** ****** ** | |

Fig. 2

| Species | Sequence | SEQ ID |
|---|---|---|
| Amborella trichopoda | TREDCCKRYLKEKGMRRPSWNKYQAIQQ | (SEQ ID NO: 167) |
| Picea sitchensis | TREDCCKRYLKEKGMRRPSWNKSQAIQQ | (SEQ ID NO: 168) |
| Spirodela polyrhiza | TREDCCKRFLKEKGMRRPSWNKSQAIQQ | (SEQ ID NO: 169) |
| Selaginella moellendorffii PPD1 | TREDCCKRYLKERGMRRPSWNKAQAVQQ | (SEQ ID NO: 170) |
| Selaginella moellendorffii PPD2 | TREDCCKRYLKEKGMRRPSWNKAQAVQQ | (SEQ ID NO: 171) |
| Musa species | TREDCCKRFLKAKGMRRPSWNKSQAIQQ | (SEQ ID NO: 172) |
| Elaeis guineensis | TREDCCKRFLKEKGMRRPSWNKSQAIQQ | (SEQ ID NO: 173) |
| Phalaenopsis aphrodite | TREDCCKRFLKDKGMRRPSWNKSQAIQQ | (SEQ ID NO: 174) |
| Nicotiana tabacum | TREDCCKRYLKEKGMRRPSWNKSQAIQQ | (SEQ ID NO: 175) |
| Solanum lycopersicum | TREDCCKRFLKAKGMRRPSWNKSQAIQQ | (SEQ ID NO: 176) |
| Solanum tuberosum | TREDCCKRYLQKGMRRPSWNKSQAIQQ | (SEQ ID NO: 177) |
| Aquilegia coerulea | TREDCCKRFLRDKGMRRPSWNKSQAIQQ | (SEQ ID NO: 178) |
| Populus trichocarpa | TREDCCKRYLEEKGMRRPSWNKSQAIQQ | (SEQ ID NO: 179) |
| Glycine max | TREDCCKRFLKEKGMRRPSWNKSQAIQQ | (SEQ ID NO: 180) |
| Medicago truncatula | TREDCCKRFLKDKGMRRPSWNKSQAIQQ | (SEQ ID NO: 181) |
| Trifolium repens | TREDCCKKFLKDKGMRRPSWNKSQAIQQ | (SEQ ID NO: 182) |
| Arabidopsis thaliana PPD1 | TREDCCKKFLKDKGMRRPSWNKSQAIQQ | (SEQ ID NO: 183) |
| Arabidopsis thaliana PPD2 | TREDCCKKFLKEKGMRRPSWNKSQAIQQ | (SEQ ID NO: 184) |
| Gossypium raimondii | TREDCCKKFLKEKGMRRPSWNKSQAIQQ | (SEQ ID NO: 185) |
| Theobroma cacao | TREDCCKKFLKEKGMRRPSWNKSQAIQQ | (SEQ ID NO: 186) |
| Citrus clementine | TREDCCKKYLKEKGMRRPSWNKSQAIQQ | (SEQ ID NO: 187) |
| Morus notabilis | TREDCCKKYLKEKGMRRPSWNKSQAIQQ | (SEQ ID NO: 188) |
| Ricinus communis | TREDCCKKYLKEKGMRRPSWNKSQAIQQ | (SEQ ID NO: 189) |
| Vitis vinifera | TREDCCKKYLKEKGMRRPSWNKSQAIQQ | (SEQ ID NO: 190) |
| Identical amino acids | ***  ** *     *   *** ****** ** * | |

Fig. 3

| | | |
|---|---|---|
| Amborella trichopoda | TIFYAG | (SEQ ID NO: 191) |
| Picea sitchensis | TIFYAG | (SEQ ID NO: 192) |
| Spirodela polyrhiza | TIFYDG | (SEQ ID NO: 193) |
| Selaginella moellendorffii PPD1 | TIFYSG | (SEQ ID NO: 194) |
| Selaginella moellendorffii PPD2 | TMFYDG | (SEQ ID NO: 195) |
| Musa species | TIFYDG | (SEQ ID NO: 196) |
| Elaeis guineensis | TIFYDG | (SEQ ID NO: 197) |
| Phalaenopsis aphrodite | TIFYGG | (SEQ ID NO: 198) |
| Nicotiana tabacum | TIFYCG | (SEQ ID NO: 199) |
| Solanum lycopersicum | TIFYCG | (SEQ ID NO: 200) |
| Solanum tuberosum | TIFYRG | (SEQ ID NO: 201) |
| Aquilegia coerulea | TIFYCG | (SEQ ID NO: 202) |
| Populus trichocarpa | TIFYCG | (SEQ ID NO: 203) |
| Glycine max | TIFYCG | (SEQ ID NO: 204) |
| Medicago truncatula | TIFYCG | (SEQ ID NO: 205) |
| Trifolium repens | TIFYCG | (SEQ ID NO: 206) |
| Arabidopsis thaliana PPD1 | TIFYSG | (SEQ ID NO: 207) |
| Arabidopsis thaliana PPD2 | TIFYSG | (SEQ ID NO: 208) |
| Gossypium raimondii | TIFYCG | (SEQ ID NO: 209) |
| Theobroma cacao | TIFYCG | (SEQ ID NO: 210) |
| Citrus clementine | TIFYCG | (SEQ ID NO: 211) |
| Morus notabilis | TIFYCG | (SEQ ID NO: 212) |
| Ricinus communis | TIFYCG | (SEQ ID NO: 213) |
| Vitis vinifera | TIFYCG | (SEQ ID NO: 214) |
| Identical amino acids | * ** * | |

Fig. 4

SEQUENCE LISTING

<160> NUMBER OF SEQ ID NOS: 217

<210> SEQ ID NO 1
<211> LENGTH: 313
<212> TYPE: PRT
<213> ORGANISM: Arabidopsis thaliana

<400> SEQUENCE: 1

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe

```
        145                 150                 155                 160
    Tyr Ser Gly Lys Val Asn Val Tyr Asp Gly Ile Pro Pro Glu Lys Ala
                    165                 170                 175
    Arg Ser Ile Met His Phe Ala Ala Asn Pro Ile Asp Leu Pro Glu Asn
                    180                 185                 190
    Gly Ile Phe Ala Ser Ser Arg Met Ile Ser Lys Leu Ile Ser Lys Glu
                    195                 200                 205
    Lys Met Met Glu Leu Pro Gln Lys Gly Leu Lys Ala Asn Ser Ser
        210                 215                 220
    Arg Asp Ser Gly Met Glu Gly Gln Ala Asn Arg Lys Val Ser Leu Gln
    225                 230                 235                 240
    Arg Tyr Arg Glu Lys Arg Lys Asp Arg Lys Phe Ser Lys Ala Lys Lys
                    245                 250                 255
    Cys Pro Gly Val Ala Ser Ser Leu Glu Met Phe Leu Asn Cys Gln
                    260                 265                 270
    Pro Arg Met Lys Ala Ala Tyr Ser Gln Asn Leu Gly Cys Thr Gly Ser
                    275                 280                 285
    Pro Leu His Ser Gln Ser Pro Glu Ser Gln Thr Lys Ser Pro Asn Leu
                    290                 295                 300
    Ser Val Asp Leu Asn Ser Glu Gly Ile
    305                 310

<210> SEQ ID NO 2
<211> LENGTH: 315
<212> TYPE: PRT
<213> ORGANISM: Arabidopsis thaliana

<400> SEQUENCE: 2

Met Asp Val Gly Val Thr Thr Ala Lys Ser Ile Leu Glu Lys Pro Leu
    1               5                   10                  15
    Lys Leu Leu Thr Glu Glu Asp Ile Ser Gln Leu Thr Arg Glu Asp Cys
                    20                  25                  30
    Arg Lys Phe Leu Lys Glu Lys Gly Met Arg Arg Pro Ser Trp Asn Lys
                    35                  40                  45
    Ser Gln Ala Ile Gln Gln Val Leu Ser Leu Lys Ala Leu Tyr Glu Pro
        50                  55                  60
    Gly Asp Asp Ser Gly Ala Gly Ile Leu Arg Lys Ile Leu Val Ser Gln
    65                  70                  75                  80
    Pro Pro Asn Pro Pro Arg Val Thr Thr Thr Leu Ile Glu Pro Arg Asn
                    85                  90                  95
    Glu Leu Glu Ala Cys Gly Arg Ile Pro Leu Gln Glu Asp Gly Ala
                    100                 105                 110
    Cys His Arg Arg Asp Ser Pro Arg Ser Ala Glu Phe Ser Gly Ser Ser
                    115                 120                 125
    Gly Gln Phe Val Ala Asp Lys Asp Ser His Lys Thr Val Ser Val Ser
        130                 135                 140
    Pro Arg Ser Pro Ala Glu Thr Asn Ala Val Val Gly Gln Met Thr Ile
    145                 150                 155                 160
    Phe Tyr Ser Gly Lys Val Asn Val Tyr Asp Gly Val Pro Pro Glu Lys
                    165                 170                 175
    Ala Arg Ser Ile Met His Phe Ala Ala Asn Pro Ile Asp Leu Pro Glu
                    180                 185                 190
    Asn Gly Ile Phe Ala Ser Ser Arg Met Ile Ser Lys Pro Met Ser Lys
                    195                 200                 205
```

```
Glu Lys Met Val Glu Leu Pro Gln Tyr Gly Leu Glu Lys Ala Pro Ala
    210                 215                 220

Ser Arg Asp Ser Asp Val Glu Gly Gln Ala Asn Arg Lys Val Ser Leu
225                 230                 235                 240

Gln Arg Tyr Leu Glu Lys Arg Lys Asp Arg Phe Ser Lys Thr Lys
                245                 250                 255

Lys Ala Pro Gly Val Ala Ser Ser Leu Glu Met Phe Leu Asn Arg
                260                 265                 270

Gln Pro Arg Met Asn Ala Ala Tyr Ser Gln Asn Leu Ser Gly Thr Gly
                275                 280                 285

His Cys Glu Ser Pro Glu Asn Gln Thr Lys Ser Pro Asn Ile Ser Val
290                 295                 300

Asp Leu Asn Ser Asp Leu Asn Ser Glu Asp Asn
305                 310                 315

<210> SEQ ID NO 3
<211> LENGTH: 375
<212> TYPE: PRT
<213> ORGANISM: Populus trichocarpa

<400> SEQUENCE: 3

Met Gln Pro Gly Glu Thr Val Phe Arg Ser Ala Leu Asp Lys Pro Leu
1               5                   10                  15

His Gln Leu Thr Glu Asp Asp Ile Ser Gln Val Thr Arg Glu Asp Cys
                20                  25                  30

Arg Arg Tyr Leu Lys Glu Lys Gly Met Arg Arg Pro Ser Trp Asn Lys
            35                  40                  45

Ser Gln Ala Ile Gln Gln Val Ile Ser Leu Lys Thr Leu Leu Glu Ala
50                  55                  60

Thr Pro Glu Thr Glu Ser Pro Arg Arg Arg Leu Tyr Ile Pro Arg Pro
65                  70                  75                  80

Pro Pro His Pro Pro Asp Asn Thr Pro Arg Val Arg Phe Ser Ala Val
                85                  90                  95

Pro Pro Asn Ser Ser Val Ser Glu Arg Gly Ala Ser Ala Glu Thr Pro
            100                 105                 110

Ile Ser Val Pro Ala Glu Glu Pro Val Pro Cys Arg Gln His Asp Pro
        115                 120                 125

Pro Asn Pro Asp Asp Pro Ala Asp Pro Leu Pro Pro Val His Ala Ala
    130                 135                 140

Val Thr Glu Asn Ala Ser Val Ser Pro Arg Thr Thr Gly Met Ala Glu
145                 150                 155                 160

Glu Ser Ala Gly Gln Met Thr Ile Phe Tyr Cys Gly Lys Val Asn Val
                165                 170                 175

Tyr Asp Asp Val Pro Gly Asp Lys Ala Gln Ala Ile Met His Leu Ala
            180                 185                 190

Ala Ser Pro Phe Ala Pro Pro Gln Asp Ala Ser Ser Asp Val Ile Pro
        195                 200                 205

Thr Leu Arg Pro Leu Gln Cys Gln Leu Asp Thr Pro Gly Val Lys Ala
    210                 215                 220

Ala Pro Asn Ser Ile Val Ala Asn Phe Pro Thr Leu Pro Thr Val Lys
225                 230                 235                 240

Gly Ala Asp Ser Gly Gln Leu Leu Trp Glu Glu Ser Asn Ile Ala Arg
                245                 250                 255

Glu Asp Asn Leu Glu Gly Ser Thr Ser Arg Lys Ala Ser Leu Gln Arg
            260                 265                 270
```

-continued

```
Tyr Phe Glu Lys Lys Asp Arg Phe Lys Asn Lys Arg Lys Val Ala
            275                 280                 285
Val Pro Ser Ala Ser Leu Asp Val Phe Leu Ser His Leu Val Gly Asp
290                 295                 300
Gln Ile Ser Asn Asp His Trp Asn Leu Asn Asp Ala Cys Ser Pro Ser
305                 310                 315                 320
Gln Pro Arg Pro Pro Gln Thr Pro Asn Arg Cys Asn Ser Val Asp Asn
            325                 330                 335
Val Ala Lys Asn Gly Ile Leu Lys Ala Asp Leu Asn Asn Lys Gly Asp
            340                 345                 350
Ala Asp Leu Ser Cys Cys Leu Asp Phe Ser Ser Lys Gln Ile Asn Ala
            355                 360                 365
Trp Cys Leu Cys Leu Gly Cys
            370                 375

<210> SEQ ID NO 4
<211> LENGTH: 346
<212> TYPE: PRT
<213> ORGANISM: Picea abies

<400> SEQUENCE: 4

Met Arg Gly Gly Gly Ala Asp Arg Leu Pro Ala Arg Ala Asn Leu
1               5                   10                  15
Glu Lys Pro Leu Glu Asp Leu Ser His Glu Asp Ile Met Gln Leu Thr
                20                  25                  30
Arg Glu Asp Cys Arg Arg Tyr Leu Ile Glu Lys Gly Met Arg Arg Pro
            35                  40                  45
Ser Trp Asn Lys Ser Gln Ala Ile Gln Gln Val Leu Ser Leu Lys Lys
    50                  55                  60
Leu Phe Glu Ser Gly Pro Asn Asp Glu Lys Arg Ser Ala Ala Thr Asn
65                  70                  75                  80
Arg Pro Asn Pro Asp Glu Asn Leu Lys Glu Ala Ala Ser Val Ser Leu
                85                  90                  95
Leu Tyr Gly Ser Gln Pro Glu Ser Pro Ser Val Val Phe Ala Ser Lys
            100                 105                 110
Asp Ser Asp Thr Phe Asn Leu Glu Trp Leu Ala Lys Thr Glu Leu Pro
        115                 120                 125
Val Leu Ala Ser Gln Pro Arg His Ile Ala Gln Gln Asn Val Phe Leu
    130                 135                 140
Ser Ser Leu Ser Ala Gln Gln Ser Gly Ala Gln Leu Thr Ile Phe Tyr
145                 150                 155                 160
Ser Gly Asn Val Asn Val Tyr Asp Asp Val Pro Ala Glu Lys Ala Gln
                165                 170                 175
Glu Ile Met Leu Leu Ala Gly Ser Gly Asn Tyr Pro Pro Ser Ser Thr
            180                 185                 190
Cys Gln Ser Thr Arg Asn Thr Gln Gln Asn Ala Val Arg Ala Ala Tyr
        195                 200                 205
Pro Ser Asn Pro Thr Asn Thr Pro Phe Ile His Gly Val Gly Pro Pro
    210                 215                 220
Leu Ala Thr Val Ala Ser Ser Val Met Ser Ser Pro Ile His Lys
225                 230                 235                 240
Glu Ser Pro Ile Thr Arg Lys Ala Ser Leu Gln Arg Phe Leu Glu Lys
                245                 250                 255
Arg Lys Asp Arg Ser Arg Gly Lys Leu Gly Ala Pro Thr Ile Ser Lys
```

```
            260                 265                 270
Lys Pro Leu Leu Met Gly Met Phe Met His Pro Ser Ile Val His Arg
                275                 280                 285

Gln Tyr Trp Thr Asp Thr Ala Lys Arg Lys Ser Gly Lys Pro Asp Ile
            290                 295                 300

Pro Ala Ser Ile Ser Pro Thr Arg Pro Pro His Thr Pro Arg Arg Thr
305                 310                 315                 320

Ser Ser Asp Glu Gln Leu Ser Ala Arg His Ala Arg Gly Asp Ile Ser
                325                 330                 335

Ala Gln Gly Gly Ser Leu His Asn Ser Asn
                340                 345

<210> SEQ ID NO 5
<211> LENGTH: 222
<212> TYPE: PRT
<213> ORGANISM: Picea sitchensis

<400> SEQUENCE: 5

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
            20                  25                  30

Asp Cys Arg Arg Tyr Leu Lys Glu Lys Gly Met Arg Arg Pro Ser Trp
        35                  40                  45

Asn Lys Ser Gln Ala Ile Gln Gln Val Leu Ser Leu Lys Ser Leu Phe
    50                  55                  60

Glu Ser Lys Pro Asn Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175

Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
        195                 200                 205

Gly Met Val Asn Val Tyr Asp Asp Val Pro Leu Asp Lys Ala
    210                 215                 220

<210> SEQ ID NO 6
<211> LENGTH: 365
<212> TYPE: PRT
<213> ORGANISM: Gossypium raimondii

<400> SEQUENCE: 6

Met Glu Ala Gly Val Thr Thr Thr Ala Thr Thr Thr Ala Ser Phe Ser
1               5                   10                  15

Ser Ile Leu Asp Lys Pro Leu Ser Gln Leu Thr Glu Glu Asp Ile Ser
```

```
        20                  25                  30
Gln Leu Thr Arg Glu Asp Cys Arg Lys Phe Leu Lys Glu Lys Gly Met
         35                  40                  45

Arg Arg Pro Ser Trp Asn Lys Ser Gln Ala Ile Gln Gln Val Ile Ser
 50                  55                  60

Phe Lys Ala Leu Leu Glu Ser Asn Glu Asp Ser Gly Ala Gly Ala Arg
 65                  70                  75                  80

Arg Lys Ile Leu Val Cys Pro Pro Ser His Phe Pro Pro Gln Asn
                 85                  90                  95

Ala Val Ala Ser Asn Ser Gly Glu Ser Val Lys Glu Ala Val Phe Gly
            100                 105                 110

Glu Glu Glu Ser Leu Tyr Gly Gln Lys Asp Leu Ser Leu Lys Ala Ala
            115                 120                 125

Pro Val Val Gln Met Asn Cys Gln Gly Gly Asp Thr Asp Asp Lys Thr
        130                 135                 140

Leu Ser Pro Ser Leu Gly Ser Pro Arg Glu Tyr Ser Lys Leu Pro Gly
145                 150                 155                 160

Arg Ser Gln Cys Glu Thr Asn Glu Leu Gly Gly Gln Met Thr Ile Phe
                165                 170                 175

Tyr Cys Gly Lys Ile Asn Val Tyr Asp Gly Val Pro Leu Ala Lys Ala
            180                 185                 190

Arg Ala Ile Met His Leu Ala Ala Ser Pro Ile Asp Phe Pro Gln Gly
        195                 200                 205

Asn Leu Cys Asn Gln Asn Gly Ala Phe Arg Ser Phe Leu Gly His Val
    210                 215                 220

Gln Glu Ala Glu Asp Lys Asn Asp Leu Thr Ser Ser Ile Ala Leu Asn
225                 230                 235                 240

Leu Asn Ser His Thr Met His Thr Glu Lys Met Thr Glu Tyr Gln Gln
                245                 250                 255

Gln Phe Arg Gly Lys Ala Asn Ile Ser Arg Asp Ser Asp Val Asp Gly
            260                 265                 270

Gln Val Ser Arg Lys Glu Ser Leu Gln Arg Tyr Leu Glu Lys Arg Lys
        275                 280                 285

Asp Arg Gly Arg Phe Phe Lys Gly Arg Lys Asn Ala Gly Gln Ala Leu
    290                 295                 300

Ser Ser Ser Glu Met Tyr Leu Asn His Gln Ile Arg Ala His Tyr Leu
305                 310                 315                 320

Asn Gly Gln Thr Asn Gln Ser Arg Thr Ser Ser Pro Pro Gln Ser Gly
                325                 330                 335

Val Pro His Ala Phe Tyr Ser Ser Ala Asp Asn Gln Glu Leu Val Asn
            340                 345                 350

Phe Ser Val Asp Leu Asn Asp Glu Gly Gly Gln Glu His
        355                 360                 365

<210> SEQ ID NO 7
<211> LENGTH: 357
<212> TYPE: PRT
<213> ORGANISM: Aquilegia coerulea

<400> SEQUENCE: 7

Met Lys Pro Asp Glu Thr Val Ser Arg Ser Pro Leu Asp Lys Pro Leu
1                 5                  10                  15

Phe Gln Leu Thr Asp Glu Asp Ile Ser Gln Leu Thr Arg Glu Asp Cys
            20                  25                  30
```

Arg Lys Phe Leu Arg Asp Lys Gly Met Arg Arg Pro Ser Trp Asn Lys
            35                   40                  45

Ser Gln Ala Ile Glu Gln Val Ile Ser Leu Lys Thr Leu Leu Glu Pro
    50                   55                  60

Arg Thr Glu Ser Asp Thr Asn Ala Thr Gly Ile Arg Gln Lys Leu Leu
65                  70                  75                  80

Val Ser Arg Leu Glu Asn Ser Thr Gln Val Pro Leu Asn Asp Lys Thr
                85                  90                  95

Asn Ala Ser Asn Leu Lys Thr Ser Val Gln Ala Ile Asn Ser Gly Lys
            100                 105                 110

Ala Asp Ile His Gly Asp Arg Pro Cys Arg Val Pro Val Pro Val Pro
            115                 120                 125

Asp Asp Asn Thr Ile Thr Val Pro Val Pro Asp Asn Asn Thr Ile Thr
130                 135                 140

Val Pro Val Pro Asp Asn Asn Ile Thr Ser Ser Arg Asn Leu Asn Ser
145                 150                 155                 160

Thr Asn Gly Leu Val Gly Gln Met Thr Ile Phe Tyr Cys Gly Lys Val
                165                 170                 175

Ile Val Tyr Asp Asp Met Pro Ala Glu Lys Ala His Ala Ile Met Lys
            180                 185                 190

Phe Ala Gly Ser His Ile Asn Val Pro Glu Asp Ser Ser Pro Ala Gly
            195                 200                 205

Ala Ala Val Ile Gln Ser Phe Ala Cys Gln Leu Gln Ala Ala Ser Ile
            210                 215                 220

Arg His Gly Leu Ala Phe Pro Ser Ala Val Ser Pro Pro Leu His Asn
225                 230                 235                 240

Val Val Ala Asp Thr Ser Gln His Cys Arg Glu Glu Val Thr Val Ser
                245                 250                 255

Arg Glu Val Glu Pro Glu Gly Pro Val Ser Arg Lys Ala Ser Val Gln
            260                 265                 270

Arg Tyr Leu Glu Lys Arg Lys Asp Arg Gly Arg Phe Lys Asn Lys Arg
            275                 280                 285

Lys Ile Glu Ser Ser Ser Ser Leu Glu Ile Tyr Leu Asn His Gln Leu
290                 295                 300

Gly Asp Gln Tyr Leu Asn Glu Lys Ser Ser Gln Ser Arg Ala Cys Ser
305                 310                 315                 320

Pro Pro Gln Pro Arg Ala Pro His Thr Pro Thr Arg Cys Ser Ser Val
                325                 330                 335

Glu Asn Gln Val Thr Asn Val Val Phe Ser Ile Asp Leu Asn Asp Asn
            340                 345                 350

Asp Val Arg Glu Gly
        355

<210> SEQ ID NO 8
<211> LENGTH: 347
<212> TYPE: PRT
<213> ORGANISM: Aquilegia coerulea

<400> SEQUENCE: 8

Met Lys Pro Asp Glu Thr Val Ser Arg Ser Pro Leu Asp Lys Pro Leu
1               5                   10                  15

Phe Gln Leu Thr Asp Glu Asp Ile Ser Gln Leu Thr Arg Glu Asp Cys
            20                  25                  30

Arg Lys Phe Leu Arg Asp Lys Gly Met Arg Arg Pro Ser Trp Asn Lys
            35                  40                  45

```
Ser Gln Ala Ile Glu Gln Val Ile Ser Leu Lys Thr Leu Leu Glu Pro
     50                  55                  60

Arg Thr Glu Ser Asp Thr Asn Ala Thr Gly Ile Arg Gln Lys Leu Leu
 65                  70                  75                  80

Val Ser Arg Leu Glu Asn Ser Thr Gln Val Pro Leu Asn Asp Lys Thr
                 85                  90                  95

Asn Ala Ser Asn Leu Lys Thr Ser Val Gln Ala Ile Asn Ser Gly Glu
             100                 105                 110

Ala Asp Ile His Gly Asp Arg Pro Cys Arg Val Pro Val Pro Val Pro
         115                 120                 125

Asp Asp Asn Thr Ile Thr Val Pro Val Pro Asp Asn Asn Ile Thr Ser
     130                 135                 140

Ser Arg Asn Leu Asn Ser Thr Asn Gly Leu Val Gly Gln Met Thr Ile
145                 150                 155                 160

Phe Tyr Cys Gly Lys Val Ile Val Tyr Asp Gly Met Pro Ala Glu Lys
                 165                 170                 175

Ala His Ala Ile Met Lys Phe Ala Gly Ser His Ile Asn Val Pro Glu
             180                 185                 190

Asp Ser Pro Ala Gly Ala Ala Val Ile Gln Ser Phe Ala Cys Gln
         195                 200                 205

Leu Gln Ala Ala Ser Ile Arg His Gly Leu Ala Phe Pro Ser Ala Val
     210                 215                 220

Ser Pro Pro Leu His Asn Val Val Ala Asp Thr Ser Gln His Cys Arg
225                 230                 235                 240

Glu Glu Val Thr Val Ser Arg Glu Val Glu Pro Glu Gly Pro Val Ser
                 245                 250                 255

Arg Lys Ala Ser Val Gln Arg Tyr Leu Glu Lys Arg Lys Asp Arg Gly
             260                 265                 270

Arg Phe Lys Asn Lys Arg Lys Ile Glu Ser Ser Ser Leu Glu Ile
     275                 280                 285

Tyr Leu Asn His Gln Leu Gly Asp Gln Tyr Leu Asn Glu Lys Ser Ser
     290                 295                 300

Gln Ser Arg Ala Cys Ser Pro Pro Gln Pro Arg Ala Pro His Thr Pro
305                 310                 315                 320

Thr Arg Cys Ser Ser Val Glu Asn Gln Val Thr Asn Val Val Phe Ser
                 325                 330                 335

Ile Asp Leu Asn Asp Asn Asp Val Arg Glu Gly
             340                 345

<210> SEQ ID NO 9
<211> LENGTH: 328
<212> TYPE: PRT
<213> ORGANISM: Medicago truncatula

<400> SEQUENCE: 9

Met Asn Gly Gly Ser Thr Val Ser Phe Arg Ser Ile Leu Asp Arg Pro
 1               5                  10                  15

Leu Asn Gln Leu Thr Glu Asp Asp Ile Ser Gln Leu Thr Arg Glu Asp
                 20                  25                  30

Cys Arg Arg Phe Leu Lys Asp Lys Gly Met Arg Arg Pro Ser Trp Asn
             35                  40                  45

Lys Ser Gln Ala Ile Gln Gln Val Ile Ser Leu Lys Ala Leu Leu Glu
     50                  55                  60

Pro Thr Asp Asp Asp Ile Pro Ala Thr Val Gly Val Gly Val Ser Ser
```

```
              65                  70                  75                  80
Ala Ile His His His His His His Pro Pro Gln Pro Pro Lys
                    85                  90                  95
Ala Leu Asp Pro Glu Asp Thr Ala Leu Glu Leu Gln Lys Ser Thr Ser
                100                 105                 110
Pro Val Ala Glu Arg Pro Thr Glu Thr Asn Asp Ala Asn Val Val Asn
                115                 120                 125
Asn Pro Gly Gly Cys Ala Pro Ser Gly Ser Phe Gly Gln Met Thr Ile
            130                 135                 140
Phe Tyr Cys Gly Lys Val Asn Val Tyr Asp Gly Val Ser Pro Asp Lys
145                 150                 155                 160
Ala Arg Ser Ile Met Gln Leu Ala Ala Ala Cys Pro Ser Ser Phe Pro
                165                 170                 175
Gln Asp Asn Pro Ser Asn Lys Asn Ala Ala Val Trp Ala Ser Pro Cys
            180                 185                 190
Asn Leu Pro Ile Asp Lys Glu Val Leu Phe Pro Thr Asp Thr Ala Ile
            195                 200                 205
Leu Gln Val Ala Gln Thr Asp Lys Met Val Glu Tyr Pro Leu Gln Tyr
    210                 215                 220
Arg Glu Lys Gly Ser Thr Ala Arg Asp Ala Glu Gly Gln Ala Ser Arg
225                 230                 235                 240
Lys Val Ser Leu Gln Arg Tyr Leu Glu Lys Lys Asp Arg Gly Arg
                245                 250                 255
Ser Lys Gly Lys Lys Leu Thr Gly Ile Thr Ser Ser Asn Phe Glu Met
            260                 265                 270
Tyr Leu Asn Leu Pro Val Lys Leu His Ala Ser Asn Gly Asn Ser Ser
    275                 280                 285
Arg Ser Ser Thr Asp Ser Pro Pro Gln Pro Arg Leu Pro Leu Val Ser
        290                 295                 300
Ser Gly Ser Ala Glu Asn Gln Pro Lys Val Thr Leu Pro Ile Asp Leu
305                 310                 315                 320
Asn Asp Lys Asp Val Gln Glu Cys
                325

<210> SEQ ID NO 10
<211> LENGTH: 339
<212> TYPE: PRT
<213> ORGANISM: Solanum lycopersicum

<400> SEQUENCE: 10

Met Ser Leu Glu Gln Thr Val Tyr Lys Ser Pro Leu Asp Lys Pro Leu
1               5                   10                  15
Tyr Leu Leu Thr Asp Asp Ile Ser Gln Leu Thr Arg Glu Asp Cys
            20                  25                  30
Arg Arg Phe Leu Lys Ala Lys Gly Met Arg Lys Pro Ser Trp Asn Lys
        35                  40                  45
Ser Gln Ala Ile Gln Gln Val Ile Ser Leu Lys Ala Leu Phe Glu Thr
    50                  55                  60
Thr Pro Glu Ser Asp Thr Gly Gln Arg Lys Lys Arg His Ile Pro Arg
65                  70                  75                  80
Pro Asp Thr Ser Leu Gln Arg Val Gln Lys Glu Thr Ser Ile Asp Ala
                85                  90                  95
Glu Phe Ala Glu Ser Ala Glu Gly Thr Val Pro Tyr Gly Arg Lys Pro
                100                 105                 110
```

```
Pro Asn Lys Pro Asp Leu Ser Gly Asp Lys Ala Ala Ser Ala Val Ala
            115                 120                 125

Val Val Asn Asn Leu Ala Pro Ser Arg Thr Thr Asp Ser Gly Asn Ala
130                 135                 140

Ser Ser Gly Gln Leu Thr Ile Phe Tyr Cys Gly Lys Val Asn Val Tyr
145                 150                 155                 160

Asp Asp Val Pro Ala Glu Lys Ala Glu Ala Ile Met His Leu Ala Ala
                165                 170                 175

Ser Pro Leu Phe Val Pro Ser Glu Thr Pro Leu Asp Ala Asn Arg Ala
                180                 185                 190

Ala Gln His Ser Glu Cys His Leu Gln Ala Ala Asn Val Lys Leu Gly
            195                 200                 205

Gln Asp Ser Pro Met Val Phe Met Pro Thr Met Gln Thr Gly Lys Ile
            210                 215                 220

Thr Glu Val Thr Arg Leu His Leu Glu Glu Ser Asn Thr Ser Tyr Glu
225                 230                 235                 240

Asp Asn Pro Glu Ala Val Asn His Val Ser Arg Lys Ala Leu Leu Glu
                245                 250                 255

Arg Tyr Arg Glu Lys Arg Lys Asp Arg Phe Lys Arg Lys Met Gly Met
                260                 265                 270

Pro Ser Ser Ala Ser Leu Asp Ile Tyr Leu Asn His Arg Thr Ile Asn
            275                 280                 285

His Thr Gln Ser Glu Leu Ser Ser Arg Ser Asn Thr Cys Ser Pro Pro
            290                 295                 300

Ala Ile Arg Leu Ser Ala Ala Pro Ala Pro Ser Gly Ser Met Asp Asn
305                 310                 315                 320

Ile Leu Gln Met Asp Ala Asn Ala Ser Gly Phe Leu Asp Asp Lys Asp
                325                 330                 335

Gly Lys Glu

<210> SEQ ID NO 11
<211> LENGTH: 338
<212> TYPE: PRT
<213> ORGANISM: Trifolium repens

<400> SEQUENCE: 11

Met Asn Gly Gly Ser Thr Val Ser Phe Arg Ser Ile Leu Asp Lys Pro
1               5                   10                  15

Leu Asn Gln Leu Thr Glu Asp Asp Ile Ser Gln Leu Thr Arg Glu Asp
                20                  25                  30

Cys Arg Arg Phe Leu Lys Asp Lys Gly Met Arg Arg Pro Ser Trp Asn
            35                  40                  45

Lys Ser Gln Ala Ile Gln Gln Val Ile Ser Leu Lys Ala Leu Leu Glu
        50                  55                  60

Pro Thr Asp Asp Leu Pro Ala Pro Val Gly Val Ser Ser Ala Ile
65                  70                  75                  80

His His His His His His Pro Gln Pro Gln Arg Asn Leu Asn
                85                  90                  95

Glu Ala Pro Val Lys Gly Ser Asp Leu Asp Asp Thr Gly Phe His Thr
                100                 105                 110

Ala Glu Asp Leu Asn Lys Ser Thr Ser Thr Ala Val Glu Ile Pro Thr
            115                 120                 125

Glu Thr Asn Asp Ala Asn Val Val Lys Ser Ser Gly Gly Cys Val Ala
            130                 135                 140
```

```
Ser Gly Ser Phe Gly Gln Met Thr Ile Phe Tyr Cys Gly Lys Val Asn
145                 150                 155                 160

Val Tyr Asp Gly Val Ser Pro Asp Lys Ala Arg Ser Ile Met Gln Leu
            165                 170                 175

Ala Ala Cys Pro Ser Ser Phe Pro Gln Asp Asn Leu Leu Asn Lys Asn
            180                 185                 190

Ala Ala Val Trp Ala Ser Pro Cys Asn Ile Pro Ile Asp Lys Asp Val
            195                 200                 205

Leu Phe Pro Asn Asp Thr Ala Ile Leu Gln Val Ala Gln Thr Asp Lys
    210                 215                 220

Met Val Glu Tyr Pro Leu Gln Tyr Arg Glu Lys Gly Ser Ile Ala Arg
225                 230                 235                 240

Asp Ala Asp Val Glu Gly Gln Ala Ser Arg Asn Ala Ser Leu Gln Arg
            245                 250                 255

Tyr Arg Glu Lys Arg Lys Asp Arg Gly Arg Ser Lys Gly Asn Lys Leu
            260                 265                 270

Thr Gly Ile Thr Ser Ser Asn Phe Glu Met Tyr Leu Asn Leu Pro Val
            275                 280                 285

Lys Leu His Ala Ser Asn Gly Asn Ser Ser Arg Ser Ser Thr Asp Ser
    290                 295                 300

Pro Pro Gln Pro Arg Leu Pro Leu Val Ser Gly Ser Ala Glu Asn
305                 310                 315                 320

Gln Pro Lys Val Thr Leu Pro Ile Asp Leu Asn Asp Lys Asp Val Gln
            325                 330                 335

Glu Cys

<210> SEQ ID NO 12
<211> LENGTH: 311
<212> TYPE: PRT
<213> ORGANISM: Amborella trichopoda

<400> SEQUENCE: 12

Met Thr Ala Gly Asp Gly Ser Ile Arg Ser Ile Leu Asp Lys Pro Leu
1               5                   10                  15

Glu Glu Leu Thr Glu Asp Ile Ser Gln Leu Thr Arg Glu Asp Cys
            20                  25                  30

Arg Arg Tyr Leu Lys Glu Lys Gly Met Arg Arg Pro Ser Trp Asn Lys
            35                  40                  45

Tyr Gln Ala Ile Gln Gln Val Leu Ser Leu Lys Gly Leu Leu Glu Gly
    50                  55                  60

Lys Pro Cys Asp Asp Asn Ser Asp Val Phe Ser His Arg Ser Pro Ile
65                  70                  75                  80

Thr Val Ile Pro Asn Val Gly Ser Met Arg Glu Lys Glu Lys Ala Val
            85                  90                  95

Asn Ile Ala Asp Pro Glu Ile Ser Gly Ser His Gln Pro Asn Phe Arg
            100                 105                 110

Arg Glu Ile His Glu Thr Thr Arg Glu Arg Ala Leu Pro Ala Ser Asp
            115                 120                 125

Trp Pro Pro Ser Gln Glu Pro Val Ser Gln Met Thr Ile Phe Tyr Ala
    130                 135                 140

Gly Ala Val Asn Val Tyr Asn Asp Ile Pro Glu Asp Lys Val Gln Ala
145                 150                 155                 160

Ile Ile Tyr Leu Ala Gly Lys Ser Asp Ser Leu Gln Gln Thr Asn Val
            165                 170                 175
```

```
Ile Arg Thr Gly Pro Asp Gln Cys Ile Ala Ser Ala Ala Ser Pro Ser
            180                 185                 190

Leu Asn Asp Leu His Ser Arg Arg Ile His Pro Thr Ser Asn Ile Thr
        195                 200                 205

Thr Ser Gln Ser Leu Arg Val Ala Thr Ser Leu Pro Val Gly Pro His
    210                 215                 220

Ser Glu Val Pro Lys Thr Arg Lys Thr Ser Val Gln Arg Phe Leu Glu
225                 230                 235                 240

Lys Arg Lys Asp Arg Gly Arg Leu Lys Gly Thr Leu Ala Ser Gly Gly
                245                 250                 255

Ser Ser Lys Arg Gly Ser Ser Cys Leu Glu Leu Tyr Ala Thr Ser Arg
            260                 265                 270

Leu Lys Ser Glu Gly Val Ala Thr Thr Thr Thr Gln Ser Asn Met Asn
        275                 280                 285

Asn Val Val Val Ser Pro Ser Asn Pro Arg Met Pro Leu Asn Pro Gly
    290                 295                 300

Ser Cys Ser Trp Val Glu Asn
305                 310

<210> SEQ ID NO 13
<211> LENGTH: 416
<212> TYPE: PRT
<213> ORGANISM: Selaginella moellendorffii

<400> SEQUENCE: 13

Met Ala Ala Ser Ile Leu Gly Cys Gly Ser Ser Asn Gly Val Ala Val
1               5                   10                  15

Thr Gly Asn Pro Ala Pro Ala Ala Ala Glu Val Pro Ala Pro Leu
            20                  25                  30

Arg Pro Leu Glu Glu Leu Thr Glu Leu Asp Ile Arg Gln Leu Thr Arg
        35                  40                  45

Glu Asp Cys Arg Arg Tyr Leu Lys Glu Arg Gly Met Arg Arg Pro Ser
    50                  55                  60

Trp Asn Lys Ala Gln Ala Ile Gln Gln Val Leu Ser Leu Arg Ser Leu
65                  70                  75                  80

Leu Cys Pro Ser Asn Pro Val Gly Pro Ser Lys Asn Pro Gly Ser
            85                  90                  95

Ala Ala Asn Ala Pro Pro Ala Glu Ala Ala Ala Gly His Thr Lys
            100                 105                 110

Gln Leu Leu Asp Lys Val Ser Gln Gln Ser Met Pro Asp Ser Cys Pro
        115                 120                 125

Ser Asn Asn Ala Ser Asp Pro Arg Pro Leu Ala Gly Cys Phe Gly Ser
    130                 135                 140

Leu Ala Pro Thr Leu Ser Val Leu Asn Pro Asp Ala Lys Arg Asn Pro
145                 150                 155                 160

Leu Ser Ser Lys Pro Ala Ser Thr Thr Lys Pro His Ser Ala Gln Leu
                165                 170                 175

Thr Ile Phe Tyr Ser Gly Ile Val Asn Val Tyr Asp Val Pro Leu
            180                 185                 190

Asp Lys Ala Gln Ala Ile Met Leu Leu Ala Ala Ser Lys Thr Phe His
        195                 200                 205

Val Pro Thr Ser Ser Val Pro Gly His Pro Pro Phe Thr Ser Ala Thr
    210                 215                 220

Gln Gln Gln Gln Gln Gln Arg Glu Leu Asn Gln Gln Thr Glu Ala
225                 230                 235                 240
```

```
Thr Gln Lys Tyr Pro Met Gln His Gln Gln Ala Pro Gln Ile Tyr Leu
                245                 250                 255

Ser Ser Gly Ser Ala Leu Pro Asp Glu Ser Cys Thr Glu Pro Gly Leu
            260                 265                 270

Pro Gln Val Arg Ser Ala Ser Leu Gln Arg Phe Leu Ala Lys Arg Arg
        275                 280                 285

Asp Arg Leu Ser Gly Asn Pro Ser Ser Arg Arg Asn Asp Arg Ser
    290                 295                 300

Lys Lys Arg Arg Phe Ser Pro Pro Ser Pro Leu Thr Ser Ala Ser
305                 310                 315                 320

Phe Gln Phe Pro Pro Ser Ala Arg Thr Ser Gln Val Leu Arg Tyr Ser
                325                 330                 335

Thr Thr Ser Thr Thr Thr Ile Thr Thr Ala Thr Ala Thr Ala Ala Thr
            340                 345                 350

Thr Thr Thr Thr Thr Gly Thr Thr Asn Gly Gly His Cys Ser Asn Ser
            355                 360                 365

Asn Gln Ala Ser Glu Asn Ala Gly Ser Asp Thr Ser Gly Gly Ser Ser
        370                 375                 380

Gly Thr Pro Asp Thr Ser Asp Thr Thr Arg Asp Asn Asp Asn Gly Arg
385                 390                 395                 400

Val Ser Asn Glu Asn Gly Arg Val Ser Thr Thr Cys Leu Ala Ala Thr
                405                 410                 415

<210> SEQ ID NO 14
<211> LENGTH: 234
<212> TYPE: PRT
<213> ORGANISM: Selaginella moellendorffii

<400> SEQUENCE: 14

Met Ser Ser Met Val Asp Phe Leu Gly Ile Glu Glu Lys Val Ser Thr
1               5                   10                  15

Ser Val Ser Ala Glu Arg Leu Lys Lys Leu Glu Glu Leu Thr Asp Glu
            20                  25                  30

Asp Val Met Gln Leu Thr Arg Glu Asp Cys Arg Arg Tyr Leu Lys Glu
        35                  40                  45

Lys Gly Met Arg Arg Pro Ser Trp Asn Lys Ala Gln Ala Val Gln Gln
    50                  55                  60

Leu Leu Ser Leu Lys Ser Leu Cys Asp Pro Ser Pro Ala Ser Ser Gly
65                  70                  75                  80

Ala Ala Lys Arg Ser Pro Ser Pro Pro Leu Asp Glu Ala Pro Ala Lys
                85                  90                  95

Lys Pro Met Ala Met Thr Ser Ile Asp Leu Lys Ala Ala Ala Ala Val
            100                 105                 110

Asp Ala Ala Asn Leu Thr Met Phe Tyr Asp Gly Ala Val Ser Val Phe
        115                 120                 125

Asp Asp Val Ser Pro Asp Lys Ala Ser Leu Phe Pro Leu Ala Tyr Ala
    130                 135                 140

Ile Met Leu Leu Ala Gly Asn Val Lys Ser Trp Pro Ser Ile Asn Val
145                 150                 155                 160

Ala Ala Asn Thr Asn Lys Val Val Ile Ser Tyr Glu Leu Pro Gln
                165                 170                 175

Ala Arg Lys Ala Ser Leu Gln Arg Phe Leu Gln Arg Arg Glu Lys
            180                 185                 190

Thr Ala Lys Glu Ala Ala Ser Lys Gly Asn Ser Asn Lys Ser Pro Cys
```

195                 200                 205
His Gly Glu Ser Ser Gly Lys His Ala Ser Asp Ala Thr Asp Pro Ala
    210                 215                 220

Thr Ser Pro Leu Leu Thr Glu Val Ser Ser
225                 230

<210> SEQ ID NO 15
<211> LENGTH: 271
<212> TYPE: PRT
<213> ORGANISM: Nicotiana tabacum

<400> SEQUENCE: 15

Met Pro Pro Glu Glu Thr Val Ser Lys Ser Pro Leu Asp Lys Pro Leu
1               5                   10                  15

His Leu Leu Thr Asp Asp Ile Ser Gln Leu Thr Arg Glu Asp Cys
                20                  25                  30

Arg Arg Tyr Leu Lys Glu Lys Gly Met Arg Arg Pro Ser Trp Asn Lys
            35                  40                  45

Ser Gln Ala Ile Gln Gln Val Ile Ser Leu Lys Ala Leu Leu Glu Thr
    50                  55                  60

Thr Pro Asp Ser Asp Thr Gly Pro Arg Arg Lys Leu His Ile Pro Arg
65                  70                  75                  80

Pro Asp Thr Arg Val Gln Gln Val Gln Lys Gly Thr Asp Thr Asp Ala
                85                  90                  95

Glu Phe Ser Lys Ser Ala Glu Gly Met Val Pro Tyr Gly Arg Lys His
            100                 105                 110

Ser Lys Lys Pro Asp Ile Pro Gly Asp Ile Ala Ala Gly Ser Val Ala
    115                 120                 125

Val Ala Ala Gly Asn Asn Leu Ala Pro Ser Arg Thr Thr Asp Leu Gly
130                 135                 140

Asn Thr Pro Ala Ser Gln Leu Thr Ile Phe Tyr Cys Gly Lys Val Asn
145                 150                 155                 160

Val Tyr Asp Asp Val Pro Ala Glu Lys Ala Gln Ala Ile Met His Leu
                165                 170                 175

Ala Ala Thr Pro Leu Phe Val Pro Ser Glu Thr Pro Leu Gly Ala Thr
            180                 185                 190

Leu Ala Ala Arg His Ser Glu Cys His Leu Gln Ala Ala Ser Val Lys
    195                 200                 205

Gln Gly Pro Asp Ser Ala Met Val Leu Met Pro Thr Met Gln Thr Gly
210                 215                 220

Lys Met Ser Glu Val Thr Arg Leu Arg Leu Glu Ser Asn Thr Phe
225                 230                 235                 240

Tyr Glu Asp Asn Ser Ala Asn Tyr Ala Glu Ala Val Glu Gly His Pro
                245                 250                 255

Ser Arg Lys Ala Ser Val Gln Arg Tyr Leu Glu Lys Arg Lys Asp
            260                 265                 270

<210> SEQ ID NO 16
<211> LENGTH: 327
<212> TYPE: PRT
<213> ORGANISM: Solanum tuberosum

<400> SEQUENCE: 16

Met Pro Pro Glu Glu Thr Val Ser Lys Ser Pro Leu Asp Lys Pro Leu
1               5                   10                  15

Asn Gln Leu Thr Asp Asp Ile Ser Gln Leu Thr Arg Glu Asp Cys

```
            20                  25                  30
Arg Arg Tyr Leu Lys Gln Lys Gly Met Arg Lys Pro Ser Trp Asn Lys
            35                  40                  45

Ser Gln Ala Ile Gln Gln Val Ile Ser Leu Lys Ala Leu Leu Glu Pro
        50                  55                  60

Asp Thr Asp Ala Gly Thr Arg Lys Lys Leu His Ile Pro Arg Ala Asp
65                  70                  75                  80

Thr His Val Gln Ser Gly Lys Asn Thr Tyr Gly Glu Pro Ser Glu Pro
                85                  90                  95

Val Pro Asp Arg Arg Asn Gln Gln Asp Arg Pro Asp Leu Ser Ser His
            100                 105                 110

Ile Thr Ala Leu Pro Val Ala Val Asp Asn Ser Ala Pro Ser Arg
        115                 120                 125

Thr Ile Gly Ser Ala Asp Lys Pro Val Gly Gln Met Thr Ile Phe Tyr
        130                 135                 140

Arg Gly Lys Val Asn Val Tyr Asp Asp Val Pro Ala Asp Lys Ala Gln
145                 150                 155                 160

Lys Ile Met Cys Leu Ala Ser Ser Pro Leu Cys Val Pro Ser Glu Thr
                165                 170                 175

Pro Ser Asn Ala Thr Val Ala Ala Arg His Ser Ala Cys Cys Leu Gln
            180                 185                 190

Ala Ala Asn Ser Lys Leu Arg Leu Asp Thr Asn Ile Val Pro Thr Ile
            195                 200                 205

Gln Thr Val Lys Met Ser Glu Val Ser Arg Val Pro Ile Glu Glu Ser
    210                 215                 220

Asn Arg Leu Tyr Asn Asp Asn Pro Glu Ala Val Glu Ser Pro Ala Ser
225                 230                 235                 240

Arg Lys Ala Ser Val Gln Arg Tyr Leu Glu Lys Arg Lys Glu Arg Phe
                245                 250                 255

Lys Trp Lys Arg Lys Val Glu Thr Thr Ser Ser Ala Ser Leu Asp Ile
            260                 265                 270

Tyr Leu Ser Asp Arg Ile Gly Thr Arg Thr Pro Ser Asp Tyr Ala Ser
        275                 280                 285

Gly Ala Asp Leu Cys Phe Thr Pro His Ile Thr Pro Thr Gly Ser Gly
        290                 295                 300

Pro Ile Gln Asp Asn Ile Gln Met Asn Pro Thr Phe Ser Ser Asp Leu
305                 310                 315                 320

Asn Asp Arg Asp Val Arg Glu
            325

<210> SEQ ID NO 17
<211> LENGTH: 348
<212> TYPE: PRT
<213> ORGANISM: Glycine max

<400> SEQUENCE: 17

Met Asn Gly Gly Ala Thr Thr Ala Thr Phe Arg Ser Ile Leu Asp Lys
1               5                   10                  15

Pro Leu Asn Gln Leu Thr Glu Asp Asp Ile Ser Gln Leu Thr Arg Glu
            20                  25                  30

Asp Cys Arg Arg Phe Leu Lys Glu Lys Gly Met Arg Arg Pro Ser Trp
        35                  40                  45

Asn Lys Ser Gln Ala Ile Gln Gln Val Ile Ser Leu Lys Ala Leu Leu
    50                  55                  60
```

Glu Pro Ser Asp Asp Asp Thr Pro Pro Thr Ala Met His His Arg
65                  70                  75                  80

Ser His Ala Pro Pro Pro Pro Gln Pro Gln Ser Gln Val Asn Leu
            85                  90                  95

Thr Glu Pro Pro Pro Pro Lys Ala Pro Pro Glu Glu Ser Ser
            100                 105                 110

Phe His Ala Ala Glu Asp Ile Gln Lys Pro Ala Ser Ser Gly Glu Lys
            115                 120                 125

Pro Ser Glu Thr Asn Asp Thr Asn Thr Asn Val Ala Ser Pro Lys Gly
            130                 135                 140

Cys Ala Thr Ser Gly Ser Phe Gly Gln Met Thr Ile Phe Tyr Cys Gly
145                 150                 155                 160

Lys Val Asn Val Tyr Asp Gly Val Ser Pro Asp Lys Ala Arg Ala Ile
                165                 170                 175

Met Gln Leu Ala Val Ser Pro Val Gln Phe Thr Gln Asp Asp Pro Ser
            180                 185                 190

Asn Gly Asn Ala Ala Val Trp Pro Ser Pro Cys His Leu Pro Met Asp
            195                 200                 205

Lys Asp Val Leu Ile Pro Val Asp Thr Thr Ile Leu Gln Val Ala Gln
210                 215                 220

Ser Asp Lys Met Met Glu Tyr Pro Leu Gln Tyr Arg Glu Lys Gly Ser
225                 230                 235                 240

Ile Ala Arg Asp Ala Glu Gly Gln Ala Ser Arg Lys Val Ser Leu Gln
                245                 250                 255

Arg Tyr Leu Glu Lys Arg Lys Asp Arg Gly Arg Leu Lys Gly Lys Lys
            260                 265                 270

Leu Thr Gly Ile Thr Ser Ser Asn Phe Glu Met Tyr Leu Asn Leu Pro
            275                 280                 285

Val Lys Val His Ala Ser Asn Gly Asn Ser Ser Arg Ser Ser Thr Ser
290                 295                 300

Ser Pro Pro Gln Pro Arg Leu Pro Leu Val Ser Ser Gly Ser Ala Asp
305                 310                 315                 320

Asn Gln Leu Lys Val Ala Leu Pro Ile Asp Leu Asn Asp Lys Val Ser
            325                 330                 335

Leu Gln Met Phe Lys Asn Ala Lys Thr Leu Thr Arg
            340                 345

<210> SEQ ID NO 18
<211> LENGTH: 338
<212> TYPE: PRT
<213> ORGANISM: Citrus clementine

<400> SEQUENCE: 18

Met Asp Val Asp Gly Gly Val Thr Ser Cys Arg Ser Ile Leu Glu Lys
1               5                   10                  15

Pro Leu Ser Gln Leu Thr Glu Glu Asp Ile Thr Gln Leu Thr Arg Glu
            20                  25                  30

Asp Cys Arg Lys Phe Leu Lys Glu Lys Gly Met Arg Arg Pro Ser Trp
        35                  40                  45

Asn Lys Ser Gln Ala Ile Gln Gln Val Ile Ser Leu Lys Ala Leu Leu
    50                  55                  60

Glu Ser Ser Gly Asp Ser Gly Ser Gly Val Leu Arg Arg Val Leu Val
65                  70                  75                  80

Ser Pro Pro Glu Ser Met Pro Pro Arg Val Asn Val Thr Ser Asn Ser
            85                  90                  95

```
Ala Asp Leu Val Lys Glu Pro Thr Ile Ser Val Ser Gly Asp Gln Asn
            100                 105                 110

Ser Ala Tyr Arg Arg Lys Tyr Pro Arg Asn Cys Ala Val Asp Ala Asp
        115                 120                 125

Asn Lys Thr Ile Ser Asn Arg Asn Pro Cys Glu Ala Asn Gly Ser Ile
    130                 135                 140

Gly Gln Met Thr Ile Phe Tyr Cys Gly Lys Val Asn Val Tyr Glu Gly
145                 150                 155                 160

Val Pro Thr Asp Lys Ala Gln Glu Ile Met His Leu Ala Ala Thr Pro
                165                 170                 175

Ile Asp Phe Ser Gln Asn Gly Ser Phe Gly Ile Thr Ala Tyr Arg
            180                 185                 190

Ala Ile Pro Cys His Leu Gln Val Thr Ser Asn Arg His Val Ser Leu
        195                 200                 205

Pro Leu Arg Pro Ala Ala Met Ile Ser Gln Phe Met Gln Thr Gly Lys
    210                 215                 220

Ile Ala Asp Tyr Ser Gln Glu Tyr Arg Glu Lys Ala Ile Ser Thr His
225                 230                 235                 240

Asp Ser Asp Val Asp Gly Gln Val Asn Arg Lys Val Ser Leu Gln Arg
                245                 250                 255

Tyr Leu Glu Lys Arg Lys Asp Arg Gly Arg Phe Phe Lys Gly Lys Lys
            260                 265                 270

Asn Thr Gly Pro Thr Pro Ser Leu Glu Met Tyr Leu Asn His Pro Gly
        275                 280                 285

Lys Thr His Ala Ser Asn Gly Gln Gln Ser Gln Ser Asn Thr Ser Ser
    290                 295                 300

Pro Thr Gln Pro Glu Leu Ser Asn Thr Leu Gly Thr Ser Pro Asp Asn
305                 310                 315                 320

Gln Ala Lys Thr Val Met Leu Pro Val Asp Leu Asn Asn Glu Asp Ile
                325                 330                 335

Gln Asp

<210> SEQ ID NO 19
<211> LENGTH: 335
<212> TYPE: PRT
<213> ORGANISM: Ricinus communis

<400> SEQUENCE: 19

Met Asp Ala Gly Val Thr Ser Phe Arg Ser Ile Leu Asp Lys Pro Leu
1               5                   10                  15

Thr Gln Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Thr
    50                  55                  60

Ser Glu Asp Ser Gly Ala Gly Ala Leu Arg Arg Ile Leu Val Ser Lys
65                  70                  75                  80

Pro Pro Val Thr Ser Asn Ser Val Asp Ser Ala Lys Glu Pro Ser Asp
                85                  90                  95

Ser Asn Asn Asn Asn Leu Leu Asp Glu Thr Ala Pro His Asp Ser Pro
            100                 105                 110

Lys Ser Pro Pro Pro Ala Pro Ser Leu Asp Cys Pro Leu Glu Glu Ala
        115                 120                 125
```

```
Asp Asn Lys Val Ile Ser Ser Arg Ser Pro Gly Ala Thr Asp Gly Leu
            130                 135                 140

Val Gly Gln Met Thr Ile Phe Tyr Cys Gly Lys Val Asn Val Tyr Asp
145                 150                 155                 160

Gly Val Pro Pro Asp Lys Ala Gln Ala Ile Met His Leu Ala Ala Thr
                165                 170                 175

Pro Ile His Ser Pro Leu Asp Asp Pro Ile Arg Arg Pro Val Phe Ala
                180                 185                 190

Phe Pro Tyr His Leu Gln Thr Pro Ser Asp Lys His Val Phe Val Pro
            195                 200                 205

Ser Asn Ala Ala Ile Ser Pro Thr Thr Pro Thr Glu Lys Val Thr Glu
210                 215                 220

Tyr Ser Gln Gln Cys Arg Glu Lys Gly Asn Val Thr Tyr Asp His Asp
225                 230                 235                 240

Val Glu Gly Gln Ala Asn Arg Lys Met Ser Leu Gln Arg Tyr Leu Glu
                245                 250                 255

Lys Lys Lys Asp Arg Gly Arg Phe Lys Gly Arg Lys Asn Leu Gly Pro
            260                 265                 270

Asn Ser Ser Ser Leu Asp Ala Tyr Leu Asn His Gln Met Arg Thr His
        275                 280                 285

Ile Ser Asn Glu Gln Ser Thr Arg Ser Ser Thr Ser Ser Pro Thr Gln
290                 295                 300

Pro Gly Val Pro His Thr Ser Ser Asn Ser Ala Glu Asp Gln Leu Lys
305                 310                 315                 320

Thr Ala Ser Phe Ala Val Asp Leu Asn Glu Asp Val Gln Glu Pro
                325                 330                 335

<210> SEQ ID NO 20
<211> LENGTH: 393
<212> TYPE: PRT
<213> ORGANISM: Vitis vinifera

<400> SEQUENCE: 20

Met Asn Pro Gly Val Thr Thr Leu Arg Ser Ile Leu Asp Lys Pro Leu
1               5                   10                  15

His Glu Leu Thr Glu Glu Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ser Leu Leu Glu Thr
    50                  55                  60

Ser Glu Gly Ser Gly Ala Gly Val Leu Arg Lys Ile Thr Asp Ser Pro
65                  70                  75                  80

Pro Ala Glu Asn Leu Pro Val Thr Ser Asn Ser Ala Asp Ser Gly
                85                  90                  95

Lys Glu Leu Ser Ala Asp Ile Gln Ile Ser Val Ser Ala Asp Glu Leu
            100                 105                 110

Val Pro Leu Pro Pro Lys Asp His His Pro Glu Ser Thr Pro Ser Gly
        115                 120                 125

Glu Leu Ala Ser Arg Pro Pro Glu Ala Asp Thr Lys His Thr Cys Pro
    130                 135                 140

Arg Ser Pro Gly Ala Thr Asn Cys Leu Val Gly Gln Met Thr Ile Phe
145                 150                 155                 160

Tyr Cys Gly Lys Val Asn Val Tyr Asp Gly Val Pro Asp Asp Lys Ala
```

```
                        165                 170                 175
            Gln Ala Ile Met His Leu Ala Ala Ser Pro Phe His Leu Pro Ser Asp
                        180                 185                 190

Asp Pro Phe Ser Gly Ala Ala Met Leu Cys Ser Ser Pro Cys His Leu
                        195                 200                 205

His Thr Ala Asn Val Lys His Gly His Ile Pro Pro Arg Ala Met Val
                        210                 215                 220

Ser Gln Thr Met Gln Thr Glu Lys Phe Thr Glu Tyr Ser Gln Gln Tyr
            225                 230                 235                 240

Arg Glu Glu Val Asn Phe Thr Arg Gly His Gly Ser Glu Ala Leu Ser
                        245                 250                 255

Gly Leu Arg Thr Val Gly Ser Pro Thr Ala Arg Pro Thr Glu Asp Met
                        260                 265                 270

Glu Gln Thr Thr Cys Leu Thr Ile Trp Gly Thr Phe Arg Tyr Lys Val
                        275                 280                 285

Met Pro Phe Glu Ile Tyr Glu Gly Ile Met Asp Val Glu Gly Gln Val
                        290                 295                 300

Asp Arg Lys Leu Ser Leu Gln Arg Tyr Phe Glu Lys Arg Lys Asp Arg
            305                 310                 315                 320

Phe Lys Ser Arg Lys Ile Gly Leu Pro Ser Gly Ser Leu Glu Met
                        325                 330                 335

Tyr Val Asn His Gln Ala Arg Thr Gln Pro Ser Asn Gly Gln Ser Ser
                        340                 345                 350

Arg Ser Gly Thr Ser Ser Pro Pro Gln His Gly Leu Ser His Thr Leu
                        355                 360                 365

Cys Ser Ser Ala Asp Asn His Thr Lys Asn Phe Thr Pro Phe Val Asp
                        370                 375                 380

Leu Asn Ser Lys Asp Ile Gln Glu Ser
            385                 390

<210> SEQ ID NO 21
<211> LENGTH: 343
<212> TYPE: PRT
<213> ORGANISM: Morus notabilis

<400> SEQUENCE: 21

Met Ser Ala Gly Thr Thr Ala Phe Arg Ser Ile Leu Asp Lys Pro Leu
1               5                   10                  15

Asn Gln Leu Thr Glu Asp Asp Ile Ser Gln Leu Thr Arg Glu Asp Cys
            20                  25                  30

Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
    50                  55                  60

Cys Asp Asp Ser Gly Ala Gly Ala Leu Arg Arg Ile Val Ala Ser Thr
65                  70                  75                  80

Pro Pro Pro Pro Pro Thr Gln Asn Ala Pro Arg Val Ser Thr Phe Ser
                85                  90                  95

Val Thr Ser Asn Ser Ala Asp Ser Gly Lys Glu Ala Ser Val Asp Val
            100                 105                 110

Gln Val Ser Ala Glu Glu Ser Gly Pro Cys Gln Arg Lys Glu Gln Ala
        115                 120                 125

Lys Ser Ala Pro Glu Thr Glu Glu Arg Pro Ala Asp Ala Gly Glu Arg
    130                 135                 140
```

```
Ala Ser Pro Arg Ser His Cys Ala Thr Asp Ala Leu Val Gly Gln Met
145                 150                 155                 160

Thr Ile Phe Tyr Cys Gly Lys Val Asn Val Tyr Glu Gly Val Pro Pro
                165                 170                 175

Glu Lys Ala Arg Ala Ile Met His Leu Ala Ala Ser Pro Ile Pro Leu
            180                 185                 190

Ser Arg Glu Asn Ser Phe Gly Val Leu Ala Ala Pro Arg Ser Phe Pro
        195                 200                 205

Trp His Leu His Ala Ala Ser Asp Lys Gly Gly Leu Leu Pro Pro Ser
    210                 215                 220

Ala Thr Ile Ser Gln Pro Met Gln Thr Asp Lys Leu Ala Asp Tyr Ser
225                 230                 235                 240

Gln Gln Cys Trp Glu Lys Glu Asn Asp Gly Gln Ala Ser Arg Lys Leu
                245                 250                 255

Ser Leu Gln Lys Tyr Arg Glu Lys Lys Asp Arg Gly Arg Leu Lys
            260                 265                 270

Thr Lys Arg Ser Thr Gly Phe Asn Ser Ser Met Glu Val Tyr Phe
        275                 280                 285

Asn His Gln Val Lys Thr His Met Ser Asn Gly Asn Ser Ser Arg Ser
290                 295                 300

Ser Thr Ser Ser Pro Thr Gln Pro Gly Leu Pro Gln Thr Leu Cys Ser
305                 310                 315                 320

Thr Val Asp Asn Gln Pro Lys Ile Pro Cys Leu Pro Val Asp Leu Asn
                325                 330                 335

Glu Lys Leu Thr Ile Glu Met
            340

<210> SEQ ID NO 22
<211> LENGTH: 364
<212> TYPE: PRT
<213> ORGANISM: Phoenix dactylifera

<400> SEQUENCE: 22

Met Tyr Trp Val Gly Ser Ala Gln Glu Arg Arg Asp Gly Gly Arg
1               5                   10                  15

Ser Pro Leu Asp Lys Pro Leu Ser Leu Thr Glu Glu Asp Ile Ala
            20                  25                  30

Gln Leu Thr Arg Glu Asp Cys Arg Arg Phe Leu Lys Glu Lys Gly Met
        35                  40                  45

Arg Arg Pro Ser Trp Asn Lys Ser Gln Ala Ile Gln Gln Val Ile Ser
50                  55                  60

Leu Lys Ala Leu Leu Glu Gly Arg Pro Glu Ser Gly Glu Leu Pro Val
65                  70                  75                  80

Gly Ala Gly Tyr Arg Gln Lys Pro Pro Arg Pro Ala Ser Leu
                85                  90                  95

Pro Ser Leu Gln Glu Ala Ala Gly Asp Ser Thr Ala Ala Lys Glu
            100                 105                 110

Pro Ser Pro Ser Ser Ser Leu Ser Pro Tyr Arg Arg Arg Asp Pro Ile
        115                 120                 125

Pro Pro Ile Ile Ser Ala Gly Gly Pro Ser Cys Arg Phe Pro Val Ala
130                 135                 140

Gly Arg Asp Gln Gln Pro Pro Glu Thr Pro Ser Pro Ser Leu Arg Val
145                 150                 155                 160

Thr Ala Glu Val Pro Ala Gly Gln Met Thr Ile Phe Tyr Asp Gly Lys
                165                 170                 175
```

```
Val Asn Val Tyr Ser Asp Val Thr Val Asp Lys Ala Arg Ala Ile Leu
            180                 185                 190

Leu Leu Ala Gly Arg Arg Asp Cys Tyr Gly Ala Ala Leu Pro Gly
        195                 200                 205

Pro Val His Ser Pro Gln Pro Ala Phe Leu Gly Pro Gly Gln Gly Pro
    210                 215                 220

Val Pro Thr Ala Pro Pro Leu Ala Ala Ala Leu Pro Thr Ser Pro Ala
225                 230                 235                 240

Gly Arg Leu Ala His Arg Phe Glu Gly Pro Ser Gly Val Pro Arg Gly
                245                 250                 255

Lys Ser Ser Leu Val Arg Glu Arg Ser Thr Ser Pro Glu Gly Pro Thr
            260                 265                 270

Ser Arg Lys Ala Ser Leu Gln Arg Tyr Leu Glu Lys Arg Lys Asp Arg
        275                 280                 285

Leu Lys Gly Arg Lys Thr Leu Gly Gly Ala Ser Ser Ser Met Glu
    290                 295                 300

Ile Met Phe Leu Ser Gln Lys Phe Gly Gly Gln Ile Pro Asn Glu Gln
305                 310                 315                 320

Leu Ser Arg Ser Asn Thr Ser Ser Pro Thr Gln Pro Arg Pro Pro Gly
                325                 330                 335

Thr Pro Thr Arg Cys Ser Ser Ile Glu Asn Gln Ala Gln Lys Asn His
            340                 345                 350

Leu Ser Val Asp Leu Asn Asp Asp Gly Cys Gly Asn
        355                 360

<210> SEQ ID NO 23
<211> LENGTH: 354
<212> TYPE: PRT
<213> ORGANISM: Theobroma cacao

<400> SEQUENCE: 23

Met Glu Ala Gly Val Ala Thr Thr Thr Thr Thr Glu Ser Phe Arg
1               5                   10                  15

Ser Ile Leu Asp Lys Pro Leu Ser Gln Leu Thr Glu Glu Asp Ile Ser
            20                  25                  30

Gln Leu Thr Arg Glu Asp Cys Arg Lys Phe Leu Lys Glu Lys Gly Met
        35                  40                  45

Arg Arg Pro Ser Trp Asn Lys Ser Gln Ala Ile Gln Gln Val Ile Ser
    50                  55                  60

Leu Lys Ala Leu Leu Glu Ser Asn Glu Asp Ser Gly Ala Gly Ala Ile
65                  70                  75                  80

Arg Lys Ile Leu Val Ser Pro Pro Ser Pro Ser Val Pro Pro Gln Asn
                85                  90                  95

Ala Ala Ala Arg Val Ala Ser Asn Ser Cys Asp Ser Val Lys Glu Ala
            100                 105                 110

Val Val Gly Glu Glu Gly Ser Pro Tyr Arg Arg Lys Asp Pro Pro Leu
        115                 120                 125

Lys Pro Ser Pro Val Gly Glu Ile Asn Cys Leu Gly Gly Asp Thr Asp
    130                 135                 140

Asn Lys Asn Leu Ser Pro Arg Ser Pro Cys Glu Ser Asn Glu Leu Gly
145                 150                 155                 160

Gly Gln Met Thr Ile Phe Tyr Cys Gly Lys Val Asn Val Tyr Asp Gly
                165                 170                 175

Val Pro Leu Asp Lys Ala Arg Ala Ile Met His Leu Ala Ala Thr Pro
```

```
                180               185               190
Ile Asp Phe Pro Gln Asp Asn Gln Cys Ser Gly Asn Ala Ala Leu Arg
            195                 200                 205

Ser Phe Met Cys His Val Gln Ala Val Gly Asp Lys Asn Gly Leu Val
    210                 215                 220

Ala Ser Thr Ala Leu Asn Ser His Thr Met Gln Thr Glu Lys Leu Thr
225                 230                 235                 240

Glu Tyr Gln His Gln Phe Arg Glu Lys Gly Asn Ile Ala Arg Asp Ala
                245                 250                 255

Asp Val Asp Gly Gln Val Asn Arg Lys Val Ser Leu Gln Arg Tyr Arg
            260                 265                 270

Glu Lys Arg Lys Asp Arg Gly Arg Phe Phe Lys Gly Arg Lys Asn Thr
        275                 280                 285

Gly Gln Ala Ser Ser Leu Glu Met Tyr Leu Asn His Gln Ile Arg
    290                 295                 300

Thr His Asn Ser Asn Gly Gln Ser Ser Arg Ser Ser Thr Gly Ser Pro
305                 310                 315                 320

Pro Gln Ser Gly Leu Pro His Ala Phe Cys Ser Ser Ala Asp Asn Gln
                325                 330                 335

Ala Lys Leu Val Asn Leu Ser Val Asp Leu Asn Asp Lys Ser Val Gln
            340                 345                 350

Glu His

<210> SEQ ID NO 24
<211> LENGTH: 293
<212> TYPE: PRT
<213> ORGANISM: Spirodela polyrrhiza

<400> SEQUENCE: 24

Met Ala Gly Ser Glu Ala Ala Pro Glu Ala Gly Arg Ala Gly
1               5                   10                  15

Glu Glu Glu Val Arg Ala Ala Gly Ala Ala Val Lys Ser Pro
                20                  25                  30

Leu Glu Lys Pro Leu Ser Glu Leu Thr Glu Glu Asp Ile Ala Gln Val
            35                  40                  45

Thr Arg Glu Asp Cys Arg Arg Phe Leu Lys Glu Lys Gly Met Arg Arg
    50                  55                  60

Pro Ser Trp Asn Lys Ser Gln Ala Val Gln Gln Val Ile Ser Leu Lys
65                  70                  75                  80

Ala Leu Leu Glu Pro Cys His Asp Ala Asp Asp Ala Pro Ser Ala
                85                  90                  95

Gly Ala Val Pro Ser Ile Ser Ser Phe Phe Ser Lys Arg Pro Ser Asp
                100                 105                 110

Ala Leu Leu Pro Ala Ala Ala Gln Phe Pro Val Ser Ser Pro Met
            115                 120                 125

Arg Gly Glu Pro Ala Gly Gly Ala Pro Gln Ile Val Ser Glu Arg Pro
    130                 135                 140

His Gly Arg Asp Pro Leu Ala Asn Val Phe Thr Cys Ser Asp Ala Leu
145                 150                 155                 160

Gly Arg Phe Pro Ala Thr Gly Asn Gly Ala Leu Pro Pro Asn Ser Ala
                165                 170                 175

Thr Leu Pro Pro Arg Gly Val Ala Ser Ala Glu Thr Leu Glu Gly Gln
            180                 185                 190

Leu Thr Ile Phe Tyr Asp Gly Lys Ile Asn Val Tyr Asp Gly Val Thr
```

```
              195                 200                 205
Pro Glu Lys Val Arg Ser Gly Gln Lys Gly Pro Thr Ser Arg Ala Ala
    210                 215                 220

Ser Leu Gln Arg Tyr Leu Glu Lys Arg Lys Asp Arg Arg Asp Pro Gly
225                 230                 235                 240

Pro Ala Ala Val Ala Thr Leu Tyr Arg Lys Val Phe Leu Ser Ala Thr
                245                 250                 255

Ala Leu Leu Ile Gly Cys Ser Ser Gly Ala Asn Val Val Leu Pro Arg
                260                 265                 270

Ala Glu Gly Pro Thr Ser Arg Ala Ala Ser Leu Gln Arg Tyr Leu Glu
                275                 280                 285

Lys Arg Lys Asp Arg
            290

<210> SEQ ID NO 25
<211> LENGTH: 293
<212> TYPE: PRT
<213> ORGANISM: Musa acuminata

<400> SEQUENCE: 25

Met Asn Pro Gly Glu Thr Thr Pro Pro Ser Pro Leu Asp Lys Pro Leu
1               5                   10                  15

Ala Glu Leu Thr Glu Glu Asp Ile Ala Gln Leu Thr Arg Glu Asp Cys
                20                  25                  30

Arg Arg Phe Leu Lys Ala Lys Gly Met Arg Arg Pro Ser Trp Asn Lys
            35                  40                  45

Ser Gln Ala Ile Gln Gln Val Ile Ser Leu Lys Ala Leu Leu Glu Gly
    50                  55                  60

Arg Pro Gly Cys Asp Asp Cys Pro Ala Gly Gly Ile Leu Gln Lys
65              70                  75                  80

Leu Leu Thr Ser Ser Pro Ser Glu Pro Leu Ser Pro Pro Gln Asp Ser
                85                  90                  95

Pro Pro Pro Ala Pro Lys Glu Gly Gly Ser Gly Ser Gln Pro Leu Ala
                100                 105                 110

Lys Glu Pro Ser Pro Tyr Arg Arg Arg Asp Pro Ile Pro Pro Pro Tyr
            115                 120                 125

Ser Ala Gly Asn Pro Thr Cys Gln Thr Pro Ile Ala Gly Ala Asp Leu
    130                 135                 140

Pro His Pro Pro Glu Lys Arg Cys Pro Ser Pro Arg Leu Thr Ala Glu
145                 150                 155                 160

Val Pro Val Gly Gln Met Thr Ile Phe Tyr Asp Gly Met Val Asn Val
                165                 170                 175

Tyr Asp Gly Val Ser Ala Asp Gln Ala Arg Ser Ile Met Glu Leu Ala
                180                 185                 190

Ala Ser Pro Val Cys Phe Asp Asp Pro Thr Gly Ala Phe Ser Pro Ala
                195                 200                 205

Arg Pro Pro Ala Phe Arg Phe Pro Pro Gly Leu Pro Arg Pro Ala Pro
            210                 215                 220

Val Pro Thr Ala Pro Ser Phe Val Gly Thr Phe Pro Ile Ser Pro Ala
225                 230                 235                 240

Gly Lys Arg Cys Tyr Ser Tyr Cys Ser Phe Arg Ser Ser Val Ser Leu
                245                 250                 255

Leu Thr Thr Thr Glu Gly Pro Thr Ser Arg Lys Ala Ser Leu Gln Arg
                260                 265                 270
```

```
Tyr Leu Glu Lys Arg Lys Asp Arg Tyr Gly His Leu Pro Thr Glu Ser
        275                 280                 285

Ile Leu Leu Val Ser
    290

<210> SEQ ID NO 26
<211> LENGTH: 171
<212> TYPE: PRT
<213> ORGANISM: Phalaenopsis aphrodite
<220> FEATURE:
<221> NAME/KEY: misc_feature
<222> LOCATION: (72)..(87)
<223> OTHER INFORMATION: Xaa can be any naturally occurring amino acid

<400> SEQUENCE: 26

Met Asn Ser Asp Ala Ile Thr Met Gly Lys Ser Leu Leu Glu Lys Pro
1               5                   10                  15

Leu Ser Leu Leu Thr Glu Asp Asp Ile Ala Gln Ile Thr Arg Glu Glu
            20                  25                  30

Cys Arg Arg Phe Leu Lys Asp Arg Gly Met Arg Arg Pro Ser Trp Asn
        35                  40                  45

Lys Ser Gln Ala Ile Gln Gln Val Ile Ser Leu Lys Ala Leu Phe Glu
    50                  55                  60

Asn Arg Ser Asp Leu Glu Asp Xaa Xaa Xaa Xaa Xaa Xaa Xaa Xaa
65                  70                  75                  80

Xaa Xaa Xaa Xaa Xaa Xaa Phe Pro Glu His Ala Asp Leu Ser Ser
                85                  90                  95

Ile Ser Pro Thr Ala Glu Ala Lys Glu Pro Glu Lys Ala Gln Leu Thr
            100                 105                 110

Ile Phe Tyr Gly Gly Lys Val Leu Val Phe Asp Asn Phe Pro Val Asn
        115                 120                 125

Lys Ala Gln Asp Leu Met Gln Ile Ala Gly Lys Glu Gln Asn Gln Asn
    130                 135                 140

Tyr Gly Thr Ala Asn Thr Val Ala Pro Ser Ala Pro Ala Ala Asp Leu
145                 150                 155                 160

His Ser Leu Pro Leu Pro Ala Lys Pro Pro Ala
                165                 170

<210> SEQ ID NO 27
<211> LENGTH: 46
<212> TYPE: PRT
<213> ORGANISM: Arabidopsis thaliana

<400> SEQUENCE: 27

Leu Lys Leu Leu Thr Glu Glu Asp Ile Ser Gln Leu Thr Arg Glu Asp
1               5                   10                  15

Cys Arg Lys Phe Leu Lys Asp Lys Gly Met Arg Arg Pro Ser Trp Asn
            20                  25                  30

Lys Ser Gln Ala Ile Gln Gln Val Leu Ser Leu Lys Ala Leu
        35                  40                  45

<210> SEQ ID NO 28
<211> LENGTH: 46
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(3)
<223> OTHER INFORMATION: X is any amino acid
```

```
<220> FEATURE:
<221> NAME/KEY: MISC_FEATURE
<222> LOCATION: (5)..(7)
<223> OTHER INFORMATION: X is any amino acid
<220> FEATURE:
<221> NAME/KEY: MISC_FEATURE
<222> LOCATION: (9)..(10)
<223> OTHER INFORMATION: X is any amino acid
<220> FEATURE:
<221> NAME/KEY: MISC_FEATURE
<222> LOCATION: (12)..(12)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (19)..(20)
<223> OTHER INFORMATION: X is any amino acid
<220> FEATURE:
<221> NAME/KEY: MISC_FEATURE
<222> LOCATION: (22)..(24)
<223> OTHER INFORMATION: X is any amino acid
<220> FEATURE:
<221> NAME/KEY: MISC_FEATURE
<222> LOCATION: (28)..(28)
<223> OTHER INFORMATION: X is any amino acid
<220> FEATURE:
<221> NAME/KEY: MISC_FEATURE
<222> LOCATION: (34)..(34)
<223> OTHER INFORMATION: X is any amino acid
<220> FEATURE:
<221> NAME/KEY: MISC_FEATURE
<222> LOCATION: (37)..(38)
<223> OTHER INFORMATION: X is any amino acid
<220> FEATURE:
<221> NAME/KEY: MISC_FEATURE
<222> LOCATION: (40)..(41)
<223> OTHER INFORMATION: X is any amino acid
<220> FEATURE:
<221> NAME/KEY: MISC_FEATURE
<222> LOCATION: (43)..(45)
<223> OTHER INFORMATION: X is any amino acid

<400> SEQUENCE: 28

Leu Xaa Xaa Leu Xaa Xaa Xaa Asp Xaa Xaa Gln Xaa Thr Arg Glu Xaa
1               5                   10                  15

Cys Arg Xaa Xaa Leu Xaa Xaa Xaa Gly Met Arg Xaa Pro Ser Trp Asn
            20                  25                  30

Lys Xaa Gln Ala Xaa Xaa Gln Xaa Xaa Ser Xaa Xaa Xaa Leu
        35                  40                  45

<210> SEQ ID NO 29
<211> LENGTH: 46
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Glu, Phe, His, Tyr, Asn, Trp, Ser, Lys
      or Thr
<220> FEATURE:
<221> NAME/KEY: MISC_FEATURE
<222> LOCATION: (3)..(3)
<223> OTHER INFORMATION: Xaa is Glu, Gln, or Leu
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
```

```
<223> OTHER INFORMATION: Xaa is Glu or Asp
<220> FEATURE:
<221> NAME/KEY: MISC_FEATURE
<222> LOCATION: (7)..(7)
<223> OTHER INFORMATION: Xaa is Glu, Leu or Asp
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Ser, Phe, Arg, Met or Thr
<220> FEATURE:
<221> NAME/KEY: MISC_FEATURE
<222> LOCATION: (12)..(12)
<223> OTHER INFORMATION: Xaa is Leu or Val
<220> FEATURE:
<221> NAME/KEY: MISC_FEATURE
<222> LOCATION: (16)..(16)
<223> OTHER INFORMATION: Xaa is Asp or Glu
<220> FEATURE:
<221> NAME/KEY: MISC_FEATURE
<222> LOCATION: (19)..(19)
<223> OTHER INFORMATION: Xaa is Arg or Lys
<220> FEATURE:
<221> NAME/KEY: MISC_FEATURE
<222> LOCATION: (20)..(20)
<223> OTHER INFORMATION: Xaa is Tyr or Phe
<220> FEATURE:
<221> NAME/KEY: MISC_FEATURE
<222> LOCATION: (22)..(22)
<223> OTHER INFORMATION: Xaa is Lys or Arg
<220> FEATURE:
<221> NAME/KEY: MISC_FEATURE
<222> LOCATION: (23)..(23)
<223> OTHER INFORMATION: Xaa is Glu, Asp, Gln or Ala
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa is Arg or Lys
<220> FEATURE:
<221> NAME/KEY: MISC_FEATURE
<222> LOCATION: (34)..(34)
<223> OTHER INFORMATION: Xaa is Tyr, Ser or Ala
<220> FEATURE:
<221> NAME/KEY: MISC_FEATURE
<222> LOCATION: (37)..(37)
<223> OTHER INFORMATION: Xaa is Ile or Val
<220> FEATURE:
<221> NAME/KEY: MISC_FEATURE
<222> LOCATION: (38)..(38)
<223> OTHER INFORMATION: Xaa is Gln or Glu
<220> FEATURE:
<221> NAME/KEY: MISC_FEATURE
<222> LOCATION: (40)..(40)
<223> OTHER INFORMATION: Xaa is Val or Leu
<220> FEATURE:
<221> NAME/KEY: MISC_FEATURE
<222> LOCATION: (41)..(41)
<223> OTHER INFORMATION: Xaa is Leu or Ile
<220> FEATURE:
<221> NAME/KEY: MISC_FEATURE
<222> LOCATION: (43)..(43)
<223> OTHER INFORMATION: Xaa is Leu or Phe
<220> FEATURE:
<221> NAME/KEY: MISC_FEATURE
<222> LOCATION: (44)..(44)
<223> OTHER INFORMATION: Xaa is Lys or Arg
<220> FEATURE:
<221> NAME/KEY: MISC_FEATURE
<222> LOCATION: (45)..(45)
<223> OTHER INFORMATION: Xaa is Gly, Ser, Thr or Ala

<400> SEQUENCE: 29
```

Leu Xaa Xaa Leu Xaa Xaa Xaa Asp Xaa Xaa Gln Xaa Thr Arg Glu Xaa
1               5                   10                  15

Cys Arg Xaa Xaa Leu Xaa Xaa Xaa Gly Met Arg Xaa Pro Ser Trp Asn
            20                  25                  30

Lys Xaa Gln Ala Xaa Xaa Gln Xaa Xaa Ser Xaa Xaa Xaa Leu
        35                  40                  45

<210> SEQ ID NO 30
<211> LENGTH: 27
<212> TYPE: PRT
<213> ORGANISM: Arabidopsis thaliana

<400> SEQUENCE: 30

Thr Arg Glu Asp Cys Arg Lys Phe Leu Lys Asp Lys Gly Met Arg Arg
1               5                   10                  15

Pro Ser Trp Asn Lys Ser Gln Ala Ile Gln Gln
            20                  25

<210> SEQ ID NO 31
<211> LENGTH: 27
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (7)..(8)
<223> OTHER INFORMATION: X is any amino acid
<220> FEATURE:
<221> NAME/KEY: MISC_FEATURE
<222> LOCATION: (10)..(12)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (22)..(22)
<223> OTHER INFORMATION: X is any amino acid
<220> FEATURE:
<221> NAME/KEY: MISC_FEATURE
<222> LOCATION: (25)..(26)
<223> OTHER INFORMATION: X is any amino acid

<400> SEQUENCE: 31

Thr Arg Glu Xaa Cys Arg Xaa Xaa Leu Xaa Xaa Xaa Gly Met Arg Xaa
1               5                   10                  15

Pro Ser Trp Asn Lys Xaa Gln Ala Xaa Xaa Gln
            20                  25

<210> SEQ ID NO 32
<211> LENGTH: 27
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Lys or Arg

```
<220> FEATURE:
<221> NAME/KEY: MISC_FEATURE
<222> LOCATION: (8)..(8)
<223> OTHER INFORMATION: Xaa is Phe or Tyr
<220> FEATURE:
<221> NAME/KEY: MISC_FEATURE
<222> LOCATION: (10)..(10)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Asp, Ala, Glu or Gln
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MISC_FEATURE
<222> LOCATION: (22)..(22)
<223> OTHER INFORMATION: Xaa is Tyr, Ser or Ala
<220> FEATURE:
<221> NAME/KEY: MISC_FEATURE
<222> LOCATION: (25)..(25)
<223> OTHER INFORMATION: Xaa is Ile or Val
<220> FEATURE:
<221> NAME/KEY: MISC_FEATURE
<222> LOCATION: (26)..(26)
<223> OTHER INFORMATION: Xaa is Gln or Glu

<400> SEQUENCE: 32

Thr Arg Glu Xaa Cys Arg Xaa Xaa Leu Xaa Xaa Xaa Gly Met Arg Xaa
1               5                   10                  15

Pro Ser Trp Asn Lys Xaa Gln Ala Xaa Xaa Gln
            20                  25

<210> SEQ ID NO 33
<211> LENGTH: 6
<212> TYPE: PRT
<213> ORGANISM: Artificial Sequence
<220> FEATURE:
<223> OTHER INFORMATION: Consensus sequence

<400> SEQUENCE: 33

Thr Ile Phe Tyr Ser Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 34

Thr Xaa Phe Tyr Xaa Gly
1               5

<210> SEQ ID NO 35
<211> LENGTH: 6
<212> TYPE: PRT
```

```
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Ile or Met
<220> FEATURE:
<221> NAME/KEY: MISC_FEATURE
<222> LOCATION: (5)..(5)
<223> OTHER INFORMATION: Xaa is Ala, Ser, Asp, Cys, Arg or Gly

<400> SEQUENCE: 35

Thr Xaa Phe Tyr Xaa Gly
1               5

<210> SEQ ID NO 36
<211> LENGTH: 355
<212> TYPE: PRT
<213> ORGANISM: Artificial Sequence
<220> FEATURE:
<223> OTHER INFORMATION: Consensus sequence

<400> SEQUENCE: 36

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Glu Lys Ala Asn Ser Ser
    210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
```

```
                275                 280                 285
Pro Leu His Ser Gln Ser Pro Glu Ser Gln Thr Lys Ser Pro Asn Leu
    290                 295                 300

Ser Val Asp Leu Asn Ser Glu Gly Ile Gly Ser Gly Gly Gly Ser Ala
305                 310                 315                 320

Lys Gly Glu Leu Arg Gly His Pro Phe Glu Gly Lys Pro Ile Pro Asn
                325                 330                 335

Pro Leu Leu Gly Leu Asp Ser Thr Arg Thr Gly His His His His
            340                 345                 350

His Gly Ser
        355

<210> SEQ ID NO 37
<211> LENGTH: 42
<212> TYPE: PRT
<213> ORGANISM: Artificial Sequence
<220> FEATURE:
<223> OTHER INFORMATION: Consensus sequence

<400> SEQUENCE: 37

Gly Ser Gly Gly Gly Ser Ala Lys Gly Glu Leu Arg Gly His Pro Phe
1               5                   10                  15

Glu Gly Lys Pro Ile Pro Asn Pro Leu Leu Gly Leu Asp Ser Thr Arg
            20                  25                  30

Thr Gly His His His His His Gly Ser
        35                  40

<210> SEQ ID NO 38
<211> LENGTH: 315
<212> TYPE: PRT
<213> ORGANISM: Artificial Sequence
<220> FEATURE:
<223> OTHER INFORMATION: Consensus sequence

<400> SEQUENCE: 38

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175
```

```
Arg Ser Ile Met His Phe Ala Ala Asn Pro Ile Asp Leu Pro Glu Asn
                180                 185                 190
Gly Ile Phe Ala Ser Ser Arg Met Ile Ser Lys Leu Ile Ser Lys Glu
            195                 200                 205
Lys Met Met Glu Leu Pro Gln Lys Gly Leu Glu Lys Ala Asn Ser Ser
210                 215                 220
Arg Asp Ser Gly Met Glu Gly Gln Ala Asn Arg Lys Val Ser Leu Gln
225                 230                 235                 240
Arg Tyr Arg Glu Lys Arg Lys Asp Arg Lys Phe Ser Lys Ala Lys Lys
                245                 250                 255
Cys Pro Gly Val Ala Ser Ser Leu Glu Met Phe Leu Asn Cys Gln
                260                 265                 270
Pro Arg Met Lys Ala Ala Tyr Ser Gln Asn Leu Gly Cys Thr Gly Ser
            275                 280                 285
Pro Leu His Ser Gln Ser Pro Glu Ser Gln Thr Lys Ser Pro Asn Leu
290                 295                 300
Ser Val Asp Leu Asn Ser Glu Gly Ile Gly Ser
305                 310                 315

<210> SEQ ID NO 39
<211> LENGTH: 86
<212> TYPE: DNA
<213> ORGANISM: Artificial Sequence
<220> FEATURE:
<223> OTHER INFORMATION: Consensus sequence

<400> SEQUENCE: 39
gtaatgttca gctctgctat agtgtgtgcc accctgcttg tttaataatg cgttctcttc      60
gtttttatga tatcttattc ttccag                                           86

<210> SEQ ID NO 40
<211> LENGTH: 1157
<212> TYPE: DNA
<213> ORGANISM: Artificial Sequence
<220> FEATURE:
<223> OTHER INFORMATION: Consensus sequence

<400> SEQUENCE: 40
atggacgtgg gcgtgtcccc ggccaagtct attctcgcca agccggtaat gttcagctct      60
gctatagtgt gtgccaccct gcttgtttaa taatgcgttc tcttcgtttt tatgatatct     120
tattcttcca gctcaagctc ctcaccgagg aggacatctc tcagctcaca agagaggact     180
gccgcaagtt cctgaaggac aaggggatga aaggccttc tggaacaag tcccaggcca      240 tccagcaagt gctcagcctc aaggcccttt acgagccagg cgacgactcc ggcgctggca     300
ttttcagaaa gatcctcgtg tcccagccgg tgaacccacc aagggtgacc accacactca     360
tcgagccgtc caatgagctt gaggcttgcg gcagagtgtc ctacccagag ataatggcg     420 cctgccacag gatggattct ccaaggtctg ctgagttctc tggcggctcc ggccatttcg     480
tgtctgagaa ggatggccac aagaccacca tctccccaag atccccagcc gagacatctg     540
agcttgtggg ccagatgacc atcttctact ccggcaaggt gaacgtgtac gacggcatcc     600
caccagagaa ggcccgctcc attatgcact tcgccgccaa cccaatcgac ctcccagaga     660
atggcatctt cgcctccagc cgcatgatct ccaagctcat ctccaaggag aagatgatgg     720
agctgccgca gaagggcctc gagaaggcta ttcctctcg cgactccggc atggagggcc     780
aggctaatag aaaggtgtcc ctccaacgct accgcgagaa gaggaaggac cgcaagttct     840
```

| | |
|---|---|
| ccaaggccaa gaagtgccca ggcgttgcct cttccagcct cgagatgttc ctcaactgcc | 900 |
| agccgagaat gaaggccgcc tactcccaaa atctcggctg cacaggctcc ccactccatt | 960 |
| ctcagtcccc agagtctcag accaagtccc cgaacctctc cgtggacctt aactccgagg | 1020 |
| gcatcggatc cggcggcggc tctgctaagg gcgagctgag gggccacccg ttcgagggca | 1080 |
| agccaattcc aaatccactc ctcggcctcg actctaccag gaccggccac catcaccatc | 1140 |
| accacggatc ctaatga | 1157 |

<210> SEQ ID NO 41
<211> LENGTH: 2771
<212> TYPE: DNA
<213> ORGANISM: Artificial Sequence
<220> FEATURE:
<223> OTHER INFORMATION: Consensus sequence

<400> SEQUENCE: 41

| | |
|---|---|
| tcgaggtcat tcatatgctt gagaagagag tcgggatagt ccaaaataaa acaaaggtaa | 60 |
| gattacctgg tcaaaagtga aaacatcagt taaaggtgg tataagtaaa atatcggtaa | 120 |
| taaaaggtgg cccaaagtga aatttactct tttctactat tataaaaatt gaggatgttt | 180 |
| tgtcggtact tgatacgtc attttgtat gaattggttt ttaagtttat tcgcgatttg | 240 |
| gaaatgcata tctgtatttg agtcggtttt taagttcgtt gcttttgtaa atacagaggg | 300 |
| atttgtataa gaaatatctt taaaaaaccc atatgctaat ttgacataat ttttgagaaa | 360 |
| aatatatatt caggcgaatt ccacaatgaa caataataag attaaaatag cttgcccccg | 420 |
| ttgcagcgat gggtattttt tctagtaaaa taaaagataa acttagactc aaaacattta | 480 |
| caaaaacaac ccctaaagtc ctaaagccca agtgctatg cacgatccat agcaagccca | 540 |
| gcccaaccca acccaccca acccaccca gtgcagccaa ctggcaaata gtctccaccc | 600 |
| ccggcactat caccgtgagt tgtccgcacc accgcacgtc tcgcagccaa aaaaaaaaaa | 660 |
| agaaagaaaa aaagaaaaa gaaaacagc aggtgggtcc gggtcgtggg ggccggaaaa | 720 |
| gcgaggagga tcgcgagcag cgacgaggcc cggccctccc tccgcttcca agaaacgcc | 780 |
| ccccatcgcc actatataca tacccccccc tctcctccca tcccccaac cctaccacca | 840 |
| ccaccaccac cacctcctcc cccctcgctg ccggacgacg agctcctccc ccctccccct | 900 |
| ccgccgccgc cggtaaccac cccgcccctc tcctctttct ttctccgttt ttttttttcgt | 960 |
| ctcggtctcg atctttggcc ttggtagttt gggtgggcga gagcggcttc gtcgcccaga | 1020 |
| tcggtgcgcg ggaggggcgg gatctcgcgg ctggcgtctc cggcgtgag tcggcccgga | 1080 |
| tcctcgcggg gaatggggct ctcggatgta gatcttcttt ctttcttctt tttgtggtag | 1140 |
| aatttgaatc cctcagcatt gttcatcggt agttttctt ttcatgattt gtgacaaatg | 1200 |
| cagcctcgtg cggagctttt ttgtaggtag acaagcttga tatcacaagt ttgtacaaaa | 1260 |
| aagcaggctt caaaaaaaac catgacgtg ggcgtgtccc cggccaagtc tattctcgcc | 1320 |
| aagccggtaa tgttcagctc tgctatagtg tgtgccaccc tgcttgttta ataatgcgtt | 1380 |
| ctcttcgttt ttatgatatc ttattcttcc agctcaagct cctcaccgag gaggacatct | 1440 |
| ctcagctcac aagagaggac tgccgcaagt tcctgaagga caaggggatg agaaggcctt | 1500 |
| cctggaacaa gtcccaggcc atccagcaag tgctcagcct caaggccctt tacgagccag | 1560 |
| gcgacgactc cggcgctggc attttcagaa agatcctcgt gtcccagccg gtgaacccac | 1620 |
| caagggtgac caccacactc atcgagccgt ccaatgagct tgaggcttgc ggcagagtgt | 1680 |
| cctacccaga ggataatggc gcctgccaca ggatggattc tccaaggtct gctgagttct | 1740 |

```
ctggcggctc cggccatttc gtgtctgaga aggatggcca caagaccacc atctccccaa    1800
gatccccagc cgagacatct gagcttgtgg gccagatgac catcttctac tccggcaagg    1860
tgaacgtgta cgacggcatc ccaccagaga aggcccgctc cattatgcac ttcgccgcca    1920
acccaatcga cctcccagag aatggcatct tcgcctccag ccgcatgatc tccaagctca    1980
tctccaagga gaagatgatg gagctgccgc agaagggcct cgagaaggct aattcctctc    2040
gcgactccgg catggagggc caggctaata gaaaggtgtc cctccaacgc taccgcgaga    2100
agaggaagga ccgcaagttc tccaaggcca agaagtgccc aggcgttgcc tcttccagcc    2160
tcgagatgtt cctcaactgc cagccgagaa tgaaggccgc ctactcccaa aatctcggct    2220
gcacaggctc cccactccat tctcagtccc cagagtctca gaccaagtcc ccgaacctct    2280
ccgtggacct taactccgag ggcatcggat ccggcggcgg ctctgctaag ggcgagctga    2340
ggggccaccc gttcgagggc aagccaattc caaatccact cctcggcctc gactctacca    2400
ggaccggcca ccatcaccat caccacggat cctaatgaag acccagcttt cttgtacaaa    2460
gtggtgatat cgaattcctg cagcccgggg gatccactag ttctaggtac cgagctcgga    2520
tcgttcaaac attggcaata aagtttctta agattgaatc ctgttgccgg tcttgcgatg    2580
attatcatat aatttctgtt gattacgtta agcatgtaat aattaacatg taatgcatga    2640
cgttatttat gagatgggtt tttatgatta gagtcccgca attatacatt taatacgcga    2700
tagaaaacaa aatatagcgc gcaaactagg ataaattatc gcgcgcggtg tcatctatgt    2760
gactagatcg g                                                         2771
```

<210> SEQ ID NO 42
<211> LENGTH: 2921
<212> TYPE: DNA
<213> ORGANISM: Artificial Sequence
<220> FEATURE:
<223> OTHER INFORMATION: Consensus sequence

<400> SEQUENCE: 42

```
gcggccgctc tagaactagt ccccttattg tacttcaatt aattatcatt atatcagcat      60
aaacattata ataagtttct tgcgtgttgg aacgtcattt tagttattct aaagaggaaa     120
tagtttcttt tttgctcatg acatcagaca tctggactac tatactggag tttaccttt     180 cttctcctct ttttcttatt gttcctctaa aaaaattat cacttttta atgcattagt     240 taaacttatc tcaacaacgt ttaaaattca tttcttgaat gcccattaca atgtaatagt     300
ataacttaat tagtcgtctc catgaaccat taatacgtac ggagtaatat aaaacaccat     360
tggggagttc aatttgcaat aatttcttgc aaaaatgtaa agtaccttt tgttcttgca     420 aaattttaca aataaaaatt tgcagctctt ttttttctct ctctccaaat actagctcaa     480 aaccccacaaa tattttttgaa tttatggcat acttttagaa tgcgtttgat gcaactattt     540
tcctttagga aatattcaca acaatctaag acaatcaaaa agtagaaaat agtttgtaaa     600
aagggatgtg gaggacatct taatcaaata ttttcagttt aaaacttgaa atgaaaaaa     660 cacccgaaag gaaatgattc gttctttaat atgtcctaca caatgtgaat ttgaattagt     720
ttggtcatac ggtatatcat atgattataa ataaaaaaaa ttagcaaaag aatataattt     780
attaaatatt ttacaccata ccaaacacaa ccgcattata tataatctta attatcatta     840
tcaccagcat caacattata atgattcccc tatgcgttgg aacgtcatta tagttattct     900
aaacaagaaa gaaatttgtt cttgacatca gacatctagt attataactc tagtggagct     960
```

```
tacctttct     ttccttctt    ttttttcttc    ttaaaaaaat    tatcacttt     taaatcttgt      1020 atattagtta    agcttatcta   aacaaagttt    taaattcatt    tcttaaacgt    ccattacaat      1080
gtaatataac    ttagtcgtct   caattaaacc    attaatgtga    aatataaatc    aaaaaaagcc      1140
aaagggcggt    gggacggcgc   caatcatttg    tcctagtcca    ctcaaataag    gcccatggtc      1200
ggcaaaacca    acacaaaat    gtgttatttt    taattttttc    ctcttttatt    gttaaagttg       1260
caaaatgtgt    tattttttggt aagaccctat    ggatatataa    agacaggtta    tgtgaaactt       1320
ggaaaaccat    caagttttaa   gcaaaaccct    cttaagaact    taaattgagc    ttcttttggg      1380
gcatttttct    agtgagaact   aaaaacaagt    ttgtacaaaa    aagcaggcta    aaaaaaacca      1440
tggacgtggg    cgtgtccccg   gccaagtcta    ttctcgccaa    gccggtaatg    ttcagctctg      1500
ctatagtgtg    tgccaccctg   cttgtttaat    aatgcgttct    cttcgttttt    atgatatctt      1560
attcttccag    ctcaagctcc   tcaccgagga    ggacatctct    cagctcacaa    gagaggactg      1620
ccgcaagttc    ctgaaggaca   aggggatgag    aaggccttcc    tggaacaagt    cccaggccat      1680
ccagcaagtg    ctcagcctca   aggccccttta  cgagccaggc    gacgactccg    cgcgctggcat     1740 tttcagaaag    atcctcgtgt   cccagccggt    gaacccacca    agggtgacca    ccacactcat      1800
cgagccgtcc    aatgagcttg   aggcttgcgc    cagagtgtcc    tacccagagg    ataatggcgc      1860
ctgccacagg    atggattctc   caaggtctgc    tgagttctct    ggcggctccg    gccatttcgt      1920
gtctgagaag    gatggccaca   agaccaccat    ctccccaaga    tccccagccg    agacatctga      1980
gcttgtgggc    cagatgacca   tcttctactc    cggcaaggtg    aacgtgtacg    acggcatccc      2040
accagagaag    gcccgctcca   ttatgcactt    cgccgccaac    ccaatcgacc    tcccagagaa      2100
tggcatcttc    gcctccagcc   gcatgatctc    caagctcatc    tccaaggaga    agatgatgga      2160
gctgccgcag    aagggcctcg   agaaggctaa    ttcctctcgc    gactccggca    tggagggcca      2220
ggctaataga    aaggtgtccc   tccaacgcta    ccgcgagaag    aggaaggacc    gcaagttctc      2280
caaggccaag    aagtgcccag   gcgttgcctc    ttccagcctc    gagatgttcc    tcaactgcca      2340
gccgagaatg    aaggccgcct   actcccaaaa    tctcggctgc    acaggctccc    cactccattc      2400
tcagtcccca    gagtctcaga   ccaagtcccc    gaacctctcc    gtggacctta    actccgaggg      2460
catcggatcc    ggcggcggct   ctgctaaggg    cgagctgagg    ggccacccgt    tcgagggcaa      2520
gccaattcca    aatccactcc   tcggcctcga    ctctaccagg    accggccacc    atcaccatca      2580
ccacggatcc    taatgaaccc   agctttcttg    tacaaagtgg    tctagtgggt    accgcgaatt      2640
tccccgatcg    ttcaaacatt   tggcaataaa    gtttcttaag    attgaatcct    gttgccggtc      2700
ttgcgatgat    tatcatataa   tttctgttga    attacgttaa    gcatgtaata    attaacatgt      2760
aatgcatgac    gttatttatg   agatgggttt    ttatgattag    agtcccgcaa    ttatacatttt     2820 aatacgcgat    agaaaacaaa   atatagcgcg    caaactagga    taaattatcg    cgcgcggtgt      2880
catctatgtt    actagatcga   agcggccgct    ctagaactag    t                              2921
```

<210> SEQ ID NO 43
<211> LENGTH: 2249
<212> TYPE: DNA
<213> ORGANISM: Artificial Sequence
<220> FEATURE:
<223> OTHER INFORMATION: Consensus sequence

<400> SEQUENCE: 43

```
gcggccgctc    tagaactagt   gtcctacaca    atgtgaattt    gaattagttt    ggtcatacgg       60
tatatcatat    gattataaat   aaaaaaaatt    agcaaaagaa    tataatttat    taaatatttt      120
```

```
acaccatacc aaacacaacc gcattatata taatcttaat tatcattatc accagcatca    180
acattataat gattcccta tgcgttggaa cgtcattata gttattctaa acaagaaaga    240
aatttgttct tgacatcaga catctagtat tataactcta gtggagctta cctttctttt    300
tccttctttt ttttcttctt aaaaaaatta tcacttttta aatcttgtat attagttaag    360
cttatctaaa caaagtttta aattcatttc ttaaacgtcc attacaatgt aatataactt    420
agtcgtctca attaaaccat taatgtgaaa tataaatcaa aaaagccaa aggggcggtgg    480 gacggcgcca atcatttgtc ctagtccact caaataaggc ccatggtcgg caaaaccaaa    540
cacaaaatgt gttattttta atttttttcct cttttattgt taaagttgca aaatgtgtta    600
tttttggtaa gaccctatgg atatataaag acaggttatg tgaaacttgg aaaaccatca    660
agttttaagc aaaaccctct taagaactta aattgagctt cttttggggc attttttctag    720 tgagaactaa aaacaagttt gtacaaaaaa gcaggctaaa aaaaaccatg gacgtgggcg    780
tgtccccggc caagtctatt ctcgccaagc cggtaatgtt cagctctgct atagtgtgtg    840
ccaccctgct tgtttaataa tgcgttctct tcgtttttat gatatcttat tcttccagct    900
caagctcctc accgaggagg acatctctca gctcacaaga gaggactgcc gcaagttcct    960
gaaggacaag gggatgagaa ggccttcctg gaacaagtcc caggccatcc agcaagtgct    1020
cagcctcaag gccctttacg agccaggcga cgactccggc gctggcattt tcagaaagat    1080
cctcgtgtcc cagccggtga acccaccaag ggtgaccacc acactcatcg agccgtccaa    1140
tgagcttgag gcttgcggca gagtgtccta cccagaggat aatggcgcct gccacaggat    1200
ggattctcca aggtctgctg agttctctgg cggctccggc catttcgtgt ctgagaagga    1260
tggccacaag accaccatct cccaagatc cccagccgag acatctgagc ttgtgggcca    1320
gatgaccatc ttctactccg gcaaggtgaa cgtgtacgac ggcatcccac cagagaaggc    1380
ccgctccatt atgcacttcg ccgccaaccc aatcgacctc ccagagaatg gcatcttcgc    1440
ctccagccgc atgatctcca agctcatctc caaggagaag atgatggagc tgccgcagaa    1500
gggcctcgag aaggctaatt cctctcgcga ctccggcatg gagggccagg ctaatagaaa    1560
ggtgtccctc caacgctacc gcgagaagag gaaggaccgc aagttctcca aggccaagaa    1620
gtgcccaggc gttgcctctt ccagcctcga gatgttcctc aactgccagc cgagaatgaa    1680
ggccgcctac tcccaaaatc tcggctgcac aggctcccca ctccattctc agtccccaga    1740
gtctcagacc aagtccccga acctctccgt ggaccttaac tccgagggca tcggatccgg    1800
cggcggctct gctaagggcg agctgagggg ccacccgttc gagggcaagc caattccaaa    1860
tccactcctc ggcctcgact ctaccaggac cggccaccat caccatcacc acggatccta    1920
atgaacccag ctttcttgta caaagtggtc tagtgggtac cgcgaatttc cccgatcgtt    1980
caaacatttg gcaataaagt ttcttaagat tgaatcctgt tgccggtctt gcgatgatta    2040
tcatataatt tctgttgaat tacgttaagc atgtaataat taacatgtaa tgcatgacgt    2100
tatttatgag atgggttttt atgattagag tcccgcaatt atacatttaa tacgcgatag    2160
aaaacaaaat atagcgcgca aactaggata aattatcgcg cgcggtgtca tctatgttac    2220
tagatcgaag cggccgctct agaactagt                                        2249
```

<210> SEQ ID NO 44
<211> LENGTH: 2852
<212> TYPE: DNA
<213> ORGANISM: Artificial Sequence
<220> FEATURE:

<223> OTHER INFORMATION: Consensus sequence

<400> SEQUENCE: 44

```
gcggccgctc tagaactagt tcacgtggaa cgcgccgcag taaacggagc ggtggatcaa    60
acttttcgtc cgtttgatca aacagaagag aactagtcaa tgctctttct tcatatcaca   120
atttaatagt ctcaagacga ttacgccaca taaccatttt ctcgtgattt cgacatcaaa   180
atttaataaa aggaactgat tgattggtca tcatgttaca agtgtcaaat gagctaatcc   240
gttttacagt ggcatagttt acgatcaatt tacaaatttt tggttttata acatacttgt   300
agttaaaact atttataagc tatttatagt gagttagctt ataaaccct attcttttat    360
ctaaaattat gttttgactc gtttcatgat aaaatttat cctttcatc ggaataaaaa     420
actttattat ttatttggca aaataattgg tgtaaaaatt atgtatatgt taataacaaa   480
aaatattaat ctgattcata atcttaaaaa agaaaaattt cttgaaataa actttagaca   540
ttgtaaataa aaaacatta tttttatata atgggatgtt tatatgtaat ttttataaa     600
aaaataaaag ttgtttacta gtaatccgat tggctttaac tatcgtcgcc aaaagaataa   660
tgtagaactg actttgaggt aaaactaaaa gaaatttgta agataatagt cacattaaat   720
gctaaaatta atacatactg atatatcgta taaaatttat gaaaactaca ccttaacctg   780
aatcatacac tgtaataaaa aaaacaaatt atatataaac cctaaaaact aatcataaat   840
cccaaacggt gtactctcta ttagctttga aaggattgcc caattgtttg ttaaaaattt   900
ctaataatag tacaatgttt tgtttcattt ttccttttcg tcaacctgtt acccaatagc   960
aaatgaagtt tttatgtgtg tgtgtgtgtg tgaatttcca tgaaaatgaa acgggcttag  1020
aatcccggtg tattatgggt cgggtcgtaa ccgggcaatg acgcaggatc tgacgtaaaa  1080
ctcccaagaa ttttttaaa aagtctccgg aaaataaaat caaagttcat taacttaaaa   1140
agaaaaaaca aaatcggtcc acgtcccaaa ccctttttat aggagagtct tatgttctgg  1200
cagaagactt cacagactct ttcttaatct ctctctcttt caaccaaacc cctaaacaaa  1260
aaaaaaatac attttctgat ctctctaaaa atctttctcc ttcgttaatc tcgtgatctc  1320
tttctttttc tatatacaag tttgtacaaa aaagcaggct aaaaaaaacc atggacgtgg  1380
gcgtgtcccc ggccaagtct attctcgcca agccggtaat gttcagctct gctatagtgt  1440
gtgccaccct gcttgtttaa taatgcgttc tcttcgtttt tatgatatct tattcttcca  1500
gctcaagctc ctcaccgagg aggacatctc tcagctcaca agagaggact gccgcaagtt  1560
cctgaaggac aaggggatga aaggccttc ctggaacaag tcccaggcca tccagcaagt  1620
gctcagcctc aaggccctt acgagccagg cgacgactcc ggcgctggca ttttcagaaa  1680
gatcctcgtg tcccagccgg tgaacccacc aagggtgacc accacactca tcgagccgtc  1740
caatgagctt gaggcttgcg gcagagtgtc ctacccagag gataatggcg cctgccacag  1800
gatggattct ccaaggtctg ctgagttctc tggcggctcc ggccatttcg tgtctgagaa  1860
ggatggccac aagaccacca tctccccaag atccccagcc gagacatctg agcttgtggg  1920
ccagatgacc atcttctact ccggcaaggt gaacgtgtac gacggcatcc accagagaa   1980
ggcccgctcc attatgcact cgccgccaa cccaatcgac ctcccagaga atggcatctt   2040
cgcctccagc cgcatgatct ccaagctcat ctccaaggag aagatgatgg agctgccgca  2100
gaagggcctc gagaaggcta attcctctcg cgactccggc atggagggcc aggctaatag  2160
aaaggtgtcc ctccaacgct accgcgagaa gaggaaggac cgcaagttct ccaaggccaa  2220
gaagtgccca ggcgttgcct cttccagcct cgagatgttc ctcaactgcc agccgagaat  2280
```

```
gaaggccgcc tactcccaaa atctcggctg cacaggctcc ccactccatt ctcagtcccc    2340
agagtctcag accaagtccc cgaacctctc cgtggacctt aactccgagg gcatcggatc    2400
cggcggcggc tctgctaagg gcgagctgag gggccacccg ttcgagggca agccaattcc    2460
aaatccactc ctcggcctcg actctaccag gaccggccac catcaccatc accacggatc    2520
ctaatgaacc cagcttttct gtacaaagtg gtctagtggg taccgcgaat tccccgatc     2580 gttcaaacat ttggcaataa agtttcttaa gattgaatcc tgttgccggt cttgcgatga    2640
ttatcatata atttctgttg aattacgtta agcatgtaat aattaacatg taatgcatga    2700
cgttatttat gagatgggtt tttatgatta gagtcccgca attatacatt taatacgcga    2760
tagaaaacaa aatatagcgc gcaaactagg ataaattatc gcgcgcggtg tcatctatgt    2820
tactagatcg aagcggccgc tctagaacta gt                                  2852

<210> SEQ ID NO 45
<211> LENGTH: 2330
<212> TYPE: DNA
<213> ORGANISM: Artificial Sequence
<220> FEATURE:
<223> OTHER INFORMATION: Consensus sequence

<400> SEQUENCE: 45
ggtaatgagc cctatctgat gtcagtgggg attgtttaca gtaccgcagc aaacactgac      60
gtatgggtct ggacccatat gttagccacc gctactgcat cagcagtatt gcagagaatt     120
tgcatcagca gtactgcatc agcagtatta cagatggggg tgcacaaagc cgggtcagtt     180
tacccaacta ccttcctcct cttaactata acttatattc aatttatgtc tctcgaaaat     240
agatatgaac atacttttt aaaaaataat actacatatt gtgaatttgt gatccttacc      300
tttacatttg agttatgacg aacaacttta tcgattatat aaaagaaagg atgacttctt     360
atccaaacaa atcctatagt aatgtctttt taactttcag tgactaacat ataaaccatc     420
aaacgagtcc atattaaagg ataatactac gaagaattgt catcccacat ttttacactg     480
ccactatcag ttaaaactga aaccagctc acccccaagct caccaagaat cttcgagaaa     540
cttataaact ccgccgaaaa atctcggaca aaccccgcggc tcacacgcct ccacgcaccc    600 aaacccacc ctagaatatc ctctccttgg ccaccgcgcc gccacatcag cctccccaat      660
ctccccgccc cacgcgcgag cgccaatcgc gagccgcctt tagatttccc aagataagga    720
ctcgatcccc cctcacttcc cgcgctattt aaactcccgc gccatctcca actcccaact    780
cacactcgct cgctcatcgc catctctctc agctctcaca gctcactgca tcaacaagtt    840
tgtacaaaaa agcaggctaa aaaaaaccat ggacgtgggc gtgtcccccgg ccaagtctat   900 tctcgccaag ccggtaatgt tcagctctgc tatagtgtgt gccaccctgc ttgtttaata    960
atgcgttctc ttcgtttttta tgatatctta ttcttccagc tcaagctcct caccgaggag    1020
gacatctctc agctcacaag agaggactgc cgcaagttcc tgaaggacaa ggggatgaga    1080
aggccttcct ggaacaagtc ccaggccatc cagcaagtgc tcagcctcaa ggcccttac     1140 gagccaggcg acgactccgg cgctggcatt ttcagaaaga tcctcgtgtc ccagccggtg    1200
aacccaccaa gggtgaccac cacactcatc gagccgtcca atgagcttga ggcttgcggc    1260
agagtgtcct acccagagga taatggcgcc tgccacagga tggattctcc aaggtctgct    1320
gagttctctg gcggctccgg ccattcgtg tctgagaagg atggcacaa gaccaccatc      1380 tccccaagat ccccagccga gacatctgag cttgtgggcc agatgaccat cttctactcc    1440
```

| | | | | |
|---|---|---|---|---|
| ggcaaggtga | acgtgtacga | cggcatccca | ccagagaagg | cccgctccat tatgcacttc | 1500 |
| gccgccaacc | caatcgacct | cccagagaat | ggcatcttcg | cctccagccg catgatctcc | 1560 |
| aagctcatct | ccaaggagaa | gatgatggag | ctgccgcaga | agggcctcga gaaggctaat | 1620 |
| tcctctcgcg | actccggcat | ggagggccag | gctaatagaa | aggtgtccct ccaacgctac | 1680 |
| cgcgagaaga | ggaaggaccg | caagttctcc | aaggccaaga | agtgcccagg cgttgcctct | 1740 |
| tccagcctcg | agatgttcct | caactgccag | ccgagaatga | aggccgccta ctcccaaaat | 1800 |
| ctcggctgca | caggctcccc | actccattct | cagtccccag | agtctcagac caagtccccg | 1860 |
| aacctctccg | tggaccttaa | ctccgagggc | atcggatccg | gcggcggctc tgctaagggc | 1920 |
| gagctgaggg | gccacccgtt | cgagggcaag | ccaattccaa | atccactcct cggcctcgac | 1980 |
| tctaccagga | ccgccacca | tcaccatcac | cacggatcct | aatgaaccca gctttcttgt | 2040 |
| acaaagtggt | ctagtgggta | ccgcgaattt | ccccgatcgt | tcaaacattt ggcaataaag | 2100 |
| tttcttaaga | ttgaatcctg | ttgccggtct | tgcgatgatt | atcatataat ttctgttgaa | 2160 |
| ttacgttaag | catgtaataa | ttaacatgta | atgcatgacg | ttatttatga gatgggtttt | 2220 |
| tatgattaga | gtcccgcaat | tatacattta | atacgcgata | gaaaacaaaa tatagcgcgc | 2280 |
| aaactaggat | aaattatcgc | gcgcggtgtc | atctatgtta | ctagatcgaa | 2330 |

<210> SEQ ID NO 46
<211> LENGTH: 3088
<212> TYPE: DNA
<213> ORGANISM: Artificial Sequence
<220> FEATURE:
<223> OTHER INFORMATION: Consensus sequence

<400> SEQUENCE: 46

| | | | | |
|---|---|---|---|---|
| aaatgcccaa | ataggtgcaa | atctcagata | gaaatgtttc | aaaagtaaaa aaggtcccta | 60 |
| tcataaacat | aattgatatg | taagtgagtt | ggaaaaagat | aagtacggtg tgagagagac | 120 |
| ggggatcaaa | ttcctggtgt | aataatgtat | gtattcacgt | ccaataaaaa attggtagca | 180 |
| gtagttgggg | ctctgtatat | tataccggta | aggtagggta | ggtagtagaa taattctttt | 240 |
| tttgttttta | gttttttctg | gtccaaaatt | tcaaatttca | aatttggatc ccttacttgt | 300 |
| accaactaat | attaatgagt | gttgagggta | gtagaggtgc | aactttacca taatccctct | 360 |
| gtttcaggtt | ataagacgtt | ttgacttta a | atttgaccaa | gttatgcgc aaatatagta | 420 |
| atatttataa | tactatatta | gtttcattaa | ataaataatt | gaatatattt tcataataaa | 480 |
| tttgtgttga | gttcaaaata | ttattaattt | tttctacaaa | cttggtcaaa cttgaagcag | 540 |
| tttgactttg | accaaagtca | acgtcttata | acttgaaacg | gatggattaa cctttttttt | 600 |
| gtgggaacaa | gttacaaag | tttaataaag | cacaatccat | cttaatgttt tcaagctgaa | 660 |
| tattgtaaaa | ttcatggata | aaccaggctt | ataaatgttt | aaccgggaaa atgcgaacgg | 720 |
| caaattaata | tttttaagtg | atggggagta | ttaattaagg | agtgacaact caactttcaa | 780 |
| tatcgtacta | aactgtggga | tttatttct | aaaattttat | accctgccaa ttcacgtgtt | 840 |
| gtagatcttt | ttttttcact | aaccgacacc | aggtatatca | attttattga atatagcagc | 900 |
| aaaaagaatg | tgttgtactt | gtaaacaaaa | agcaaactgt | acataaaaaa aaatgcactc | 960 |
| ctatataatt | aagctcataa | agatgctttg | cttcgtgagg | gcccaaggtt ttgatgacct | 1020 |
| tttgcttgat | ctcgaaatta | aaatttaagt | actgttaagg | gagttcacac caccatcaat | 1080 |
| tttcagcctg | aagaaacagt | taaacaaacg | gaccccgatg | accagtctac tgctctccac | 1140 |
| atactagctg | cattattgat | cacaaaacaa | aacaaaacga | aataaaaatc agcagcgaga | 1200 |

| | |
|---|---|
| gtgtgcagag agagacaaag gtgatctggg cgtggatatc tccccatcca tcctcacccg | 1260 |
| cgctgcccat cactcgccgc cgcatactcc atcatgtgga gagaggaaga cgaggaccac | 1320 |
| agccagagcc cgggtcgaga tgccaccacg gccacaaccc acgagcccgg cgcgacacca | 1380 |
| ccgcgcgcgt gagccagcca caaacgcccg cggataggcg cgccgcacgc ggccaatcct | 1440 |
| accacatccc cggcctccgc ggctcgagcg ccgctgccat ccgatccgct gagttttggc | 1500 |
| tatttatacg taccgcggga gcctgtgtgc agagcagtgc atctcaagaa gtactcgagc | 1560 |
| aaagaaggag agagcttggt gagctgcaga gacaagtttg tacaaaaaag caggctaaaa | 1620 |
| aaaaccatgg acgtgggcgt gtccccggcc aagtctattc tcgccaagcc ggtaatgttc | 1680 |
| agctctgcta tagtgtgtgc caccctgctt gtttaataat gcgttctctt cgtttttatg | 1740 |
| atatcttatt cttccagctc aagctcctca ccgaggagga catctctcag ctcacaagag | 1800 |
| aggactgccg caagttcctg aaggacaagg ggatgagaag gccttcctgg aacaagtccc | 1860 |
| aggccatcca gcaagtgctc agcctcaagg cccttacga gccaggcgac gactccggcg | 1920 |
| ctggcatttt cagaaagatc ctcgtgtccc agccggtgaa cccaccaagg gtgaccacca | 1980 |
| cactcatcga gccgtccaat gagcttgagg cttgcggcag agtgtcctac ccagaggata | 2040 |
| atggcgcctg ccacaggatg gattctccaa ggtctgctga gttctctggc ggctccggcc | 2100 |
| atttcgtgtc tgagaaggat ggccacaaga ccaccatctc cccaagatcc ccagccgaga | 2160 |
| catctgagct tgtgggccag atgaccatct tctactccgg caaggtgaac gtgtacgacg | 2220 |
| gcatcccacc agagaaggcc cgctccatta tgcacttcgc cgccaaccca atcgacctcc | 2280 |
| cagagaatgg catcttcgcc tccagccgca tgatctccaa gctcatctcc aaggagaaga | 2340 |
| tgatggagct gccgcagaag ggcctcgaga aggctaattc ctctcgcgac tccggcatgg | 2400 |
| agggccaggc taatagaaag gtgtccctcc aacgctaccg cgagaagagg aaggaccgca | 2460 |
| agttctccaa ggccaagaag tgcccaggcg ttgcctcttc cagcctcgag atgttcctca | 2520 |
| actgccagcc gagaatgaag gccgcctact cccaaaatct cggctgcaca ggctcccac | 2580 |
| tccattctca gtccccagag tctcagacca agtccccgaa cctctccgtg gaccttaact | 2640 |
| ccgagggcat cggatccggc ggcggctctg ctaagggcga gctgagggc cacccgttcg | 2700 |
| agggcaagcc aattccaaat ccactcctcg gcctcgactc taccaggacc ggccaccatc | 2760 |
| accatcacca cggatcctaa tgaacccagc tttcttgtac aaagtggtct agtgggtacc | 2820 |
| gcgaatttcc ccgatcgttc aaacatttgg caataaagtt tcttaagatt gaatcctgtt | 2880 |
| gccggtcttg cgatgattat catataattt ctgttgaatt acgttaagca tgtaataatt | 2940 |
| aacatgtaat gcatgacgtt atttatgaga tgggttttta tgattagagt cccgcaatta | 3000 |
| tacatttaat acgcgataga aaacaaaata tagcgcgcaa actaggataa attatcgcgc | 3060 |
| gcggtgtcat ctatgttact agatcgaa | 3088 |

<210> SEQ ID NO 47
<211> LENGTH: 2651
<212> TYPE: DNA
<213> ORGANISM: Artificial Sequence
<220> FEATURE:
<223> OTHER INFORMATION: Consensus sequence

<400> SEQUENCE: 47

| | |
|---|---|
| tcgaggtcat tcatatgctt gagaagagag tcgggatagt ccaaaataaa acaaaggtaa | 60 |
| gattacctgg tcaaaagtga aaacatcagt taaaaggtgg tataagtaaa atatcggtaa | 120 |

```
taaaaggtgg cccaaagtga aatttactct tttctactat tataaaaatt gaggatgttt      180
tgtcggtact ttgatacgtc atttttgtat gaattggttt ttaagtttat tcgcgatttg      240
gaaatgcata tctgtatttg agtcggtttt taagttcgtt gcttttgtaa atacagaggg      300
atttgtataa gaaatatctt taaaaaaccc atatgctaat ttgacataat ttttgagaaa      360
aatatatatt caggcgaatt ccacaatgaa caataataag attaaaatag cttgcccccg      420
ttgcagcgat gggtattttt tctagtaaaa taaaagataa acttagactc aaaacattta      480
caaaaacaac ccctaaagtc ctaaagccca aagtgctatg cacgatccat agcaagccca      540
gcccaaccca acccaaccca acccacccca gtgcagccaa ctggcaaata gtctccaccc      600
ccggcactat caccgtgagt tgtccgcacc accgcacgtc tcgcagccaa aaaaaaaaaa      660
agaaagaaaa aaaagaaaaa gaaaacagc aggtgggtcc gggtcgtggg ggccggaaaa      720
gcgaggagga tcgcgagcag cgacgaggcc cggccctccc tccgcttcca aagaaacgcc      780
ccccatcgcc actatataca tacccccccc tctcctccca tcccccaac cctaccacca      840 ccaccaccac cacctcctcc cccctcgctg ccggacgacg agctcctccc ccctcccct      900 ccgccgccgc cggtaaccac cccgcccctc tcctctttct ttctccgttt ttttttttcgt     960 ctcggtctcg atctttggcc ttggtagttt gggtgggcga gagcggcttc gtcgcccaga     1020
tcggtgcgcg ggaggggcgg gatctcgcgg ctggcgtctc cgggcgtgag tcggcccgga     1080
tcctcgcggg gaatggggct ctcggatgta gatcttcttt cttcttcttt tttgtggtag     1140
aatttgaatc cctcagcatt gttcatcggt agttttctt ttcatgattt gtgacaaatg      1200
cagcctcgtg cggagctttt ttgtaggtag acaagcttga tatcacaagt ttgtacaaaa     1260
aagcaggctt caaaaaaaac catggacgtg ggcgtgtccc cggccaagtc tattctcgcc     1320
aagccggtaa tgttcagctc tgctatagtg tgtgccaccc tgcttgttta ataatgcgtt     1380
ctcttcgttt ttatgatatc ttattcttcc agctcaagct cctcaccgag gaggacatct     1440
ctcagctcac aagagaggac tgccgcaagt tcctgaagga caaggggatg agaaggcctt     1500
cctggaacaa gtcccaggcc atccagcaag tgctcagcct caaggccctt tacgagccag     1560
gcgacgactc cggcgctggc attttcagaa agatcctcgt gtcccagccg gtgaaccac      1620 caagggtgac caccacactc atcgagccgt ccaatgagct tgaggcttgc ggcagagtgt     1680
cctacccaga ggataatggc gcctgccaca ggatggattc tccaaggtct gctgagttct     1740
ctggcggctc cggccatttc gtgtctgaga aggatggcca caagaccacc atctccccaa     1800
gatccccagc cgagacatct gagcttgtgg gccagatgac catcttctac tccggcaagg     1860
tgaacgtgta cgacggcatc ccaccagaga aggcccgctc cattatgcac ttcgccgcca     1920
acccaatcga cctcccagag aatggcatct tcgcctccag ccgcatgatc tccaagctca     1980
tctccaagga gaagatgatg gagctgccgc agaagggcct cgagaaggct aattcctctc     2040
gcgactccgg catggagggc caggctaata gaaaggtgtc cctccaacgc taccgcgaga     2100
agaggaagga ccgcaagttc tccaaggcca agaagtgccc aggcgttgcc tcttccagcc     2160
tcgagatgtt cctcaactgc agccgagaa tgaaggccgc ctactcccaa aatctcggct     2220
gcacaggctc cccactccat tctcagtccc cagagtctca gaccaagtcc ccgaacctct     2280
ccgtggacct taactccgag ggcatcggat cctaatgaag acccagcttt cttgtacaaa     2340
gtggtgatat cgaattcctg cagcccgggg gatccactag ttctaggtac cgagctcgga     2400
tcgttcaaac attggcaata aagtttctta agattgaatc ctgttgccgg tcttgcgatg     2460
attatcatat aatttctgtt gattacgtta agcatgtaat aattaacatg taatgcatga     2520
```

```
cgttatttat gagatgggtt tttatgatta gagtcccgca attatacatt taatacgcga    2580
tagaaaacaa aatatagcgc gcaaactagg ataaattatc gcgcgcggtg tcatctatgt    2640
gactagatcg g                                                         2651
```

<210> SEQ ID NO 48
<211> LENGTH: 2801
<212> TYPE: DNA
<213> ORGANISM: Artificial Sequence
<220> FEATURE:
<223> OTHER INFORMATION: Consensus sequence

<400> SEQUENCE: 48

```
gcggccgctc tagaactagt ccccttattg tacttcaatt aattatcatt atatcagcat      60
aaacattata ataagtttct tgcgtgttgg aacgtcattt tagttattct aaagaggaaa     120
tagtttcttt tttgctcatg acatcagaca tctggactac tatactggag tttacctttt     180
cttctcctct ttttcttatt gttcctctaa aaaaattat cacttttaa atgcattagt       240 taaacttatc tcaacaacgt ttaaaattca tttcttgaat gcccattaca atgtaatagt     300
ataacttaat tagtcgtctc catgaaccat taatacgtac ggagtaatat aaaacaccat     360
tggggagttc aatttgcaat aatttcttgc aaaaatgtaa agtaccttt tgttcttgca      420 aaattttaca aataaaaatt tgcagctctt tttttctct ctctccaaat actagctcaa      480
aacccacaaa tatttttgaa tttatggcat acttttagaa tgcgtttgat gcaactattt     540
tcctttagga aatattcaca acaatctaag acaatcaaaa agtagaaaat agtttgtaaa     600
aagggatgtg gaggacatct taatcaaata ttttcagttt aaaacttgaa aatgaaaaaa     660
cacccgaaag gaaatgattc gttctttaat atgtcctaca caatgtgaat ttgaattagt     720
ttggtcatac ggtatatcat atgattataa ataaaaaaaa ttagcaaaag aatataattt     780
attaaatatt ttacaccata ccaaacacaa ccgcattata tataatctta attatcatta    840
tcaccagcat caacattata atgattcccc tatgcgttgg aacgtcatta tagttattct    900
aaacaagaaa gaaatttgtt cttgacatca gacatctagt attataactc tagtggagct    960
taccttttct tttccttctt ttttttcttc ttaaaaaaat tatcacttttt taaatcttgt   1020 atattagtta agcttatcta aacaaagttt taaattcatt tcttaaacgt ccattacaat    1080
gtaatataac ttagtcgtct caattaaacc attaatgtga aatataaatc aaaaaaagcc    1140
aaagggcggt gggacggcgc caatcatttg tcctagtcca ctcaaataag gcccatggtc    1200
ggcaaaacca aacacaaaat gtgttatttt taatttttc ctcttttatt gttaaagttg    1260
caaaatgtgt tattttggt aagaccctat ggatatataa agacaggtta tgtgaaactt    1320
ggaaaaccat caagttttaa gcaaaaccct cttaagaact taaattgagc ttcttttggg   1380
gcatttttct agtgagaact aaaaacaagt ttgtacaaaa aagcaggcta aaaaaaacca   1440
tggacgtggg cgtgtccccg gccaagtcta ttctcgccaa gccggtaatg ttcagctctg   1500
ctatagtgtg tgccacccctg cttgtttaat aatgcgttct cttcgttttt atgatatctt   1560
attcttccag ctcaagctcc tcaccgagga ggacatctct cagctcacaa gagaggactg   1620
ccgcaagttc ctgaaggaca aggggatgag aaggccttcc tggaacaagt cccaggccat   1680
ccagcaagtg ctcagcctca aggcccttta cgagccaggc gacgactccg gcgctggcat   1740
tttcagaaag atcctcgtgt cccagccggt gaacccacca agggtgacca ccacactcat   1800
cgagccgtcc aatgagcttg aggcttgcgg cagagtgtcc tacccagagg ataatggcgc   1860
```

```
ctgccacagg atggattctc caaggtctgc tgagttctct ggcggctccg gccatttcgt    1920
gtctgagaag gatggccaca agaccaccat ctccccaaga tccccagccg agacatctga    1980
gcttgtgggc cagatgacca tcttctactc cggcaaggtg aacgtgtacg acggcatccc    2040
accagagaag gcccgctcca ttatgcactt cgccgccaac ccaatcgacc tcccagagaa    2100
tggcatcttc gcctccagcc gcatgatctc caagctcatc tccaaggaga gatgatgga    2160 gctgccgcag aagggcctcg agaaggctaa ttcctctcgc gactccggca tggagggcca    2220
ggctaataga aaggtgtccc tccaacgcta ccgcgagaag aggaaggacc gcaagttctc    2280
caaggccaag aagtgcccag cgttgcctc ttccagcctc gagatgttcc tcaactgcca    2340
gccgagaatg aaggccgcct actcccaaaa tctcggctgc acaggctccc cactccattc    2400
tcagtcccca gagtctcaga ccaagtcccc gaacctctcc gtggacctta actccgaggg    2460
catcggatcc taatgaaccc agcttcttg tacaaagtgg tctagtgggt accgcgaatt    2520
tccccgatcg ttcaaacatt tggcaataaa gtttcttaag attgaatcct gttgccggtc    2580
ttgcgatgat tatcatataa tttctgttga attacgttaa gcatgtaata attaacatgt    2640
aatgcatgac gttatttatg agatgggttt ttatgattag agtcccgcaa ttatacattt    2700
aatacgcgat agaaaacaaa atatagcgcg caaactagga taaattatcg cgcgcggtgt    2760
catctatgtt actagatcga agcggccgct ctagaactag t                        2801
```

<210> SEQ ID NO 49
<211> LENGTH: 2129
<212> TYPE: DNA
<213> ORGANISM: Artificial Sequence
<220> FEATURE:
<223> OTHER INFORMATION: Consensus sequence

<400> SEQUENCE: 49

```
gcggccgctc tagaactagt gtcctacaca atgtgaattt gaattagttt ggtcatacgg     60
tatatcatat gattataaat aaaaaaaatt agcaaaagaa tataatttat taaatatttt    120
acaccatacc aaacacaacc gcattatata taatcttaat tatcattatc accagcatca    180
acattataat gattccccta tgcgttggaa cgtcattata gttattctaa acaagaaaga    240
aatttgttct tgacatcaga catctagtat tataactcta gtggagctta cctttttcttt   300 tccttctttt ttttcttctt aaaaaaatta tcacttttta aatcttgtat attagttaag    360
cttatctaaa caaagtttta aattcatttc ttaaacgtcc attacaatgt aatataactt    420
agtcgtctca attaaaccat taatgtgaaa tataaatcaa aaaaagccaa agggcggtgg    480
gacggcgcca atcatttgtc ctagtccact caaataaggc ccatggtcgg caaaaccaaa    540
cacaaaatgt gttattttta atttttttcct cttttattgt taaagttgca aaatgtgtta    600
tttttggtaa gaccctatgg atatataaag acaggttatg tgaaacttgg aaaaccatca    660
agttttaagc aaaaccctct taagaactta aattgagctt cttttggggc atttttctag    720
tgagaactaa aaacaagttt gtacaaaaaa gcaggctaaa aaaaaccatg gacgtgggcg    780
tgtccccggc caagtctatt ctcgccaagc cggtaatgtt cagctctgct atagtgtgtg    840 ccacccctgct tgtttaataa tgcgttctct tcgttttat gatatcttat tcttccagct    900
caagctcctc accgaggagg acatctctca gctcacaaga gaggactgcc gcaagttcct    960
gaaggacaag gggatgagaa ggccttcctg aacaagtcc caggccatcc agcaagtgct   1020
cagcctcaag gcccttttacg agccaggcga cgactccggc gctggcattt tcagaaagat   1080
cctcgtgtcc cagccggtga acccaccaag ggtgaccacc acactcatcg agccgtccaa   1140
```

```
tgagcttgag gcttgcggca gagtgtccta cccagaggat aatggcgcct gccacaggat    1200
ggattctcca aggtctgctg agttctctgg cggctccggc catttcgtgt ctgagaagga    1260
tggccacaag accaccatct ccccaagatc cccagccgag acatctgagc ttgtgggcca    1320
gatgaccatc ttctactccg gcaaggtgaa cgtgtacgac ggcatcccac cagagaaggc    1380
ccgctccatt atgcacttcg ccgccaaccc aatcgacctc ccagagaatg catcttcgc    1440 ctccagccgc atgatctcca agctcatctc caaggagaag atgatggagc tgccgcagaa    1500
gggcctcgag aaggctaatt cctctcgcga ctccggcatg gagggccagg ctaatagaaa    1560
ggtgtccctc caacgctacc gcgagaagag gaaggaccgc aagttctcca aggccaagaa    1620
gtgcccaggc gttgcctctt ccagcctcga gatgttcctc aactgccagc cgagaatgaa    1680
ggccgcctac tcccaaaatc tcggctgcac aggctcccca ctccattctc agtccccaga    1740
gtctcagacc aagtccccga acctctccgt ggaccttaac tccgagggca tcggatccta    1800
atgaacccag ctttcttgta caaagtggtc tagtgggtac cgcgaatttc cccgatcgtt    1860
caaacatttg gcaataaagt ttcttaagat tgaatcctgt tgccggtctt gcgatgatta    1920
tcatataatt tctgttgaat tacgttaagc atgtaataat taacatgtaa tgcatgacgt    1980
tatttatgag atgggttttt atgattagag tcccgcaatt atacatttaa tacgcgatag    2040
aaaacaaaat atagcgcgca aactaggata aattatcgcg cgcggtgtca tctatgttac    2100
tagatcgaag cggccgctct agaactagt                                      2129

<210> SEQ ID NO 50
<211> LENGTH: 2732
<212> TYPE: DNA
<213> ORGANISM: Artificial Sequence
<220> FEATURE:
<223> OTHER INFORMATION: Consensus sequence

<400> SEQUENCE: 50
gcggccgctc tagaactagt tcacgtggaa cgcgccgcag taaacggagc ggtggatcaa      60
acttttcgtc cgtttgatca aacagaagag aactagtcaa tgctctttct tcatatcaca    120
atttaatagt ctcaagacga ttacgccaca taaccatttt ctcgtgattt cgacatcaaa    180
atttaataaa aggaactgat tgattggtca tcatgttaca agtgtcaaat gagctaatcc    240
gttttacagt ggcatagttt acgatcaatt tacaaatttt tggttttata acatacttgt    300
agttaaaact atttataagc tatttatagt gagttagctt ataaaaccct attcttttat    360
ctaaaattat gttttgactc gtttcatgat aaaattttat cctttcatc ggaataaaaa    420 actttattat ttatttggca aaataattgg tgtaaaaatt atgtatatgt taataacaaa    480
aaatattaat ctgattcata atcttaaaaa agaaaaattt cttgaaataa actttagaca    540
ttgtaaataa aaaaacatta tttttatata atgggatgtt tatatgtaat tttttataaa    600
aaaataaaag ttgtttacta gtaatccgat tggctttaac tatcgtcgcc aaaagaataa    660
tgtagaactg acttttgaggt aaaactaaaa gaaatttgta agataatagt cacattaaat    720
gctaaaatta atacatactg atatatcgta taaaatttat gaaaactaca ccttaacctg    780
aatcatacac tgtaataaaa aaaacaaatt atatataaac cctaaaaact aatcataaat    840
cccaaacggt gtactctcta ttagctttga aaggattgcc caattgtttg ttaaaaattt    900 ctaataaatag tacaatgttt tgtttcattt ttcctttcg tcaacctgtt acccaatagc    960
aaatgaagtt tttatgtgtg tgtgtgtgtg tgaatttcca tgaaaatgaa acgggcttag   1020
```

```
aatcccggtg tattatgggt cgggtcgtaa ccgggcaatg acgcaggatc tgacgtaaaa    1080
ctcccaagaa ttttttaaa aagtctccgg aaaataaaat caaagttcat taacttaaaa    1140
agaaaaaaca aaatcggtcc acgtcccaaa ccctttttat aggagagtct tatgttctgg    1200
cagaagactt cacagactct ttcttaatct ctctctcttt caaccaaacc cctaaacaaa    1260
aaaaaaatac attttctgat ctctctaaaa atctttctcc ttcgttaatc tcgtgatctc    1320 tttcttttc tatatacaag tttgtacaaa aaagcaggct aaaaaaaacc atggacgtgg    1380
gcgtgtcccc ggccaagtct attctcgcca agccggtaat gttcagctct gctatagtgt    1440
gtgccaccct gcttgtttaa taatgcgttc tcttcgtttt tatgatatct tattcttcca    1500
gctcaagctc ctcaccgagg aggacatctc tcagctcaca agagaggact gccgcaagtt    1560
cctgaaggac aaggggatga aaggccttc ctggaacaag tcccaggcca tccagcaagt    1620
gctcagcctc aaggccctt acgagccagg cgacgactcc ggcgctggca ttttcagaaa    1680
gatcctcgtg tcccagccgg tgaacccacc aagggtgacc accacactca tcgagccgtc    1740
caatgagctt gaggcttgcg gcagagtgtc ctacccagag ataatggcg cctgccacag    1800 gatggattct ccaaggtctg ctgagttctc tggcggctcc ggccatttcg tgtctgagaa    1860
ggatggccac aagaccacca tctccccaag atccccagcc gagacatctg agcttgtggg    1920
ccagatgacc atcttctact ccggcaaggt gaacgtgtac gacggcatcc caccagagaa    1980
ggcccgctcc attatgcact cgccgccaa ccccaatcgac ctcccagaga atggcatctt    2040
cgcctccagc cgcatgatct ccaagctcat ctccaaggag aagatgatgg agctgccgca    2100
gaagggcctc gagaaggcta attcctctcg cgactccggc atggagggcc aggctaatag    2160
aaaggtgtcc ctccaacgct accgcgagaa gaggaaggac cgcaagttct ccaaggccaa    2220
gaagtgccca ggcgttgcct cttccagcct cgagatgttc ctcaactgcc agccgagaat    2280
gaaggccgcc tactcccaaa atctcggctg cacaggctcc ccactccatt ctcagtcccc    2340
agagtctcag accaagtccc cgaacctctc cgtggacctt aactccgagg catcggatc    2400 ctaatgaacc cagctttctt gtacaaagtg gtctagtggg taccgcgaat tccccgatc    2460 gttcaaacat ttggcaataa agtttcttaa gattgaatcc tgttgccggt cttgcgatga    2520
ttatcatata atttctgttg aattacgtta agcatgtaat aattaacatg taatgcatga    2580
cgttatttat gagatgggtt tttatgatta gagtcccgca attatacatt taatacgcga    2640
tagaaaacaa aatatagcgc gcaaactagg ataaattatc gcgcgcggtg tcatctatgt    2700
tactagatcg aagcggccgc tctagaacta gt                                 2732
```

<210> SEQ ID NO 51
<211> LENGTH: 2210
<212> TYPE: DNA
<213> ORGANISM: Artificial Sequence
<220> FEATURE:
<223> OTHER INFORMATION: Consensus sequence

<400> SEQUENCE: 51

```
ggtaatgagc cctatctgat gtcagtgggg attgtttaca gtaccgcagc aaacactgac      60
gtatgggtct ggaccatat gttagccacc gctactgcat cagcagtatt gcagagaatt     120
tgcatcagca gtactgcatc agcagtatta cagatggggg tgcacaaagc cgggtcagtt     180
tacccaacta ccttcctcct cttaactata acttatattc aatttatgtc tctcgaaaat     240
agatatgaac atacttttt aaaaaataat actacatatt gtgaatttgt gatccttacc     300
tttacatttg agttatgacg aacaacttta tcgattatat aaaagaaagg atgacttctt     360
```

```
atccaaacaa atcctatagt aatgtctttt taactttcag tgactaacat ataaaccatc      420
aaacgagtcc atattaaagg ataatactac gaagaattgt catcccacat ttttacactg      480
ccactatcag ttaaaactga aaaccagctc accccaagct caccaagaat cttcgagaaa      540
cttataaact ccgccgaaaa atctcggaca aacccgcggc tcacacgcct ccacgcaccc      600 aaacccacc ctagaatatc ctctccttgg ccaccgcgcc gccacatcag cctccccaat       660
ctccccgccc cacgcgcgag cgccaatcgc gagccgcctt tagatttccc aagataagga     720
ctcgatcccc cctcacttcc cgcgctattt aaactcccgc gccatctcca actcccaact     780
cacactcgct cgctcatcgc catctctctc agctctcaca gctcactgca tcaacaagtt     840
tgtacaaaaa agcaggctaa aaaaaaccat ggacgtgggc gtgtccccgg ccaagtctat     900
tctcgccaag ccggtaatgt tcagctctgc tatagtgtgt gccaccctgc ttgtttaata     960
atgcgttctc ttcgtttta  tgatatctta ttcttccagc tcaagctcct caccgaggag    1020
gacatctctc agctcacaag agaggactgc cgcaagttcc tgaaggacaa ggggatgaga    1080
aggccttcct ggaacaagtc ccaggccatc cagcaagtgc tcagcctcaa ggcccttac    1140 gagccaggcg acgactccgg cgctggcatt ttcagaaaga tcctcgtgtc ccagccggtg    1200
aacccaccaa gggtgaccac cacactcatc gagccgtcca atgagcttga ggcttgcggc    1260
agagtgtcct acccgagga  taatggcgcc tgccacagga tggattctcc aaggtctgct    1320
gagttctctg gcggctccgg ccatttcgtg tctgagaagg atggccacaa gaccaccatc    1380
tccccaagat ccccagccga gacatctgag cttgtgggcc agatgaccat cttctactcc    1440
ggcaaggtga acgtgtacga cggcatccca ccagagaagg cccgctccat tatgcacttc    1500
gccgccaacc caatcgacct cccagagaat ggcatcttcg cctccagccg catgatctcc    1560
aagctcatct ccaaggagaa gatgatggag ctgccgcaga agggcctcga aaggctaat    1620 tcctctcgcg actccggcat ggagggccaa gctaatagaa aggtgtccct ccaacgctac    1680
cgcgagaaga ggaaggaccg caagttctcc aaggccaaga agtgcccagg cgttgcctct    1740
tccagcctcg agatgttcct caactgccag ccgagaatga aggccgccta ctcccaaaat    1800
ctcggctgca caggctcccc actccattct cagtccccag agtctcagac caagtccccg    1860
aacctctccg tggaccttaa ctccgagggc atcggatcct aatgaaccca gctttcttgt    1920
acaaagtggt ctagtgggta ccgcgaattt ccccgatcgt tcaaacattt ggcaataaag    1980
tttcttaaga ttgaatcctg ttgccggtct tgcgatgatt atcatataat ttctgttgaa    2040
ttacgttaag catgtaataa ttaacatgta atgcatgacg ttatttatga gatgggtttt    2100
tatgattaga gtcccgcaat tatacattta atacgcgata gaaaacaaaa tatagcgcgc    2160
aaactaggat aaattatcgc gcgcggtgtc atctatgtta ctagatcgaa              2210
```

<210> SEQ ID NO 52
<211> LENGTH: 2968
<212> TYPE: DNA
<213> ORGANISM: Artificial Sequence
<220> FEATURE:
<223> OTHER INFORMATION: Consensus sequence

<400> SEQUENCE: 52

```
aaatgcccaa ataggtgcaa atctcagata gaaatgtttc aaaagtaaaa aaggtcccta      60
tcataaacat aattgatatg taagtgagtt ggaaaaagat aagtacggtg tgagagagac     120
ggggatcaaa ttcctggtgt aataatgtat gtattcacgt ccaataaaaa attggtagca     180
```

```
gtagttgggg ctctgtatat tataccggta aggtagggta ggtagtagaa taattctttt    240
tttgttttta gtttttctg gtccaaaatt tcaaatttca aatttggatc ccttacttgt    300
accaactaat attaatgagt gttgagggta gtagaggtgc aactttacca taatccctct    360
gtttcaggtt ataagacgtt ttgactttaa atttgaccaa gttatgcgc aaatatagta    420
atatttataa tactatatta gtttcattaa ataaataatt gaatatattt tcataataaa    480
tttgtgttga gttcaaaata ttattaattt tttctacaaa cttggtcaaa cttgaagcag    540
tttgactttg accaaagtca acgtcttata acttgaaacg gatggattaa ccttttttt    600
gtgggaacaa gttacaaag tttaataaag cacaatccat cttaatgttt tcaagctgaa    660
tattgtaaaa ttcatggata aaccaggctt ataaatgttt aaccgggaaa atgcgaacgg    720
caaattaata tttttaagtg atggggagta ttaattaagg agtgacaact caactttcaa    780
tatcgtacta aactgtggga tttatttct aaaattttat accctgccaa ttcacgtgtt    840
gtagatcttt ttttttcact aaccgacacc aggtatatca attttattga atatagcagc    900
aaaaagaatg tgttgtactt gtaaacaaaa agcaaactgt acataaaaaa aaatgcactc    960
ctatataatt aagctcataa agatgctttg cttcgtgagg gcccaaggtt ttgatgacct   1020
tttgcttgat ctcgaaatta aaatttaagt actgttaagg gagttcacac caccatcaat   1080
tttcagcctg aagaaacagt taaacaaacg gaccccgatg accagtctac tgctctccac   1140
atactagctg cattattgat cacaaaacaa aacaaaacga aataaaaatc agcagcgaga   1200
gtgtgcagag agagacaaag gtgatctggg cgtggatatc tccccatcca tcctcacccg   1260
cgctgcccat cactcgccgc cgcatactcc atcatgtgga gagaggaaga cgaggaccac   1320
agccagagcc cgggtcgaga tgccaccacg gccacaaccc acgagcccgg cgcgacacca   1380
ccgcgcgcgt gagccagcca caaacgcccg cggataggcg cgccgcacgc ggccaatcct   1440
accacatccc cggcctccgc ggctcgagcg ccgctgccat ccgatccgct gagttttggc   1500
tatttatacg taccgcggga gcctgtgtgc agagcagtgc atctcaagaa gtactcgagc   1560
aaagaaggag agagcttggt gagctgcaga gacaagtttg tacaaaaaag caggctaaaa   1620
aaaccatgg acgtgggcgt gtccccggcc aagtctattc tcgccaagcc ggtaatgttc   1680
agctctgcta tagtgtgtgc caccctgctt gtttaataat gcgttctctt cgttttatg   1740
atatcttatt cttccagctc aagctcctca ccgaggagga catctctcag ctcacaagag   1800
aggactgccg caagttcctg aaggacaagg ggatgagaag gccttcctgg aacaagtccc   1860
aggccatcca gcaagtgctc agcctcaagg ccctttacga gccaggcgac gactccggcg   1920
ctggcatttt cagaaagatc ctcgtgtccc agccggtgaa cccaccaagg gtgaccacca   1980
cactcatcga gccgtccaat gagcttgagg cttgcggcag agtgtcctac ccagaggata   2040
atggcgcctg ccacaggatg gattctccaa ggtctgctga gttctctggc ggctccggcc   2100
atttcgtgtc tgagaaggat ggccacaaga ccaccatctc cccaagatcc ccagccgaga   2160
catctgagct tgtgggccag atgaccatct tctactccgg caaggtgaac gtgtacgacg   2220
gcatcccacc agagaaggcc cgctccatta tgcacttcgc cgccaaccca atcgacctcc   2280
cagagaatgg catcttcgcc tccagccgca tgatctccaa gctcatctcc aaggagaaga   2340
tgatggagct gccgcagaag ggcctcgaga aggctaattc ctctcgcgac tccggcatgg   2400
agggccaggc taatagaaag gtgtccctcc aacgctaccg cgagaagagg aaggaccgca   2460
agttctccaa ggccaagaag tgcccaggcg ttgcctcttc cagccgag atgttcctca   2520
actgccagcc gagaatgaag gccgcctact cccaaaatct cggctgcaca ggctccccac   2580
```

-continued

```
tccattctca gtccccagag tctcagacca agtccccgaa cctctccgtg gaccttaact    2640
ccgagggcat cggatcctaa tgaacccagc tttcttgtac aaagtggtct agtgggtacc    2700
gcgaatttcc ccgatcgttc aaacatttgg caataaagtt tcttaagatt gaatcctgtt    2760
gccggtcttg cgatgattat catataattt ctgttgaatt acgttaagca tgtaataatt    2820
aacatgtaat gcatgacgtt atttatgaga tgggttttta tgattagagt cccgcaatta    2880
tacatttaat acgcgataga aaacaaaata tagcgcgcaa actaggataa attatcgcgc    2940
gcggtgtcat ctatgttact agatcgaa                                      2968
```

<210> SEQ ID NO 53
<211> LENGTH: 161
<212> TYPE: PRT
<213> ORGANISM: Artificial Sequence
<220> FEATURE:
<223> OTHER INFORMATION: Consensus sequence

<400> SEQUENCE: 53

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser

<210> SEQ ID NO 54
<211> LENGTH: 139
<212> TYPE: PRT
<213> ORGANISM: Artificial Sequence
<220> FEATURE:
<223> OTHER INFORMATION: Consensus sequence

<400> SEQUENCE: 54

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

```
Glu Ile Thr Ala Ser Lys Ile Asp Asp Gly Asn Asn Ser Lys Pro Leu
 65                  70                  75                  80

Ser Pro Gly Trp Thr Asp Gln Thr Ala Tyr Asn Ala Phe Gly Ile Thr
                 85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser
    130                 135
```

<210> SEQ ID NO 55
<211> LENGTH: 474
<212> TYPE: PRT
<213> ORGANISM: Artificial Sequence
<220> FEATURE:
<223> OTHER INFORMATION: Consensus sequence

<400> SEQUENCE: 55

```
Met Lys Leu Leu Ser Ser Ile Glu Glu Ala Cys Asn Ile Cys Arg Leu
 1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240

Gln Pro Val Asn Pro Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285
```

```
Ser Gly His Phe Val Ser Glu Lys Asp Gly His Lys Thr Thr Ile Ser
    290                 295                 300

Pro Arg Ser Pro Ala Glu Thr Ser Glu Leu Val Gly Gln Met Thr Ile
305                 310                 315                 320

Phe Tyr Ser Gly Lys Val Asn Val Tyr Asp Gly Ile Pro Pro Glu Lys
                325                 330                 335

Ala Arg Ser Ile Met His Phe Ala Ala Asn Pro Ile Asp Leu Pro Glu
            340                 345                 350

Asn Gly Ile Phe Ala Ser Ser Arg Met Ile Ser Lys Leu Ile Ser Lys
            355                 360                 365

Glu Lys Met Met Glu Leu Pro Gln Lys Gly Leu Glu Lys Ala Asn Ser
    370                 375                 380

Ser Arg Asp Ser Gly Met Glu Gly Gln Ala Asn Arg Lys Val Ser Leu
385                 390                 395                 400

Gln Arg Tyr Arg Glu Lys Arg Lys Asp Arg Lys Phe Ser Lys Ala Lys
                405                 410                 415

Lys Cys Pro Gly Val Ala Ser Ser Ser Leu Glu Met Phe Leu Asn Cys
            420                 425                 430

Gln Pro Arg Met Lys Ala Ala Tyr Ser Gln Asn Leu Gly Cys Thr Gly
            435                 440                 445

Ser Pro Leu His Ser Gln Ser Pro Glu Ser Gln Thr Lys Ser Pro Asn
    450                 455                 460

Leu Ser Val Asp Leu Asn Ser Glu Gly Ile
465                 470

<210> SEQ ID NO 56
<211> LENGTH: 452
<212> TYPE: PRT
<213> ORGANISM: Artificial Sequence
<220> FEATURE:
<223> OTHER INFORMATION: Consensus sequence

<400> SEQUENCE: 56

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
                20                  25                  30

Ser Asn Gly Pro Asn Leu Ile Thr Thr Gln Thr Asn Ser Gln Ala Leu
            35                  40                  45

Ser Gln Pro Ile Ala Ser Ser Asn Val His Asp Asn Phe Met Asn Asn
50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
                100                 105                 110

Phe Asp Asp Glu Asp Thr Pro Pro Asn Pro Lys Lys Glu Gly Gly Ser
            115                 120                 125

Asn Gln Thr Ser Leu Tyr Lys Lys Ala Gly Ser Met Asp Val Gly Val
    130                 135                 140

Ser Pro Ala Lys Ser Ile Leu Ala Lys Pro Leu Lys Leu Leu Thr Glu
145                 150                 155                 160

Glu Asp Ile Ser Gln Leu Thr Arg Glu Asp Cys Arg Lys Phe Leu Lys
                165                 170                 175
```

```
Asp Lys Gly Met Arg Arg Pro Ser Trp Asn Lys Ser Gln Ala Ile Gln
            180                 185                 190

Gln Val Leu Ser Leu Lys Ala Leu Tyr Glu Pro Gly Asp Asp Ser Gly
        195                 200                 205

Ala Gly Ile Phe Arg Lys Ile Leu Val Ser Gln Pro Val Asn Pro Pro
    210                 215                 220

Arg Val Thr Thr Thr Leu Ile Glu Pro Ser Asn Glu Leu Glu Ala Cys
225                 230                 235                 240

Gly Arg Val Ser Tyr Pro Glu Asp Asn Gly Ala Cys His Arg Met Asp
            245                 250                 255

Ser Pro Arg Ser Ala Glu Phe Ser Gly Gly Ser Gly His Phe Val Ser
        260                 265                 270

Glu Lys Asp Gly His Lys Thr Thr Ile Ser Pro Arg Ser Pro Ala Glu
    275                 280                 285

Thr Ser Glu Leu Val Gly Gln Met Thr Ile Phe Tyr Ser Gly Lys Val
290                 295                 300

Asn Val Tyr Asp Gly Ile Pro Pro Glu Lys Ala Arg Ser Ile Met His
305                 310                 315                 320

Phe Ala Ala Asn Pro Ile Asp Leu Pro Glu Asn Gly Ile Phe Ala Ser
            325                 330                 335

Ser Arg Met Ile Ser Lys Leu Ile Ser Lys Glu Lys Met Met Glu Leu
        340                 345                 350

Pro Gln Lys Gly Leu Glu Lys Ala Asn Ser Ser Arg Asp Ser Gly Met
    355                 360                 365

Glu Gly Gln Ala Asn Arg Lys Val Ser Leu Gln Arg Tyr Arg Glu Lys
370                 375                 380

Arg Lys Asp Arg Lys Phe Ser Lys Ala Lys Lys Cys Pro Gly Val Ala
385                 390                 395                 400

Ser Ser Ser Leu Glu Met Phe Leu Asn Cys Gln Pro Arg Met Lys Ala
            405                 410                 415

Ala Tyr Ser Gln Asn Leu Gly Cys Thr Gly Ser Pro Leu His Ser Gln
        420                 425                 430

Ser Pro Glu Ser Gln Thr Lys Ser Pro Asn Leu Ser Val Asp Leu Asn
    435                 440                 445

Ser Glu Gly Ile
    450

<210> SEQ ID NO 57
<211> LENGTH: 391
<212> TYPE: PRT
<213> ORGANISM: Artificial Sequence
<220> FEATURE:
<223> OTHER INFORMATION: Consensus sequence

<400> SEQUENCE: 57

Met Pro Lys Lys Arg Lys Val Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80
```

```
Ser Pro Gly Trp Thr Asp Gln Thr Ala Tyr Asn Ala Phe Gly Ile Thr
                85                  90                  95

Thr Gly Met Phe Asn Thr Thr Met Asp Asp Val Tyr Asn Tyr Leu
           100                 105                 110

Phe Asp Asp Glu Asp Thr Pro Pro Asn Pro Lys Lys Glu Gly Gly Ser
       115                 120                 125

Asn Gln Thr Ser Leu Tyr Lys Lys Ala Gly Ser Tyr Glu Pro Gly Asp
   130                 135                 140

Asp Ser Gly Ala Gly Ile Phe Arg Lys Ile Leu Val Ser Gln Pro Val
145                 150                 155                 160

Asn Pro Pro Arg Val Thr Thr Thr Leu Ile Glu Pro Ser Asn Glu Leu
               165                 170                 175

Glu Ala Cys Gly Arg Val Ser Tyr Pro Glu Asp Asn Gly Ala Cys His
           180                 185                 190

Arg Met Asp Ser Pro Arg Ser Ala Glu Phe Ser Gly Gly Ser Gly His
       195                 200                 205

Phe Val Ser Glu Lys Asp Gly His Lys Thr Thr Ile Ser Pro Arg Ser
   210                 215                 220

Pro Ala Glu Thr Ser Glu Leu Val Gly Gln Met Thr Ile Phe Tyr Ser
225                 230                 235                 240

Gly Lys Val Asn Val Tyr Asp Gly Ile Pro Pro Glu Lys Ala Arg Ser
               245                 250                 255

Ile Met His Phe Ala Ala Asn Pro Ile Asp Leu Pro Glu Asn Gly Ile
           260                 265                 270

Phe Ala Ser Ser Arg Met Ile Ser Lys Leu Ile Ser Lys Glu Lys Met
       275                 280                 285

Met Glu Leu Pro Gln Lys Gly Leu Glu Lys Ala Asn Ser Ser Arg Asp
   290                 295                 300

Ser Gly Met Glu Gly Gln Ala Asn Arg Lys Val Ser Leu Gln Arg Tyr
305                 310                 315                 320

Arg Glu Lys Arg Lys Asp Arg Lys Phe Ser Lys Ala Lys Lys Cys Pro
               325                 330                 335

Gly Val Ala Ser Ser Ser Leu Glu Met Phe Leu Asn Cys Gln Pro Arg
           340                 345                 350

Met Lys Ala Ala Tyr Ser Gln Asn Leu Gly Cys Thr Gly Ser Pro Leu
       355                 360                 365

His Ser Gln Ser Pro Glu Ser Gln Thr Lys Ser Pro Asn Leu Ser Val
   370                 375                 380

Asp Leu Asn Ser Glu Gly Ile
385                 390

<210> SEQ ID NO 58
<211> LENGTH: 427
<212> TYPE: PRT
<213> ORGANISM: Artificial Sequence
<220> FEATURE:
<223> OTHER INFORMATION: Consensus sequence

<400> SEQUENCE: 58

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
               20                  25                  30

Ser Asn Gly Pro Asn Leu Ile Thr Thr Gln Thr Asn Ser Gln Ala Leu
           35                  40                  45
```

```
Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Met Asp Asp Val Tyr Asn Tyr Leu
            100                 105                 110

Phe Asp Asp Glu Asp Thr Pro Pro Asn Pro Lys Lys Glu Gly Gly Ser
                115                 120                 125

Asn Gln Thr Ser Leu Tyr Lys Lys Ala Gly Ser Met Asp Val Gly Val
        130                 135                 140

Ser Pro Ala Lys Ser Ile Leu Ala Lys Pro Leu Lys Leu Leu Thr Glu
145                 150                 155                 160

Glu Asp Ile Ser Gln Leu Thr Arg Glu Asp Cys Arg Lys Phe Leu Lys
                165                 170                 175

Asp Lys Gly Met Arg Arg Pro Ser Trp Asn Lys Ser Gln Ala Ile Gln
            180                 185                 190

Gln Val Leu Ser Leu Lys Ala Leu Tyr Glu Pro Gly Asp Asp Ser Gly
        195                 200                 205

Ala Gly Ile Phe Arg Lys Ile Leu Val Ser Gln Pro Val Asn Pro Pro
    210                 215                 220

Arg Val Thr Thr Thr Leu Ile Glu Pro Ser Asn Glu Leu Glu Ala Cys
225                 230                 235                 240

Gly Arg Val Ser Tyr Pro Glu Asp Asn Gly Ala Cys His Arg Met Asp
                245                 250                 255

Ser Pro Arg Ser Ala Glu Phe Ser Gly Gly Ser Gly His Phe Val Ser
            260                 265                 270

Glu Lys Asp Gly His Lys Thr Thr Ile Ser Pro Arg Ser Pro Ala Glu
        275                 280                 285

Thr Ser Glu Leu Ile Met His Phe Ala Ala Asn Pro Ile Asp Leu Pro
    290                 295                 300

Glu Asn Gly Ile Phe Ala Ser Ser Arg Met Ile Ser Lys Leu Ile Ser
305                 310                 315                 320

Lys Glu Lys Met Met Glu Leu Pro Gln Lys Gly Leu Glu Lys Ala Asn
                325                 330                 335

Ser Ser Arg Asp Ser Gly Met Glu Gly Gln Ala Asn Arg Lys Val Ser
            340                 345                 350

Leu Gln Arg Tyr Arg Glu Lys Arg Lys Asp Arg Lys Phe Ser Lys Ala
        355                 360                 365

Lys Lys Cys Pro Gly Val Ala Ser Ser Ser Leu Glu Met Phe Leu Asn
370                 375                 380

Cys Gln Pro Arg Met Lys Ala Ala Tyr Ser Gln Asn Leu Gly Cys Thr
385                 390                 395                 400

Gly Ser Pro Leu His Ser Gln Ser Pro Glu Ser Gln Thr Lys Ser Pro
                405                 410                 415

Asn Leu Ser Val Asp Leu Asn Ser Glu Gly Ile
                420                 425

<210> SEQ ID NO 59
<211> LENGTH: 427
<212> TYPE: PRT
<213> ORGANISM: Artificial Sequence
<220> FEATURE:
<223> OTHER INFORMATION: Consensus sequence
```

<400> SEQUENCE: 59

```
Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Met Asp Val Gly Val
    130                 135                 140

Ser Pro Ala Lys Ser Ile Leu Ala Lys Pro Leu Lys Leu Leu Thr Glu
145                 150                 155                 160

Glu Asp Ile Ser Gln Leu Thr Arg Glu Asp Cys Arg Lys Phe Leu Lys
                165                 170                 175

Asp Lys Gly Met Arg Arg Pro Ser Trp Asn Lys Ser Gln Ala Ile Gln
            180                 185                 190

Gln Val Leu Ser Leu Lys Ala Leu Tyr Glu Pro Gly Asp Asp Ser Gly
    195                 200                 205

Ala Gly Ile Phe Arg Lys Ile Leu Val Ser Gln Pro Val Asn Pro Pro
    210                 215                 220

Arg Val Thr Thr Thr Leu Ile Glu Pro Ser Asn Glu Leu Glu Ala Cys
225                 230                 235                 240

Gly Arg Val Ser Tyr Pro Glu Asp Asn Gly Ala Cys His Arg Met Asp
                245                 250                 255

Ser Pro Arg Ser Ala Glu Phe Ser Gly Gly Ser Gly His Phe Val Ser
            260                 265                 270

Glu Lys Asp Gly His Lys Thr Thr Ile Ser Pro Arg Ser Pro Ala Glu
    275                 280                 285

Thr Ser Glu Leu Ile Met His Phe Ala Ala Asn Pro Ile Asp Leu Pro
290                 295                 300

Glu Asn Gly Ile Phe Ala Ser Ser Arg Met Ile Ser Lys Leu Ile Ser
305                 310                 315                 320

Lys Glu Lys Met Met Glu Leu Pro Gln Lys Gly Leu Glu Lys Ala Asn
                325                 330                 335

Ser Ser Arg Asp Ser Gly Met Gly Gln Ala Asn Arg Lys Val Ser
            340                 345                 350

Leu Gln Arg Tyr Arg Glu Lys Arg Lys Asp Arg Lys Phe Ser Lys Ala
    355                 360                 365

Lys Lys Cys Pro Gly Val Ala Ser Ser Leu Glu Met Phe Leu Asn
        370                 375                 380

Cys Gln Pro Arg Met Lys Ala Ala Tyr Ser Gln Asn Leu Gly Cys Thr
385                 390                 395                 400

Gly Ser Pro Leu His Ser Gln Ser Pro Glu Ser Gln Thr Lys Ser Pro
```

```
                        405                 410                 415
Asn Leu Ser Val Asp Leu Asn Ser Glu Gly Ile
                420                 425

<210> SEQ ID NO 60
<211> LENGTH: 1131
<212> TYPE: PRT
<213> ORGANISM: Artificial Sequence
<220> FEATURE:
<223> OTHER INFORMATION: Consensus sequence

<400> SEQUENCE: 60

Met Ser Ser Leu Ser Arg Glu Leu Val Phe Leu Ile Leu Gln Phe Leu
1               5                   10                  15

Asp Glu Glu Lys Phe Lys Glu Thr Val His Lys Leu Gln Gln Glu Ser
            20                  25                  30

Gly Phe Phe Phe Asn Met Lys Tyr Phe Glu Asp Glu Val His Asn Gly
        35                  40                  45

Asn Trp Asp Glu Val Lys Tyr Leu Ser Gly Phe Thr Lys Val Asp
    50                  55                  60

Asp Asn Arg Tyr Ser Met Lys Ile Phe Phe Glu Ile Arg Lys Gln Lys
65                  70                  75                  80

Tyr Leu Glu Ala Leu Asp Lys His Asp Arg Pro Lys Ala Val Asp Ile
                85                  90                  95

Leu Val Lys Asp Leu Lys Val Phe Ser Thr Phe Asn Glu Glu Leu Phe
            100                 105                 110

Lys Glu Ile Thr Gln Leu Leu Thr Leu Glu Asn Phe Arg Glu Asn Glu
        115                 120                 125

Gln Leu Ser Lys Tyr Gly Asp Thr Lys Ser Ala Arg Ala Ile Met Leu
    130                 135                 140

Val Glu Leu Lys Lys Leu Ile Glu Ala Asn Pro Leu Phe Arg Asp Lys
145                 150                 155                 160

Leu Gln Phe Pro Thr Leu Arg Asn Ser Arg Leu Arg Thr Leu Ile Asn
                165                 170                 175

Gln Ser Leu Asn Trp Gln His Gln Leu Cys Lys Asn Pro Arg Pro Asn
            180                 185                 190

Pro Asp Ile Lys Thr Leu Phe Val Asp His Ser Cys Gly Pro Pro Asn
        195                 200                 205

Gly Ala Arg Ala Pro Ser Pro Val Asn Asn Pro Leu Leu Gly Gly Ile
    210                 215                 220

Pro Lys Ala Gly Gly Phe Pro Leu Gly Ala His Gly Pro Phe Gln
225                 230                 235                 240

Pro Thr Ala Ser Pro Val Pro Thr Pro Leu Ala Gly Trp Met Ser Ser
                245                 250                 255

Pro Ser Ser Val Pro His Pro Ala Val Ser Ala Gly Ala Ile Ala Leu
            260                 265                 270

Gly Gly Pro Ser Ile Pro Ala Ala Leu Lys His Pro Arg Thr Pro Pro
        275                 280                 285

Thr Asn Ala Ser Leu Asp Tyr Pro Ser Ala Asp Ser Glu His Val Ser
    290                 295                 300

Lys Arg Thr Arg Pro Met Gly Ile Ser Asp Glu Val Asn Leu Gly Val
305                 310                 315                 320

Asn Met Leu Pro Met Ser Phe Ser Gly Gln Ala His Gly His Ser Pro
                325                 330                 335

Ala Phe Lys Ala Pro Asp Asp Leu Pro Lys Thr Val Ala Arg Thr Leu
```

```
              340                 345                 350
Ser Gln Gly Ser Ser Pro Met Ser Met Asp Phe His Pro Ile Lys Gln
            355                 360                 365

Thr Leu Leu Leu Val Gly Thr Asn Val Gly Asp Ile Gly Leu Trp Glu
        370                 375                 380

Val Gly Ser Arg Glu Arg Leu Val Gln Lys Thr Phe Lys Val Trp Asp
385                 390                 395                 400

Leu Ser Lys Cys Ser Met Pro Leu Gln Ala Ala Leu Val Lys Glu Pro
                405                 410                 415

Val Val Ser Val Asn Arg Val Ile Trp Ser Pro Asp Gly Ser Leu Phe
            420                 425                 430

Gly Val Ala Tyr Ser Arg His Ile Val Gln Leu Tyr Ser Tyr His Gly
        435                 440                 445

Gly Glu Asp Met Arg Gln His Leu Glu Ile Asp Ala His Val Gly Gly
    450                 455                 460

Val Asn Asp Ile Ser Phe Ser Thr Pro Asn Lys Gln Leu Cys Val Ile
465                 470                 475                 480

Thr Cys Gly Asp Asp Lys Thr Ile Lys Val Trp Asp Ala Ala Thr Gly
                485                 490                 495

Val Lys Arg His Thr Phe Glu Gly His Glu Ala Pro Val Tyr Ser Val
            500                 505                 510

Cys Pro His Tyr Lys Glu Asn Ile Gln Phe Ile Phe Ser Thr Ala Leu
        515                 520                 525

Asp Gly Lys Ile Lys Ala Trp Leu Tyr Asp Asn Met Gly Ser Arg Val
    530                 535                 540

Asp Tyr Asp Ala Pro Gly Arg Trp Cys Thr Thr Met Ala Tyr Ser Ala
545                 550                 555                 560

Asp Gly Thr Arg Leu Phe Ser Cys Gly Thr Ser Lys Asp Gly Glu Ser
                565                 570                 575

Phe Ile Val Glu Trp Asn Glu Ser Glu Gly Ala Val Lys Arg Thr Tyr
            580                 585                 590

Gln Gly Phe His Lys Arg Ser Leu Gly Val Val Gln Phe Asp Thr Thr
        595                 600                 605

Lys Asn Arg Tyr Leu Ala Ala Gly Asp Asp Phe Ser Ile Lys Phe Trp
    610                 615                 620

Asp Met Asp Ala Val Gln Leu Leu Thr Ala Ile Asp Gly Asp Gly Gly
625                 630                 635                 640

Leu Gln Ala Ser Pro Arg Ile Arg Phe Asn Lys Glu Gly Ser Leu Leu
                645                 650                 655

Ala Val Ser Gly Asn Glu Asn Val Ile Lys Ile Met Ala Asn Ser Asp
            660                 665                 670

Gly Leu Arg Leu Leu His Thr Phe Glu Asn Ile Ser Ser Glu Ser Ser
        675                 680                 685

Lys Pro Ala Ile Asn Ser Ile Ala Ala Ala Ala Ala Ala Ala Ala Thr
    690                 695                 700

Ser Ala Gly His Ala Asp Arg Ser Ala Asn Val Val Ser Ile Gln Gly
705                 710                 715                 720

Met Asn Gly Asp Ser Arg Asn Met Val Asp Val Lys Pro Val Ile Thr
                725                 730                 735

Glu Glu Ser Asn Asp Lys Ser Lys Ile Trp Lys Leu Thr Glu Val Ser
            740                 745                 750

Glu Pro Ser Gln Cys Arg Ser Leu Arg Leu Pro Glu Asn Leu Arg Val
        755                 760                 765
```

Ala Lys Ile Ser Arg Leu Ile Phe Thr Asn Ser Gly Asn Ala Ile Leu
770                 775                 780

Ala Leu Ala Ser Asn Ala Ile His Leu Leu Trp Lys Trp Gln Arg Asn
785                 790                 795                 800

Glu Arg Asn Ala Thr Gly Lys Ala Thr Ala Ser Leu Pro Pro Gln Gln
            805                 810                 815

Trp Gln Pro Ala Ser Gly Ile Leu Met Thr Asn Asp Val Ala Glu Thr
            820                 825                 830

Asn Pro Glu Glu Ala Val Pro Cys Phe Ala Leu Ser Lys Asn Asp Ser
        835                 840                 845

Tyr Val Met Ser Ala Ser Gly Gly Lys Ile Ser Leu Phe Asn Met Met
850                 855                 860

Thr Phe Lys Thr Met Ala Thr Phe Met Pro Pro Pro Ala Ala Thr
865                 870                 875                 880

Phe Leu Ala Phe His Pro Gln Asp Asn Asn Ile Ile Ala Ile Gly Met
                885                 890                 895

Asp Asp Ser Thr Ile Gln Ile Tyr Asn Val Arg Val Asp Glu Val Lys
            900                 905                 910

Ser Lys Leu Lys Gly His Ser Lys Arg Ile Thr Gly Leu Ala Phe Ser
            915                 920                 925

Asn Val Leu Asn Val Leu Val Ser Ser Gly Ala Asp Ala Gln Leu Cys
930                 935                 940

Val Trp Asn Thr Asp Gly Trp Glu Lys Gln Arg Ser Lys Val Leu Pro
945                 950                 955                 960

Leu Pro Gln Gly Arg Pro Asn Ser Ala Pro Ser Asp Thr Arg Val Gln
                965                 970                 975

Phe His Gln Asp Gln Ala His Phe Leu Val Val His Glu Thr Gln Leu
            980                 985                 990

Ala Ile Tyr Glu Thr Thr Lys Leu Glu Cys Met Lys Gln Trp Ala Val
            995                 1000                1005

Arg Glu Ser Leu Ala Pro Ile Thr His Ala Thr Phe Ser Cys Asp
    1010                1015                1020

Ser Gln Leu Val Tyr Ala Ser Phe Met Asp Ala Thr Val Cys Val
    1025                1030                1035

Phe Ser Ser Ala Asn Leu Arg Leu Arg Cys Arg Val Asn Pro Ser
    1040                1045                1050

Ala Tyr Leu Pro Ala Ser Leu Ser Asn Ser Asn Val His Pro Leu
    1055                1060                1065

Val Ile Ala Ala His Pro Gln Glu Pro Asn Met Phe Ala Val Gly
    1070                1075                1080

Leu Ser Asp Gly Gly Val His Ile Phe Glu Pro Leu Glu Ser Glu
    1085                1090                1095

Gly Lys Trp Gly Val Ala Pro Pro Ala Glu Asn Gly Ser Ala Ser
    1100                1105                1110

Gly Ala Pro Thr Ala Pro Ser Val Gly Ala Ser Ala Ser Asp Gln
    1115                1120                1125

Pro Gln Arg
    1130

<210> SEQ ID NO 61
<211> LENGTH: 1292
<212> TYPE: PRT
<213> ORGANISM: Artificial Sequence
<220> FEATURE:

<223> OTHER INFORMATION: Consensus sequence

<400> SEQUENCE: 61

```
Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Glu Glu Ser Ser Asn Lys Gly Gln Arg Gln Leu
        130                 135                 140

Thr Val Ser Ser Arg Ser Asn Gln Thr Ser Leu Tyr Lys Lys Ala Gly
145                 150                 155                 160

Ser Met Ser Ser Leu Ser Arg Glu Leu Val Phe Leu Ile Leu Gln Phe
                165                 170                 175

Leu Asp Glu Glu Lys Phe Lys Glu Thr Val His Lys Leu Glu Gln Glu
                180                 185                 190

Ser Gly Phe Phe Phe Asn Met Lys Tyr Phe Glu Asp Glu Val His Asn
            195                 200                 205

Gly Asn Trp Asp Glu Val Glu Lys Tyr Leu Ser Gly Phe Thr Lys Val
210                 215                 220

Asp Asp Asn Arg Tyr Ser Met Lys Ile Phe Phe Glu Ile Arg Lys Gln
225                 230                 235                 240

Lys Tyr Leu Glu Ala Leu Asp Lys His Asp Arg Pro Lys Ala Val Asp
                245                 250                 255

Ile Leu Val Lys Asp Leu Lys Val Phe Ser Thr Phe Asn Glu Glu Leu
                260                 265                 270

Phe Lys Glu Ile Thr Gln Leu Leu Thr Leu Glu Asn Phe Arg Glu Asn
                275                 280                 285

Glu Gln Leu Ser Lys Tyr Gly Asp Thr Lys Ser Ala Arg Ala Ile Met
290                 295                 300

Leu Val Glu Leu Lys Lys Leu Ile Glu Ala Asn Pro Leu Phe Arg Asp
305                 310                 315                 320

Lys Leu Gln Phe Pro Thr Leu Arg Asn Ser Arg Leu Arg Thr Leu Ile
                325                 330                 335

Asn Gln Ser Leu Asn Trp Gln His Gln Leu Cys Lys Asn Pro Arg Pro
            340                 345                 350

Asn Pro Asp Ile Lys Thr Leu Phe Val Asp His Ser Cys Gly Pro Pro
            355                 360                 365

Asn Gly Ala Arg Ala Pro Ser Pro Val Asn Asn Pro Leu Leu Gly Gly
        370                 375                 380

Ile Pro Lys Ala Gly Gly Phe Pro Pro Leu Gly Ala His Gly Pro Phe
385                 390                 395                 400
```

```
Gln Pro Thr Ala Ser Pro Val Pro Thr Pro Leu Ala Gly Trp Met Ser
                405                 410                 415
Ser Pro Ser Ser Val Pro His Pro Ala Val Ser Ala Gly Ala Ile Ala
            420                 425                 430
Leu Gly Gly Pro Ser Ile Pro Ala Ala Leu Lys His Pro Arg Thr Pro
        435                 440                 445
Pro Thr Asn Ala Ser Leu Asp Tyr Pro Ser Ala Asp Ser Glu His Val
    450                 455                 460
Ser Lys Arg Thr Arg Pro Met Gly Ile Ser Asp Glu Val Asn Leu Gly
465                 470                 475                 480
Val Asn Met Leu Pro Met Ser Phe Ser Gly Gln Ala His Gly His Ser
                485                 490                 495
Pro Ala Phe Lys Ala Pro Asp Asp Leu Pro Lys Thr Val Ala Arg Thr
            500                 505                 510
Leu Ser Gln Gly Ser Ser Pro Met Ser Met Asp Phe His Pro Ile Lys
        515                 520                 525
Gln Thr Leu Leu Leu Val Gly Thr Asn Val Gly Asp Ile Gly Leu Trp
    530                 535                 540
Glu Val Gly Ser Arg Glu Arg Leu Val Gln Lys Thr Phe Lys Val Trp
545                 550                 555                 560
Asp Leu Ser Lys Cys Ser Met Pro Leu Gln Ala Ala Leu Val Lys Glu
                565                 570                 575
Pro Val Val Ser Val Asn Arg Val Ile Trp Ser Pro Asp Gly Ser Leu
            580                 585                 590
Phe Gly Val Ala Tyr Ser Arg His Ile Val Gln Leu Tyr Ser Tyr His
        595                 600                 605
Gly Gly Glu Asp Met Arg Gln His Leu Glu Ile Asp Ala His Val Gly
    610                 615                 620
Gly Val Asn Asp Ile Ser Phe Ser Thr Pro Asn Lys Gln Leu Cys Val
625                 630                 635                 640
Ile Thr Cys Gly Asp Asp Lys Thr Ile Lys Val Trp Asp Ala Ala Thr
                645                 650                 655
Gly Val Lys Arg His Thr Phe Glu Gly His Glu Ala Pro Val Tyr Ser
            660                 665                 670
Val Cys Pro His Tyr Lys Glu Asn Ile Gln Phe Ile Phe Ser Thr Ala
        675                 680                 685
Leu Asp Gly Lys Ile Lys Ala Trp Leu Tyr Asp Asn Met Gly Ser Arg
    690                 695                 700
Val Asp Tyr Asp Ala Pro Gly Arg Trp Cys Thr Thr Met Ala Tyr Ser
705                 710                 715                 720
Ala Asp Gly Thr Arg Leu Phe Ser Cys Gly Thr Ser Lys Asp Gly Glu
                725                 730                 735
Ser Phe Ile Val Glu Trp Asn Glu Ser Glu Gly Ala Val Lys Arg Thr
            740                 745                 750
Tyr Gln Gly Phe His Lys Arg Ser Leu Gly Val Gln Phe Asp Thr
        755                 760                 765
Thr Lys Asn Arg Tyr Leu Ala Ala Gly Asp Asp Phe Ser Ile Lys Phe
    770                 775                 780
Trp Asp Met Asp Ala Val Gln Leu Leu Thr Ala Ile Asp Gly Asp Gly
785                 790                 795                 800
Gly Leu Gln Ala Ser Pro Arg Ile Arg Phe Asn Lys Glu Gly Ser Leu
                805                 810                 815
Leu Ala Val Ser Gly Asn Glu Asn Val Ile Lys Ile Met Ala Asn Ser
```

```
                820                 825                 830
Asp Gly Leu Arg Leu Leu His Thr Phe Glu Asn Ile Ser Ser Glu Ser
            835                 840                 845
Ser Lys Pro Ala Ile Asn Ser Ile Ala Ala Ala Ala Ala Ala Ala Ala
850                 855                 860
Thr Ser Ala Gly His Ala Asp Arg Ser Ala Asn Val Val Ser Ile Gln
865                 870                 875                 880
Gly Met Asn Gly Asp Ser Arg Asn Met Val Asp Val Lys Pro Val Ile
                885                 890                 895
Thr Glu Glu Ser Asn Asp Lys Ser Lys Ile Trp Lys Leu Thr Glu Val
            900                 905                 910
Ser Glu Pro Ser Gln Cys Arg Ser Leu Arg Leu Pro Glu Asn Leu Arg
            915                 920                 925
Val Ala Lys Ile Ser Arg Leu Ile Phe Thr Asn Ser Gly Asn Ala Ile
            930                 935                 940
Leu Ala Leu Ala Ser Asn Ala Ile His Leu Leu Trp Lys Trp Gln Arg
945                 950                 955                 960
Asn Glu Arg Asn Ala Thr Gly Lys Ala Thr Ala Ser Leu Pro Pro Gln
                965                 970                 975
Gln Trp Gln Pro Ala Ser Gly Ile Leu Met Thr Asn Asp Val Ala Glu
            980                 985                 990
Thr Asn Pro Glu Glu Ala Val Pro  Cys Phe Ala Leu Ser  Lys Asn Asp
            995                 1000                1005
Ser Tyr  Val Met Ser Ala Ser  Gly Gly Lys Ile Ser  Leu Phe Asn
   1010                1015                1020
Met Met  Thr Phe Lys Thr Met  Ala Thr Phe Met Pro  Pro Pro Pro
   1025                1030                1035
Ala Ala  Thr Phe Leu Ala Phe  His Pro Gln Asp Asn  Asn Ile Ile
   1040                1045                1050
Ala Ile  Gly Met Asp Asp Ser  Thr Ile Gln Ile Tyr  Asn Val Arg
   1055                1060                1065
Val Asp  Glu Val Lys Ser Lys  Leu Lys Gly His Ser  Lys Arg Ile
   1070                1075                1080
Thr Gly  Leu Ala Phe Ser Asn  Val Leu Asn Val Leu  Val Ser Ser
   1085                1090                1095
Gly Ala  Asp Ala Gln Leu Cys  Val Trp Asn Thr Asp  Gly Trp Glu
   1100                1105                1110
Lys Gln  Arg Ser Lys Val Leu  Pro Leu Pro Gln Gly  Arg Pro Asn
   1115                1120                1125
Ser Ala  Pro Ser Asp Thr Arg  Val Gln Phe His Gln  Asp Gln Ala
   1130                1135                1140
His Phe  Leu Val Val His Glu  Thr Gln Leu Ala Ile  Tyr Glu Thr
   1145                1150                1155
Thr Lys  Leu Glu Cys Met Lys  Gln Trp Ala Val Arg  Glu Ser Leu
   1160                1165                1170
Ala Pro  Ile Thr His Ala Thr  Phe Ser Cys Asp Ser  Gln Leu Val
   1175                1180                1185
Tyr Ala  Ser Phe Met Asp Ala  Thr Val Cys Val Phe  Ser Ser Ala
   1190                1195                1200
Asn Leu  Arg Leu Arg Cys Arg  Val Asn Pro Ser Ala  Tyr Leu Pro
   1205                1210                1215
Ala Ser  Leu Ser Asn Ser Asn  Val His Pro Leu Val  Ile Ala Ala
   1220                1225                1230
```

```
His Pro Gln Glu Pro Asn Met Phe Ala Val Gly Leu Ser Asp Gly
    1235                1240                1245

Gly Val His Ile Phe Glu Pro Leu Glu Ser Glu Gly Lys Trp Gly
    1250                1255                1260

Val Ala Pro Pro Ala Glu Asn Gly Ser Ala Ser Gly Ala Pro Thr
    1265                1270                1275

Ala Pro Ser Val Gly Ala Ser Ala Ser Asp Gln Pro Gln Arg
    1280                1285                1290

<210> SEQ ID NO 62
<211> LENGTH: 425
<212> TYPE: PRT
<213> ORGANISM: Artificial Sequence
<220> FEATURE:
<223> OTHER INFORMATION: Consensus sequence

<400> SEQUENCE: 62

Met Asp Asp Asn Gly Leu Glu Leu Ser Leu Gly Leu Ser Cys Gly
1               5                   10                  15

Gly Ser Thr Gly Lys Ala Lys Gly Asn Asn Asn Asn Ala Gly Ser
            20                  25                  30

Ser Ser Glu Asn Tyr Arg Ala Glu Gly Gly Asp Arg Ser Ala Lys Val
        35                  40                  45

Ile Asp Asp Phe Lys Asn Phe Leu His Pro Thr Ser Gln Arg Pro Ala
    50                  55                  60

Glu Pro Ser Ser Gly Ser Gln Arg Ser Asp Ser Gly Gln Gln Pro Pro
65                  70                  75                  80

Gln Asn Phe Phe Asn Asp Leu Ser Lys Ala Pro Thr Thr Glu Ala Glu
                85                  90                  95

Ala Ser Thr Lys Pro Leu Trp Val Glu Asp Glu Ser Arg Lys Glu Ala
                100                 105                 110

Gly Asn Lys Arg Lys Phe Gly Phe Pro Gly Met Asn Asp Asp Lys Lys
            115                 120                 125

Lys Glu Lys Asp Ser Ser His Val Asp Met His Glu Lys Lys Thr Lys
    130                 135                 140

Ala Ser His Val Ser Thr Ala Thr Asp Glu Gly Ser Thr Ala Glu Asn
145                 150                 155                 160

Glu Asp Val Ala Glu Ser Glu Val Gly Gly Ser Ser Asn His
                165                 170                 175

Ala Lys Glu Val Val Arg Pro Pro Thr Asp Thr Asn Ile Val Asp Asn
            180                 185                 190

Leu Thr Gly Gln Arg Arg Ser Asn His Gly Gly Ser Gly Thr Glu Glu
        195                 200                 205

Phe Thr Met Arg Asn Met Ser Tyr Thr Val Pro Phe Thr Val His Pro
    210                 215                 220

Gln Asn Val Val Thr Ser Met Pro Tyr Ser Leu Pro Thr Lys Glu Ser
225                 230                 235                 240

Gly Gln His Ala Ala Ala Thr Ser Leu Leu Gln Pro Asn Ala Asn Ala
                245                 250                 255

Gly Asn Leu Pro Ile Met Phe Gly Tyr Ser Pro Val Gln Leu Pro Met
            260                 265                 270

Leu Asp Lys Asp Gly Ser Gly Gly Ile Val Ala Leu Ser Gln Ser Pro
        275                 280                 285

Phe Ala Gly Arg Val Pro Ser Asn Ser Ala Thr Ala Lys Gly Glu Gly
    290                 295                 300
```

```
Lys Gln Pro Val Ala Glu Gly Ser Ser Glu Asp Ala Ser Glu Arg
305                 310                 315                 320

Pro Thr Gly Asp Asn Ser Asn Leu Asn Thr Ala Phe Ser Phe Asp Phe
                325                 330                 335

Ser Ala Ile Lys Pro Gly Met Ala Ala Asp Val Lys Phe Gly Gly Ser
                340                 345                 350

Gly Ala Arg Pro Asn Leu Pro Trp Val Ser Thr Thr Gly Ser Gly Pro
                355                 360                 365

His Gly Arg Thr Ile Ser Gly Val Thr Tyr Arg Tyr Asn Ala Asn Gln
                370                 375                 380

Ile Lys Ile Val Cys Ala Cys His Gly Ser His Met Ser Pro Glu Glu
385                 390                 395                 400

Phe Val Arg His Ala Ser Glu Glu Tyr Val Ser Pro Glu Ser Ser Met
                405                 410                 415

Gly Met Thr Ala Ala Ser Ala His Thr
                420                 425

<210> SEQ ID NO 63
<211> LENGTH: 564
<212> TYPE: PRT
<213> ORGANISM: Artificial Sequence
<220> FEATURE:
<223> OTHER INFORMATION: Consensus sequence

<400> SEQUENCE: 63

Met Pro Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
                20                  25                  30

Ser Asn Gly Pro Asn Leu Ile Thr Thr Gln Thr Asn Ser Gln Ala Leu
                35                  40                  45

Ser Gln Pro Ile Ala Ser Ser Asn Val His Asp Asn Phe Met Asn Asn
                50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
                100                 105                 110

Phe Asp Asp Glu Asp Thr Pro Pro Asn Pro Lys Lys Glu Gly Gly Ser
                115                 120                 125

Asn Gln Thr Ser Leu Tyr Lys Lys Ala Gly Ser Met Asp Asp Asp Asn
130                 135                 140

Gly Leu Glu Leu Ser Leu Gly Leu Ser Cys Gly Gly Ser Thr Gly Lys
145                 150                 155                 160

Ala Lys Gly Asn Asn Asn Asn Ala Gly Ser Ser Ser Glu Asn Tyr
                165                 170                 175

Arg Ala Glu Gly Gly Asp Arg Ser Ala Lys Val Ile Asp Asp Phe Lys
                180                 185                 190

Asn Phe Leu His Pro Thr Ser Gln Arg Pro Ala Glu Pro Ser Ser Gly
                195                 200                 205

Ser Gln Arg Ser Asp Ser Gly Gln Gln Pro Gln Asn Phe Phe Asn
                210                 215                 220

Asp Leu Ser Lys Ala Pro Thr Thr Glu Ala Glu Ala Ser Thr Lys Pro
225                 230                 235                 240
```

-continued

```
Leu Trp Val Glu Asp Glu Ser Arg Lys Glu Ala Gly Asn Lys Arg Lys
            245                 250                 255

Phe Gly Phe Pro Gly Met Asn Asp Asp Lys Lys Lys Glu Lys Asp Ser
        260                 265                 270

Ser His Val Asp Met His Glu Lys Lys Thr Lys Ala Ser His Val Ser
    275                 280                 285

Thr Ala Thr Asp Glu Gly Ser Thr Ala Glu Asn Glu Asp Val Ala Glu
290                 295                 300

Ser Glu Val Gly Gly Gly Ser Ser Asn His Ala Lys Glu Val Val
305                 310                 315                 320

Arg Pro Pro Thr Asp Thr Asn Ile Val Asp Asn Leu Thr Gly Gln Arg
                325                 330                 335

Arg Ser Asn His Gly Gly Ser Gly Thr Glu Glu Phe Thr Met Arg Asn
            340                 345                 350

Met Ser Tyr Thr Val Pro Phe Thr Val His Pro Gln Asn Val Val Thr
        355                 360                 365

Ser Met Pro Tyr Ser Leu Pro Thr Lys Glu Ser Gly Gln His Ala Ala
    370                 375                 380

Ala Thr Ser Leu Leu Gln Pro Asn Ala Asn Ala Gly Asn Leu Pro Ile
385                 390                 395                 400

Met Phe Gly Tyr Ser Pro Val Gln Leu Pro Met Leu Asp Lys Asp Gly
                405                 410                 415

Ser Gly Gly Ile Val Ala Leu Ser Gln Ser Pro Phe Ala Gly Arg Val
            420                 425                 430

Pro Ser Asn Ser Ala Thr Ala Lys Gly Glu Gly Lys Gln Pro Val Ala
        435                 440                 445

Glu Glu Gly Ser Ser Glu Asp Ala Ser Glu Arg Pro Thr Gly Asp Asn
    450                 455                 460

Ser Asn Leu Asn Thr Ala Phe Ser Phe Asp Phe Ser Ala Ile Lys Pro
465                 470                 475                 480

Gly Met Ala Ala Asp Val Lys Phe Gly Gly Ser Gly Ala Arg Pro Asn
                485                 490                 495

Leu Pro Trp Val Ser Thr Thr Gly Ser Gly Pro His Gly Arg Thr Ile
            500                 505                 510

Ser Gly Val Thr Tyr Arg Tyr Asn Ala Asn Gln Ile Lys Ile Val Cys
        515                 520                 525

Ala Cys His Gly Ser His Met Ser Pro Glu Glu Phe Val Arg His Ala
    530                 535                 540

Ser Glu Glu Tyr Val Ser Pro Glu Ser Ser Met Gly Met Thr Ala Ala
545                 550                 555                 560

Ser Ala His Thr

<210> SEQ ID NO 64
<211> LENGTH: 475
<212> TYPE: PRT
<213> ORGANISM: Artificial Sequence
<220> FEATURE:
<223> OTHER INFORMATION: Consensus sequence

<400> SEQUENCE: 64

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30
```

```
Ser Asn Gly Pro Asn Leu Ile Thr Thr Gln Thr Asn Ser Gln Ala Leu
         35                  40                  45

Ser Gln Pro Ile Ala Ser Ser Asn Val His Asp Asn Phe Met Asn Asn
 50                  55                  60

Glu Ile Thr Ala Ser Lys Ile Asp Asp Gly Asn Asn Ser Lys Pro Leu
 65                  70                  75                  80

Ser Pro Gly Trp Thr Asp Gln Thr Ala Tyr Asn Ala Phe Gly Ile Thr
                 85                  90                  95

Thr Gly Met Phe Asn Thr Thr Thr Met Asp Asp Val Tyr Asn Tyr Leu
             100                 105                 110

Phe Asp Asp Glu Asp Thr Pro Pro Asn Pro Lys Lys Glu Gly Gly Ser
         115                 120                 125

Asn Gln Thr Ser Leu Tyr Lys Lys Ala Gly Ser Met Thr Ser Asp Gly
     130                 135                 140

Ala Thr Ser Thr Ser Ala Ala Ala Ala Ala Ala Ala Ala Ala Ala Ala
145                 150                 155                 160

Arg Arg Lys Pro Ser Trp Arg Glu Arg Glu Asn Asn Arg Arg Arg Glu
                 165                 170                 175

Arg Arg Arg Arg Ala Val Ala Ala Lys Ile Tyr Thr Gly Leu Arg Ala
             180                 185                 190

Gln Gly Asp Tyr Asn Leu Pro Lys His Cys Asp Asn Asn Glu Val Leu
         195                 200                 205

Lys Ala Leu Cys Val Glu Ala Gly Trp Val Val Glu Glu Asp Gly Thr
     210                 215                 220

Thr Tyr Arg Lys Gly Cys Lys Pro Leu Pro Gly Glu Ile Ala Gly Thr
225                 230                 235                 240

Ser Ser Arg Val Thr Pro Tyr Ser Ser Gln Asn Gln Ser Pro Leu Ser
                 245                 250                 255

Ser Ala Phe Gln Ser Pro Ile Pro Ser Tyr Gln Val Ser Pro Ser Ser
             260                 265                 270

Ser Ser Phe Pro Ser Pro Ser Arg Gly Glu Pro Asn Asn Asn Met Ser
         275                 280                 285

Ser Thr Phe Phe Pro Phe Leu Arg Asn Gly Gly Ile Pro Ser Ser Leu
     290                 295                 300

Pro Ser Leu Arg Ile Ser Asn Ser Cys Pro Val Thr Pro Pro Val Ser
305                 310                 315                 320

Ser Pro Thr Ser Lys Asn Pro Lys Pro Leu Pro Asn Trp Glu Ser Ile
                 325                 330                 335

Ala Lys Gln Ser Met Ala Ile Ala Lys Gln Ser Met Ala Ser Phe Asn
             340                 345                 350

Tyr Pro Phe Tyr Ala Val Ser Ala Pro Ala Ser Pro Thr His Arg His
         355                 360                 365

Gln Phe His Thr Pro Ala Thr Ile Pro Glu Cys Asp Glu Ser Asp Ser
     370                 375                 380

Ser Thr Val Asp Ser Gly His Trp Ile Ser Phe Gln Lys Phe Ala Gln
385                 390                 395                 400

Gln Gln Pro Phe Ser Ala Ser Met Val Pro Thr Ser Pro Thr Phe Asn
                 405                 410                 415

Leu Val Lys Pro Ala Pro Gln Gln Met Ser Pro Asn Thr Ala Ala Phe
             420                 425                 430

Gln Glu Ile Gly Gln Ser Ser Glu Phe Lys Phe Glu Asn Ser Gln Val
         435                 440                 445

Lys Pro Trp Glu Gly Glu Arg Ile His Asp Val Gly Met Glu Asp Leu
```

```
            450                 455                 460
Glu Leu Thr Leu Gly Asn Gly Lys Ala Arg Gly
465                 470                 475

<210> SEQ ID NO 65
<211> LENGTH: 475
<212> TYPE: PRT
<213> ORGANISM: Artificial Sequence
<220> FEATURE:
<223> OTHER INFORMATION: Consensus sequence

<400> SEQUENCE: 65

Met Pro Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
                20                  25                  30

Ser Asn Gly Pro Asn Leu Ile Thr Thr Gln Thr Asn Ser Gln Ala Leu
            35                  40                  45

Ser Gln Pro Ile Ala Ser Ser Asn Val His Asp Asn Phe Met Asn Asn
        50                  55                  60

Glu Ile Thr Ala Ser Lys Ile Asp Asp Gly Asn Asn Ser Lys Pro Leu
65              70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
                100                 105                 110

Phe Asp Asp Glu Asp Thr Pro Pro Asn Pro Lys Lys Glu Gly Gly Ser
            115                 120                 125

Asn Gln Thr Ser Leu Tyr Lys Lys Ala Gly Ser Met Thr Ser Asp Gly
        130                 135                 140

Ala Thr Ser Thr Ser Ala Ala Ala Ala Ala Ala Ala Ala Ala Ala Ala
145                 150                 155                 160

Arg Arg Lys Pro Ser Trp Arg Glu Arg Glu Asn Asn Arg Arg Arg Glu
                165                 170                 175

Arg Arg Arg Arg Ala Val Ala Ala Lys Ile Tyr Thr Gly Leu Arg Ala
            180                 185                 190

Gln Gly Asp Tyr Asn Leu Pro Lys His Cys Asp Asn Asn Glu Val Leu
        195                 200                 205

Lys Ala Leu Cys Val Glu Ala Gly Trp Val Val Glu Glu Asp Gly Thr
    210                 215                 220

Thr Tyr Arg Lys Gly Cys Lys Pro Leu Pro Gly Glu Ile Ala Gly Thr
225                 230                 235                 240

Ser Ser Arg Val Thr Pro Tyr Ser Ser Gln Asn Gln Ser Pro Leu Ser
                245                 250                 255

Ser Ala Phe Gln Ser Pro Ile Pro Ser Tyr Gln Val Ser Pro Ser Ser
            260                 265                 270

Ser Ser Phe Pro Ser Pro Ser Arg Gly Glu Pro Asn Asn Asn Met Ser
        275                 280                 285

Ser Thr Phe Phe Pro Phe Leu Arg Asn Gly Gly Ile Pro Ser Ser Leu
    290                 295                 300

Pro Ser Leu Arg Ile Ser Asn Ser Cys Pro Val Thr Pro Val Ser
305                 310                 315                 320

Ser Pro Thr Ser Lys Asn Pro Lys Pro Leu Pro Asn Trp Glu Ser Ile
                325                 330                 335

Ala Lys Gln Ser Met Ala Ile Ala Lys Gln Ser Met Ala Ser Phe Asn
```

```
            340                 345                 350
Tyr Pro Phe Tyr Ala Val Ser Ala Pro Ala Ser Pro Thr His Arg His
        355                 360                 365

Gln Phe His Thr Pro Ala Thr Ile Pro Glu Cys Asp Glu Ser Asp Ser
    370                 375                 380

Ser Thr Val Asp Ser Gly His Trp Ile Ser Phe Gln Lys Phe Ala Gln
385                 390                 395                 400

Gln Gln Pro Phe Ser Ala Ser Met Val Pro Thr Ser Pro Thr Phe Asn
            405                 410                 415

Leu Val Lys Pro Ala Pro Gln Gln Met Ser Pro Asn Thr Ala Ala Phe
        420                 425                 430

Gln Glu Ile Gly Gln Ser Ser Glu Phe Lys Phe Glu Asn Ser Gln Val
    435                 440                 445

Lys Pro Trp Glu Gly Glu Arg Ile His Asp Val Gly Met Glu Asp Leu
    450                 455                 460

Glu Leu Thr Leu Gly Asn Gly Lys Ala Arg Gly
465                 470                 475

<210> SEQ ID NO 66
<211> LENGTH: 726
<212> TYPE: PRT
<213> ORGANISM: Artificial Sequence
<220> FEATURE:
<223> OTHER INFORMATION: Consensus sequence

<400> SEQUENCE: 66

Met Pro Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Met Lys Arg Asp His
    130                 135                 140

His Gln Phe Gln Gly Arg Leu Ser Asn His Gly Thr Ser Ser Ser Ser
145                 150                 155                 160

Ser Ser Ile Ser Lys Asp Lys Met Met Met Val Lys Lys Glu Glu Asp
                165                 170                 175

Gly Gly Gly Asn Met Asp Asp Glu Leu Leu Ala Val Leu Gly Tyr Lys
            180                 185                 190

Val Arg Ser Ser Glu Met Ala Glu Val Ala Leu Lys Leu Glu Gln Leu
        195                 200                 205

Glu Thr Met Met Ser Asn Val Gln Glu Asp Gly Leu Ser His Leu Ala
    210                 215                 220

Thr Asp Thr Val His Tyr Asn Pro Ser Glu Leu Tyr Ser Trp Leu Asp
```

```
                225                 230                 235                 240
Asn Met Leu Ser Glu Leu Asn Pro Pro Leu Pro Ala Ser Ser Asn
                    245                 250                 255
Gly Leu Asp Pro Val Leu Pro Ser Pro Glu Ile Cys Gly Phe Pro Ala
                    260                 265                 270
Ser Asp Tyr Asp Leu Lys Val Ile Pro Gly Asn Ala Ile Tyr Gln Phe
                    275                 280                 285
Pro Ala Ile Asp Ser Ser Ser Ser Asn Asn Gln Asn Lys Arg Leu
                290                 295                 300
Lys Ser Cys Ser Ser Pro Asp Ser Met Val Thr Ser Thr Ser Thr Gly
305                 310                 315                 320
Thr Gln Ile Gly Gly Val Ile Gly Thr Thr Val Thr Thr Thr Thr
                    325                 330                 335
Thr Thr Thr Ala Ala Gly Glu Ser Thr Arg Ser Val Ile Leu Val Asp
                340                 345                 350
Ser Gln Glu Asn Gly Val Arg Leu Val His Ala Leu Met Ala Cys Ala
                355                 360                 365
Glu Ala Ile Gln Gln Asn Asn Leu Thr Leu Ala Glu Ala Leu Val Lys
            370                 375                 380
Gln Ile Gly Cys Leu Ala Val Ser Gln Ala Gly Ala Met Arg Lys Val
385                 390                 395                 400
Ala Thr Tyr Phe Ala Glu Ala Leu Ala Arg Arg Ile Tyr Arg Leu Ser
                    405                 410                 415
Pro Pro Gln Asn Gln Ile Asp His Cys Leu Ser Asp Thr Leu Gln Met
                420                 425                 430
His Phe Tyr Glu Thr Cys Pro Tyr Leu Lys Phe Ala His Phe Thr Ala
            435                 440                 445
Asn Gln Ala Ile Leu Glu Ala Phe Glu Gly Lys Lys Arg Val His Val
                450                 455                 460
Ile Asp Phe Ser Met Asn Gln Gly Leu Gln Trp Pro Ala Leu Met Gln
465                 470                 475                 480
Ala Leu Ala Leu Arg Glu Gly Gly Pro Pro Thr Phe Arg Leu Thr Gly
                    485                 490                 495
Ile Gly Pro Pro Ala Pro Asp Asn Ser Asp His Leu His Glu Val Gly
                500                 505                 510
Cys Lys Leu Ala Gln Leu Ala Glu Ala Ile His Val Glu Phe Glu Tyr
                515                 520                 525
Arg Gly Phe Val Ala Asn Ser Leu Ala Asp Leu Asp Ala Ser Met Leu
            530                 535                 540
Glu Leu Arg Pro Ser Asp Thr Glu Ala Val Ala Val Asn Ser Val Phe
545                 550                 555                 560
Glu Leu His Lys Leu Leu Gly Arg Pro Gly Gly Ile Glu Lys Val Leu
                    565                 570                 575
Gly Val Val Lys Gln Ile Lys Pro Val Ile Phe Thr Val Val Glu Gln
                580                 585                 590
Glu Ser Asn His Asn Gly Pro Val Phe Leu Asp Arg Phe Thr Glu Ser
            595                 600                 605
Leu His Tyr Tyr Ser Thr Leu Phe Asp Ser Leu Glu Gly Val Pro Asn
                610                 615                 620
Ser Gln Asp Lys Val Met Ser Glu Val Tyr Leu Gly Lys Gln Ile Cys
625                 630                 635                 640
Asn Leu Val Ala Cys Glu Gly Pro Asp Arg Val Glu Arg His Glu Thr
                    645                 650                 655
```

```
Leu Ser Gln Trp Gly Asn Arg Phe Gly Ser Ser Gly Leu Ala Pro Ala
            660                 665                 670

His Leu Gly Ser Asn Ala Phe Lys Gln Ala Ser Met Leu Leu Ser Val
            675                 680                 685

Phe Asn Ser Gly Gln Gly Tyr Arg Val Glu Glu Ser Asn Gly Cys Leu
            690                 695                 700

Met Leu Gly Trp His Thr Arg Pro Leu Ile Thr Thr Ser Ala Trp Lys
705                 710                 715                 720

Leu Ser Thr Ala Ala Tyr
                725

<210> SEQ ID NO 67
<211> LENGTH: 413
<212> TYPE: PRT
<213> ORGANISM: Artificial Sequence
<220> FEATURE:
<223> OTHER INFORMATION: Consensus sequence

<400> SEQUENCE: 67

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asn Leu Asn Met Ile
65              70                  75                  80

Leu Lys Met Asp Ser Leu Gln Asp Ile Lys Ala Leu Leu Thr Gly Leu
            85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
        130                 135                 140

Thr Val Ser Ser Arg Ser Asn Gln Thr Ser Leu Tyr Lys Lys Ala Gly
145                 150                 155                 160

Ser Tyr Glu Pro Gly Asp Asp Ser Gly Ala Gly Ile Phe Arg Lys Ile
                165                 170                 175

Leu Val Ser Gln Pro Val Asn Pro Pro Arg Val Thr Thr Thr Leu Ile
            180                 185                 190

Glu Pro Ser Asn Glu Leu Glu Ala Cys Gly Arg Val Ser Tyr Pro Glu
            195                 200                 205

Asp Asn Gly Ala Cys His Arg Met Asp Ser Pro Arg Ser Ala Glu Phe
        210                 215                 220

Ser Gly Gly Ser Gly His Phe Val Ser Glu Lys Asp Gly His Lys Thr
225                 230                 235                 240

Thr Ile Ser Pro Arg Ser Pro Ala Glu Thr Ser Glu Leu Val Gly Gln
                245                 250                 255

Met Thr Ile Phe Tyr Ser Gly Lys Val Asn Val Tyr Asp Gly Ile Pro
            260                 265                 270

Pro Glu Lys Ala Arg Ser Ile Met His Phe Ala Ala Asn Pro Ile Asp
            275                 280                 285
```

```
Leu Pro Glu Asn Gly Ile Phe Ala Ser Ser Arg Met Ile Ser Lys Leu
    290                 295                 300

Ile Ser Lys Glu Lys Met Met Glu Leu Pro Gln Lys Gly Leu Glu Lys
305                 310                 315                 320

Ala Asn Ser Ser Arg Asp Ser Gly Met Glu Gly Gln Ala Asn Arg Lys
                325                 330                 335

Val Ser Leu Gln Arg Tyr Arg Glu Lys Arg Lys Asp Arg Lys Phe Ser
            340                 345                 350

Lys Ala Lys Lys Cys Pro Gly Val Ala Ser Ser Leu Glu Met Phe
        355                 360                 365

Leu Asn Cys Gln Pro Arg Met Lys Ala Ala Tyr Ser Gln Asn Leu Gly
    370                 375                 380

Cys Thr Gly Ser Pro Leu His Ser Gln Ser Pro Glu Ser Gln Thr Lys
385                 390                 395                 400

Ser Pro Asn Leu Ser Val Asp Leu Asn Ser Glu Gly Ile
                405                 410

<210> SEQ ID NO 68
<211> LENGTH: 449
<212> TYPE: PRT
<213> ORGANISM: Artificial Sequence
<220> FEATURE:
<223> OTHER INFORMATION: Consensus sequence

<400> SEQUENCE: 68

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240
```

```
Gln Pro Val Asn Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285

Ser Gly His Phe Val Ser Glu Lys Asp Gly His Lys Thr Thr Ile Ser
    290                 295                 300

Pro Arg Ser Pro Ala Glu Thr Ser Glu Leu Ile Met His Phe Ala Ala
305                 310                 315                 320

Asn Pro Ile Asp Leu Pro Glu Asn Gly Ile Phe Ala Ser Ser Arg Met
                325                 330                 335

Ile Ser Lys Leu Ile Ser Lys Glu Lys Met Met Glu Leu Pro Gln Lys
            340                 345                 350

Gly Leu Glu Lys Ala Asn Ser Ser Arg Asp Ser Gly Met Glu Gly Gln
        355                 360                 365

Ala Asn Arg Lys Val Ser Leu Gln Arg Tyr Arg Glu Lys Arg Lys Asp
    370                 375                 380

Arg Lys Phe Ser Lys Ala Lys Lys Cys Pro Gly Val Ala Ser Ser Ser
385                 390                 395                 400

Leu Glu Met Phe Leu Asn Cys Gln Pro Arg Met Lys Ala Ala Tyr Ser
                405                 410                 415

Gln Asn Leu Gly Cys Thr Gly Ser Pro Leu His Ser Gln Ser Pro Glu
            420                 425                 430

Ser Gln Thr Lys Ser Pro Asn Leu Ser Val Asp Leu Asn Ser Glu Gly
        435                 440                 445

Ile

<210> SEQ ID NO 69
<211> LENGTH: 390
<212> TYPE: PRT
<213> ORGANISM: Artificial Sequence
<220> FEATURE:
<223> OTHER INFORMATION: Consensus sequence

<400> SEQUENCE: 69

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140
```

```
Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240

Gln Pro Val Asn Pro Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285

Ser Gly His Phe Val Ser Glu Lys Asp Gly His Lys Thr Thr Ile Ser
    290                 295                 300

Pro Arg Ser Pro Ala Glu Thr Ser Glu Leu Val Gly Gln Met Thr Ile
305                 310                 315                 320

Phe Tyr Ser Gly Lys Val Asn Val Tyr Asp Gly Ile Pro Pro Glu Lys
                325                 330                 335

Ala Arg Ser Ile Met His Phe Ala Ala Asn Pro Ile Asp Leu Pro Glu
            340                 345                 350

Asn Gly Ile Phe Ala Ser Ser Arg Met Ile Ser Lys Leu Ile Ser Lys
        355                 360                 365

Glu Lys Met Met Glu Leu Pro Gln Lys Gly Leu Glu Lys Ala Asn Ser
    370                 375                 380

Ser Arg Asp Ser Gly Met
385                 390

<210> SEQ ID NO 70
<211> LENGTH: 142
<212> TYPE: PRT
<213> ORGANISM: Artificial Sequence
<220> FEATURE:
<223> OTHER INFORMATION: Consensus sequence

<400> SEQUENCE: 70

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Asp Asp Gly Asn
            35                  40                  45

Tyr Lys Thr Arg Ala Glu Val Lys Phe Glu Gly Asp Thr Leu Val Asn
        50                  55                  60

Arg Ile Glu Leu Lys Gly Ile Asp Phe Lys Glu Asp Gly Asn Ile Leu
65                  70                  75                  80

Gly His Lys Leu Glu Tyr Asn Tyr Asn Ser His Asn Val Tyr Ile Thr
                85                  90                  95

Ala Asp Lys Gln Lys Asn Gly Ile Lys Ala Asn Phe Lys Ile Arg His
            100                 105                 110
```

```
Asn Ile Glu Glu Gln Lys Leu Ile Ser Glu Glu Asp Leu Gly Pro Arg
            115                 120                 125

Pro Thr Ser Gly Ser Val Asp Leu Glu Gly Thr Ala Pro Gly
        130                 135                 140

<210> SEQ ID NO 71
<211> LENGTH: 111
<212> TYPE: PRT
<213> ORGANISM: Artificial Sequence
<220> FEATURE:
<223> OTHER INFORMATION: Consensus sequence

<400> SEQUENCE: 71

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly
            100                 105                 110

<210> SEQ ID NO 72
<211> LENGTH: 568
<212> TYPE: PRT
<213> ORGANISM: Artificial Sequence
<220> FEATURE:
<223> OTHER INFORMATION: Consensus sequence

<400> SEQUENCE: 72

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Asp Asp Gly Asn
        35                  40                  45

Tyr Lys Thr Arg Ala Glu Val Lys Phe Glu Gly Asp Thr Leu Val Asn
    50                  55                  60

Arg Ile Glu Leu Lys Gly Ile Asp Phe Lys Glu Asp Gly Asn Ile Leu
65                  70                  75                  80

Gly His Lys Leu Glu Tyr Asn Tyr Asn Ser His Asn Val Tyr Ile Thr
                85                  90                  95

Ala Asp Lys Gln Lys Asn Gly Ile Lys Ala Asn Phe Lys Ile Arg His
            100                 105                 110

Asn Ile Glu Glu Gln Lys Leu Ile Ser Glu Glu Asp Leu Gly Pro Arg
            115                 120                 125

Pro Thr Ser Gly Ser Val Asp Leu Glu Gly Thr Ala Pro Gly Ser Met
        130                 135                 140

Asp Asp Asp Asn Gly Leu Glu Leu Ser Leu Gly Leu Ser Cys Gly Gly
145                 150                 155                 160

Ser Thr Gly Lys Ala Lys Gly Asn Asn Asn Asn Asn Ala Gly Ser Ser
                165                 170                 175
```

Ser Glu Asn Tyr Arg Ala Glu Gly Gly Asp Arg Ser Ala Lys Val Ile
            180                 185                 190

Asp Asp Phe Lys Asn Phe Leu His Pro Thr Ser Gln Arg Pro Ala Glu
        195                 200                 205

Pro Ser Ser Gly Ser Gln Arg Ser Asp Ser Gly Gln Gln Pro Pro Gln
        210                 215                 220

Asn Phe Phe Asn Asp Leu Ser Lys Ala Pro Thr Thr Glu Ala Glu Ala
225                 230                 235                 240

Ser Thr Lys Pro Leu Trp Val Glu Asp Glu Ser Arg Lys Glu Ala Gly
                245                 250                 255

Asn Lys Arg Lys Phe Gly Phe Pro Gly Met Asn Asp Lys Lys Lys
        260                 265                 270

Glu Lys Asp Ser Ser His Val Asp Met His Glu Lys Lys Thr Lys Ala
        275                 280                 285

Ser His Val Ser Thr Ala Thr Asp Glu Gly Ser Thr Ala Glu Asn Glu
        290                 295                 300

Asp Val Ala Glu Ser Glu Val Gly Gly Gly Ser Ser Asn His Ala
305                 310                 315                 320

Lys Glu Val Val Arg Pro Pro Thr Asp Thr Asn Ile Val Asp Asn Leu
                325                 330                 335

Thr Gly Gln Arg Arg Ser Asn His Gly Gly Ser Gly Thr Glu Glu Phe
                340                 345                 350

Thr Met Arg Asn Met Ser Tyr Thr Val Pro Phe Thr Val His Pro Gln
                355                 360                 365

Asn Val Val Thr Ser Met Pro Tyr Ser Leu Pro Thr Lys Glu Ser Gly
        370                 375                 380

Gln His Ala Ala Ala Thr Ser Leu Leu Gln Pro Asn Ala Asn Ala Gly
385                 390                 395                 400

Asn Leu Pro Ile Met Phe Gly Tyr Ser Pro Val Gln Leu Pro Met Leu
                405                 410                 415

Asp Lys Asp Gly Ser Gly Gly Ile Val Ala Leu Ser Gln Ser Pro Phe
                420                 425                 430

Ala Gly Arg Val Pro Ser Asn Ser Ala Thr Ala Lys Gly Glu Gly Lys
        435                 440                 445

Gln Pro Val Ala Glu Glu Gly Ser Ser Glu Asp Ala Ser Glu Arg Pro
        450                 455                 460

Thr Gly Asp Asn Ser Asn Leu Asn Thr Ala Phe Ser Phe Asp Phe Ser
465                 470                 475                 480

Ala Ile Lys Pro Gly Met Ala Ala Asp Val Lys Phe Gly Gly Ser Gly
                485                 490                 495

Ala Arg Pro Asn Leu Pro Trp Val Ser Thr Thr Gly Ser Gly Pro His
        500                 505                 510

Gly Arg Thr Ile Ser Gly Val Thr Tyr Arg Tyr Asn Ala Asn Gln Ile
        515                 520                 525

Lys Ile Val Cys Ala Cys His Gly Ser His Met Ser Pro Glu Glu Phe
        530                 535                 540

Val Arg His Ala Ser Glu Glu Tyr Val Ser Pro Glu Ser Ser Met Gly
545                 550                 555                 560

Met Thr Ala Ala Ser Ala His Thr
                565

<210> SEQ ID NO 73
<211> LENGTH: 479

```
<212> TYPE: PRT
<213> ORGANISM: Artificial Sequence
<220> FEATURE:
<223> OTHER INFORMATION: Consensus sequence

<400> SEQUENCE: 73
```

| | | | | | | | | | | | | | | |
|---|---|---|---|---|---|---|---|---|---|---|---|---|---|---|
| Met | Val | Ser | Lys | Gly | Glu | Glu | Leu | Phe | Thr | Gly | Val | Val | Pro | Ile | Leu |
| 1 | | | | 5 | | | | | 10 | | | | | 15 |

Val Glu Leu Asp Gly Asp Val Asn Gly His Lys Phe Ser Val Ser Gly
              20                  25                  30

Glu Gly Glu Gly Asp Ala Thr Tyr Gly Lys Leu Thr Asp Asp Gly Asn
          35                  40                  45

Tyr Lys Thr Arg Ala Glu Val Lys Phe Glu Gly Asp Thr Leu Val Asn
 50                  55                  60

Arg Ile Glu Leu Lys Gly Ile Asp Phe Lys Glu Asp Gly Asn Ile Leu
 65                  70                  75                  80

Gly His Lys Leu Glu Tyr Asn Tyr Asn Ser His Asn Val Tyr Ile Thr
              85                  90                  95

Ala Asp Lys Gln Lys Asn Gly Ile Lys Ala Asn Phe Lys Ile Arg His
              100                 105                 110

Asn Ile Glu Glu Gln Lys Leu Ile Ser Glu Glu Asp Leu Gly Pro Arg
              115                 120                 125

Pro Thr Ser Gly Ser Val Asp Leu Glu Gly Thr Ala Pro Gly Ser Met
 130                 135                 140

Thr Ser Asp Gly Ala Thr Ser Thr Ser Ala Ala Ala Ala Ala Ala Ala
 145                 150                 155                 160

Ala Ala Ala Arg Arg Lys Pro Ser Trp Arg Glu Arg Glu Asn Asn
              165                 170                 175

Arg Arg Arg Glu Arg Arg Arg Ala Val Ala Ala Lys Ile Tyr Thr
              180                 185                 190

Gly Leu Arg Ala Gln Gly Asp Tyr Asn Leu Pro Lys His Cys Asp Asn
              195                 200                 205

Asn Glu Val Leu Lys Ala Leu Cys Val Glu Ala Gly Trp Val Val Glu
              210                 215                 220

Glu Asp Gly Thr Thr Tyr Arg Lys Gly Cys Lys Pro Leu Pro Gly Glu
 225                 230                 235                 240

Ile Ala Gly Thr Ser Ser Arg Val Thr Pro Tyr Ser Ser Gln Asn Gln
              245                 250                 255

Ser Pro Leu Ser Ser Ala Phe Gln Ser Pro Ile Pro Ser Tyr Gln Val
              260                 265                 270

Ser Pro Ser Ser Ser Ser Phe Pro Ser Pro Ser Arg Gly Glu Pro Asn
              275                 280                 285

Asn Asn Met Ser Ser Thr Phe Phe Pro Phe Leu Arg Asn Gly Gly Ile
              290                 295                 300

Pro Ser Ser Leu Pro Ser Leu Arg Ile Ser Asn Ser Cys Pro Val Thr
 305                 310                 315                 320

Pro Pro Val Ser Ser Pro Thr Ser Lys Asn Pro Lys Pro Leu Pro Asn
              325                 330                 335

Trp Glu Ser Ile Ala Lys Gln Ser Met Ala Ile Ala Lys Gln Ser Met
              340                 345                 350

Ala Ser Phe Asn Tyr Pro Phe Tyr Ala Val Ser Ala Pro Ala Ser Pro
              355                 360                 365

Thr His Arg His Gln Phe His Thr Pro Ala Thr Ile Pro Glu Cys Asp
              370                 375                 380

```
Glu Ser Asp Ser Ser Thr Val Asp Ser Gly His Trp Ile Ser Phe Gln
385                 390                 395                 400

Lys Phe Ala Gln Gln Gln Pro Phe Ser Ala Ser Met Val Pro Thr Ser
            405                 410                 415

Pro Thr Phe Asn Leu Val Lys Pro Ala Pro Gln Gln Met Ser Pro Asn
            420                 425                 430

Thr Ala Ala Phe Gln Glu Ile Gly Gln Ser Ser Glu Phe Lys Phe Glu
            435                 440                 445

Asn Ser Gln Val Lys Pro Trp Glu Gly Glu Arg Ile His Asp Val Gly
            450                 455                 460

Met Glu Asp Leu Glu Leu Thr Leu Gly Asn Gly Lys Ala Arg Gly
465                 470                 475

<210> SEQ ID NO 74
<211> LENGTH: 425
<212> TYPE: PRT
<213> ORGANISM: Artificial Sequence
<220> FEATURE:
<223> OTHER INFORMATION: Consensus sequence

<400> SEQUENCE: 74

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
            35                  40                  45

Ser Tyr Gln Ser Ala Leu Ser Lys Asp Pro Asn Glu Lys Arg Asp His
50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Val Gly Val Ser Pro Ala Lys Ser Ile Leu Ala Lys Pro Leu
            115                 120                 125

Lys Leu Leu Thr Glu Glu Asp Ile Ser Gln Leu Thr Arg Glu Asp Cys
130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                165                 170                 175

Gly Asp Asp Ser Gly Ala Gly Ile Phe Arg Lys Ile Leu Val Ser Gln
            180                 185                 190

Pro Val Asn Pro Pro Arg Val Thr Thr Thr Leu Ile Glu Pro Ser Asn
            195                 200                 205

Glu Leu Glu Ala Cys Gly Arg Val Ser Tyr Pro Glu Asp Asn Gly Ala
            210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                245                 250                 255

Arg Ser Pro Ala Glu Thr Ser Glu Leu Val Gly Gln Met Thr Ile Phe
            260                 265                 270
```

```
Tyr Ser Gly Lys Val Asn Val Tyr Asp Gly Ile Pro Pro Glu Lys Ala
            275                 280                 285

Arg Ser Ile Met His Phe Ala Ala Asn Pro Ile Asp Leu Pro Glu Asn
            290                 295                 300

Gly Ile Phe Ala Ser Ser Arg Met Ile Ser Lys Leu Ile Ser Lys Glu
305                 310                 315                 320

Lys Met Met Glu Leu Pro Gln Lys Gly Leu Glu Lys Ala Asn Ser Ser
                325                 330                 335

Arg Asp Ser Gly Met Glu Gly Gln Ala Asn Arg Lys Val Ser Leu Gln
            340                 345                 350

Arg Tyr Arg Glu Lys Arg Lys Asp Arg Lys Phe Ser Lys Ala Lys Lys
            355                 360                 365

Cys Pro Gly Val Ala Ser Ser Ser Leu Glu Met Phe Leu Asn Cys Gln
            370                 375                 380

Pro Arg Met Lys Ala Ala Tyr Ser Gln Asn Leu Gly Cys Thr Gly Ser
385                 390                 395                 400

Pro Leu His Ser Gln Ser Pro Glu Ser Gln Thr Lys Ser Pro Asn Leu
                405                 410                 415

Ser Val Asp Leu Asn Ser Glu Gly Ile
            420                 425

<210> SEQ ID NO 75
<211> LENGTH: 425
<212> TYPE: PRT
<213> ORGANISM: Artificial Sequence
<220> FEATURE:
<223> OTHER INFORMATION: Consensus sequence

<400> SEQUENCE: 75

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Val Gly Val Ser Pro Ala Lys Ser Ile Leu Ala Lys Pro Leu
            115                 120                 125

Lys Leu Leu Thr Glu Glu Asp Ile Ser Gln Leu Thr Arg Glu Asp Cys
130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                165                 170                 175

Gly Asp Asp Ser Gly Ala Gly Ile Phe Arg Lys Ile Leu Val Ser Gln
            180                 185                 190

Pro Val Asn Pro Pro Arg Val Thr Thr Leu Ile Glu Pro Ser Asn
        195                 200                 205
```

```
Glu Leu Glu Ala Cys Gly Arg Val Ser Tyr Pro Glu Asp Asn Gly Ala
    210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                245                 250                 255

Arg Ser Pro Ala Glu Thr Ser Glu Leu Val Gly Gln Met Thr Ile Phe
                260                 265                 270

Tyr Ser Gly Lys Val Asn Val Tyr Asp Gly Ile Pro Pro Glu Lys Ala
                275                 280                 285

Arg Ser Ile Met His Phe Ala Ala Asn Pro Ile Asp Leu Pro Glu Asn
290                 295                 300

Gly Ile Phe Ala Ser Ser Arg Met Ile Ser Lys Leu Ile Ser Lys Glu
305                 310                 315                 320

Lys Met Met Glu Leu Pro Gln Lys Gly Leu Glu Lys Ala Asn Ser Ser
                325                 330                 335

Arg Asp Ser Gly Met Glu Gly Gln Ala Asn Arg Lys Val Ser Leu Gln
                340                 345                 350

Arg Tyr Arg Glu Lys Arg Lys Asp Arg Lys Phe Ser Lys Ala Lys Lys
                355                 360                 365

Cys Pro Gly Val Ala Ser Ser Leu Glu Met Phe Leu Asn Cys Gln
370                 375                 380

Pro Arg Met Lys Ala Ala Tyr Ser Gln Asn Leu Gly Cys Thr Gly Ser
385                 390                 395                 400

Pro Leu His Ser Gln Ser Pro Glu Ser Gln Thr Lys Ser Pro Asn Leu
                405                 410                 415

Ser Val Asp Leu Asn Ser Glu Gly Ile
                420                 425

<210> SEQ ID NO 76
<211> LENGTH: 448
<212> TYPE: PRT
<213> ORGANISM: Artificial Sequence
<220> FEATURE:
<223> OTHER INFORMATION: Consensus sequence

<400> SEQUENCE: 76

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
                20                  25                  30

Thr Pro Ile Gly Asp Gly Pro Val Leu Leu Pro Asp Asn His Tyr Leu
                35                  40                  45

Ser Tyr Gln Ser Ala Leu Ser Lys Asp Pro Asn Glu Lys Arg Asp His
            50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
                100                 105                 110

Met Thr Ser Asp Gly Ala Thr Ser Thr Ser Ala Ala Ala Ala Ala Ala
            115                 120                 125

Ala Ala Ala Ala Ala Arg Arg Lys Pro Ser Trp Arg Glu Arg Glu Asn
130                 135                 140
```

Asn Arg Arg Arg Glu Arg Arg Arg Ala Val Ala Ala Lys Ile Tyr
145                 150                 155                 160

Thr Gly Leu Arg Ala Gln Gly Asp Tyr Asn Leu Pro Lys His Cys Asp
            165                 170                 175

Asn Asn Glu Val Leu Lys Ala Leu Cys Val Glu Ala Gly Trp Val Val
            180                 185                 190

Glu Glu Asp Gly Thr Thr Tyr Arg Lys Gly Cys Lys Pro Leu Pro Gly
            195                 200                 205

Glu Ile Ala Gly Thr Ser Ser Arg Val Thr Pro Tyr Ser Ser Gln Asn
        210                 215                 220

Gln Ser Pro Leu Ser Ser Ala Phe Gln Ser Pro Ile Pro Ser Tyr Gln
225                 230                 235                 240

Val Ser Pro Ser Ser Ser Phe Pro Ser Pro Ser Arg Gly Glu Pro
            245                 250                 255

Asn Asn Asn Met Ser Ser Thr Phe Phe Pro Phe Leu Arg Asn Gly Gly
            260                 265                 270

Ile Pro Ser Ser Leu Pro Ser Leu Arg Ile Ser Asn Ser Cys Pro Val
        275                 280                 285

Thr Pro Pro Val Ser Ser Pro Thr Ser Lys Asn Pro Lys Pro Leu Pro
        290                 295                 300

Asn Trp Glu Ser Ile Ala Lys Gln Ser Met Ala Ile Ala Lys Gln Ser
305                 310                 315                 320

Met Ala Ser Phe Asn Tyr Pro Phe Tyr Ala Val Ser Ala Pro Ala Ser
                325                 330                 335

Pro Thr His Arg His Gln Phe Thr Pro Ala Thr Ile Pro Glu Cys
            340                 345                 350

Asp Glu Ser Asp Ser Ser Thr Val Asp Ser Gly His Trp Ile Ser Phe
            355                 360                 365

Gln Lys Phe Ala Gln Gln Pro Phe Ser Ala Ser Met Val Pro Thr
            370                 375                 380

Ser Pro Thr Phe Asn Leu Val Lys Pro Ala Pro Gln Gln Met Ser Pro
385                 390                 395                 400

Asn Thr Ala Ala Phe Gln Glu Ile Gly Gln Ser Ser Glu Phe Lys Phe
                405                 410                 415

Glu Asn Ser Gln Val Lys Pro Trp Glu Gly Glu Arg Ile His Asp Val
            420                 425                 430

Gly Met Glu Asp Leu Glu Leu Thr Leu Gly Asn Gly Lys Ala Arg Gly
            435                 440                 445

<210> SEQ ID NO 77
<211> LENGTH: 364
<212> TYPE: PRT
<213> ORGANISM: Artificial Sequence
<220> FEATURE:
<223> OTHER INFORMATION: Consensus sequence

<400> SEQUENCE: 77

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

```
Met Val Leu Leu Glu Phe Val Thr Ala Ala Gly Ile Thr Leu Gly Met
 65                  70                  75                  80

Asp Glu Leu Tyr Lys Tyr Pro Tyr Asp Val Pro Asp Tyr Ala Gly Pro
                 85                  90                  95

Arg Pro Thr Ser Gly Ser Val Asp Leu Glu Gly Thr Ala Pro Gly Ser
            100                 105                 110

Tyr Glu Pro Gly Asp Asp Ser Gly Ala Gly Ile Phe Arg Lys Ile Leu
        115                 120                 125

Val Ser Gln Pro Val Asn Pro Arg Val Thr Thr Thr Leu Ile Glu
130                 135                 140

Pro Ser Asn Glu Leu Glu Ala Cys Gly Arg Val Ser Tyr Pro Glu Asp
145                 150                 155                 160

Asn Gly Ala Cys His Arg Met Asp Ser Pro Arg Ser Ala Glu Phe Ser
                165                 170                 175

Gly Gly Ser Gly His Phe Val Ser Glu Lys Asp Gly His Lys Thr Thr
            180                 185                 190

Ile Ser Pro Arg Ser Pro Ala Glu Thr Ser Glu Leu Val Gly Gln Met
        195                 200                 205

Thr Ile Phe Tyr Ser Gly Lys Val Asn Val Tyr Asp Gly Ile Pro Pro
    210                 215                 220

Glu Lys Ala Arg Ser Ile Met His Phe Ala Ala Asn Pro Ile Asp Leu
225                 230                 235                 240

Pro Glu Asn Gly Ile Phe Ala Ser Ser Arg Met Ile Ser Lys Leu Ile
                245                 250                 255

Ser Lys Glu Lys Met Met Glu Leu Pro Gln Lys Gly Leu Glu Lys Ala
            260                 265                 270

Asn Ser Ser Arg Asp Ser Gly Met Glu Gly Gln Ala Asn Arg Lys Val
        275                 280                 285

Ser Leu Gln Arg Tyr Arg Glu Lys Arg Lys Asp Arg Lys Phe Ser Lys
    290                 295                 300

Ala Lys Lys Cys Pro Gly Val Ala Ser Ser Leu Glu Met Phe Leu
305                 310                 315                 320

Asn Cys Gln Pro Arg Met Lys Ala Ala Tyr Ser Gln Asn Leu Gly Cys
                325                 330                 335

Thr Gly Ser Pro Leu His Ser Gln Ser Pro Glu Ser Gln Thr Lys Ser
            340                 345                 350

Pro Asn Leu Ser Val Asp Leu Asn Ser Glu Gly Ile
        355                 360

<210> SEQ ID NO 78
<211> LENGTH: 400
<212> TYPE: PRT
<213> ORGANISM: Artificial Sequence
<220> FEATURE:
<223> OTHER INFORMATION: Consensus sequence

<400> SEQUENCE: 78

Met Asp Lys Gln Lys Asn Gly Ile Lys Ala Asn Phe Lys Ile Arg His
  1               5                  10                  15

Asn Ile Glu Asp Gly Gly Val Gln Leu Ala Asp His Tyr Gln Gln Asn
             20                  25                  30

Thr Pro Ile Gly Asp Gly Pro Val Leu Leu Pro Asp Asn His Tyr Leu
         35                  40                  45

Ser Tyr Gln Ser Ala Leu Ser Lys Asp Pro Asn Glu Lys Arg Asp His
     50                  55                  60
```

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Val Gly Val Ser Pro Ala Lys Ser Ile Leu Ala Lys Pro Leu
        115                 120                 125

Lys Leu Leu Thr Glu Glu Asp Ile Ser Gln Leu Thr Arg Glu Asp Cys
130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                165                 170                 175

Gly Asp Asp Ser Gly Ala Gly Ile Phe Arg Lys Ile Leu Val Ser Gln
            180                 185                 190

Pro Val Asn Pro Pro Arg Val Thr Thr Leu Ile Glu Pro Ser Asn
        195                 200                 205

Glu Leu Glu Ala Cys Gly Arg Val Ser Tyr Pro Glu Asp Asn Gly Ala
210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                245                 250                 255

Arg Ser Pro Ala Glu Thr Ser Glu Leu Ile Met His Phe Ala Ala Asn
            260                 265                 270

Pro Ile Asp Leu Pro Glu Asn Gly Ile Phe Ala Ser Ser Arg Met Ile
        275                 280                 285

Ser Lys Leu Ile Ser Lys Glu Lys Met Met Glu Leu Pro Gln Lys Gly
290                 295                 300

Leu Glu Lys Ala Asn Ser Ser Arg Asp Ser Gly Met Glu Gly Gln Ala
305                 310                 315                 320

Asn Arg Lys Val Ser Leu Gln Arg Tyr Arg Glu Lys Arg Lys Asp Arg
                325                 330                 335

Lys Phe Ser Lys Ala Lys Lys Cys Pro Gly Val Ala Ser Ser Ser Leu
            340                 345                 350

Glu Met Phe Leu Asn Cys Gln Pro Arg Met Lys Ala Ala Tyr Ser Gln
        355                 360                 365

Asn Leu Gly Cys Thr Gly Ser Pro Leu His Ser Gln Ser Pro Glu Ser
370                 375                 380

Gln Thr Lys Ser Pro Asn Leu Ser Val Asp Leu Asn Ser Glu Gly Ile
385                 390                 395                 400

<210> SEQ ID NO 79
<211> LENGTH: 341
<212> TYPE: PRT
<213> ORGANISM: Artificial Sequence
<220> FEATURE:
<223> OTHER INFORMATION: Consensus sequence

<400> SEQUENCE: 79

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
                20                  25                  30

```
Thr Pro Ile Gly Asp Gly Pro Val Leu Leu Pro Asp Asn His Tyr Leu
             35                  40                  45

Ser Tyr Gln Ser Ala Leu Ser Lys Asp Pro Asn Glu Lys Arg Asp His
 50                  55                  60

Met Val Leu Leu Glu Phe Val Thr Ala Ala Gly Ile Thr Leu Gly Met
 65                  70                  75                  80

Asp Glu Leu Tyr Lys Tyr Pro Tyr Asp Val Pro Asp Tyr Ala Gly Pro
                 85                  90                  95

Arg Pro Thr Ser Gly Ser Val Asp Leu Glu Gly Thr Ala Pro Gly Ser
             100                 105                 110

Met Asp Val Gly Val Ser Pro Ala Lys Ser Ile Leu Ala Lys Pro Leu
         115                 120                 125

Lys Leu Leu Thr Glu Glu Asp Ile Ser Gln Leu Thr Arg Glu Asp Cys
130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                 165                 170                 175

Gly Asp Asp Ser Gly Ala Gly Ile Phe Arg Lys Ile Leu Val Ser Gln
             180                 185                 190

Pro Val Asn Pro Pro Arg Val Thr Thr Thr Leu Ile Glu Pro Ser Asn
         195                 200                 205

Glu Leu Glu Ala Cys Gly Arg Val Ser Tyr Pro Glu Asp Asn Gly Ala
210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                 245                 250                 255

Arg Ser Pro Ala Glu Thr Ser Glu Leu Val Gly Gln Met Thr Ile Phe
             260                 265                 270

Tyr Ser Gly Lys Val Asn Val Tyr Asp Gly Ile Pro Pro Glu Lys Ala
         275                 280                 285

Arg Ser Ile Met His Phe Ala Ala Asn Pro Ile Asp Leu Pro Glu Asn
290                 295                 300

Gly Ile Phe Ala Ser Ser Arg Met Ile Ser Lys Leu Ile Ser Lys Glu
305                 310                 315                 320

Lys Met Met Glu Leu Pro Gln Lys Gly Leu Glu Lys Ala Asn Ser Ser
                 325                 330                 335

Arg Asp Ser Gly Met
             340

<210> SEQ ID NO 80
<211> LENGTH: 942
<212> TYPE: DNA
<213> ORGANISM: Arabidopsis thaliana

<400> SEQUENCE: 80
atggatgtcg gagtttcacc ggcgaagtct atacttgcga aacctctgaa gctactcact       60
gaagaggaca tttctcagct cactcgcgaa gactgccgca aattcctcaa agacaaagga      120
atgcgaagac cgtcgtggaa caaatctcag gcgatccagc aagtttttatc tcttaaagct      180 ctctatgagc ctggagacga ttccggcgcc ggtatcttcc gcaagatcct cgtttctcag      240
ccagtaaatc cgcctcgcgt cacaacaacg ttgattgagc aagcaacga gctgaaagct      300 tgtggccggg tttcttatcc ggaagataac ggcgcgtgcc atagaatgga ttctccaaga      360
```

```
tcagctgagt tttccggtgg gtctggtcac tttgtatccg agaaagatgg ccacaagacg    420
actatttctc ccagaagccc agctgaaaca agtgagctcg ttgggcaaat gacgatattc    480
tatagtggaa aagtgaatgt gtatgatgga ataccacctg aaaaggcccg gtcaatcatg    540
cactttgcag ccaatccaat tgatttgcct gaaaacggta ttttgcttc cagtagaatg    600 atttcaaagc tcataagtaa agagaagatg atggaacttc cccaaaaagg ccttgagaag    660
gcgaattctt ctcgtgattc tggtatgagg ggccaggcga acagaaaggt atctttgcaa    720
agatatcgtg aaaagcggaa agacagaaaa ttctcaaagg ccaaaaagtg tccaggagtt    780
gcgtcctcta gcttggagat gtttctgaat tgtcagccac ggatgaaagc tgcatattcg    840
caaaacctag gctgcaccgg atctccactg catagccagt cacctgaaag ccagacaaaa    900
agtcccaatc tttcagttga tctaaacagt gaaggcattt aa                      942
```

```
<210> SEQ ID NO 81
<211> LENGTH: 950
<212> TYPE: DNA
<213> ORGANISM: Arabidopsis thaliana

<400> SEQUENCE: 81
agggatatgg atgtaggagt tactacggcg aagtctatac ttgagaagcc tctgaagctt     60
ctcactgaag aagacatttc tcagcttact cgcgaagatt gccgcaaatt cctcaaagag    120
aaaggaatgc gcaggcctttc gtggaataaa tctcaggcga tccagcaagt tttatctctt    180
aaagctctct atgaacctgg agatgattcc ggcgccggaa tcctccgcaa gatccttgtt    240
tctcagccgc caaatccgcc tcgcgttaca acaacgttga ttgagccaag gaacgagctc    300
gaagcttgtg aaggattcc tttacaggaa gatgatggtg cgtgccatag aagggattct    360
ccaagatcag ctgagtttc tggtagttct ggtcagtttg ttgcggataa agatagccac    420
aagactgttt ctgtttcccc cagaagccca gctgaaacaa atgcggtggt tgggcaaatg    480
acgatatttt atagtggcaa agtgaatgta tatgatggag taccacctga aaaggcccgg    540
tctatcatgc attttgcagc caatccaatt gatttgcctg aaaatggtat ttttgcttct    600
agtagaatga tttcgaaacc catgagtaaa gagaagatgt ggagcttcc ccaatatgga    660 cttgaaaagg cacctgcttc tcgtgattct gatgttgagg gtcaggcgaa cagaaaagta    720
tcgttgcaaa gatatcttga aaagcggaaa gacagaagat tttctaagac caagaaggct    780
ccaggagttg cgtcctctag cttggagatg tttctgaatc gtcagccacg gatgaacgct    840
gcatattcac aaaaccttag tggcacaggg cattgcgagt cacctgaaaa tcaaacaaaa    900
agtcccaata tctcagttga tctaaacagt gatctaaaca gcgaagataa                950
```

```
<210> SEQ ID NO 82
<211> LENGTH: 1128
<212> TYPE: DNA
<213> ORGANISM: Populus trichocarpa

<400> SEQUENCE: 82
atgcagccgg agagacagt tttccggtca gctctggaca aaccccctaca ccagctaaca     60 gaagatgata tttctcaggt cactcgcgaa gattgccgcc gttacctcaa agaaaaaggt    120
atgagaaggc cgtcgtggaa caaatcgcag gcaatacagc aagtgatttc actcaaaaca    180
ctcctggaag cgacgccgga gactgaatct ccaaggcgac gactctacat tccccgccct    240
cctcctcatc ctcctgataa tactcctcgt gtgcgtttct ctgccgtccc tccaaattcc    300
```

```
tctgtttcag agagggagc aagtgctgaa acgccgatct cggtgccagc cgaggagcca      360
gttccgtgcc ggcaacacga tcctccaaat cccgatgatc ctgccgatcc tctgcctcct     420
gtccatgccg ccgtcaccga gaatgcttcg gtttcaccaa gaactacagg catggcagaa     480
gaatcagcag gacagatgac aatttttttac tgtgggaagg taaacgtcta tgatgatgta    540
ccgggagaca aggcgcaagc aataatgcat cttgctgcaa gcccatttgc tccacctcag     600
gatgcttctt cagatgtaat tcctacatta aggcctttac aatgccagtt agacactcca     660
ggtgtcaaag ctgctccaaa ttcaattgtg gcgaactttc caaccctgcc aacagtgaaa     720
ggggcagata gtggtcagct ctctctgggaa gaaagcaaca tagctcgtga agacaaccta    780
gaaggctcta caagcagaaa agcatcctta caaagatatt ttgagaagaa gaaagacagg     840
ttcaagaaca agagaaaggt ggcagtgcct tctgctagct tggacgtctt cttaagccat     900
ctggttggag atcaaatctc aaatgatcat tggaacctaa atgatgcctg ctctccttcc     960
caacccaggc ctccccaaac gcctaaccgg tgcaactctg ttgacaatgt agcaaaaaat    1020
ggcatcctca aagctgacct taacaacaaa ggtgatgcag atttatcttg ttgtcttgac    1080
tttagttcca agcagattaa tgcgtggtgc ttatgcttgg gatgttga                 1128
```

<210> SEQ ID NO 83
<211> LENGTH: 2114
<212> TYPE: DNA
<213> ORGANISM: Picea abies

<400> SEQUENCE: 83

```
atgcgaggag gaggaggcgc ggacagactc cccgctagag ctaacctcga gaaacccttg      60
gaagatctca gccatgaaga cattatgcag ctcaccaggg aagactgccg gcgatacttg     120
atagaaaaag gtagcttcca aaatcttttg ctttctcctc aaataacgct ttgctctgag     180
taaatatatg aatataaatg aatgtaatct agtaatcgag ccctaagcgc gacatttaaa     240
gtatttgtaa aggtctgcgg ctgttttggc tttgtctacg gagacaaaaa tcttttttcc     300
gttgggttga gctcagaatc aatggcggtt cttctcgtgg atttgatttt gtttcgtttg     360
gcttgacttt tgccagtatt tacgccctgc cttgtcctaa aatgcttttta cagaaaaaat    420 taaatcctct aaattttctt taaacctttc cagtgttaac ctctgaacat tgccaataaa     480
agcgtatagg aaaattttca attaaagctt tatataccgt aaggccatgt agaatctttt     540 aattttttgcc gtttcagaaa acggtttaaa gggataaatt tcttagaagc tcttaaaata    600
gaaaatagag cttgaaatac cactgatcca atgccagaat tgtatataat ttgacttcag     660 accttaaaata ctgcttattc ggacggacat ttgctcagaa atcgttttaa tatttatgca    720
taacagattt taaattttctt tgtaggcatg cgacggcctt cgtggaacaa gtctcaggcg    780
attcagcagg tactctcgtt gaagaaattg tttgaatccg ggccgaacga tgaaaagagg     840
tcggcggcaa caaatcggcc gaatccggat gaaaacttaa atgaaaagag gtcggcggca    900
acaaatcggc cgaatccgga tgaaaactta aggaagctg cgtccgtttc tttgctttac     960
ggttcacagc ctgaaagtcc ttcggtaggc tttttctttt aaacaatgtc gtctaatcga    1020
gcttaaacct gcagaaacgc tggcattgtc tttaatttgg ctaggtattt caaagttgaa    1080
catttctgtc tccattgtaa tgtttgttca ggttgtcttc gccagtaaag actcagacac    1140
ttttaatttg gagtggttgg cgaagacaga gttgccagta ttagcaagcc aaccccgaca    1200
catagcacag cagaatgttt tcttaagctc tttatctgct cagcaatccg gagctcagct    1260
caccattttt tactcgggaa atgttaatgt ctacgacgat gtgcctgcag aaaaggtatc    1320
```

```
tacagattta cagttcgatt ctcgtaaaga tgtgcttaaa atttccaatg atataggctt    1380
aaaattctca agatctatat ttgcaggcac aagaaataat gctgttggcc gggagcggaa    1440
attatcctcc gtcgtcgacg tgtcagtcca cacgaaatac acaacaaaac gcagtacgtg    1500
cggcgtatcc atcaaatcct acgaatacgc cgttcattca cggagtaggg ccgcctcttg    1560
caactgtggc gagctcttcc gtcatgagca gtccaataca taaaggtatc gtccattgta    1620
tcccaatgcg gaatgaaacg aaactaaaaa attgacccaa atttatcaaa atttgggcgt    1680
ccgaacataa tttggttgtt tccgatgcag agagtccgat tacaagaaaa gcatcgctgc    1740
aaagatttct ggagaaaaga aaggacaggt acagatagaa aaggttttac tccattatca    1800
tgagattcgt ggttaaaaat gcaatgaatg caattaaata tttttgattg caggagtcgt    1860
ggcaagttgg gggctcccac tatatcgaaa aagcctctgc tgatgggtat gtttatgcat    1920
ccctccattg ttcatcgtca gtattggact gatacggcca agaggaaatc cggaaaaccg    1980
gacatacctg cttctatttc tccgacccgg cctcctcaca cgccgcgtcg gacttcgtcg    2040
gacgaacaac ttagtgcacg ccatgctcgt ggtgatataa gtgcgcaggg ggggtcgcta    2100
cataattcca acta                                                    2114

<210> SEQ ID NO 84
<211> LENGTH: 1098
<212> TYPE: DNA
<213> ORGANISM: Gossypium raimondii

<400> SEQUENCE: 84
atggaggctg gggtaacgac gacggcgact acaacagcgt cgttcagttc gatacttgat      60
aaacccctca gccaactaac cgaagaagac atttctcaac tcactcgcga agactgtcgc     120
aaattcctca agaaaaaagg aatgcgtagg ccgtcatgga acaaatcgca ggcgatccag     180
caagtgattt cgttcaaggc gttgttggaa agcaacgaag attccggcgc cggagctcgc     240
cggaaaatcc ttgtttgtcc accaccgtca cattttcctc cgcaaaatgc ggtagcttca     300
aattctggtg agtcagtaaa agaagcagtc tttggagaag aagaaagcct gtacggccaa     360
aaagatcttt ctttgaaagc tgctccggtg gtgcagatga attgtcaggg cggtgacacg     420
gatgacaaga ctcttttcgcc tagtttaggc tctccacggg agtattcaaa attgcctggc     480
agaagtcaat gtgaaacaaa tgagttgggt ggcaaatga caattttta ctgtggaaag     540 atcaatgtgt acgatggtgt accacttgct aaggcacgag caatcatgca cctggcagct     600
tctcctattg attttcctca gggcaatcta tgtaatcaaa atggtgcctt taggtccttt     660
ctgggtcatg tacaagaagc cgaagacaaa aacgacctta cttcatctat tgctttgaac     720
ttgaattctc ataccatgca cactgagaag atgacagaat atcagcagca gtttagggga     780
aaagcaaaca tcagtcgtga ttctgatgta gatggacagg tgagcagaaa agaatcattg     840
cagcgatatc ttgaaaagcg aaaagacagg ggaagattct ttaaaggcag gaaaaatgca     900
ggacaagctt tgtctagctc ggagatgtac ctgaaccatc agataagagc tcactactta     960
aatggacaaa caaccagag cagaacaagt tctccaccac agtctggagt gccacatgca    1020
ttttatagct cagctgacaa ccaagagctt gtgaattttt ctgtagatct caatgatgaa    1080
ggtggtcaag aacactga                                                1098

<210> SEQ ID NO 85
<211> LENGTH: 1074
<212> TYPE: DNA
```

<213> ORGANISM: Aquilegia coerulea

<400> SEQUENCE: 85

| | |
|---|---|
| atgaaacctg acgagacagt tcccggtca ccacttgata aacctttgtt tcaacttact | 60 |
| gatgaagata tttcacagct cactcgtgaa gattgccgga aatttctcag agacaaaggt | 120 |
| atgagacgtc cttcatggaa caaatctcag gcgattgaac aagtgatctc acttaaaacg | 180 |
| ttgctagaac caagaacgga atctgataca aatgccaccg gaatccggca gaaattactt | 240 |
| gtttctcggc tagaaaattc tacccaagta cctttaaatg caagacaaa tgcctcaaat | 300 |
| ttaaagacat ctgttcaggc aataaactcc gggaaagccg atattcatgg tgacaggccg | 360 |
| tgtcgggtcc ctgttccagt ccctgacgat aacacaatca ctgttccagt ccctgacaat | 420 |
| aacacaatca ctgttccagt ccctgacaat aacatcactt catccagaaa cctgaactcc | 480 |
| accaatggac tggttggtca gatgacaatt ttctactgcg gcaaggtgat cgtctacgat | 540 |
| gatatgcctg ctgagaaggc acatgcaatc atgaaatttg caggaagcca tatcaatgtg | 600 |
| cctgaggatt cttcaccagc tggagctgca gtaattcaat cctttgcatg ccaattacag | 660 |
| gcagcatcca tcagacatgg acttgctttc ccgtcagcgg tctctccacc cttgcacaat | 720 |
| gtggtagccg atacttctca gcattgcagg gaggaagtga cagtttctcg tgaagttgaa | 780 |
| cccgagggtc cagtgagtag aaaagcatct gtacaaagat atttggagaa gcgaaaagac | 840 |
| aggggggcggt ttaagaacaa gcgaaagata gagtcatctt ctagcttaga gatatacttg | 900 |
| aaccatcaac tgggggatca gtaccttaat gagaaatcaa gtcagagcag ggcatgttcc | 960 |
| ccaccccaac ctagagcacc acacactccc actcgttgca gttcagttga gaaccaggtc | 1020 |
| acaaatgtcg tgttctccat tgatctcaat gataacgatg ttcgggaagg ctga | 1074 |

<210> SEQ ID NO 86
<211> LENGTH: 1044
<212> TYPE: DNA
<213> ORGANISM: Aquilegia coerulea

<400> SEQUENCE: 86

| | |
|---|---|
| atgaaacctg acgagacagt tcccggtca ccacttgata aacctttgtt tcaacttact | 60 |
| gatgaagata tttcacagct cactcgtgaa gattgccgga aatttctcag agacaaaggt | 120 |
| atgagacgtc cttcatggaa caaatctcag gcgattgaac aagtgatctc acttaaaacg | 180 |
| ttgctagaac caagaacgga atctgacaca aatgccaccg gaatccggca gaaattactt | 240 |
| gtttctcggc tagaaaattc tacccaagta cctttaaatg caagacaaa tgcctcaaat | 300 |
| ttaaagacat ctgttcaggc aataaactcc ggggaagccg atattcatgg tgacaggccg | 360 |
| tgtcgggtcc ctgttccagt ccctgacgat aacacaatca ctgttccagt ccctgacaat | 420 |
| aacatcactt catccagaaa cctgaactcc accaatggac tggttggtca gatgacaatt | 480 |
| ttctactgcg gcaaggtgat cgtctacgat ggtatgcctg ctgagaaggc acatgcaatc | 540 |
| atgaaatttg caggaagcca tatcaatgtg cctgaggatt cttcaccagc tggagctgca | 600 |
| gtaattcaat cctttgcatg ccaattacag gcagcatcca tcagacatgg acttgctttc | 660 |
| ccgtcagcgg tctctccacc cttgcacaat gtggtagccg atacttctca gcattgcagg | 720 |
| gaggaagtga cagtttctcg tgaagttgaa cccgagggtc cagtgagtag aaaagcatct | 780 |
| gtacaaagat atttggagaa gcgaaaagac aggggggcggt ttaagaacaa gcgaaagata | 840 |
| gagtcatctt ctagcttaga gatatacttg aaccatcaac tgggggatca gtaccttaat | 900 |
| gagaaatcaa gtcagagcag ggcatgttcc ccaccccaac ctagagcacc acacactccc | 960 |

| actcgttgca gttcagttga gaaccaggtc acaaatgtcg tgttctccat tgatctcaat | 1020 |
| gataacgatg ttcgggaagg ctga | 1044 |

<210> SEQ ID NO 87
<211> LENGTH: 987
<212> TYPE: DNA
<213> ORGANISM: Medicago truncatula

<400> SEQUENCE: 87

| atgaacggcg gaagcaccgt ttccttccga tccatcctcg acagacctct taaccaactc | 60 |
| actgaagatg acatttctca actcactcgc gaagactgtc gcagattcct caagataaaa | 120 |
| gggatgcgca ggccttcctg aacaaatca caggcgatcc agcaggtgat ttctctcaaa | 180 |
| gcgcttctag aacctaccga cgatgatatc ccggctaccg tcggcgttgg tgtctcctcc | 240 |
| gccattcacc accatcacca ccaccaccct cctcaacctc cgccgaaggc tttggatccc | 300 |
| gaagatactg cttggaact acagaaatcc acttcacctg ttgctgagag acccacggaa | 360 |
| accaatgatg ccaatgttgt taacaatccc ggagggtgcg cacctagtgg gtcatttggg | 420 |
| caaatgacaa ttttctactg tggtaaggtg aatgtctatg atggagtctc gccggataag | 480 |
| gcacgatcaa tcatgcagct tgctgctgca tgtccgtcct cctttcctca ggataatcct | 540 |
| tcaaataaaa atgcagcagt ttgggcttct ccttgcaact tacctattga taaggaagtc | 600 |
| ctcttcccta ctgacacagc aatccttcaa gttgctcaaa cagataagat ggtggaatac | 660 |
| cctctgcaat acagggagaa aggaagcaca gctcgtgatg ctgagggtca ggcaagcaga | 720 |
| aaagtgtcac tgcagcgata tcttgaaaag cgaaaggaca ggggaagatc gaagggcaag | 780 |
| aaactgactg gcataacttc atctaacttt gagatgtatt tgaaccttcc agtgaagctc | 840 |
| catgcctcaa atgggaattc aagtcgtagt agcactgact ctccaccaca gcctagactg | 900 |
| cctttagttt ccagtggctc agctgaaaac cagccaaaag ttacccttcc cattgatttg | 960 |
| aatgataaag atgttcaaga tgctaa | 987 |

<210> SEQ ID NO 88
<211> LENGTH: 1020
<212> TYPE: DNA
<213> ORGANISM: Solanum lycopersicum

<400> SEQUENCE: 88

| atgtcgctgg aacaaactgt ttacaagtct cctctggaca aaccgcttta cctacttacc | 60 |
| gatgacgaca tttctcagct cactcgcgaa gattgccgac gttttcttaa agctaaagga | 120 |
| atgagaaagc cgtcatggaa taaatcacag gcgattcagc aggtgatttc actgaaggcg | 180 |
| ttgttgaga cgacgccgga atccgacacc ggtcagcgga aaaagcgtca cattcctcgc | 240 |
| ccggacacta gtttacagcg agtccagaaa gaaacgagta tcgatgcaga atttgctgaa | 300 |
| tcggctgaag aaacggtgcc gtacggtaga aaacctccca ataaacctga tctttccggc | 360 |
| gacaaagctg caagtgctgt tgccgttgtc aataacttag ctccttctag aaccacagat | 420 |
| tcaggaaatg catcatcagg tcaattgaca atcttctatt gtggcaaggt gaatgtgtat | 480 |
| gatgatgtac ctgctgaaaa ggcagaagca atcatgcatc ttgctgcaag cccactcttt | 540 |
| gtcccttcag aaactccatt ggatgctaac agagcagctc aacattccga atgccatttg | 600 |
| caagctgcaa atgttaaact gggtcaagat tctcctatgg tgttcatgcc aaccatgcaa | 660 |
| acagggaaaa taactgaagt tactcgcctg catttggagg aaagcaacac ttcctatgaa | 720 |

```
gacaatcctg aagcagtgaa ccacgtaagc aggaaagcat tactggaaag atatcgtgag    780
aagcggaaag acaggttcaa gagaaagatg ggaatgcctt catctgctag cttggacatc    840
tatttgaacc atcgaaccat aaatcatacc caaagcgagc tctcaagtag gagcaacact    900
tgttccccgc ccgcaattag attatctgct gcgcctgctc caagtggttc aatggataac    960
attctccaaa tggatgccaa tgcttctggt tttctcgacg acaaagatgg taaagagtga   1020
```

<210> SEQ ID NO 89
<211> LENGTH: 1018
<212> TYPE: DNA
<213> ORGANISM: Trifolium repens

<400> SEQUENCE: 89

```
atgaacggcg aagcaccgt ttccttccga tccatcctcg acaaaccccct taaccagctc     60 accgaagatg acatttctca actcactcgt gaagactgtc gcagattcct caaagataaa    120
gggatgcgca ggccttcctg gaacaaatct caggcgatcc agcaagtcat ttctctcaaa    180
gcacttctag aacctaccga cgatgatctc cctgctcccg tcggtgtctc ctccgccatt    240
caccaccatc atcaccacca ccctcaacct cctcagagga atttgaatga agctccggtg    300
aagggctccg atctcgatga taccggtttt catactgcgg aggatcttaa caaatctact    360
tcaactgctg tggaaattcc tactgaaacg aatgatgcca atgttgttaa atcctctggg    420
gggtgcgtag ctagtgggtc gtttgggcaa atgacaattt tctactgtgg taaggtgaat    480
gtctatgatg gagtctcacc ggataaggca cgatcaatca tgcagcttgc tgcatgtcca    540
tcctcgtttc ctcaggataa tctttttaaat aaaaatgcag cagtgtgggc ttctccttgc    600
aacataccaa ttgataagga tgtcctcttt cccaatgaca cagcaatcct tcaggttgct    660
caaacagata agatggtgga atatcctctg caatacaggg agaaagggag catagctcgt    720
gatgctgatg tagagggtca ggcaagcaga aatgcgtcgc tgcagcgata tcgtgaaaag    780
cgaaaggaca ggggaagatc gaaaggcaac aaactgactg gcataacttc atctaacttt    840
gagatgtatt tgaaccttcc agtgaagctc catgcctcaa atggtaattc aagtcgtagt    900
agcactgact ctccaccaca gcctagactg cctctagttt ccggtggctc agctgaaaac    960
cagccaaaag ttacccttcc cattgatttg aatgataaag atgttcaaga atgctaat   1018
```

<210> SEQ ID NO 90
<211> LENGTH: 936
<212> TYPE: DNA
<213> ORGANISM: Amborella trichopoda

<400> SEQUENCE: 90

```
atgacggccg gtgatggctc catacgatca atattggaca agcccttgga agagctcacg     60
gaggaggaca tctcgcagct cactcgtgaa gactgtcgca ggtacctcaa agaaaaaggg    120
atgcgaaggc cttcgtggaa caagtatcag gcaattcagc aggttctctc tctaaaaggc    180
ctcttagagg ggaagccttg cgatgacaac agcgatgttt tcagtcaccg atcaccgatc    240
acggtcattc ccaatgttgg gagcatgaga gagaaagaaa aggccgtaaa tattgcggat    300
ccggagatat cggggtctca tcagccgaat tttcgccgag aaattcacga aaccaccgg    360 gaaagagctt taccggcttc cgactggcca ccttctcagg agccggtatc tcagatgacc    420 atttttctatg ctggagccgt taacgtatac aacgacattc ctgaagataa ggtgcaagcc    480 atcattttatc ttgctgggaa gtcagactcc ttacagcaaa ctaatgttat cagaacggga    540
ccggaccaat gcatagcatc tgctgcaagc ccctcattga acgatctcca cagtagacga    600
```

| | |
|---|---|
| atccacccaa cttcaaacat caccacttct cagtctcttc gtgttgcaac ttcccttcct | 660 |
| gttgggcctc attcagaggt tcctaagacg aggaaaacct cggtgcagcg attcttggag | 720 |
| aagcggaagg acaggggggcg cttgaaggga acattggcga gtggtgggag ctctaagagg | 780 |
| ggttcctcat gcctagaatt gtatgcaact tcaagattaa agagtgaggg ggtggccacg | 840 |
| actacaactc aatccaatat gaacaatgtg gtcgtatcac cttctaaccc aagaatgcct | 900 |
| ctaaatcccg ggagttgcag ctgggttgag aactaa | 936 |

<210> SEQ ID NO 91
<211> LENGTH: 1251
<212> TYPE: DNA
<213> ORGANISM: Selaginella moellendorffii

<400> SEQUENCE: 91

| | |
|---|---|
| atggcggcct cgattctagg ttgcggttct agcaatggcg tcgcggtcac cggtaatcct | 60 |
| gctccagccg cggcggccga ggtgcccgcg cctctcaggc cgctggagga gctcacggag | 120 |
| ctggatatca ggcagctcac gcgggaggac tgtagacgct atctcaagga acggggaatg | 180 |
| cgcaggccgt cttggaacaa ggcacaggcg atccagcaag tgctgtcttt gaggagtttg | 240 |
| ctttgtcctt ccaatccggt aggcccttcc tccaagaacc cgggaagtgc cgcgaacgcc | 300 |
| cctccggctg aagcagctgc tgctggtcac accaaacaat tactggacaa ggtctctcag | 360 |
| caaagcatgc cagattcttg tccatctaac aacgcctctg atcctaggcc gctcgccgga | 420 |
| tgctttggat ctcttgcccc gacgttatca gttctcaatc ccgatgcgaa acgtaacccg | 480 |
| ctgagttcta aacccgcgtc aacgacaaag cctcacagtg cccagctgac cattttctac | 540 |
| tccggtattg tgaacgtgta cgacgatgtc ccgcttgaca aggcacaagc tataatgctt | 600 |
| cttgccgcga gtaaaacgtt tcacgttccg acaagttcag tgcctggcca tccgccgttt | 660 |
| acgagtgcaa cccaacaaca acaacaacaa caacgagagc ttaaccaaca aaccgaagcc | 720 |
| acgcaaaagt acccgatgca gcaccaacaa gctcctcaaa tatatctaag ctcgggttca | 780 |
| gctctacccg acgaaagctg cacggaacct gggcttccac aggtcagaag tgcatcgcta | 840 |
| cagagattcc tggctaaacg acgagacagg ttgtcaggga atccttcctc gtctaggcgg | 900 |
| aacgacagat ccaaaaagcg gaggttctcc ccgccaccgt caccgttaac ttcggcttcg | 960 |
| ttccagtttc ctccaagtgc tagaacatcg caagttttaa gatactccac tacttctaca | 1020 |
| actacgatca ctactgccac tgctactgcc gctactacca ctactactac gggtaccacg | 1080 |
| aatggtggac actgttccaa ttccaatcaa gcaagcgaga atgcaggcag cgatacctcc | 1140 |
| ggtggaagtt ctggaacgcc ggacacaagc gacacaacaa gggacaacga caatggacga | 1200 |
| gtttccaacg aaaatggacg agtgtccacc acttgtctcg cagcaacgtg a | 1251 |

<210> SEQ ID NO 92
<211> LENGTH: 705
<212> TYPE: DNA
<213> ORGANISM: Selaginella moellendorffii

<400> SEQUENCE: 92

| | |
|---|---|
| atgtctagca tggtcgattt cctggggatc gaggagaagg tgtccaccag cgtcagcgcc | 60 |
| gagaggttga agaagctgga ggagctcacg gacgaggacg tgatgcagct cactcgggag | 120 |
| gattgccggc gctacctcaa ggagaaggga atgcgtcgtc cgtcttggaa caaggcccag | 180 |
| gccgtgcagc aacttctctc gctcaagagc ctgtgcgatc cttccccggc ttccagtgga | 240 |

| | |
|---|---|
| gccgccaaga ggagcccatc tccgccgctc gacgaggctc cagcgaagaa acccatggca | 300 |
| atgacaagca tcgatctcaa ggctgccgct gctgtggacg ccgccaatct tacgatgttt | 360 |
| tatgatggag cagtgtccgt gtttgacgac gtttcgccag acaaggcatc tcttttccct | 420 |
| ttggcttatg cgatcatgct cctggccggg aatgtgaagt cgtggccttc gatcaacgtt | 480 |
| gctgctaaca ccaacaaagt tgtgatctct tcttatgagt tgccacaggc gcgaaaggca | 540 |
| tcactccagc gttttcttca gagacgccgt gagaaaactg cgaaagaggc agcatccaaa | 600 |
| gggaactcta ataagtcgcc ttgtcatggc gagagctcgg ggaagcacgc atcggatgct | 660 |
| actgatccag ccacttctcc cttgctcacg gaggtctctt cctag | 705 |

<210> SEQ ID NO 93
<211> LENGTH: 813
<212> TYPE: DNA
<213> ORGANISM: Nicotiana tabacum

<400> SEQUENCE: 93

| | |
|---|---|
| atgccgccgg aagaaacagt ttccaaatca cctctggaca aaccgctcca cctacttacc | 60 |
| gatgacgaca tttctcagct tactcgcgaa gattgccgcc gttaccttaa agaaaaagga | 120 |
| atgagaaggc cgtcatggaa taaatcacag gcgattcagc aggtgatttc actgaaggcg | 180 |
| cttctcgaga cgacaccgga ttccgacacc ggccctcgga gaaaacttca cattcctcgc | 240 |
| ccagacacta gagtacaaca agtccagaaa ggaacggata ccgatgcaga attttcgaaa | 300 |
| tctgctgaag ggatggtgcc atacggaaga aacattcga aaaacctga tattcccggt | 360 |
| gatatagctg ccggttcagt tgccgttgcc gccggcaata acttagctcc ttctagaacc | 420 |
| acagatttgg gaaacacacc agcaagtcaa ttgacaatct tctattgtgg caaggtgaat | 480 |
| gtgtacgatg atgtgcccgc tgaaaaggca caagcaatca tgcatcttgc tgcaactcca | 540 |
| ctctttgtgc cttcagaaac tccattgggt gctaccttag cggctcgaca ttccgaatgc | 600 |
| catttgcaag ctgcaagtgt taaacagggt ccagattctg ctatggtgct catgccaacc | 660 |
| atgcaaacag ggaaaatgag tgaagtgact cgcctgcgtc tggaggaaag caataccttc | 720 |
| tatgaagaca actctgccaa ttatgcagaa gcagtggaag gccacccaag caggaaagca | 780 |
| tcagtacaaa gatatcttga aagcggaaa gac | 813 |

<210> SEQ ID NO 94
<211> LENGTH: 984
<212> TYPE: DNA
<213> ORGANISM: Solanum tuberosum

<400> SEQUENCE: 94

| | |
|---|---|
| atgccgccgg aagaaacagt ttccaagtca cctctcgata aacctctcaa tcaactcact | 60 |
| gacgatgaca tttctcagct cacacgcgaa gactgccgtc gttacctcaa acaaaaagga | 120 |
| atgagaaagc cgtcatggaa taaatcacag gcgattcagc aagttatatc gttgaaggct | 180 |
| ctcctcgagc cggatactga cgccggaact cggaagaaac ttcacattcc tcgtgcagat | 240 |
| actcatgtcc agagcgggaa aaatacctat ggcgaacctt ctgaaccagt gcctgataga | 300 |
| agaaatcagc aggacagacc tgatcttttcc agtcatatta ctgcccttcc ggtcgctgtt | 360 |
| gtggataatt cagctccttc tagaacaata ggttcagcag ataaaccagt aggacaaatg | 420 |
| acaatcttct atagaggcaa ggtgaatgtc tatgatgatg tgcctgccga caaggcacaa | 480 |
| aaaatcatgt gtcttgcttc aagccctctt tgtgtgcctt cagaaactcc atcgaatgcc | 540 |
| actgtagcag ctcgacattc agcatgctgc ttacaagctg caaatagtaa actacgccta | 600 |

```
gatactaata ttgtaccgac tattcaaaca gtgaaaatga gtgaggtttc tcgagttcct      660
atagaagaaa gcaaccgctt atacaatgat aatcctgaag cagtggagag ccccgcaagc      720
aggaaagcat cagtacaaag atatcttgag aagcgaaaag aaaggttcaa gtggaagaga      780
aaggtagaaa caacttcatc agctagcttg gatatctatt taagtgatcg aattgggact      840
cgtacgccaa gtgactatgc aagtggggct gatctttgct tcacacccca cattacacct      900
acaggaagtg gtcctataca agacaatatt cagatgaatc ccacttttc tagtgatctc       960 aatgacagag atgttagaga gtga                                             984
```

<210> SEQ ID NO 95
<211> LENGTH: 1047
<212> TYPE: DNA
<213> ORGANISM: Glycine max

<400> SEQUENCE: 95

```
atgaacggcg gtgccaccac cgccaccttc cgatccatcc tcgacaagcc cctcaaccag       60
ctcaccgagg atgacatttc tcagctcact cgcgaagact gtcgcagatt cctcaaagaa      120
aaagggatgc gcaggccttc ctggaacaaa tcgcaggcga tccaacaggt catttccctg      180
aaagcgctgc tggaaccttc cgacgatgat actcctcctc ctaccgccat gcaccaccgt      240
agtcatgctc ctcccccttcc acctcaacct caatctcaag tgaatttgac tgaacctcct      300
cctccgccca aggctccgcc acctgaagaa tcctctttttc atgctgctga agacattcag      360
aaacctgcgt cgtctgggga aaaaccttcg gaaactaatg acaccaacac caacgttgct      420
agccccaaag ggtgtgcaac tagtggatca tttgggcaaa tgacaatttt ctattgtggt      480
aaggtgaatg tctatgatgg agtctcgcct gataaggcac gagcaatcat gcagcttgcg      540
gtgagtcctg tccagtttac tcaagatgat ccttcaaatg gaaatgcagc tgtttggcct      600
tctccttgcc acttaccaat ggataaggat gtcctcattc ctgtagatac aacaatcctt      660
caggttgctc aatcagataa gatgatggaa tatcctctgc aatatagaga gaaaggtagc      720
atagctcgtg atgctgaggg tcaggcaagc agaaaagtgt cattgcagcg atatcttgaa      780
aagcgtaagg acagggggag attgaaaggc aagaaattga ctgggataac ttcatctaac      840
ttcgagatgt atttgaacct tccagtgaag gtccatgcct caaatgggaa ttcaagccgt      900
agcagtacta gctctccacc acagcctaga ctgcctctag tatctagtgg ttcagctgac      960
aaccagctaa aggttgccct tcccattgat ctcaatgaca aagtgtcatt gcagatgttc     1020
aagaatgcta aaactctaac tagatag                                         1047
```

<210> SEQ ID NO 96
<211> LENGTH: 1017
<212> TYPE: DNA
<213> ORGANISM: Citrus clementine

<400> SEQUENCE: 96

```
atggacgtgg acggtggcgt gacgtcgtgc cggtcaatac tcgagaaacc tctcagtcag       60
ctcactgaag aggacattac gcagctcaca cgcgaagatt gccgcaaatt tctcaaggag      120
aaaggaatgc gcagaccatc gtggaacaaa tcgcaggcga tccagcaggt gatctctctc      180
aaagctttgc tcgagtccag cggcgattcc ggctcaggtg ttttacgcag agtactcgtc      240
tcgcctccgg aaagtatgcc gccgcgcgtg aatgtgactt caaattcagc tgatttagta      300
aaggaaccga ccatctcagt ttctggagac caaaacagtg cgtataggcg gaagtaccct      360
```

| | |
|---|---:|
| cgcaactgtg ctgttgatgc agataacaag accatctcta acagaaatcc ctgtgaagca | 420 |
| aatgggtcca tagggcagat gacgattttc tattgtggca aggtgaacgt gtacgaagga | 480 |
| gtgccaactg ataaggcaca ggagattatg caccttgcag caactccaat tgattttcc | 540 |
| cagaacggtt catttggtgg aattacggca tataggcca ttccatgcca tttacaagtg | 600 |
| acaagcaaca gacatgtgtc tctccctctt cgtcctgctg ccatgatctc tcagttcatg | 660 |
| caaacaggga agatagcaga ttattctcag gagtataggg agaaagcgat tagtactcat | 720 |
| gactctgatg tggatggtca ggttaaccga aaagtctcgt tgcagaggta tcttgaaaag | 780 |
| cggaaagaca ggggaaggtt tttcaaggga aagaaaaata caggaccaac tcctagtttg | 840 |
| gagatgtacc tgaaccatcc ggggaagaca catgcctcca atggacaaca gagccagagc | 900 |
| aacacaagct ctccgaccca gcctgagttg tccaacacat tggggacctc cccagacaac | 960 |
| caggcgaaga ctgtcatgct tccggttgat ctcaacaatg aagatattca agactga | 1017 |

<210> SEQ ID NO 97
<211> LENGTH: 1008
<212> TYPE: DNA
<213> ORGANISM: Ricinus communis

<400> SEQUENCE: 97

| | |
|---|---:|
| atggacgccg gagtgacgtc gttcaggtca atactagata aacccctaac tcagctaact | 60 |
| gaagaagaca tttctcaact cacacgcgaa gattgccgca ataccctcaa agaaaaagga | 120 |
| atgcgaagac cttcatggaa caaatcgcaa gcgatccagc aagtgatttc tctaaaagca | 180 |
| cttcttgaaa ctagtgaaga ttccggtgcc ggtgctctcc gtagaatctt agtttctaaa | 240 |
| cctccggtta cttcaaattc tgttgattca gctaaggaac caagtgatag caacaataat | 300 |
| aacttactag atgagacagc tcctcatgat tctcccaaat ctcctcctcc ggcgccatcg | 360 |
| ttggattgtc cactggaaga ggcagataat aaagtcattt cttcaagaag tcctggtgca | 420 |
| acagatgggt tggtcgggca aatgacgatt ttctattgtg gaaaggtgaa tgtttatgat | 480 |
| ggagtcccac ccgataaggc ccaggcgatc atgcatcttg cagcgactcc aattcactca | 540 |
| cctttagacg atccaattcg tagacctgta tttgcttttc cgtatcattt acagaccca | 600 |
| agtgacaaac atgtctttgt tccttctaat gctgcaattt ctccaaccac accaacagag | 660 |
| aaggtgacag aatattctca gcagtgtagg gagaaaggaa atgtaactta tgatcatgat | 720 |
| gtagagggtc aagcaaaccg aaaaatgtca ttgcagagat atctggagaa gaaaaaggat | 780 |
| aggggaagat tcaagggtag gaaaaattta gggcctaatt cgtctagctt ggatgcatat | 840 |
| ttgaaccatc aaatgaggac acatatctca aacgagcaat caaccaggag cagtacaagc | 900 |
| tctccaaccc agcctggagt gccacatact tcgagtaact cggccgaaga tcagctgaag | 960 |
| actgccagtt tgctgttga tcttaatgaa gatgtccaag aaccttga | 1008 |

<210> SEQ ID NO 98
<211> LENGTH: 1182
<212> TYPE: DNA
<213> ORGANISM: Vitis vinifera

<400> SEQUENCE: 98

| | |
|---|---:|
| atgaatcccg gcgtcaccac tctccgctct atactggaca aaccccttca cgaactcacc | 60 |
| gaagaagaca tttctcagct cactcgtgaa gattgtcgca ataccctcaa agaaaaagga | 120 |
| atgcgtcgtc cttcctggaa caaatcgcag gcgatccagc aggttatttc gcttaaatcg | 180 |
| ttgctcgaaa ccagtgaggg cagcggtgcc ggagtttga ggaagatcac cgattcaccg | 240 |

```
ccggcggaaa atctacctcc ggttacctcc aattcagctg attcaggcaa ggagctgagt        300
gctgatatcc agatctcagt atcagctgat gaactggttc cccttccgcc aaaagatcat        360
catccagaat ccacccctte tggcgaatta gccagccggc tccagaggc agacaccaag         420 catacttgtc ccagaagtcc aggtgcaaca aattgtttgg ttgggcagat gacaattttc        480
tactgtggaa aggtgaatgt gtatgatgga gttccagatg ataaggcaca agcaatcatg       540
catcttgcag caagcccatt ccatttgcct tcagatgacc cctttagtgg tgctgctatg        600
ctttgctcct ctccatgcca tttgcatact gccaatgtta acatggcca tattcctcct         660 cgagccatgg tttctcagac tatgcaaaca gagaaattta ctgaatattc tcaacagtac        720
agagaagaag tgaactttac ccgtggacat ggatcggaag cactttctgg cttaggacg        780 gtaggaagcc caacggccag gcctaccgaa gatatggaac agaccacttg tctcactata        840
tggggtacct tccgctacaa ggttatgcca ttcgagatat atgagggcat catggatgtt       900
gaaggtcagt tgacagaaa attatcattg caaagatatt tcgaaaagcg aaaagacaga        960
tttaagagca ggaaaaaaat aggactacct tctggtagct tggagatgta tgtgaaccat       1020
caagcaagga cacaaccctc gaatgggcaa tcaagccgga gtggcacaag ctctccaccc       1080
cagcatggat tgtcgcacac cctgtgcagc tcagctgaca accatacaaa gaatttcact      1140 cctttttgttg atctaaacag taaagatatc caagaaagtt ga                         1182
```

<210> SEQ ID NO 99
<211> LENGTH: 1029
<212> TYPE: DNA
<213> ORGANISM: Morus notabilis

<400> SEQUENCE: 99

```
atgagcgccg gcacgacggc gtttcggtcc atactggaca agcccctgaa ccagctcacc         60
gaggatgaca tttctcagct cacccgtgaa gattgccgca atacctcaa ggaaaaaggg         120 atgcgaaggc cgtcgtggaa caaatcgcag gcgatccagc aagtgatttc gctcaaggct        180
ttgttggagc cctgcgacga ttccggcgcc ggagccctaa ggaggatcgt cgcttcgacg        240
ccgccgccac cgccgacaca aaacgcgcca cgtgtctcca ctttcagtgt tacttcgaac        300
tcggcagatt cgggtaagga agcaagtgtt gatgtccagg tttcggcgga ggaatcggga        360
ccgtgtcaga ggaaggagca ggcgaaatct gctccggaga ctgaggaaag accggctgat       420
gcgggtgaga gggcaagtcc aagaagtcat tgtgcaactg atgcattggt cggacaaatg       480
acaattttct attgtggcaa agtgaatgtg tacgaagggg ttccacctga aaggcacga        540 gcaatcatgc accttgctgc aagtccaatc ccttatctc gagaaaattc atttggggtc        600
cttgcagcac ctagatcttt tccatggcat ttacatgctg cgagtgacaa gggtggcctt       660
ctccctccta gtgccacaat atcacaaccc atgcagacag ataagctagc cgactacagc      720
caacagtgct gggagaaaga aaatgatggt caggcgagca gaaaactctc attgcagaaa      780
taccgtgaaa agaaaaaaga taggggggagg ttgaagacca agagaagcac gggatttaat      840
tcttctagca tggaggtcta ttttaaccac caggtaaaga cccacatgtc aaatggtaat       900
tcaagtcgaa gtagcacaag ctctccgacc cagcctggac taccacaaac attgtgtagc      960
acagtcgaca atcagccaaa gattccctgt cttcctgttg atctcaatga aaaactaact      1020
attgagatg                                                              1029
```

<210> SEQ ID NO 100

<211> LENGTH: 1095
<212> TYPE: DNA
<213> ORGANISM: Phoenix dactylifera

<400> SEQUENCE: 100

```
atgtattggg ttggatcggc tcaagaacgc cgccgagacg ggggccggtc gccgctcgac      60
aagccactca gcctgctcac agaggaggat atcgcccagc tcaccgcga ggactgccgc     120
cgattcctca agagaaagg catgcgacgg ccgtcctgga ataagtcgca ggcgatccaa     180
caggtcatct ccctcaaggc cctcctcgag ggacgaccgg agtccggcga actcccgtc     240
ggcgccggct accgccagaa gcctccccct cggcggccgg cctctcttcc ttcgctgcag    300
gaggcggccg gcgactcgac ggcggcggcg aaggagccgt cgccgtcgtc gtcgctgtct    360
ccgtaccgga gaagagatcc gatcccgccg atcatctccg ccggcgggcc gtcttgccgg    420
ttcccggtcg ccggcaggga ccaacaaccg ccagagaccc cctcccccctc gctcagggtg   480
acggcggaag taccggcggg tcagatgacg atcttctacg acggcaaggt gaacgtctac    540
agcgacgtga cggtcgataa ggcgcggcg atcctgctgc tcgcggggag acgagactgc     600
tacggcgctg cggctctacc gggtccggtt cactcgcccc agccggcttt tctcggaccg    660
ggtcagggcc cggtccccac cgctcccccg ctggccgctg cttttacccac ctcgccagct   720
gggaggttag cccaccgttt cgagggaccg agtggagtgc cgcgcgggaa atcgagcctg    780
gtaagagagc ggagcacgtc accggagggt ccaacaagta gaaaagcatc attgcagcgg    840
tacctggaga aaaggaagga caggttaaaa ggtagaaaaa ctcttggagg ggcatcttct    900
tcaagcatgg aaataatgtt cttgagccaa aaatttgggg gtcagatacc aaatgagcag    960
ttaagtagga gcaacactag ctcccctacc caacccagac cacctggcac accaactaga   1020
tgcagttcaa tagagaacca ggctcagaaa aatcatctct cagttgatct caatgatgat  1080
ggttgcggca actga                                                   1095
```

<210> SEQ ID NO 101
<211> LENGTH: 1065
<212> TYPE: DNA
<213> ORGANISM: Theobroma cacao

<400> SEQUENCE: 101

```
atggaggcgg gggtagcgac gacgacgaca acgacggagt cgtttaggtc gatacttgat    60
aaaccccctca gccaactaac agaagaagac atttctcagc tcactcggga agattgtcga   120
aaattcctca aggaaaaagg aatgcggagg ccgtcgtgga acaaatcgca ggcgatccag   180
caagtaattt cactcaaggc gttgttggag agcaacgaag attccggcgc cggagctatc   240
cggaagatcc tcgtttctcc accatcaccg tcagtgcctc cgcaaaatgc agcggcgcgt   300
gtggcttcca attcatgtga ttcagtaaaa gaagcggttg tcggagaaga aggaagcccg   360
tatcggcgaa aagatcctcc tttgaaacct tctccggtgg gggagataaa ttgccttggc   420
ggtgacacgg ataacaagaa tctctctcct agaagtccat gtgaatcaaa tgagttgggt  480
gggcaaatga caattttcta ctgtggaaag gtcaatgtgt atgatggagt accacttgat  540
aaggcacggg caatcatgca tctggcagcg actcctattg attttcctca ggacaatcaa  600
tgtagtggaa atgcagccct taggtccttt atgtgccatg tccaagcagt cggtgacaaa  660
aatggccttg ttgcttctac tgccttgaac tctcatacca tgcaaacaga gaagttgaca  720
gaatatcagc atcagtttag ggaaaaagga aatatcgctc gtgacgctga tgtagatggg  780
caggtgaaca gaaaagtatc attgcagaga tatcgtgaaa agcgaaaaga caggggaaga  840
```

```
tttttaagg gcaggaagaa tacaggacaa gcttcctcta gcttggagat gtacctgaac    900
catcagataa gaactcacaa ctcaaatgga caatcaagcc ggagcagcac gggttctcca    960
ccacagtctg gattgccaca tgcattttgt agctcagctg acaaccaagc aaaacttgtg   1020
aatctttctg tagatctcaa tgacaaaagt gttcaagaac actga                   1065

<210> SEQ ID NO 102
<211> LENGTH: 3789
<212> TYPE: DNA
<213> ORGANISM: Spirodela polyrrhiza

<400> SEQUENCE: 102
atggccggga gcgaggcggc ggcgccggag gaggccggaa gggcggggga ggaggaggtg     60
agagcggcgg cggggctgc ggcggtgaag tcgccgctgg agaagccgct gtcggagctc    120
acggaggagg acatcgcgca ggtcacgcgc gaggactgcc gtcggttcct caaggaaaaa    180
ggtgctctag tccttttcct ttggttttcc tccttgtttc tcttcttttc ctttggaggt    240
cgcggtggag ctgatctcga tatccacgtg gccgcccgcg gtgacggcgg ctcccgtttt    300
ctctgtgcaa acgaatgcag gtatgcgccg cccttcgtgg aacaagtcgc aggccgtcca    360
gcaggtcatc tccctcaagg cgctcctgga gccctgccac gatgcagacg acgacgcacc    420
ttccgccggt gctgttccct ccatctcctc cttcttctcg aaaaggccgt ccgacgccct    480
gcttccggcc gccgcggcgc aggtgaggag gggtatcctg ttccaaactt ccgtcgcctt    540
ctcttctagc tcgagctggc aacattttgt gaaattgttc cttctcgatt tagttggaga    600
aacgcgtgtg gtttattgtg ttctgtttac ttctcagttt cccgtctctt ctccaatgag    660
gggtgaacct gccggcggcg cgccccaaat tgtctccgaa cgtccccacg aagggaccc    720 gctggcgaac gtcttcacct gctccgacgc cctcggtcga ttcccggcaa cggggaacgg    780
tgctcttccg ccaaacagtg ccaccctccc gcccaggtgc gtcccttctc agcacaacgc    840
cccctctatt caactctttt atttccccgg attgtccctc agatgttaac gggcgcccat    900
ggtgttgtag aggggttgct tccgctgaga cgctggaggg acagctgaca atcttctacg    960
atggcaagat taatgtctat gatggtgtga cgccggagaa ggtgaggtcc ggtcagagta   1020
agttggcggt gacccttcc tgtggtagat ctaggcactc atggcagtgt atttcccgtc   1080
tttgaaggcg cgggtgatcg tacaatttgc ggggagcccg agctgctacg atatgccgcc   1140
gatgccttcg ccgtctttct acccaaaccg accccctaaa tgccacgacc tggctctgcc   1200
agcgttatct caagcgacag gtggtggttc cttcaatccg ccaccgcctc cgccgccgtt   1260
gcagccaccg ccgtctcatc ctgcccagcc tatcggctat tcccaggttc cccagaacgc   1320
tggtacgttt ttttctccgt catgactttc ctgcgggttc gcctatgctt gatcacgttc   1380
acgataacgc cctgcggtgg ccctcctgct cacgttgagt tctattgccc tggcaggaag   1440
gttcccgcag caattcgggg aaggcatgga agagtggaga agctcgcgag aagttgaacc   1500
aggtgagaga ccttggaccc ttttcttcag tatcagtcgt tattctcgtt tctctctgct   1560
taactgacct atgcacccgg cctgaacagg cagggtatgc tgggtgattg aggagattac   1620
gcctatatgt cagtctatta ccatgctact gtttaagggt gtccttctgt ctaagttaac   1680
tagagtgacc ttaagctcct ggatttctta acctaccaca ccctgatggt acatggtaca   1740
ctcacagttg acctcaaagc ctttctcatt cctgcggggg aagagggtgg gggtgggcgt   1800
tgactgagaa aattttgaaa gcaaattgct aattctctgtt gttctttata atgacatttt   1860
```

-continued

| | |
|---|---|
| aggcattgcg cgcaagatag ctctttttc cttttaaga actgtgcttc ttgattccat | 1920 |
| tagcccggga tttaggttcc gttcattgct tagttagcct ccccaattgg cgctgtttat | 1980 |
| gaacgattgg cctcgaccct cttcagcatc cttatcaggg atcttgagat tgagcttaat | 2040 |
| cttatcgcct cttctcaaat gattatggct gccgcgtttt tttccaattt ccagttgatt | 2100 |
| tacctatttt ttggggagag atgactggt acagtatggc aacttatcca gttttgaatt | 2160 |
| gatgctgata ctgttcttct ttataaggcc tagaaattga tggtaattaa agtaacgtgt | 2220 |
| cagtgattcc atggatcaca ttaatgccct aaacttctgt gtcttatgct attccaaatc | 2280 |
| tgaaaacctt atgaatcaga ccaacaatag tatgaagaaa atttatttca tgctagggtc | 2340 |
| catggtgttc tattcaagaa ctacccttt tttggatcat gcagatgatc tattaagaga | 2400 |
| acaaaatgca gtagaaataa gttaacgaaa gacaacaagg tcatgtcatt tgacgaatga | 2460 |
| agaatttcag aatcaaattg aagcacatta catcttctca tgagttaaaa aaaatgctca | 2520 |
| tgcactgctt ttaatgctcc tttataatac ctgtcatagg ctgaattatt tcaaagtttc | 2580 |
| cttgtatggg aagttctact gggtggttct tttgtatgaa tcttcgtaaa taatcaaagc | 2640 |
| ctgtttattg ttcttcatga cgtggaaata attatttta tgtatcactc acgaaatgga | 2700 |
| tacagcacct atggttacat gatatttaac ttacgtccgc tcaaataaat gagcaataat | 2760 |
| aagataacct accatttctc tccttcattc ccattttgca aagcgtctgt tggtcgtatg | 2820 |
| ggaaaccaca tttctacaag aggaatccat catcttctat cacatctccc ttgagtgggc | 2880 |
| gcattttatg tggatccaaa tatctcaatt aataataatg tttactggat cattatatag | 2940 |
| tttttttat gcattcctct gatgatctta gtggctctcg gaattttttt attcatgaat | 3000 |
| agaaattttg tcatccctga agctgctgc cctttgcgt tcatcatttc tattctatta | 3060 |
| ttctcccttc ttcctgtatg gcctcctgaa gagttcttct tcatgcgaga gaaaaactat | 3120 |
| ggtcttaccc gaatagggtg ggatatttgt atgatcttcc caaggttttg tgtgggcccc | 3180 |
| atatggggc ggtggcgaag cgggcttttcg ggccggcgag cctagagaga cccgggcccg | 3240 |
| gcggctgttg ctaccctcta tagaaaagtt ttcctcagtg ctaccgcgct actgattggt | 3300 |
| tgctcttctg gtgccaatgt cgtcttgccg cgagcagagg gccccaccag cagagccgca | 3360 |
| tcgctccagc ggtacctgga gaaacggaag gataggtaaa gatggtgggc gtgggggtt | 3420 |
| gaccgactgg ttgactgccg ccgccgctgg ctgacttcgc cctctttccc tgtcggaagg | 3480 |
| ttcaagtgca agaagcacgc cggcgggggc tcttccggcg tggagctcct cctgagccag | 3540 |
| cggatcaggg accagattcc ggccgcccac ctctcatgcg gagagatgta cgcggcggcg | 3600 |
| ccgccggccc cgcggccccc tcccccgccg gcccgctgta gcgccgccgg ccacctccgc | 3660 |
| ttctccatcg acctcaacga cggcggtgag cgctctctct atctctctca cctcttttc | 3720 |
| atcgcctctg cttttgaaga gagtacccat gccaccgccg cctgcgtttc agatgtccgg | 3780 |
| gaagcttga | 3789 |

<210> SEQ ID NO 103
<211> LENGTH: 882
<212> TYPE: DNA
<213> ORGANISM: Musa acuminata

<400> SEQUENCE: 103

| | |
|---|---|
| atgaacccg gggagaccac gccccgtcg ccgctcgaca agcccctcgc cgagctcacc | 60 |
| gaggaggaca tcgcccagct caccgcgag gactgccgcc gcttcctcaa agcgaaaggc | 120 |
| atgcgacggc cgtcgtggaa caagtcgcag gcgatccagc aggtcatctc tctcaaggcc | 180 |

```
cttctcgagg ggcggcccgg ctgtgacgac tgccctgctg gcggcggaat cctccaaaag      240
ctgctcactt cttctccttc ggagccgcta tcgccaccgc aggactcacc tcctcccgcg      300
ccgaaggagg gcggtagcgg atcacagccg ctggcgaagg agccgtcgcc gtatcgaagg      360
agggacccga tcccaccgcc ctattcagcc ggaaatccga cgtgccagac cccaattgcc      420
ggagctgacc ttccccaccc gccggagaag cgctgcccct ccccaggtt gacggcggaa       480 gtaccggtcg gccagatgac gatcttctac gacgggatgg tcaacgtata cgacggcgtc      540
tcggccgatc aggccaggtc gatcatggaa cttgcggcca gcccggtctg cttcgacgat      600
ccgaccggtg cattctctcc ggcccggccg ccggccttcc gcttccctcc gggtctcccc      660
cgaccggccc cggtccccac cgctccctcg ttcgtgggga ccttcccgat ctcgccggct      720
ggtaaacgtt gctactccta ctgttcgttc cggtcaagcg tcagccttt aaccacaaca       780 gagggcccaa caagcagaaa agcatcattg cagagatact tggagaaaag gaaagacagg      840
tatggtcatt taccaacaga aagtatacta cttgttagct ga                         882
```

<210> SEQ ID NO 104  
<211> LENGTH: 498  
<212> TYPE: DNA  
<213> ORGANISM: Phalaenopsis aphrodite  
<220> FEATURE:  
<221> NAME/KEY: misc_feature  
<222> LOCATION: (214)..(243)  
<223> OTHER INFORMATION: n is a, c, g, or t

<400> SEQUENCE: 104

```
atgaactccg atgcaataac catggggaaa tctctgcttg agaaacccct tagccttcta       60
accgaagacg atatcgcaca gattacaaga gaagaatgcc gtagattcct caaagataga      120
ggcatgcgtc gcccctcttg aacaagtcg caggcgatcc agcaagtgat ttctctcaaa       180
gccctgttcg aaaaccgatc agatctagaa gatnnnnnnn nnnnnnnnnn nnnnnnnnnn      240
nnntttcccg aacacgcaga tctcagttcg atctcgccga ctgcggaggc caaggaacca      300
gagaaagctc agctcactat attctacggg gggaaggtgc ttgtgttcga cattttccg       360 gttaataagg cacaggattt gatgcagatt gcaggaaaag agcagaatca aaattacggg      420
acagcaaaca ctgtggctcc atctgcccct gcagcagacc tccatagttt acctctgccg      480
gctaagcctc cggcgtaa                                                    498
```

<210> SEQ ID NO 105  
<211> LENGTH: 355  
<212> TYPE: PRT  
<213> ORGANISM: Arabidopsis thaliana

<400> SEQUENCE: 105

```
Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
```

```
                        85                  90                  95
Glu Leu Glu Ala Cys Gly Arg Val Ser Tyr Pro Glu Asp Asn Gly Ala
                100                 105                 110

Cys His Arg Met Asp Ser Pro Arg Ser Ala Glu Phe Ser Gly Gly Ser
            115                 120                 125

Gly His Phe Val Ser Glu Lys Asp Gly His Lys Thr Thr Ile Ser Pro
        130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Glu Lys Ala Asn Ser Ser
210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
        275                 280                 285

Pro Leu His Ser Gln Ser Pro Glu Ser Gln Thr Lys Ser Pro Asn Leu
    290                 295                 300

Ser Val Asp Leu Asn Ser Glu Gly Ile Gly Ser Gly Gly Ser Ala
305                 310                 315                 320

Lys Gly Glu Leu Arg Gly His Pro Phe Glu Gly Lys Pro Ile Pro Asn
                325                 330                 335

Pro Leu Leu Gly Leu Asp Ser Thr Arg Thr Gly His His His His His
            340                 345                 350

His Gly Ser
        355

<210> SEQ ID NO 106
<211> LENGTH: 380
<212> TYPE: PRT
<213> ORGANISM: Trifolium repens

<400> SEQUENCE: 106

Met Asn Gly Gly Ser Thr Val Ser Phe Arg Ser Ile Leu Asp Lys Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn
        35                  40                  45

Lys Ser Gln Ala Ile Gln Gln Val Ile Ser Leu Lys Ala Leu Leu Glu
    50                  55                  60

Pro Thr Asp Asp Leu Pro Ala Pro Val Gly Val Ser Ser Ala Ile
65                  70                  75                  80

His His His His His His Pro Gln Pro Gln Arg Asn Leu Asn
                85                  90                  95
```

-continued

```
Glu Ala Pro Val Lys Gly Ser Asp Leu Asp Asp Thr Gly Phe His Thr
            100                 105                 110

Ala Glu Asp Leu Asn Lys Ser Thr Ser Thr Ala Val Glu Ile Pro Thr
        115                 120                 125

Glu Thr Asn Asp Ala Asn Val Val Lys Ser Ser Gly Gly Cys Val Ala
    130                 135                 140

Ser Gly Ser Phe Gly Gln Met Thr Ile Phe Tyr Cys Gly Lys Val Asn
145                 150                 155                 160

Val Tyr Asp Gly Val Ser Pro Asp Lys Ala Arg Ser Ile Met Gln Leu
                165                 170                 175

Ala Ala Cys Pro Ser Ser Phe Pro Gln Asp Asn Leu Leu Asn Lys Asn
            180                 185                 190

Ala Ala Val Trp Ala Ser Pro Cys Asn Ile Pro Ile Asp Lys Asp Val
        195                 200                 205

Leu Phe Pro Asn Asp Thr Ala Ile Leu Gln Val Ala Gln Thr Asp Lys
    210                 215                 220

Met Val Glu Tyr Pro Leu Gln Tyr Arg Glu Lys Gly Ser Ile Ala Arg
225                 230                 235                 240

Asp Ala Asp Val Glu Gly Gln Ala Ser Arg Asn Ala Ser Leu Gln Arg
                245                 250                 255

Tyr Arg Glu Lys Arg Lys Asp Arg Gly Arg Ser Lys Gly Asn Lys Leu
            260                 265                 270

Thr Gly Ile Thr Ser Ser Asn Phe Glu Met Tyr Leu Asn Leu Pro Val
        275                 280                 285

Lys Leu His Ala Ser Asn Gly Asn Ser Ser Arg Ser Ser Thr Asp Ser
    290                 295                 300

Pro Pro Gln Pro Arg Leu Pro Leu Val Ser Gly Ser Ala Glu Asn
305                 310                 315                 320

Gln Pro Lys Val Thr Leu Pro Ile Asp Leu Asn Asp Lys Asp Val Gln
                325                 330                 335

Glu Cys Gly Ser Gly Gly Gly Ser Ala Lys Gly Glu Leu Arg Gly His
            340                 345                 350

Pro Phe Glu Gly Lys Pro Ile Pro Asn Pro Leu Leu Gly Leu Asp Ser
        355                 360                 365

Thr Arg Thr Gly His His His His His Gly Ser
    370                 375                 380

<210> SEQ ID NO 107
<211> LENGTH: 353
<212> TYPE: PRT
<213> ORGANISM: Amborella trichopoda

<400> SEQUENCE: 107

Met Thr Ala Gly Asp Gly Ser Ile Arg Ser Ile Leu Asp Lys Pro Leu
1               5                   10                  15

Glu Glu Leu Thr Glu Glu Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Tyr Gln Ala Ile Gln Gln Val Leu Ser Leu Lys Gly Leu Leu Glu Gly
    50                  55                  60

Lys Pro Cys Asp Asp Asn Ser Asp Val Phe Ser His Arg Ser Pro Ile
65                  70                  75                  80

Thr Val Ile Pro Asn Val Gly Ser Met Arg Glu Lys Glu Lys Ala Val
                85                  90                  95
```

Asn Ile Ala Asp Pro Glu Ile Ser Gly Ser His Gln Pro Asn Phe Arg
            100                 105                 110

Arg Glu Ile His Glu Thr Thr Arg Glu Arg Ala Leu Pro Ala Ser Asp
        115                 120                 125

Trp Pro Ser Gln Glu Pro Val Ser Gln Met Thr Ile Phe Tyr Ala
130                 135                 140

Gly Ala Val Asn Val Tyr Asn Asp Ile Pro Glu Asp Lys Val Gln Ala
145                 150                 155                 160

Ile Ile Tyr Leu Ala Gly Lys Ser Asp Ser Leu Gln Gln Thr Asn Val
                165                 170                 175

Ile Arg Thr Gly Pro Asp Gln Cys Ile Ala Ser Ala Ser Pro Ser
            180                 185                 190

Leu Asn Asp Leu His Ser Arg Arg Ile His Pro Thr Ser Asn Ile Thr
        195                 200                 205

Thr Ser Gln Ser Leu Arg Val Ala Thr Ser Leu Pro Val Gly Pro His
210                 215                 220

Ser Glu Val Pro Lys Thr Arg Lys Thr Ser Val Gln Arg Phe Leu Glu
225                 230                 235                 240

Lys Arg Lys Asp Arg Gly Arg Leu Lys Gly Thr Leu Ala Ser Gly Gly
                245                 250                 255

Ser Ser Lys Arg Gly Ser Ser Cys Leu Glu Leu Tyr Ala Thr Ser Arg
            260                 265                 270

Leu Lys Ser Glu Gly Val Ala Thr Thr Thr Gln Ser Asn Met Asn
        275                 280                 285

Asn Val Val Ser Pro Ser Asn Pro Arg Met Pro Leu Asn Pro Gly
        290                 295                 300

Ser Cys Ser Trp Val Glu Asn Gly Ser Gly Gly Ser Ala Lys Gly
305                 310                 315                 320

Glu Leu Arg Gly His Pro Phe Glu Gly Lys Pro Ile Pro Asn Pro Leu
                325                 330                 335

Leu Gly Leu Asp Ser Thr Arg Thr Gly His His His His His Gly
            340                 345                 350

Ser

<210> SEQ ID NO 108
<211> LENGTH: 335
<212> TYPE: PRT
<213> ORGANISM: Musa acuminata

<400> SEQUENCE: 108

Met Asn Pro Gly Glu Thr Thr Pro Pro Ser Pro Leu Asp Lys Pro Leu
1               5                   10                  15

Ala Glu Leu Thr Glu Glu Asp Ile Ala Gln Leu Thr Arg Glu Asp Cys
                20                  25                  30

Arg Arg Phe Leu Lys Ala Lys Gly Met Arg Arg Pro Ser Trp Asn Lys
            35                  40                  45

Ser Gln Ala Ile Gln Gln Val Ile Ser Leu Lys Ala Leu Leu Glu Gly
        50                  55                  60

Arg Pro Gly Cys Asp Asp Cys Pro Ala Gly Gly Ile Leu Gln Lys
65                  70                  75                  80

Leu Leu Thr Ser Ser Pro Ser Glu Pro Leu Ser Pro Pro Gln Asp Ser
                85                  90                  95

Pro Pro Pro Ala Pro Lys Glu Gly Gly Ser Gly Ser Gln Pro Leu Ala
            100                 105                 110

-continued

```
Lys Glu Pro Ser Pro Tyr Arg Arg Asp Pro Ile Pro Pro Tyr
            115                 120                 125

Ser Ala Gly Asn Pro Thr Cys Gln Thr Pro Ile Ala Gly Ala Asp Leu
130                 135                 140

Pro His Pro Pro Glu Lys Arg Cys Pro Ser Pro Arg Leu Thr Ala Glu
145                 150                 155                 160

Val Pro Val Gly Gln Met Thr Ile Phe Tyr Asp Gly Met Val Asn Val
                165                 170                 175

Tyr Asp Gly Val Ser Ala Asp Gln Ala Arg Ser Ile Met Glu Leu Ala
            180                 185                 190

Ala Ser Pro Val Cys Phe Asp Asp Pro Thr Gly Ala Phe Ser Pro Ala
        195                 200                 205

Arg Pro Pro Ala Phe Arg Phe Pro Pro Gly Leu Pro Arg Pro Ala Pro
    210                 215                 220

Val Pro Thr Ala Pro Ser Phe Val Gly Thr Phe Pro Ile Ser Pro Ala
225                 230                 235                 240

Gly Lys Arg Cys Tyr Ser Tyr Cys Ser Phe Arg Ser Ser Val Ser Leu
                245                 250                 255

Leu Thr Thr Thr Glu Gly Pro Thr Ser Arg Lys Ala Ser Leu Gln Arg
            260                 265                 270

Tyr Leu Glu Lys Arg Lys Asp Arg Tyr Gly His Leu Pro Thr Glu Ser
        275                 280                 285

Ile Leu Leu Val Ser Gly Ser Gly Gly Ser Ala Lys Gly Glu Leu
    290                 295                 300

Arg Gly His Pro Phe Glu Gly Lys Pro Ile Pro Asn Pro Leu Leu Gly
305                 310                 315                 320

Leu Asp Ser Thr Arg Thr Gly His His His His His His Gly Ser
                325                 330                 335

<210> SEQ ID NO 109
<211> LENGTH: 264
<212> TYPE: PRT
<213> ORGANISM: Picea sitchensis

<400> SEQUENCE: 109

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
                20                  25                  30

Asp Cys Arg Arg Tyr Leu Lys Glu Lys Gly Met Arg Arg Pro Ser Trp
            35                  40                  45

Asn Lys Ser Gln Ala Ile Gln Gln Val Leu Ser Leu Lys Ser Leu Phe
50                  55                  60

Glu Ser Lys Pro Asn Gln Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

Thr Glu Gly Lys Arg Cys Ala His Asp Gly His Gly Arg Lys Ser Ala
```

```
            145                 150                 155                 160
        Gln Pro Leu Val Arg Leu Pro Ala Asn Phe Lys Asn Asp Cys Ser Asn
                        165                 170                 175

Arg Gln Ser Ser His Thr Ser Glu Ser Gln Pro Asp Thr Leu Leu Arg
                        180                 185                 190

Ser Asp Ser Phe Gln Gln Pro Thr Ala Gln Leu Thr Ile Phe Tyr Ala
                        195                 200                 205

Gly Met Val Asn Val Tyr Asp Asp Val Pro Leu Asp Lys Ala Gly Ser
                210                 215                 220

Gly Gly Gly Ser Ala Lys Gly Glu Leu Arg Gly His Pro Phe Glu Gly
        225                 230                 235                 240

Lys Pro Ile Pro Asn Pro Leu Leu Gly Leu Asp Ser Thr Arg Thr Gly
                        245                 250                 255

His His His His His His Gly Ser
                        260

<210> SEQ ID NO 110
<211> LENGTH: 276
<212> TYPE: PRT
<213> ORGANISM: Selaginella moellendorffii

<400> SEQUENCE: 110

Met Ser Ser Met Val Asp Phe Leu Gly Ile Glu Glu Lys Val Ser Thr
        1               5                   10                  15

Ser Val Ser Ala Glu Arg Leu Lys Lys Leu Glu Glu Leu Thr Asp Glu
                        20                  25                  30

Asp Val Met Gln Leu Thr Arg Glu Asp Cys Arg Arg Tyr Leu Lys Glu
                        35                  40                  45

Lys Gly Met Arg Arg Pro Ser Trp Asn Lys Ala Gln Ala Val Gln Gln
                50                  55                  60

Leu Leu Ser Leu Lys Ser Leu Cys Asp Pro Ser Pro Ala Ser Ser Gly
        65                  70                  75                  80

Ala Ala Lys Arg Ser Pro Ser Pro Leu Asp Glu Ala Pro Ala Lys
                        85                  90                  95

Lys Pro Met Ala Met Thr Ser Ile Asp Leu Lys Ala Ala Ala Val
                        100                 105                 110

Asp Ala Ala Asn Leu Thr Met Phe Tyr Asp Gly Ala Val Ser Val Phe
                        115                 120                 125

Asp Asp Val Ser Pro Asp Lys Ala Ser Leu Phe Pro Leu Ala Tyr Ala
                130                 135                 140

Ile Met Leu Leu Ala Gly Asn Val Lys Ser Trp Pro Ser Ile Asn Val
        145                 150                 155                 160

Ala Ala Asn Thr Asn Lys Val Val Ile Ser Ser Tyr Glu Leu Pro Gln
                        165                 170                 175

Ala Arg Lys Ala Ser Leu Gln Arg Phe Leu Gln Arg Arg Glu Lys
                        180                 185                 190

Thr Ala Lys Glu Ala Ala Ser Lys Gly Asn Ser Asn Lys Ser Pro Cys
                        195                 200                 205

His Gly Glu Ser Gly Lys His Ala Ser Asp Ala Thr Asp Pro Ala
                210                 215                 220

Thr Ser Pro Leu Leu Thr Glu Val Ser Ser Gly Ser Gly Gly Ser
        225                 230                 235                 240

Ala Lys Gly Glu Leu Arg Gly His Pro Phe Glu Gly Lys Pro Ile Pro
                        245                 250                 255
```

Asn Pro Leu Leu Gly Leu Asp Ser Thr Arg Thr Gly His His His
            260                 265                 270

His His Gly Ser
        275

<210> SEQ ID NO 111
<211> LENGTH: 315
<212> TYPE: PRT
<213> ORGANISM: Arabidopsis thaliana

<400> SEQUENCE: 111

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Lys Ala Asn Ser Ser
    210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Leu Glu Met Phe Leu Asn Cys Gln
            260                 265                 270

Pro Arg Met Lys Ala Ala Tyr Ser Gln Asn Leu Gly Cys Thr Gly Ser
        275                 280                 285

Pro Leu His Ser Gln Ser Pro Glu Ser Gln Thr Lys Ser Pro Asn Leu
    290                 295                 300

Ser Val Asp Leu Asn Ser Glu Gly Ile Gly Ser
305                 310                 315

<210> SEQ ID NO 112
<211> LENGTH: 340
<212> TYPE: PRT
<213> ORGANISM: Trifolium repens

<400> SEQUENCE: 112

Met Asn Gly Gly Ser Thr Val Ser Phe Arg Ser Ile Leu Asp Lys Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn
        35                  40                  45

Lys Ser Gln Ala Ile Gln Gln Val Ile Ser Leu Lys Ala Leu Leu Glu
    50                  55                  60

Pro Thr Asp Asp Asp Leu Pro Ala Pro Val Gly Val Ser Ser Ala Ile
65                  70                  75                  80

His His His His His His Pro Gln Pro Pro Gln Arg Asn Leu Asn
                85                  90                  95

Glu Ala Pro Val Lys Gly Ser Asp Leu Asp Asp Thr Gly Phe His Thr
            100                 105                 110

Ala Glu Asp Leu Asn Lys Ser Thr Ser Thr Ala Val Glu Ile Pro Thr
        115                 120                 125

Glu Thr Asn Asp Ala Asn Val Val Lys Ser Ser Gly Gly Cys Val Ala
    130                 135                 140

Ser Gly Ser Phe Gly Gln Met Thr Ile Phe Tyr Cys Gly Lys Val Asn
145                 150                 155                 160

Val Tyr Asp Gly Val Ser Pro Asp Lys Ala Arg Ser Ile Met Gln Leu
                165                 170                 175

Ala Ala Cys Pro Ser Ser Phe Pro Gln Asp Asn Leu Leu Asn Lys Asn
            180                 185                 190

Ala Ala Val Trp Ala Ser Pro Cys Asn Ile Pro Ile Asp Lys Asp Val
        195                 200                 205

Leu Phe Pro Asn Asp Thr Ala Ile Leu Gln Val Ala Gln Thr Asp Lys
    210                 215                 220

Met Val Glu Tyr Pro Leu Gln Tyr Arg Glu Lys Gly Ser Ile Ala Arg
225                 230                 235                 240

Asp Ala Asp Val Glu Gly Gln Ala Ser Arg Asn Ala Ser Leu Gln Arg
                245                 250                 255

Tyr Arg Glu Lys Arg Lys Asp Arg Gly Arg Ser Lys Gly Asn Lys Leu
            260                 265                 270

Thr Gly Ile Thr Ser Ser Asn Phe Glu Met Tyr Leu Asn Leu Pro Val
        275                 280                 285

Lys Leu His Ala Ser Asn Gly Asn Ser Ser Arg Ser Ser Thr Asp Ser
    290                 295                 300

Pro Pro Gln Pro Arg Leu Pro Leu Val Ser Gly Ser Ala Glu Asn
305                 310                 315                 320

Gln Pro Lys Val Thr Leu Pro Ile Asp Leu Asn Asp Lys Asp Val Gln
                325                 330                 335

Glu Cys Gly Ser
            340

<210> SEQ ID NO 113
<211> LENGTH: 313
<212> TYPE: PRT
<213> ORGANISM: Amborella trichopoda

<400> SEQUENCE: 113

Met Thr Ala Gly Asp Gly Ser Ile Arg Ser Ile Leu Asp Lys Pro Leu
1               5                   10                  15

Glu Glu Leu Thr Glu Glu Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Tyr Gln Ala Ile Gln Gln Val Leu Ser Leu Lys Gly Leu Leu Glu Gly
    50                  55                  60

Lys Pro Cys Asp Asp Asn Ser Asp Val Phe Ser His Arg Ser Pro Ile
65                  70                  75                  80

Thr Val Ile Pro Asn Val Gly Ser Met Arg Glu Lys Glu Lys Ala Val
                85                  90                  95

Asn Ile Ala Asp Pro Glu Ile Ser Gly Ser His Gln Pro Asn Phe Arg
            100                 105                 110

Arg Glu Ile His Glu Thr Thr Arg Glu Arg Ala Leu Pro Ala Ser Asp
        115                 120                 125

Trp Pro Pro Ser Gln Glu Pro Val Ser Gln Met Thr Ile Phe Tyr Ala
    130                 135                 140

Gly Ala Val Asn Val Tyr Asn Asp Ile Pro Glu Asp Lys Val Gln Ala
145                 150                 155                 160

Ile Ile Tyr Leu Ala Gly Lys Ser Asp Ser Leu Gln Gln Thr Asn Val
                165                 170                 175

Ile Arg Thr Gly Pro Asp Gln Cys Ile Ala Ser Ala Ser Pro Ser
            180                 185                 190

Leu Asn Asp Leu His Ser Arg Arg Ile His Pro Thr Ser Asn Ile Thr
        195                 200                 205

Thr Ser Gln Ser Leu Arg Val Ala Thr Ser Leu Pro Val Gly Pro His
    210                 215                 220

Ser Glu Val Pro Lys Thr Arg Lys Thr Ser Val Gln Arg Phe Leu Glu
225                 230                 235                 240

Lys Arg Lys Asp Arg Gly Arg Leu Lys Gly Thr Leu Ala Ser Gly Gly
                245                 250                 255

Ser Ser Lys Arg Gly Ser Ser Cys Leu Glu Leu Tyr Ala Thr Ser Arg
            260                 265                 270

Leu Lys Ser Glu Gly Val Ala Thr Thr Thr Gln Ser Asn Met Asn
        275                 280                 285

Asn Val Val Val Ser Pro Ser Asn Pro Arg Met Pro Leu Asn Pro Gly
    290                 295                 300

Ser Cys Ser Trp Val Glu Asn Gly Ser
305                 310

<210> SEQ ID NO 114
<211> LENGTH: 295
<212> TYPE: PRT
<213> ORGANISM: Musa acuminata

<400> SEQUENCE: 114

Met Asn Pro Gly Glu Thr Thr Pro Pro Ser Pro Leu Asp Lys Pro Leu
1               5                   10                  15

Ala Glu Leu Thr Glu Glu Asp Ile Ala Gln Leu Thr Arg Glu Asp Cys
            20                  25                  30

Arg Arg Phe Leu Lys Ala Lys Gly Met Arg Arg Pro Ser Trp Asn Lys
        35                  40                  45

Ser Gln Ala Ile Gln Gln Val Ile Ser Leu Lys Ala Leu Leu Glu Gly
    50                  55                  60

Arg Pro Gly Cys Asp Asp Cys Pro Ala Gly Gly Gly Ile Leu Gln Lys

```
                65                  70                  75                  80
Leu Leu Thr Ser Ser Pro Ser Glu Pro Leu Ser Pro Pro Gln Asp Ser
                85                  90                  95
Pro Pro Pro Ala Pro Lys Glu Gly Ser Gly Ser Gln Pro Leu Ala
            100                 105                 110
Lys Glu Pro Ser Pro Tyr Arg Arg Asp Pro Ile Pro Pro Pro Tyr
            115                 120                 125
Ser Ala Gly Asn Pro Thr Cys Gln Thr Pro Ile Ala Gly Ala Asp Leu
130                 135                 140
Pro His Pro Pro Glu Lys Arg Cys Pro Ser Pro Arg Leu Thr Ala Glu
145                 150                 155                 160
Val Pro Val Gly Gln Met Thr Ile Phe Tyr Asp Gly Met Val Asn Val
                165                 170                 175
Tyr Asp Gly Val Ser Ala Asp Gln Ala Arg Ser Ile Met Glu Leu Ala
                180                 185                 190
Ala Ser Pro Val Cys Phe Asp Asp Pro Thr Gly Ala Phe Ser Pro Ala
                195                 200                 205
Arg Pro Pro Ala Phe Arg Phe Pro Pro Gly Leu Pro Arg Pro Ala Pro
210                 215                 220
Val Pro Thr Ala Pro Ser Phe Val Gly Thr Phe Pro Ile Ser Pro Ala
225                 230                 235                 240
Gly Lys Arg Cys Tyr Ser Tyr Cys Ser Phe Arg Ser Ser Val Ser Leu
                245                 250                 255
Leu Thr Thr Thr Glu Gly Pro Thr Ser Arg Lys Ala Ser Leu Gln Arg
                260                 265                 270
Tyr Leu Glu Lys Arg Lys Asp Arg Tyr Gly His Leu Pro Thr Glu Ser
            275                 280                 285
Ile Leu Leu Val Ser Gly Ser
            290                 295

<210> SEQ ID NO 115
<211> LENGTH: 224
<212> TYPE: PRT
<213> ORGANISM: Picea abies

<400> SEQUENCE: 115

Met Arg Gly Gly Glu Arg Ala Pro Gly Ser Arg Pro Ser Leu Asp Lys
1               5                   10                  15
Pro Leu Glu Glu Leu Thr Glu Glu Asp Ile Phe Gln Leu Thr Arg Glu
                20                  25                  30
Asp Cys Arg Arg Tyr Leu Lys Glu Lys Gly Met Arg Arg Pro Ser Trp
            35                  40                  45
Asn Lys Ser Gln Ala Ile Gln Gln Val Leu Ser Leu Lys Ser Leu Phe
        50                  55                  60
Glu Ser Lys Pro Asn Gln Gln Ser Lys Pro Ser Lys His Lys Pro
65                  70                  75                  80
Ala Thr Leu Gln Phe Glu Thr Ala Arg Asp Ser Thr Phe Ala Gln Ser
                85                  90                  95
Ser Val Ser Gln Glu Gln Ser Leu Gly Phe Ser Trp Ser Lys Glu Val
            100                 105                 110
Leu Asp Lys Gly Thr Ala Glu Arg Gln Arg Leu Cys Ser Asp Ser Gln
        115                 120                 125
Glu Ala His Glu Ile Pro Arg Leu Gly Ser Lys Pro Pro Gln Ser Asn
    130                 135                 140
```

```
Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175

Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
        195                 200                 205

Gly Met Val Asn Val Tyr Asp Asp Val Pro Leu Asp Lys Ala Gly Ser
    210                 215                 220
```

<210> SEQ ID NO 116
<211> LENGTH: 236
<212> TYPE: PRT
<213> ORGANISM: Selaginella moellendorffii

<400> SEQUENCE: 116

```
Met Ser Ser Met Val Asp Phe Leu Gly Ile Glu Glu Lys Val Ser Thr
1               5                   10                  15

Ser Val Ser Ala Glu Arg Leu Lys Lys Leu Glu Glu Leu Thr Asp Glu
            20                  25                  30

Asp Val Met Gln Leu Thr Arg Glu Asp Cys Arg Arg Tyr Leu Lys Glu
        35                  40                  45

Lys Gly Met Arg Arg Pro Ser Trp Asn Lys Ala Gln Ala Val Gln Gln
    50                  55                  60

Leu Leu Ser Leu Lys Ser Leu Cys Asp Pro Ser Pro Ala Ser Ser Gly
65                  70                  75                  80

Ala Ala Lys Arg Ser Pro Ser Pro Pro Leu Asp Glu Ala Pro Ala Lys
                85                  90                  95

Lys Pro Met Ala Met Thr Ser Ile Asp Leu Lys Ala Ala Ala Ala Val
            100                 105                 110

Asp Ala Ala Asn Leu Thr Met Phe Tyr Asp Gly Ala Val Ser Val Phe
        115                 120                 125

Asp Asp Val Ser Pro Asp Lys Ala Ser Leu Phe Pro Leu Ala Tyr Ala
    130                 135                 140

Ile Met Leu Leu Ala Gly Asn Val Lys Ser Trp Pro Ser Ile Asn Val
145                 150                 155                 160

Ala Ala Asn Thr Asn Lys Val Val Ile Ser Ser Tyr Glu Leu Pro Gln
                165                 170                 175

Ala Arg Lys Ala Ser Leu Gln Arg Phe Leu Gln Arg Arg Glu Lys
            180                 185                 190

Thr Ala Lys Glu Ala Ala Ser Lys Gly Asn Ser Asn Lys Ser Pro Cys
    195                 200                 205

His Gly Glu Ser Ser Gly Lys His Ala Ser Asp Ala Thr Asp Pro Ala
    210                 215                 220

Thr Ser Pro Leu Leu Thr Glu Val Ser Ser Gly Ser
225                 230                 235
```

<210> SEQ ID NO 117
<211> LENGTH: 1226
<212> TYPE: DNA
<213> ORGANISM: Arabidopsis thaliana

<400> SEQUENCE: 117

```
acaagtttgt acaaaaaagc aggctcaaaa aaaaccatgg acgtgggcgt gtccccggcc      60
aagtctattc tcgccaagcc ggtaatgttc agctctgcta tagtgtgtgc caccctgctt     120
```

```
gtttaataat gcgttctctt cgtttttatg atatcttatt cttccagctc aagctcctca      180
ccgaggagga catctctcag ctcacaagag aggactgccg caagttcctc aaggacaagg      240
gcatgagaag gccgtcctgg aacaagtccc aggccatcca acaagtgctc agcctcaagg      300
ccctctacga gccaggcgac gactccggcg ctggcatttt cagaaagatc ctcgtgtccc      360
agccggtgaa cccaccaagg gtgaccacca cactcatcga gccgtccaat gagcttgagg      420
cctgcggcag agtttcctac ccagaggata atggcgcctg ccacaggatg gattctccaa      480
ggtctgctga gttctctggc ggctccggcc atttcgtgtc tgagaaggat ggccacaaga      540
ccaccatctc cccaagatcc ccagccgaga catctgagct tgtgggccag atgaccatct      600
tctactccgg caaggtgaac gtgtacgacg gcatcccacc agagaaggcc cgctccatta      660
tgcacttcgc cgccaaccca atcgacctcc agagaatgg catcttcgcc tccagccgca      720
tgatctccaa gctcatctcc aaggagaaga tgatggagct gccgcagaag ggcctcgaga      780
aggctaattc ctctcgcgac tccggcatgg agggccaggc taatagaaag gtgtccctcc      840
aacgctaccg cgagaagagg aaggaccgca agttctccaa ggccaagaag tgcccaggcg      900
ttgcctcttc cagcctcgag atgttcctca actgccagcc gagaatgaag gccgcctact      960
cccaaaatct cggctgcaca ggctccccac tccattctca gtccccagag tctcagacca     1020
agtccccgaa cctctccgtg gaccttaact ccgagggcat cggatccggc ggcggctctg     1080
ctaagggcga gctgaggggc caccccgttcg agggcaagcc aattccaaat ccactcctcg     1140
gcctcgactc taccaggacc ggccaccatc accatcacca cggatcctaa tgaagaccca     1200
gctttcttgt acaaagtggt caggct                                          1226

<210> SEQ ID NO 118
<211> LENGTH: 1295
<212> TYPE: DNA
<213> ORGANISM: Trifolium repens

<400> SEQUENCE: 118
acaagtttgt acaaaaaagc aggctcaaaa aaaaccatga acggcggctc caccgtgtcc       60
ttcagatcca tcctcgataa gccggtaatg ttcagctctg ctatagtgtg tgccaccctg      120
cttgtttaat aatgcgttct cttcgttttt atgatatctt attcttccag ctcaaccagc      180
tcaccgagga cgacatctct cagctcacac gcgaggatta ccgccgcttc cttaaggaca      240
agggcatgag aaggccgtcc tggaacaagt cccaggccat ccagcaagtg atctccctca      300
aggctctcct cgagccgacc gacgatgatc tcccagcccc ggtgggcgtg tcatctgcca      360
tccaccatca ccaccaccac catcctcaac cgccacagag gaacctcaat gaggccccag      420
ttaagggctc cgacctcgac gataccggct tccatacagc cgaggacctc aacaagtcta      480
cctccaccgc cgtcgagatc ccgaccgaga caaacgatgc caacgtggtg aagtctagcg      540
gcggctgcgt ggcctccggc tccttcggcc agatgaccat tttctactgc ggcaaggtga      600
acgtgtacga cggcgtgtca ccagataagg cccgctccat tatgcaactc gccgcttgcc      660
catctagctt cccgcaggat aacctcctca caagaacgc cgccgtttgg gcctccccat      720
gcaacatccc gatcgacaag gatgtcctct tcccgaacga caccgccatt ctccaggtgg      780
cccagaccga taagatggtc gagtacccac tccagtaccg cgagaagggc tctattgcca      840
gggatgccga tgttgagggc caggcctcca gaaatgcttc cctgcaacgc tatcgcgaga      900
agcgcaagga cagaggcaga tccaagggca acaagctgac cggcatcacc tcctccaact      960
```

```
tcgagatgta cctcaacctc ccggtgaagc tccatgcctc caacggcaac tcctctaggt    1020
cctccacaga ttccccaccg cagccaagac tcccactcgt gtccggcggc tctgccgaga    1080
accagccaaa ggtgaccctc ccgatcgacc tcaacgacaa ggacgtgcaa gagtgcggat    1140
ccggcggcgg ctctgctaag ggcgagctga ggggccaccc gttcgagggc aagccaattc    1200
caaatccact cctcggcctc gactctacca ggaccggcca ccatcaccat caccacggat    1260
cctaatgaag acccagcttt cttgtacaaa gtggt    1295
```

<210> SEQ ID NO 119
<211> LENGTH: 1214
<212> TYPE: DNA
<213> ORGANISM: Amborella trichopoda

<400> SEQUENCE: 119

```
acaagtttgt acaaaaaagc aggctcaaaa aaaaccatga cagccggcga cggctccatc     60
cgctctatcc ttgacaagcc ggtaatgttc agctctgcta tagtgtgtgc caccctgctt    120
gtttaataat gcgttctctt cgtttttatg atatcttatt cttccagctc gaggagctga    180
ccgaggagga catctctcaa ctcacccgcg aggattgccg ccgctacctc aaggagaagg    240
ggatgcgcag gccatcctgg aacaagtacc aggccatcca gcaggtcctc agcctcaagg    300
gcctcctcga gggcaagcca tgcgacgata actccgacgt gttctcccac aggtccccga    360
tcaccgtgat cccaaatgtt ggctccatgc gcgagaagga gaaggccgtc aatatcgccg    420
acccagagat ctccggctcc caccagccga actttaggcg cgagatccat gagacaacac    480
gcgagagagc cctcccagct tctgattggc cgccgtcaca gagccagtg tcccagatga    540 ccatcttcta cgctggcgcc gtgaacgtgt acaacgacat cccagaggac aaggtgcagg    600
ccatcatcta cctcgccggc aagtctgatt ccctccagca gaccaacgtg atcaggaccg    660
gcccagatca gtgcattgct tctgctgctt ccccgtccct caacgacctc cattctaggc    720
gcatccaccc gacctccaac atcaccacat ctcagtctct ccgcgtggcc acatctctcc    780
cagtgggccc gcactccgag gtgccaaaga ccagaaagac aagcgtgcag cgcttcctcg    840
agaagaggaa ggatagggc aggctcaagg gcacactcgc ctccggcggc tcctccaaga    900
ggggctcctc ctgcctcgag ctttacgcta catcccgcct taagtctgag gcgtggcca    960 ccacaaccac ccagtccaac atgaacaacg tggtggtgtc cccgtccaac ccgaggatgc    1020
cgctcaaccc gggctcctgc tcctgggtcg agaacggatc cggcggcggc tctgctaagg    1080
gcgagctgag ggggccacccg ttcgagggca agccaattcc aaatccactc ctcggcctcg    1140
actctaccag gaccggccac catcaccatc accacggatc ctaatgaaga cccagcttc    1200 ttgtacaaag tggt    1214
```

<210> SEQ ID NO 120
<211> LENGTH: 1160
<212> TYPE: DNA
<213> ORGANISM: Musa acuminata

<400> SEQUENCE: 120

```
acaagtttgt acaaaaaagc aggctcaaaa aaaaccatga cccgggcga gacaaccccg     60 ccatctccac ttgacaagcc ggtaatgttc agctctgcta tagtgtgtgc caccctgctt    120
gtttaataat gcgttctctt cgtttttatg atatcttatt cttccagctc gccgagctga    180
ccgaggagga tattgctcaa ctcacccgcg aggactgccg cagattcctt aaggctaagg    240
gcatgcgcag gccgtcctgg aacaagtctc aggccatcca gcaagtgatc tccctcaagg    300
```

```
ctctcctcga gggcaggcca ggttgcgatg actgcccggc cggcggcggc atcctccaga    360
agctcctcac ctccagcccg tctgagccgc tctcccgcc acaggactcc ccgccaccgg    420
ctccaaaaga gggcggctcc ggctcccagc ctctcgccaa ggagccgtcc ccgtacaggc    480
gcagggaccc gatcccgcca ccgtactccg ccggcaaccc gacctgccag accccgatcg    540
ctggcgccga cctcccgcac ccgccagaga agaggtgccc gtccccgagg ctcacagccg    600
aggtgccggt gggccagatg accattttct acgacggcat ggtgaacgtg tacgacggcg    660
tgtcagctga tcaggcccgc tccattatgg agcttgccgc ttctccggtg tgcttcgatg    720
atccaacagg cgcctttagc ccagccagac caccagcttt cagattccca ccaggcctcc    780
caaggccagc tccggtgccg accgccccgt ccttcgtggg caccttcccg atctccccag    840
ccggcaagag atgctactcc tactgctcct tccgctcctc cgtgtcactc ctcacaacaa    900
ccgagggccc aacatctagg aaggcctcac tccaacgcta cctcgagaag cgcaaggaca    960
ggtacggcca tctcccaacc gagtccattc tcctcgtgtc cggatccggc ggcggctctg    1020
ctaagggcga gctgaggggc caccngttcg agggcaagcc aattccaaat ccactcctcg    1080
gcctcgactc taccaggacc ggccaccatc accatcacca cggatcctaa tgaagaccca    1140
gctttcttgt acaaagtggt                                                1160
```

<210> SEQ ID NO 121
<211> LENGTH: 947
<212> TYPE: DNA
<213> ORGANISM: Picea sitchensis

<400> SEQUENCE: 121

```
acaagtttgt acaaaaaagc aggctcaaaa aaaaccatga gaggcggcga gagagcccca     60
ggctccaggc cggtaatgtt cagctctgct atagtgtgtg ccaccctgct tgtttaataa    120
tgcgttctct tcgttttttat gatatcttat tcttccagtc cctcgacaag ccgctcgagg    180
agcttaccga ggaggacatc ttccagctca cccgcgagga ttgcaggcgc tacctcaagg    240
agaaggggat gagaaggccg tcctggaaca agtcccaggc catccaacaa gtgctcagcc    300
tcaagagcct cttcgagtcc aagccgaacc agcagtccaa gaagccgtcc aagcacaagc    360
cagccacccct ccaattcgag acagccaggg attctacctt cgcccagtcc tccgtgtccc    420
aagagcaatc tctcggcttc tcctggtcca aggaggtgct cgataagggc acagccgaga    480
gacaaaggct ctgctccgat tcccaagagg cccacgagat tccaaggctc ggctctaagc    540
caccgcagtc caacaccgag ggcaagagat gcgctcatga tggccatggg agaaagtccg    600
cccaaccact cgttaggctc ccggccaact tcaagaacga ctgctccaac aggcagtcct    660
cccacacatc tgagtcccag ccagataccc tcctccgctc cgattctttc agcagccaa    720
cagcccagct caccatcttc tacgccggca tggtgaacgt gtacgacgac gtgccactcg    780
acaaggccgg atccggcggc ggctctgcta agggcgagct gaggggccac ccgttcgagg    840
gcaagccaat tccaaatcca ctcctcggcc tcgactctac caggaccggc caccatcacc    900
atcaccacgg atcctaatga agacccagct ttcttgtaca aagtggt              947
```

<210> SEQ ID NO 122
<211> LENGTH: 897
<212> TYPE: DNA
<213> ORGANISM: Selaginella moellendorffii

<400> SEQUENCE: 122

```
acaagtttgt acaaaaaagc aggctcaaaa aaaaccatgt cctcgatggt ggacttcctc      60
ggcatcgagg agaaggtgtc cacctccgtg tccgccgaga ggctcaagaa gctcgaggag     120
ctgaccgacg aggacgtgat gcaactcaca cgcgaggatt gccgccgcta ccttaaggag     180
aaggggatga aaggccgtc ctggaacaag gcccaagccg tgcaacaact cctcagcctc      240
aagtccctct gcgatccatc tccggcctcc agcggagctg ccaagaggtc cccgtccccg     300
ccactcgacg aggccccagc caagaagccg atggccatga cctccatcga tctcaaggcc     360
gctgccgccg ttgatgccgc caatctcacc atgttctacg acggcgccgt gtccgtgttc     420
gatgatgtgt ctccagacaa ggcctcctc ttcccactcg cctacgccat tatgctcctc      480
gccggcaatg tgaagtcctg gccgtctatc aacgtggccg ccaacaccaa caaggtggtg     540
atctccagct acgagctgcc gcaagctaga aaggcttccc tccagcgctt ccttcagaga     600
aggcgcgaga agacagccaa ggaggccgct tctaagggca actccaacaa gtccccatgc     660
cacggcgagt ctagcggcaa gcacgcctct gatgctaccg atccagctac ctctccactc     720
ctcacagagg tgtcatccgg atccggcggc ggctctgcta agggcgagct gaggggccac     780
ccgttcgagg gcaagccaat tccaaatcca ctcctcggcc tcgactctac caggaccggc     840
caccatcacc atcaccacgg atcctaatga agacccagct ttcttgtaca aagtggt       897
```

`<210>` SEQ ID NO 123
`<211>` LENGTH: 1134
`<212>` TYPE: DNA
`<213>` ORGANISM: Arabidopsis thaliana

`<400>` SEQUENCE: 123

```
acaagtttgt acaaaaaagc aggctcaaaa aaaaccatgg atgtgggagt gtctccagct      60
aagtctatcc ttgctaagcc ctcaagctc ctcaccgaag aggatatctc tcagctcact      120
agagaggatt gcagaaagtt cctcaaggat aagggaatga aaggccatc ttggaacaag      180
tctcaggcta tccagcaggt tctcagtctc aaggctcttt acgagcctgg tgatgattct     240
ggtgctggaa tcttcagaaa gatcctcgtg tctcagcctg tgaaccctcc tagagttact     300
actactctca tcgagccttc taacgagctt gaggcttgcg gaaagagtttc ttaccctgag    360
gataacggtg cttgccacag gatggattct ccaagatctg ctgagttctc tggtggatct     420
ggacacttcg tgtctgagaa ggatggacac aagactacta tctctccaag aagtcctgct    480
gagacttctg agcttgtggg acagatgacc atcttctact ctggaaaggt gaacgtgtac    540
gatggaatcc ctcctgagaa ggctagatct atcatgcact tcgctgctaa ccctatcgat   600
ctccctgaga acggaatctt cgcttcttct aggatgatct ctaagctcat ctctaaagaa   660
aagatgatgg aactccctca gaagggactc gagaaggcta actcttctag ggattctgga   720
atggaaggac aggctaacag aaaggtgtca ctccagaggt acagagagaa gaggaaggat  780
aggaagttct ctaaggctaa gaaatgccct ggtgtggctt cttcatctct cgagatgttc  840
cttaactgcc agcctaggat gaaggctgct tactctcaga acctcggatg tactggatct  900
ccactccatt ctcagtctcc agagtctcag accaagtctc ctaacctctc tgtggatctc  960
aactctgagg gaatcggatc cggtggtgga tctgctaagg gtgagcttag aggtcatcct 1020
ttcgagggta agcctatccc taaccctctt ctcggtctcg attctactag aactggtcat 1080
catcatcacc atcacggatc ctaatgaaga cccagctttc ttgtacaaag tggt         1134
```

`<210>` SEQ ID NO 124
`<211>` LENGTH: 1209

<212> TYPE: DNA
<213> ORGANISM: Trifolium repens

<400> SEQUENCE: 124

```
acaagtttgt acaaaaaagc aggctcaaaa aaaaccatga acggtggatc taccgtgtct    60
ttcagatcta tcctcgataa gcctctcaac cagctcaccg aggatgatat ctctcagctc   120
actagagagg attgcagaag attcctcaag gataagggaa tgagaaggcc atcttggaac   180
aagtctcagg ctatccagca ggttatctct ctcaaggctc tcctcgagcc taccgatgat   240
gatcttcctg ctcctgtggg agtgtcatct gctatccatc atcatcacca tcaccaccct   300
caacctccac agagaaatct taacgaggct cctgtgaagg atctgatct cgatgatact    360
ggattccaca ccgctgagga tctcaacaag tctacttcta ccgctgttga gatccctacc   420
gagactaacg atgctaacgt ggtgaagtca tctggtggat gtgtggcttc tggatctttc   480
ggacagatga ccatcttcta ctgcggaaag gtgaacgtgt acgatggtgt gtctcctgat   540
aaggctagat ctatcatgca gctcgctgct tgcccttcta gtttccctca ggataacctc   600
ctcaacaaga acgctgctgt ttgggcttct ccttgcaaca tccctattga taaggatgtt   660
ctcttcccta acgataccgc tatcctccaa gtggctcaga ccgataagat ggttgagtac   720
cctctccagt acagagagaa gggatctatc gctagggatg ctgatgttga gggacaggct   780
tctagaaacg cttcactcca gaggtacagg gaaaagagga aggataggg aaggtctaag    840
ggaaacaagc tcaccggaat cacctcttct aacttcgaga tgtacctcaa cctccctgtg   900
aagctccatg cttctaacgg aaactcttct aggtctagta ccgattcacc tcctcagcct   960
agactccctc ttgtttctgg tggatctgct gagaaccagc taaggttac actccctatc   1020
gatctcaacg ataaggatgt gcaagagtgc ggatccggtg gtggatctgc taagggtgag   1080
cttagaggtc atcctttcga gggtaagcct atccctaacc ctcttctcgg tctcgattct   1140
actagaactg gtcatcatca tcaccatcac ggatcctaat gaagacccag ctttcttgta   1200
caaagtggt                                                          1209
```

<210> SEQ ID NO 125
<211> LENGTH: 1128
<212> TYPE: DNA
<213> ORGANISM: Amborella trichopoda

<400> SEQUENCE: 125

```
acaagtttgt acaaaaaagc aggctcaaaa aaaaccatga ccgctggtga tggatctatc    60
agatctatcc tcgataagcc tctcgaggaa ctcaccgaag aggatatctc tcagctcacc   120
agagaggatt gcagaagata cctcaaagaa aagggtatga aaggccatc ttggaacaag    180
taccaggcta tccagcaggt tctcagtctt aagggacttc tcgagggaaa gccttgtgat   240
gataactctg atgtgttctc tcacaggtca cctatcaccg tgatccctaa cgtgggatct   300
atgagagaga aagagaaggc tgttaacatt gctgatcctg agatctctgg ttctcaccag   360
cctaactta gaagagagat ccacgagact accagagaga gagctttgcc tgcttctgat    420
tggcctccat ctcaagagcc tgtgtctcag atgaccatct tctacgctgg tgctgtgaac   480
gtgtacaacg atatccctga ggataaggtg caggctatca tctacctcgc tggaaagtct   540
gattctctcc agcagaccaa cgtgatcaga actggacctg atcagtgtat cgcttctgct   600
gcttctcctt ctctcaacga tctccactct agaagaatcc accctacctc taacatcacc   660
acctctcagt ctctcagagt ggctacttct cttcctgtgg gacctcattc tgaggtgcca   720
```

| | |
|---|---|
| aagactagaa agacctctgt gcagagattc ctcgagaaga ggaaggatag aggtaggctc | 780 |
| aagggaactc ttgcttctgg tggatcttct aagaggggat cttcttgcct cgagctttac | 840 |
| gctacctcta ggcttaagtc tgagggtgtg gctactacta ccacccagtc taacatgaac | 900 |
| aacgtggtgg tgtctccatc taaccctagg atgcctctta accctggatc ttgctcttgg | 960 |
| gttgagaacg gatccggtgg tggatctgct aagggtgagc ttagaggtca tcctttcgag | 1020 |
| ggtaagccta tccctaaccc tcttctcggt ctcgattcta ctagaactgg tcatcatcat | 1080 |
| caccatcacg gatcctaatg aagacccagc tttcttgtac aaagtggt | 1128 |

<210> SEQ ID NO 126
<211> LENGTH: 1074
<212> TYPE: DNA
<213> ORGANISM: Musa acuminata

<400> SEQUENCE: 126

| | |
|---|---|
| acaagtttgt acaaaaaagc aggctcaaaa aaaaccatga accctggtga gactacccct | 60 |
| ccatctccac ttgataagcc tctcgctgag cttaccgaag aggatatcgc tcagctcact | 120 |
| agagaggatt gcagaagatt cctcaaggct aagggaatga aaggccatc ttggaacaag | 180 |
| tctcaggcta tccagcaggt tatctctctc aaggctctcc ttgaaggtag gcctggatgt | 240 |
| gatgattgtc ctgctggtgg tggaatcctc cagaagctcc ttacttctag tccttctgag | 300 |
| cctctcagtc ctcctcaaga ttctccacct cctgctccta agagggagg atctggatct | 360 |
| cagcctcttg ctaaagagcc ttctccatac agaagaagag atcctatccc tcctccttac | 420 |
| tctgctggaa accctacttg tcagactcct atcgctggtg ctgatcttcc tcatcctcct | 480 |
| gagaagagat gcccatctcc tagacttact gctgaggttc cagtgggaca tgatgaccatc | 540 |
| ttctacgatg aatggtgaa cgtgtacgat ggtgtgtctg ctgatcaggc tagatctatt | 600 |
| atggaactcg ctgcttctcc tgtgtgcttc gatgatccta ctggtgcttt cagtcctgct | 660 |
| agacctcctg cttttagatt ccctccagga cttcctagac ctgctcctgt tcctactgct | 720 |
| ccttctttcg ttggaaccctt ccctatctct cctgctggaa agaggtgcta ctcttactgc | 780 |
| tctttcaggt ctagtgtgtc tctcttgact accactgagg gacctacctc tagaaaggct | 840 |
| tcactccaga gatacctcga agaggaag gatagatacg gacacctccc taccgagtct | 900 |
| atccttctcg tttctggatc cggtggtgga tctgctaagg gtgagcttag aggtcatcct | 960 |
| ttcgagggta gcctatccc taaccctctt ctcggtctcg attctactag aactggtcat | 1020 |
| catcatcacc atcacggatc ctaatgaaga cccagctttc ttgtacaaag tggt | 1074 |

<210> SEQ ID NO 127
<211> LENGTH: 1233
<212> TYPE: DNA
<213> ORGANISM: Picea abies

<400> SEQUENCE: 127

| | |
|---|---|
| acaagtttgt acaaaaaagc aggctcaaaa aaaaccatga ggggtggtgg tggtgctgat | 60 |
| agacttcctg ctagagctaa ccttgagaag cctctcgagg atctctctca cgaggatatc | 120 |
| atgcagctca ccagagagga ttgcagaaga tacctcatcg agaagggaat gagaaggcca | 180 |
| tcttggaaca agtctcaggc tatccagcag gttctcagtc tcaagaagct tttcgagtct | 240 |
| ggacctaacg atgagaagag gtcgctgct accaacaggc taatcctga tgagaacctc | 300 |
| aaagaggctg cttctgtttc tctcttgtac ggatctcagc tgagtctcc ttctgtggtg | 360 |
| ttcgcttcta aggattctga taccttcaac ctcgagtggc tcgctaagac tgagcttcct | 420 |

```
gttcttgctt ctcagcctag gcatatcgct cagcagaacg tgttcctctc ttcactttct      480
gctcagcagt ctggtgctca gctcaccatt ttctactctg gaaacgtgaa cgtgtacgat      540
gatgtgcctg ctgagaaggc tcaagagatc atgcttcttg ctggatctgg aaactaccct      600
ccttcatcta cttgccagtc taccagaaac acccagcaga acgctgttag agctgcttac      660
ccttctaacc ctaccaacac cccttcatc catggtgttg daccacctct tgctaccgtg       720
gcttcttctt ctgtgatgtc atctcctatc cacaaagagt ctccaatcac cagaaaggct      780
tcactccaga gattcctcga agaggaag ataggtcta ggggtaagct tggtgctcct        840
actatctcta agaaacctct cctcatggga atgttcatgc acccttctat cgtgcacaga      900
cagtactgga ctgataccgc taagaggaag tctggaaagc ctgatatccc tgcttctatc      960
tctcctacca gacctcctca cactcctaga aggacatctt ctgatgagca gctctctgct     1020
agacacgcta ggggagatat ttctgctcaa ggtggaagtc tccacaactc taacggatcc     1080
ggtggtggat ctgctaaggg tgagcttaga ggtcatcctt tcgagggtaa gcctatcct     1140 aaccctcttc tcggtctcga ttctactaga actggtcatc atcatcacca tcacggatcc     1200
taatgaagac ccagctttct tgtacaaagt ggt                                 1233
```

<210> SEQ ID NO 128
<211> LENGTH: 897
<212> TYPE: DNA
<213> ORGANISM: Selaginella moellendorffii

<400> SEQUENCE: 128

```
acaagtttgt acaaaaaagc aggctcaaaa aaaaccatgt caagtatggt ggatttcctc       60
ggaatcgaag agaaggttc aacctctgtg tctgctgaga ggcttaagaa gctcgaggaa       120
ctcactgatg aggatgtgat gcagctcacc agagaggatt gcagaagata cctcaaagaa      180
aagggtatga aaggccatc ttggaacaag gctcaagctg ttcagcagct cctcagtctt       240
aagtctctct gcgatccttc accagcttca tctggtgctg ctaagagatc tccttcacct       300
cctttggatg aggctcctgc taagaaacct atggctatga cctctatcga tctcaaggct      360
gctgctgctg ttgatgctgc taacctcacc atgttctacg atggtgctgt gtctgtgttc      420
gatgatgtgt ctcctgataa ggcttctctc ttcccactcg cttacgctat catgcttctc      480
gctggaaacg tgaagtcttg gccttctatc aacgtggcag ctaacaccaa caaggtggtg      540
atctcttctt acgaactccc tcaggctagg aaggcttcac ttcagagatt cctccagaga      600
agaagggaaa agaccgctaa agaggctgct tctaagggaa actctaacaa gtctccttgc      660
cacggtgagt ctagtggaaa gcacgcttct gatgctactg atcctgctac ttctccactc      720
ctcactgagg tgtcatctgg atccggtggt ggatctgcta agggtgagct tagaggtcat      780
cctttcgagg gtaagcctat ccctaaccct cttctcggtc tcgattctac tagaactggt      840
catcatcatc accatcacgg atcctaatga agacccagct ttcttgtaca aagtggt        897
```

<210> SEQ ID NO 129
<211> LENGTH: 1345
<212> TYPE: DNA
<213> ORGANISM: Artificial Sequence
<220> FEATURE:
<223> OTHER INFORMATION: Construct

<400> SEQUENCE: 129

```
tcgacgaatt aattccaatc ccacaaaaat ctgagcttaa cagcacagtt gctcctctca       60
```

```
gagcagaatc gggtattcaa caccctcata tcaactacta cgttgtgtat aacggtccac    120
atgccggtat atacgatgac tggggttgta caaaggcggc aacaaacggc gttcccggag    180
ttgcacacaa gaaatttgcc actattacag aggcaagagc agcagctgac gcgtacacaa    240
caagtcagca aacagacagg ttgaacttca tccccaaagg agaagctcaa ctcaagccca    300
agagctttgc taaggcccta caagcccacc aaagcaaaa agcccactgg ctcacgctag    360
gaaccaaaag gcccagcagt gatccagccc caaaagagat ctccttttgcc ccggagatta    420 caatggacga tttcctctat ctttacgatc taggaaggaa gttcgaaggt gaaggtgacg    480
acactatgtt caccactgat aatgagaagg ttagcctctt caatttcaga agaatgctg    540 acccacagat ggttagagag gcctacgcag caggtctcat caagacgatc tacccgagta    600
acaatctcca ggagatcaaa taccttccca gaaggttaa agatgcagtc aaaagattca    660
ggactaattg catcaagaac acagagaaag acatatttct caagatcaga agtactattc    720
cagtatggac gattcaaggc ttgcttcata aaccaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga agaaaatctt cgtcaacatg gtggagcacg acactctggt ctactccaaa    960
aatgtcaaag atacagtctc agaagaccaa agggctattg agacttttca acaaaggata    1020
atttcgggaa acctcctcgg attccattgc ccagctatct gtcacttcat cgaaaggaca    1080
gtagaaaagg aaggtggctc ctacaaatgc catcattgcg ataaaggaaa ggctatcatt    1140
caagatctct ctgccgacag tggtcccaaa gatggacccc cacccacgag gagcatcgtg    1200
gaaaaagaag acgttccaac cacgtcttca aagcaagtgg attgatgtga catctccact    1260
gacgtaaggg atgacgcaca atcccactat ccttcgcaag acccttcctc tatataagga    1320
agttcatttc atttggagag gacac                                          1345
```

<210> SEQ ID NO 130
<211> LENGTH: 224
<212> TYPE: PRT
<213> ORGANISM: Picea sitchensis

<400> SEQUENCE: 130

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
            20                  25                  30

Asp Cys Arg Arg Tyr Leu Lys Glu Lys Gly Met Arg Arg Pro Ser Trp
        35                  40                  45

Asn Lys Ser Gln Ala Ile Gln Gln Val Leu Ser Leu Lys Ser Leu Phe
    50                  55                  60

Glu Ser Lys Pro Asn Gln Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

-continued

```
Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175

Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
        195                 200                 205

Gly Met Val Asn Val Tyr Asp Asp Val Pro Leu Asp Lys Ala Gly Ser
    210                 215                 220
```

<210> SEQ ID NO 131
<211> LENGTH: 26
<212> TYPE: DNA
<213> ORGANISM: Artificial Sequence
<220> FEATURE:
<223> OTHER INFORMATION: Consensus sequence

<400> SEQUENCE: 131
gctggggcgt cggtttccac tatccg                                  26

<210> SEQ ID NO 132
<211> LENGTH: 27
<212> TYPE: DNA
<213> ORGANISM: Artificial Sequence
<220> FEATURE:
<223> OTHER INFORMATION: Consensus sequence

<400> SEQUENCE: 132
cgcataacag cggtcattga ctggagc                                 27

<210> SEQ ID NO 133
<211> LENGTH: 20
<212> TYPE: DNA
<213> ORGANISM: Artificial Sequence
<220> FEATURE:
<223> OTHER INFORMATION: Consensus sequence

<400> SEQUENCE: 133
ctgttgccgg tcttgcgatg                                         20

<210> SEQ ID NO 134
<211> LENGTH: 20
<212> TYPE: DNA
<213> ORGANISM: Artificial Sequence
<220> FEATURE:
<223> OTHER INFORMATION: Consensus sequence

<400> SEQUENCE: 134
gtcacataga tgacaccgcg                                         20

<210> SEQ ID NO 135
<211> LENGTH: 24
<212> TYPE: DNA
<213> ORGANISM: Artificial Sequence
<220> FEATURE:
<223> OTHER INFORMATION: Consensus sequence

<400> SEQUENCE: 135
ctcgtgcttt cagcttcgat gtag                                    24

<210> SEQ ID NO 136
<211> LENGTH: 26
<212> TYPE: DNA

```
<213> ORGANISM: Artificial Sequence
<220> FEATURE:
<223> OTHER INFORMATION: Consensus sequence

<400> SEQUENCE: 136
gctggggcgt cggtttccac tatcgg                                          26

<210> SEQ ID NO 137
<211> LENGTH: 21
<212> TYPE: DNA
<213> ORGANISM: Artificial Sequence
<220> FEATURE:
<223> OTHER INFORMATION: Consensus sequence

<400> SEQUENCE: 137
cacaggatgg attctccaag g                                               21

<210> SEQ ID NO 138
<211> LENGTH: 20
<212> TYPE: DNA
<213> ORGANISM: Artificial Sequence
<220> FEATURE:
<223> OTHER INFORMATION: Consensus sequence

<400> SEQUENCE: 138
taaggtccac ggagaggttc                                                 20

<210> SEQ ID NO 139
<211> LENGTH: 12
<212> TYPE: DNA
<213> ORGANISM: Artificial Sequence
<220> FEATURE:
<223> OTHER INFORMATION: Construct

<400> SEQUENCE: 139
gatctataga tc                                                         12

<210> SEQ ID NO 140
<211> LENGTH: 12
<212> TYPE: DNA
<213> ORGANISM: Artificial Sequence
<220> FEATURE:
<223> OTHER INFORMATION: Construct

<400> SEQUENCE: 140
ctagatatct ag                                                         12

<210> SEQ ID NO 141
<211> LENGTH: 12
<212> TYPE: DNA
<213> ORGANISM: Artificial Sequence
<220> FEATURE:
<223> OTHER INFORMATION: Construct

<400> SEQUENCE: 141
gatctataga tc                                                         12

<210> SEQ ID NO 142
<211> LENGTH: 12
<212> TYPE: DNA
<213> ORGANISM: Artificial Sequence
<220> FEATURE:
<223> OTHER INFORMATION: Construct

<400> SEQUENCE: 142
ctagatatct ag                                                         12
```

<210> SEQ ID NO 143
<211> LENGTH: 46
<212> TYPE: PRT
<213> ORGANISM: Amborella trichopoda

<400> SEQUENCE: 143

Leu Glu Glu Leu Thr Glu Glu Asp Ile Ser Gln Leu Thr Arg Glu Asp
1               5                   10                  15

Cys Arg Arg Tyr Leu Lys Glu Lys Gly Met Arg Arg Pro Ser Trp Asn
            20                  25                  30

Lys Tyr Gln Ala Ile Gln Gln Val Leu Ser Leu Lys Gly Leu
        35                  40                  45

<210> SEQ ID NO 144
<211> LENGTH: 46
<212> TYPE: PRT
<213> ORGANISM: Picea sitchensis

<400> SEQUENCE: 144

Leu Glu Glu Leu Thr Glu Glu Asp Ile Phe Gln Leu Thr Arg Glu Asp
1               5                   10                  15

Cys Arg Arg Tyr Leu Lys Glu Lys Gly Met Arg Arg Pro Ser Trp Asn
            20                  25                  30

Lys Ser Gln Ala Ile Gln Gln Val Leu Ser Leu Lys Ser Leu
        35                  40                  45

<210> SEQ ID NO 145
<211> LENGTH: 46
<212> TYPE: PRT
<213> ORGANISM: Spirodela polyrrhiza

<400> SEQUENCE: 145

Leu Ser Glu Leu Thr Glu Glu Asp Ile Ala Gln Val Thr Arg Glu Asp
1               5                   10                  15

Cys Arg Arg Phe Leu Lys Glu Lys Gly Met Arg Arg Pro Ser Trp Asn
            20                  25                  30

Lys Ser Gln Ala Val Gln Gln Val Ile Ser Leu Lys Ala Leu
        35                  40                  45

<210> SEQ ID NO 146
<211> LENGTH: 46
<212> TYPE: PRT
<213> ORGANISM: Selaginella moellendorffii

<400> SEQUENCE: 146

Leu Glu Glu Leu Thr Glu Leu Asp Ile Arg Gln Leu Thr Arg Glu Asp
1               5                   10                  15

Cys Arg Arg Tyr Leu Lys Glu Arg Gly Met Arg Arg Pro Ser Trp Asn
            20                  25                  30

Lys Ala Gln Ala Ile Gln Gln Val Leu Ser Leu Arg Ser Leu
        35                  40                  45

<210> SEQ ID NO 147
<211> LENGTH: 46
<212> TYPE: PRT
<213> ORGANISM: Selaginella moellendorffii

<400> SEQUENCE: 147

Leu Glu Glu Leu Thr Asp Glu Asp Val Met Gln Leu Thr Arg Glu Asp
1               5                   10                  15

```
Cys Arg Arg Tyr Leu Lys Glu Lys Gly Met Arg Arg Pro Ser Trp Asn
                20                  25                  30

Lys Ala Gln Ala Val Gln Gln Leu Leu Ser Leu Lys Ser Leu
        35                  40                  45

<210> SEQ ID NO 148
<211> LENGTH: 46
<212> TYPE: PRT
<213> ORGANISM: Musa species

<400> SEQUENCE: 148

Leu Ala Glu Leu Thr Glu Glu Asp Ile Ala Gln Leu Thr Arg Glu Asp
1               5                   10                  15

Cys Arg Arg Phe Leu Lys Ala Lys Gly Met Arg Arg Pro Ser Trp Asn
                20                  25                  30

Lys Ser Gln Ala Ile Gln Gln Val Ile Ser Leu Lys Ala Leu
        35                  40                  45

<210> SEQ ID NO 149
<211> LENGTH: 46
<212> TYPE: PRT
<213> ORGANISM: Elaeis guineensis

<400> SEQUENCE: 149

Leu Ser Glu Leu Thr Glu Glu Asp Ile Ala Gln Leu Thr Arg Glu Asp
1               5                   10                  15

Cys Arg Arg Phe Leu Lys Glu Lys Gly Met Arg Arg Pro Ser Trp Asn
                20                  25                  30

Lys Ser Gln Ala Ile Gln Gln Val Ile Ser Leu Lys Ala Leu
        35                  40                  45

<210> SEQ ID NO 150
<211> LENGTH: 46
<212> TYPE: PRT
<213> ORGANISM: Phalaenopsis aphrodite

<400> SEQUENCE: 150

Leu Asn Leu Leu Thr Glu Asp Asp Ile Ala Gln Ile Thr Arg Glu Glu
1               5                   10                  15

Cys Arg Arg Phe Leu Lys Asp Arg Gly Met Arg Arg Pro Ser Trp Asn
                20                  25                  30

Lys Ser Gln Ala Ile Gln Gln Val Ile Ser Leu Lys Ala Leu
        35                  40                  45

<210> SEQ ID NO 151
<211> LENGTH: 46
<212> TYPE: PRT
<213> ORGANISM: Nicotiana tabacum

<400> SEQUENCE: 151

Leu His Leu Leu Thr Asp Asp Asp Ile Ser Gln Leu Thr Arg Glu Asp
1               5                   10                  15

Cys Arg Arg Tyr Leu Lys Glu Lys Gly Met Arg Arg Pro Ser Trp Asn
                20                  25                  30

Lys Ser Gln Ala Ile Gln Gln Val Ile Ser Leu Lys Ala Leu
        35                  40                  45

<210> SEQ ID NO 152
<211> LENGTH: 46
<212> TYPE: PRT
```

<213> ORGANISM: Solanum lycopersicum

<400> SEQUENCE: 152

Leu Tyr Leu Leu Thr Asp Asp Ile Ser Gln Leu Thr Arg Glu Asp
1               5                   10                  15

Cys Arg Arg Phe Leu Lys Ala Lys Gly Met Arg Lys Pro Ser Trp Asn
            20                  25                  30

Lys Ser Gln Ala Ile Gln Gln Val Ile Ser Leu Lys Ala Leu
        35                  40                  45

<210> SEQ ID NO 153
<211> LENGTH: 46
<212> TYPE: PRT
<213> ORGANISM: Solanum tuberosum

<400> SEQUENCE: 153

Leu Asn Gln Leu Thr Asp Asp Ile Ser Gln Leu Thr Arg Glu Asp
1               5                   10                  15

Cys Arg Arg Tyr Leu Lys Gln Lys Gly Met Arg Lys Pro Ser Trp Asn
            20                  25                  30

Lys Ser Gln Ala Ile Gln Gln Val Ile Ser Leu Lys Ala Leu
        35                  40                  45

<210> SEQ ID NO 154
<211> LENGTH: 46
<212> TYPE: PRT
<213> ORGANISM: Aquilegia coerulea

<400> SEQUENCE: 154

Leu Phe Gln Leu Thr Asp Glu Asp Ile Ser Gln Leu Thr Arg Glu Asp
1               5                   10                  15

Cys Arg Lys Phe Leu Arg Asp Lys Gly Met Arg Arg Pro Ser Trp Asn
            20                  25                  30

Lys Ser Gln Ala Ile Glu Gln Val Ile Ser Leu Lys Thr Leu
        35                  40                  45

<210> SEQ ID NO 155
<211> LENGTH: 46
<212> TYPE: PRT
<213> ORGANISM: Populus trichocarpa

<400> SEQUENCE: 155

Leu His Gln Leu Thr Glu Asp Asp Ile Ser Gln Val Thr Arg Glu Asp
1               5                   10                  15

Cys Arg Arg Tyr Leu Lys Glu Lys Gly Met Arg Arg Pro Ser Trp Asn
            20                  25                  30

Lys Ser Gln Ala Ile Gln Gln Val Ile Ser Leu Lys Thr Leu
        35                  40                  45

<210> SEQ ID NO 156
<211> LENGTH: 46
<212> TYPE: PRT
<213> ORGANISM: Glycine max

<400> SEQUENCE: 156

Leu Asn Gln Leu Thr Glu Asp Asp Ile Ser Gln Leu Thr Arg Glu Asp
1               5                   10                  15

Cys Arg Arg Phe Leu Lys Glu Lys Gly Met Arg Arg Pro Ser Trp Asn
            20                  25                  30

Lys Ser Gln Ala Ile Gln Gln Val Ile Ser Leu Lys Ala Leu

<210> SEQ ID NO 157
<211> LENGTH: 46
<212> TYPE: PRT
<213> ORGANISM: Medicago truncatula

<400> SEQUENCE: 157

Leu Trp Gln Leu Thr Glu Asp Asp Ile Ser Gln Leu Thr Arg Glu Asp
1               5                   10                  15

Cys Arg Arg Phe Leu Lys Asp Lys Gly Met Arg Arg Pro Ser Trp Asn
            20                  25                  30

Lys Ser Gln Ala Ile Gln Gln Val Ile Ser Leu Lys Ala Leu
        35                  40                  45

<210> SEQ ID NO 158
<211> LENGTH: 46
<212> TYPE: PRT
<213> ORGANISM: Trifolium repens

<400> SEQUENCE: 158

Leu Asn Gln Leu Thr Glu Asp Asp Ile Ser Gln Leu Thr Arg Glu Asp
1               5                   10                  15

Cys Arg Arg Phe Leu Lys Asp Lys Gly Met Arg Arg Pro Ser Trp Asn
            20                  25                  30

Lys Ser Gln Ala Ile Gln Gln Val Ile Ser Leu Lys Ala Leu
        35                  40                  45

<210> SEQ ID NO 159
<211> LENGTH: 46
<212> TYPE: PRT
<213> ORGANISM: Arabidopsis thaliana

<400> SEQUENCE: 159

Leu Lys Leu Leu Thr Glu Glu Asp Ile Ser Gln Leu Thr Arg Glu Asp
1               5                   10                  15

Cys Arg Lys Phe Leu Lys Asp Lys Gly Met Arg Arg Pro Ser Trp Asn
            20                  25                  30

Lys Ser Gln Ala Ile Gln Gln Val Leu Ser Leu Lys Ala Leu
        35                  40                  45

<210> SEQ ID NO 160
<211> LENGTH: 46
<212> TYPE: PRT
<213> ORGANISM: Arabidopsis thaliana

<400> SEQUENCE: 160

Leu Lys Leu Leu Thr Glu Glu Asp Ile Ser Gln Leu Thr Arg Glu Asp
1               5                   10                  15

Cys Arg Lys Phe Leu Lys Glu Lys Gly Met Arg Arg Pro Ser Trp Asn
            20                  25                  30

Lys Ser Gln Ala Ile Gln Gln Val Leu Ser Leu Lys Ala Leu
        35                  40                  45

<210> SEQ ID NO 161
<211> LENGTH: 46
<212> TYPE: PRT
<213> ORGANISM: Gossypium raimondii

<400> SEQUENCE: 161

Leu Ser Gln Leu Thr Glu Glu Asp Ile Ser Gln Leu Thr Arg Glu Asp

```
                1               5                  10                  15
Cys Arg Lys Phe Leu Lys Glu Lys Gly Met Arg Arg Pro Ser Trp Asn
                20                  25                  30

Lys Ser Gln Ala Ile Gln Gln Val Ile Ser Phe Lys Ala Leu
                35                  40                  45

<210> SEQ ID NO 162
<211> LENGTH: 46
<212> TYPE: PRT
<213> ORGANISM: Theobroma cacao

<400> SEQUENCE: 162

Leu Ser Gln Leu Thr Glu Glu Asp Ile Ser Gln Leu Thr Arg Glu Asp
1               5                  10                  15

Cys Arg Lys Phe Leu Lys Glu Lys Gly Met Arg Arg Pro Ser Trp Asn
                20                  25                  30

Lys Ser Gln Ala Ile Gln Gln Val Ile Ser Leu Lys Ala Leu
                35                  40                  45

<210> SEQ ID NO 163
<211> LENGTH: 46
<212> TYPE: PRT
<213> ORGANISM: Citrus clementine

<400> SEQUENCE: 163

Leu Ser Gln Leu Thr Glu Glu Asp Ile Thr Gln Leu Thr Arg Glu Asp
1               5                  10                  15

Cys Arg Lys Phe Leu Lys Glu Lys Gly Met Arg Arg Pro Ser Trp Asn
                20                  25                  30

Lys Ser Gln Ala Ile Gln Gln Val Ile Ser Leu Lys Ala Leu
                35                  40                  45

<210> SEQ ID NO 164
<211> LENGTH: 46
<212> TYPE: PRT
<213> ORGANISM: Morus notabilis

<400> SEQUENCE: 164

Leu Asn Gln Leu Thr Glu Asp Asp Ile Ser Gln Leu Thr Arg Glu Asp
1               5                  10                  15

Cys Arg Lys Tyr Leu Lys Glu Lys Gly Met Arg Arg Pro Ser Trp Asn
                20                  25                  30

Lys Ser Gln Ala Ile Gln Gln Val Ile Ser Leu Lys Ala Leu
                35                  40                  45

<210> SEQ ID NO 165
<211> LENGTH: 46
<212> TYPE: PRT
<213> ORGANISM: Ricinus communis

<400> SEQUENCE: 165

Leu Thr Gln Leu Thr Glu Glu Asp Ile Ser Gln Leu Thr Arg Glu Asp
1               5                  10                  15

Cys Arg Lys Tyr Leu Lys Glu Lys Gly Met Arg Arg Pro Ser Trp Asn
                20                  25                  30

Lys Ser Gln Ala Ile Gln Gln Val Ile Ser Leu Lys Ala Leu
                35                  40                  45

<210> SEQ ID NO 166
<211> LENGTH: 46
```

```
<212> TYPE: PRT
<213> ORGANISM: Vitis vinifera

<400> SEQUENCE: 166

Leu His Glu Leu Thr Glu Glu Asp Ile Ser Gln Leu Thr Arg Glu Asp
1               5                   10                  15

Cys Arg Lys Tyr Leu Lys Glu Lys Gly Met Arg Arg Pro Ser Trp Asn
                20                  25                  30

Lys Ser Gln Ala Ile Gln Gln Val Ile Ser Leu Lys Ser Leu
            35                  40                  45

<210> SEQ ID NO 167
<211> LENGTH: 27
<212> TYPE: PRT
<213> ORGANISM: Amborella trichopoda

<400> SEQUENCE: 167

Thr Arg Glu Asp Cys Arg Arg Tyr Leu Lys Glu Lys Gly Met Arg Arg
1               5                   10                  15

Pro Ser Trp Asn Lys Tyr Gln Ala Ile Gln Gln
                20                  25

<210> SEQ ID NO 168
<211> LENGTH: 27
<212> TYPE: PRT
<213> ORGANISM: Picea sitchensis

<400> SEQUENCE: 168

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
                20                  25

<210> SEQ ID NO 169
<211> LENGTH: 27
<212> TYPE: PRT
<213> ORGANISM: Spirodela polyrrhiza

<400> SEQUENCE: 169

Thr Arg Glu Asp Cys Arg Arg Phe Leu Lys Glu Lys Gly Met Arg Arg
1               5                   10                  15

Pro Ser Trp Asn Lys Ser Gln Ala Val Gln Gln
                20                  25

<210> SEQ ID NO 170
<211> LENGTH: 27
<212> TYPE: PRT
<213> ORGANISM: Selaginella moellendorffii

<400> SEQUENCE: 170

Thr Arg Glu Asp Cys Arg Arg Tyr Leu Lys Glu Arg Gly Met Arg Arg
1               5                   10                  15

Pro Ser Trp Asn Lys Ala Gln Ala Ile Gln Gln
                20                  25

<210> SEQ ID NO 171
<211> LENGTH: 27
<212> TYPE: PRT
<213> ORGANISM: Selaginella moellendorffii

<400> SEQUENCE: 171

Thr Arg Glu Asp Cys Arg Arg Tyr Leu Lys Glu Lys Gly Met Arg Arg
```

```
                1               5                   10                  15

Pro Ser Trp Asn Lys Ala Gln Ala Val Gln Gln
            20                  25

<210> SEQ ID NO 172
<211> LENGTH: 27
<212> TYPE: PRT
<213> ORGANISM: Musa species

<400> SEQUENCE: 172

Thr Arg Glu Asp Cys Arg Arg Phe Leu Lys Ala Lys Gly Met Arg Arg
1               5                   10                  15

Pro Ser Trp Asn Lys Ser Gln Ala Ile Gln Gln
            20                  25

<210> SEQ ID NO 173
<211> LENGTH: 27
<212> TYPE: PRT
<213> ORGANISM: Elaeis guineensis

<400> SEQUENCE: 173

Thr Arg Glu Asp Cys Arg Arg Phe Leu Lys Glu Lys Gly Met Arg Arg
1               5                   10                  15

Pro Ser Trp Asn Lys Ser Gln Ala Ile Gln Gln
            20                  25

<210> SEQ ID NO 174
<211> LENGTH: 27
<212> TYPE: PRT
<213> ORGANISM: Phalaenopsis aphrodite

<400> SEQUENCE: 174

Thr Arg Glu Glu Cys Arg Arg Phe Leu Lys Asp Arg Gly Met Arg Arg
1               5                   10                  15

Pro Ser Trp Asn Lys Ser Gln Ala Ile Gln Gln
            20                  25

<210> SEQ ID NO 175
<211> LENGTH: 27
<212> TYPE: PRT
<213> ORGANISM: Nicotiana tabacum

<400> SEQUENCE: 175

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 176
<211> LENGTH: 27
<212> TYPE: PRT
<213> ORGANISM: Solanum lycopersicum

<400> SEQUENCE: 176

Thr Arg Glu Asp Cys Arg Arg Phe Leu Lys Ala Lys Gly Met Arg Lys
1               5                   10                  15

Pro Ser Trp Asn Lys Ser Gln Ala Ile Gln Gln
            20                  25

<210> SEQ ID NO 177
<211> LENGTH: 27
<212> TYPE: PRT
```

<213> ORGANISM: Solanum tuberosum

<400> SEQUENCE: 177

Thr Arg Glu Asp Cys Arg Arg Tyr Leu Lys Gln Lys Gly Met Arg Lys
1               5                   10                  15

Pro Ser Trp Asn Lys Ser Gln Ala Ile Gln Gln
            20                  25

<210> SEQ ID NO 178
<211> LENGTH: 27
<212> TYPE: PRT
<213> ORGANISM: Aquilegia coerulea

<400> SEQUENCE: 178

Thr Arg Glu Asp Cys Arg Lys Phe Leu Arg Asp Lys Gly Met Arg Arg
1               5                   10                  15

Pro Ser Trp Asn Lys Ser Gln Ala Ile Glu Gln
            20                  25

<210> SEQ ID NO 179
<211> LENGTH: 27
<212> TYPE: PRT
<213> ORGANISM: Populus trichocarpa

<400> SEQUENCE: 179

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 180
<211> LENGTH: 27
<212> TYPE: PRT
<213> ORGANISM: Glycine max

<400> SEQUENCE: 180

Thr Arg Glu Asp Cys Arg Arg Phe Leu Lys Glu Lys Gly Met Arg Arg
1               5                   10                  15

Pro Ser Trp Asn Lys Ser Gln Ala Ile Gln Gln
            20                  25

<210> SEQ ID NO 181
<211> LENGTH: 27
<212> TYPE: PRT
<213> ORGANISM: Medicago truncatula

<400> SEQUENCE: 181

Thr Arg Glu Asp Cys Arg Arg Phe Leu Lys Asp Lys Gly Met Arg Arg
1               5                   10                  15

Pro Ser Trp Asn Lys Ser Gln Ala Ile Gln Gln
            20                  25

<210> SEQ ID NO 182
<211> LENGTH: 27
<212> TYPE: PRT
<213> ORGANISM: Trifolium repens

<400> SEQUENCE: 182

Thr Arg Glu Asp Cys Arg Arg Phe Leu Lys Asp Lys Gly Met Arg Arg
1               5                   10                  15

Pro Ser Trp Asn Lys Ser Gln Ala Ile Gln Gln
            20                  25

<210> SEQ ID NO 183
<211> LENGTH: 27
<212> TYPE: PRT
<213> ORGANISM: Arabidopsis thaliana

<400> SEQUENCE: 183

Thr Arg Glu Asp Cys Arg Lys Phe Leu Lys Asp Lys Gly Met Arg Arg
1               5                   10                  15

Pro Ser Trp Asn Lys Ser Gln Ala Ile Gln Gln
            20                  25

<210> SEQ ID NO 184
<211> LENGTH: 27
<212> TYPE: PRT
<213> ORGANISM: Arabidopsis thaliana

<400> SEQUENCE: 184

Thr Arg Glu Asp Cys Arg Lys Phe Leu Lys Glu Lys Gly Met Arg Arg
1               5                   10                  15

Pro Ser Trp Asn Lys Ser Gln Ala Ile Gln Gln
            20                  25

<210> SEQ ID NO 185
<211> LENGTH: 27
<212> TYPE: PRT
<213> ORGANISM: Gossypium raimondii

<400> SEQUENCE: 185

Thr Arg Glu Asp Cys Arg Lys Phe Leu Lys Lys Gly Met Arg Arg
1               5                   10                  15

Pro Ser Trp Asn Lys Ser Gln Ala Ile Gln Gln
            20                  25

<210> SEQ ID NO 186
<211> LENGTH: 27
<212> TYPE: PRT
<213> ORGANISM: Theobroma cacao

<400> SEQUENCE: 186

Thr Arg Glu Asp Cys Arg Lys Phe Leu Lys Glu Lys Gly Met Arg Arg
1               5                   10                  15

Pro Ser Trp Asn Lys Ser Gln Ala Ile Gln Gln
            20                  25

<210> SEQ ID NO 187
<211> LENGTH: 27
<212> TYPE: PRT
<213> ORGANISM: Citrus clementine

<400> SEQUENCE: 187

Thr Arg Glu Asp Cys Arg Lys Phe Leu Lys Glu Lys Gly Met Arg Arg
1               5                   10                  15

Pro Ser Trp Asn Lys Ser Gln Ala Ile Gln Gln
            20                  25

<210> SEQ ID NO 188
<211> LENGTH: 27
<212> TYPE: PRT
<213> ORGANISM: Morus notabilis

<400> SEQUENCE: 188

Thr Arg Glu Asp Cys Arg Lys Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 189
<211> LENGTH: 27
<212> TYPE: PRT
<213> ORGANISM: Ricinus communis

<400> SEQUENCE: 189

Thr Arg Glu Asp Cys Arg Lys Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 190
<211> LENGTH: 27
<212> TYPE: PRT
<213> ORGANISM: Vitis vinifera

<400> SEQUENCE: 190

Thr Arg Glu Asp Cys Arg Lys Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 191
<211> LENGTH: 6
<212> TYPE: PRT
<213> ORGANISM: Amborella trichopoda

<400> SEQUENCE: 191

Thr Ile Phe Tyr Ala Gly
1               5

<210> SEQ ID NO 192
<211> LENGTH: 6
<212> TYPE: PRT
<213> ORGANISM: Picea sitchensis

<400> SEQUENCE: 192

Thr Ile Phe Tyr Ala Gly
1               5

<210> SEQ ID NO 193
<211> LENGTH: 6
<212> TYPE: PRT
<213> ORGANISM: Spirodela polyrrhiza

<400> SEQUENCE: 193

Thr Ile Phe Tyr Asp Gly
1               5

<210> SEQ ID NO 194
<211> LENGTH: 6
<212> TYPE: PRT
<213> ORGANISM: Selaginella moellendorffii

<400> SEQUENCE: 194

Thr Ile Phe Tyr Ser Gly
1               5

```
<210> SEQ ID NO 195
<211> LENGTH: 6
<212> TYPE: PRT
<213> ORGANISM: Selaginella moellendorffii

<400> SEQUENCE: 195

Thr Met Phe Tyr Asp Gly
1               5

<210> SEQ ID NO 196
<211> LENGTH: 6
<212> TYPE: PRT
<213> ORGANISM: Musa species

<400> SEQUENCE: 196

Thr Ile Phe Tyr Asp Gly
1               5

<210> SEQ ID NO 197
<211> LENGTH: 6
<212> TYPE: PRT
<213> ORGANISM: Elaeis guineensis

<400> SEQUENCE: 197

Thr Ile Phe Tyr Asp Gly
1               5

<210> SEQ ID NO 198
<211> LENGTH: 6
<212> TYPE: PRT
<213> ORGANISM: Phalaenopsis aphrodite

<400> SEQUENCE: 198

Thr Ile Phe Tyr Gly Gly
1               5

<210> SEQ ID NO 199
<211> LENGTH: 6
<212> TYPE: PRT
<213> ORGANISM: Nicotiana tabacum

<400> SEQUENCE: 199

Thr Ile Phe Tyr Cys Gly
1               5

<210> SEQ ID NO 200
<211> LENGTH: 6
<212> TYPE: PRT
<213> ORGANISM: Solanum lycopersicum

<400> SEQUENCE: 200

Thr Ile Phe Tyr Cys Gly
1               5

<210> SEQ ID NO 201
<211> LENGTH: 6
<212> TYPE: PRT
<213> ORGANISM: Solanum tuberosum

<400> SEQUENCE: 201

Thr Ile Phe Tyr Arg Gly
1               5

<210> SEQ ID NO 202
<211> LENGTH: 6
```

<210> SEQ ID NO 202
<211> LENGTH: 6
<212> TYPE: PRT
<213> ORGANISM: Aquilegia coerulea

<400> SEQUENCE: 202

Thr Ile Phe Tyr Cys Gly
1               5

<210> SEQ ID NO 203
<211> LENGTH: 6
<212> TYPE: PRT
<213> ORGANISM: Populus trichocarpa

<400> SEQUENCE: 203

Thr Ile Phe Tyr Cys Gly
1               5

<210> SEQ ID NO 204
<211> LENGTH: 6
<212> TYPE: PRT
<213> ORGANISM: Glycine max

<400> SEQUENCE: 204

Thr Ile Phe Tyr Cys Gly
1               5

<210> SEQ ID NO 205
<211> LENGTH: 6
<212> TYPE: PRT
<213> ORGANISM: Medicago truncatula

<400> SEQUENCE: 205

Thr Ile Phe Tyr Cys Gly
1               5

<210> SEQ ID NO 206
<211> LENGTH: 6
<212> TYPE: PRT
<213> ORGANISM: Trifolium repens

<400> SEQUENCE: 206

Thr Ile Phe Tyr Cys Gly
1               5

<210> SEQ ID NO 207
<211> LENGTH: 6
<212> TYPE: PRT
<213> ORGANISM: Arabidopsis thaliana

<400> SEQUENCE: 207

Thr Ile Phe Tyr Ser Gly
1               5

<210> SEQ ID NO 208
<211> LENGTH: 6
<212> TYPE: PRT
<213> ORGANISM: Arabidopsis thaliana

<400> SEQUENCE: 208

Thr Ile Phe Tyr Ser Gly
1               5

<210> SEQ ID NO 209
<211> LENGTH: 6
<212> TYPE: PRT
<213> ORGANISM: Gossypium raimondii

```
<400> SEQUENCE: 209

Thr Ile Phe Tyr Cys Gly
1               5

<210> SEQ ID NO 210
<211> LENGTH: 6
<212> TYPE: PRT
<213> ORGANISM: Theobroma cacao

<400> SEQUENCE: 210

Thr Ile Phe Tyr Cys Gly
1               5

<210> SEQ ID NO 211
<211> LENGTH: 6
<212> TYPE: PRT
<213> ORGANISM: Citrus clementine

<400> SEQUENCE: 211

Thr Ile Phe Tyr Cys Gly
1               5

<210> SEQ ID NO 212
<211> LENGTH: 6
<212> TYPE: PRT
<213> ORGANISM: Morus notabilis

<400> SEQUENCE: 212

Thr Ile Phe Tyr Cys Gly
1               5

<210> SEQ ID NO 213
<211> LENGTH: 6
<212> TYPE: PRT
<213> ORGANISM: Ricinus communis

<400> SEQUENCE: 213

Thr Ile Phe Tyr Cys Gly
1               5

<210> SEQ ID NO 214
<211> LENGTH: 6
<212> TYPE: PRT
<213> ORGANISM: Vitis vinifera

<400> SEQUENCE: 214

Thr Ile Phe Tyr Cys Gly
1               5

<210> SEQ ID NO 215
<211> LENGTH: 45
<212> TYPE: PRT
<213> ORGANISM: Artificial Sequence
<220> FEATURE:
<223> OTHER INFORMATION: Construct

<400> SEQUENCE: 215

Leu Lys Leu Leu Thr Glu Glu Asp Ile Ser Gln Leu Thr Arg Glu Asp
1               5                   10                  15

Cys Arg Lys Phe Leu Lys Asp Gly Met Arg Arg Pro Ser Trp Asn Lys
                20                  25                  30

Ser Gln Ala Ile Gln Gln Val Leu Ser Leu Lys Ala Leu
            35                  40                  45
```

```
<210> SEQ ID NO 216
<211> LENGTH: 26
<212> TYPE: PRT
<213> ORGANISM: Artificial Sequence
<220> FEATURE:
<223> OTHER INFORMATION: Construct

<400> SEQUENCE: 216

Glu Gly Gln Ala Asn Arg Lys Val Ser Leu Gln Arg Tyr Arg Glu Lys
1               5                   10                  15

Arg Lys Asp Arg Lys Phe Ser Lys Ala Lys
            20                  25

<210> SEQ ID NO 217
<211> LENGTH: 26
<212> TYPE: PRT
<213> ORGANISM: Artificial Sequence
<220> FEATURE:
<223> OTHER INFORMATION: Construct

<400> SEQUENCE: 217

Val Gly Gln Thr Ile Phe Tyr Ser Gly Ser Gly Lys Val Asn Val Tyr
1               5                   10                  15

Asp Gly Ile Pro Pro Glu Lys Ala Arg Ser
            20                  25
```

METHODS FOR MONOCOT PLANT IMPROVEMENT

TECHNICAL FIELD

The present invention relates methods for producing monocotyledonous plants from the Poaceae family with at least one of: increased root biomass and increased above-ground biomass.

BACKGROUND ART

The Poaceae (also called Gramineae or true grasses) family of monocotyledonous plants is the most economically important plant family in modern times, providing numerous human food crops, and also species useful for forage, building materials (bamboo, thatch) and biofuel production.

Some of these applications are limited in part at least, by the plant's architecture and productivity, including the amount of root biomass and above-ground biomass produced.

Poaceae plants with increased above-ground biomass would have a number of advantages, particularly for crops where above-ground parts of the plant are harvested, in biofuel crops, and in forage crops.

Poaceae plants with increased root biomass would potentially have a number of advantages including better anchorage, more efficient water uptake, more efficient nutrient uptake, and improved drought tolerance. A combination of these features may also result in improved yield, including grain and leaf biomass.

At present there is limited understanding of the genetic mechanisms controlling production of root and above-ground biomass in Poaceae plants.

It would therefore be beneficial to have available alternative methods for controlling root and above-ground biomass in Poaceae plants.

It is therefore an object of the invention to provide methods and materials for altering the production of at least one of root biomass and above-ground biomass in Poaceae plants, and/or at least to provide the public with a useful choice.

SUMMARY OF THE INVENTION

Previously, White (2006) discovered two adjacent homologous genes in *Arabidopsis* (named PEAPOD, PPD1 and PPD2) that regulate the cell proliferation of meristemoids during the late stages of leaf and seed pod development. Homologs of these genes were found in mosses, all dicotyledonous plants, conifers and palms but were found to be absent from the grass family (Poaceae).

Deletion of these genes in *Arabidopsis* resulted in enlarged leaves and wide seed pods while over expression of PPD1 resulted in a reduction in the size of the leaves and siliques (White, 2006). In addition a reduction in PPD expression combined with over expression of either the brassinosteroid receptor (BRI1) or a member of the auxin responsive gene family (SAUR19) demonstrated positive epistasis with respect to leaf growth in *Arabidopsis* (Vanhaeren et al 2014).

The applicants have now surprisingly shown that the expression of PEAPOD proteins in Poaceae plants results in an increase in the production of root and above-ground biomass.

The applicant's invention therefore relates to a method for increasing at least one of root biomass and above-ground biomass in Poaceae plants by ectopic expression of PEAPOD. In particular the invention relates to expressing PEAPOD proteins that are characterized by presence of at least one consensus amino acid motif common to all PEAPOD proteins disclosed from a wide range of plant species.

Because Poaceae plants do not naturally contain PEAPOD genes, the plants used in, or produced by the methods of the invention do not occur in nature.

Methods

In the first aspect the invention provides a method for increasing at least one of root biomass and above-ground biomass and in a Poaceae plant, the method comprising the step of expressing a PEAPOD protein in the Poaceae plant.

In one embodiment at least one of root biomass and above-ground biomass is increased relative to that in a control plant, of the same species or variety, which does not express the PEAPOD protein.

In one embodiment the PEAPOD protein is expressed as a consequence of the plant, or its ancestor plant or plant cell having been transformed with a polynucleotide encoding the PEAPOD protein.

In a further embodiment, the plant is transgenic for a polynucleotide expressing the PEAPOD protein.

In a further aspect the invention provides a method for producing a Poaceae plant with at least one of increased root biomass and increased above-ground biomass, the method comprising the step of expressing a PEAPOD protein in the Poaceae plant.

In one embodiment the Poaceae plant is transformed with a polynucleotide encoding the PEAPOD protein.

In a further embodiment the method comprises the step of transforming the Poaceae plant, or transforming a Poaceae plant cell which is regenerated into the Poaceae plant, with a polynucleotide encoding the PEAPOD protein.

In one embodiment the method includes the additional step of testing or assessing the plant for at least one of increased root biomass and increased above-ground biomass. In one embodiment the method includes the additional step of testing or assessing the plant for increased above-ground biomass. In one embodiment the method includes the additional step of testing or assessing the plant for increased root biomass.

In a further embodiment the method includes the step producing further plants with at least one of increased root biomass and increased above-ground biomass, by asexually or sexually multiplying the plants tested for at least one of increased root biomass and increased above-ground biomass.

PEAPOD Proteins

In one embodiment the PEAPOD protein is a polypeptide comprising the sequence of at least one of SEQ ID NO: 28, 29, 31, 32, 34 and 35.

In a further embodiment the PEAPOD protein comprises the sequence of SEQ ID NO: 28. In a further embodiment the PEAPOD protein comprises the sequence of SEQ ID NO: 29. In a further embodiment the PEAPOD protein comprises the sequence of SEQ ID NO:31. In a further embodiment the PEAPOD protein comprises the sequence of SEQ ID NO:32. In a further embodiment the PEAPOD protein comprises the sequence of SEQ ID NO:34. In a further embodiment the PEAPOD protein comprises the sequence of SEQ ID NO:35.

In a further embodiment the PEAPOD protein is a polypeptide comprising a sequence with at least 70% identity to any one of SEQ ID NO: 1 to 26.

In a further embodiment the PEAPOD protein is a polypeptide comprising a sequence selected from any one of SEQ ID NO: 1 to 26.

In a further embodiment the PEAPOD protein is a polypeptide comprising a sequence with at least 70% identity to SEQ ID NO: 1.

In a further embodiment the PEAPOD protein is a polypeptide comprising the sequence of SEQ ID NO: 1.

Expressing PEAPOD

Methods for expressing proteins in plants are well known to those skilled in the art, and are described herein. All of such methods are included within the scope of the invention.

Increasing Expression of PEAPOD by Introducing a Polynucleotide

In one embodiment expression is increased by introducing a polynucleotide into the plant cell or plant.

In a preferred embodiment the polynucleotide encodes a PEAPOD protein as herein defined.

In a further embodiment the polynucleotide comprises a sequence with at least 70% identity to the coding sequence of any one of SEQ ID NO: 80 to 104.

In a further embodiment the polynucleotide comprises a sequence with at least 70% identity to the sequence of any one of SEQ ID NO: 80 to 104.

In a further embodiment the polynucleotide comprises the coding sequence of any one of SEQ ID NO: 80 to 104.

In a further embodiment the polynucleotide comprises the sequence of any one of SEQ ID NO: 80 to 104.

In a further embodiment the polynucleotide comprises a fragment of the sequences described above, that is capable of encoding a polypeptide with the same function as a PEAPOD protein. In one embodiment the fragment encodes a polypeptide capable of increasing at least one of leaf and root biomass.

Expressing PEAPOD Via an Expression Construct

In a preferred embodiment the polynucleotide is introduced into the plant as part of an expression construct.

In a preferred embodiment the expression construct comprises a promoter operatively linked to the polynucleotide.

Promoter for Increasing Expression of PEAPOD

In one embodiment the promoter is capable of driving, or drives, expression of the operatively linked polynucleotide constitutively in all tissues of the plant.

In a further embodiment the promoter is a tissue-preferred promoter.

In a further embodiment the promoter is capable of driving, or drives, expression of the operatively linked polynucleotide in the above-ground parts of the plant.

In a further embodiment the promoter is capable of driving, or drives, expression of the operatively linked polynucleotide in the leaves of the plant.

In one embodiment the promoter is an above-ground parts-preferred promoter.

In one embodiment the promoter is a leaf-preferred promoter.

In a further embodiment the promoter is a leaf specific promoter.

In a further embodiment the promoter is capable of driving, or drives, expression of the operatively linked polynucleotide in the below ground tissues of the plant.

In one embodiment the promoter is a below ground tissues-preferred promoter.

In a further embodiment the promoter is a below ground tissue-specific promoter.

In one embodiment the promoter is a light-repressed promoter.

In a further embodiment the promoter is capable of driving, or drives, expression of the operatively linked polynucleotide in the roots of the plant.

In one embodiment the promoter is a root-preferred promoter.

In a further embodiment the promoter is a root-specific promoter.

Source of Polynucleotides and Polypeptides

The polynucleotides and variants of polynucleotides of the invention, or used in the methods of the invention, may be derived from any species. The polynucleotides and variants may also be synthetically or recombinantly produced, and also may be the products of "gene shuffling" approaches.

The polypeptides and variants of polypeptides of the invention, or used in the methods of the invention, may be derived from any species. The polypeptides and variants may also be recombinantly produced and also may also be expressed from the products of "gene shuffling" approaches.

In one embodiment the polynucleotide, polypeptide or variant, is derived from a plant species.

In a further embodiment the polynucleotide, polypeptide or variant, is derived from gymnosperm plant species.

In a further embodiment the polynucleotide, polypeptide or variant, is derived from an angiosperm plant species.

In a further embodiment the polynucleotide, polypeptide or variant, is derived from a dicotyledonous species.

In a preferred embodiment the polynucleotide, polypeptide or variant, is derived from a eudicot species.

In a further embodiment the polynucleotide, polypeptide or variant, is derived from a monocotyledonous species. Preferred monocot plants include: palm, banana, duckweed and orchid species.

Poaceae Plant Cells and Plants to be Transformed

Preferred Poaceae subfamilies include the: Anomochlooideae, Pharoideae, Puelioideae, Bambusoideae, Pooideae, Ehrhartoideae, Aristidoideae, Arundinoideae, Chloridoideae, Panicoideae, Danthonioideae, and Micrairoideae.

A preferred Poaceae family is the subfamily pooideae. Preferred pooideae plants include wheat, barley, oats, brome grass and reed grass.

Another preferred Poaceae family is the subfamily ehrhartoideae. Preferred ehrhartoideae plants include rice.

Another preferred Poaceae family is the subfamily panicoideae. Preferred panicoideae plants include panic grass, maize, sorghum, sugar cane, energy cane, millet, fonio and bluestem grasses.

Another preferred Poaceae family is the subfamily Arundinoideae. Preferred Arundinoideae plants include *Arundo donax*.

Another preferred Poaceae family is the subfamily Bambusoideae. Preferred Bambusoideae plants include bamboo.

Preferred Poacea species include those form the *Lolium* genera. Preferred *Lolium* species include *Lolium longiflorum, Lolium multiflorum, Lolium perenne, Lolium westerwoldicum, Lolium temulentum*, and *Lolium hybridum*.

Other preferred Poacea species include those form the *Festuca* genera. Preferred *Festuca* species include *Festuca arundinacea, Festuca ovina, Festuca pratensis* and *Festuca rubra*.

Plants and Plant Parts

In a further aspect the invention provides a Poaceae plant expressing a PEAPOD protein, or fragment thereof, that has at least one of:

a) increased root biomass, and b) increased above-ground biomass, as a result of expressing the PEAPOD protein, or fragment thereof.

In one embodiment the PEAPOD protein, or fragment thereof, is expressed as a consequence of the plant, or its ancestor plant or plant cell, having been transformed with a polynucleotide encoding the PEAPOD protein, or fragment thereof.

In a further embodiment the Poaceae plant is transgenic for a polynucleotide expressing the PEAPOD protein, or fragment thereof.

In a further embodiment the polynucleotide or fragment thereof is operatively linked polynucleotide to a tissue-preferred promoter.

In one embodiment the promoter is capable of driving, or drives, expression of the operatively linked polynucleotide, or a fragment thereof, in the above-ground parts of the plant.

In a further embodiment the promoter is capable of driving, or drives, expression of the operatively linked polynucleotide, or a fragment thereof, in the below ground tissues of the plant.

In a further embodiment the PEAPOD protein is as herein defined.

In a further embodiment the polynucleotide, encoding the PEAPOD protein, is as herein defined.

In a further embodiment the Poaceae plant is as herein defined.

In a further aspect the invention provides a cell, part, propagule or progeny of the plant that is transgenic for at least one of:
a) the polynucleotide, and
b) the polynucleotide and operatively linked promoter.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Increased Root Biomass

A plant with "increased root biomass" produces more root biomass than does a control plant of the same type and age. Thus "increased" means increased relative to a control plant of the same type and age.

Preferably the plant with "increased root biomass" produces at least 10%, preferably at least 20%, more preferably at least 30%, more preferably at least 40%, more preferably at least 50%, more preferably at least 60%, more preferably at least 70%, more preferably at least 80%, more preferably at least 90%, more preferably at least 100%, more preferably at least 150%, more preferably at least 200%, more preferably at least 300%, more preferably at least 400% more root biomass than does a control plant of the same type and age.

In one embodiment the plant with "increased root biomass" has at least one of: larger roots, longer roots, more roots, more lateral roots, or a more extensive root system, than does a control plant.

Root Biomass

The term root biomass refers to total mass of root tissue produced by the plant. This can be assessed by dry weight or wet weight.

Root

The term root as used herein encompasses the primary root, secondary roots, adventitious roots, root branches and root hairs. Roots are generally below ground, but the term also encompasses aerial roots. In one embodiment the term root encompasses non-leaf, non-node bearing parts of the plant.

Increased Drought Tolerance

In one embodiment the plant with "increased root biomass" also has increased drought tolerance. Again "increased" means increased relative to a control plant of the same type and age.

The term "increased drought tolerance" is intended to describe a plant, or plants, which perform more favourably in any aspect of their growth and development under sub-optimal hydration conditions than do suitable control plants in the same conditions.

Increased Above-Ground Biomass

A plant with "increased above-ground biomass" produces more above-ground biomass than does a control plant of the same type and age. Thus "increased" means increased relative to a control plant of the same type and age.

Preferably the plant with "increased above-ground biomass" produces at least 10%, preferably at least 20%, more preferably at least 30%, more preferably at least 40%, more preferably at least 50%, more preferably at least 60%, more preferably at least 70%, more preferably at least 80%, more preferably at least 90%, more preferably at least 100%, more preferably at least 150%, more preferably at least 200%, more preferably at least 300%, more preferably at least 400% more above-ground biomass than does a control plant of the same type and age.

In one embodiment the plant with "increased above-ground biomass" has at least one of: larger leaves, more leaves, a longer stem (culm), a thicker stem (culm), more tillers, larger tillers, more stolons, larger stolons than does a control plant.

Preferably the plant with "increased above-ground biomass" has larger leaves than does a control plant.

Above-Ground Biomass

The term above-ground biomass refers to total mass of above-ground tissue produced by the plant. This can be assessed by dry weight or wet weight.

Above ground biomass can be contributed to by any one of leaves, stems/culms/tillers/and stolons.

Leaf

The term leaf as used herein means the same as standard usage of the term. Preferably the term leaf includes the leaf blade (or leaf lamina) and any leaf stalk.

Stem/Culm

The stem (or culm) is the central axis of the mature grass shoot, comprised of nodes and internodes, each node bearing a leaf.

Tiller

A tiller is a daughter plant, a shoot capable of producing a new plant.

Stolon

A stolon is a prostrate or creeping, above-ground stem, rooting at the nodes, and is a means of vegetative reproduction.

Increased Flower Branching

In one embodiment the plant with at least one of increased root biomass and increased above-ground biomass" also has "increased flower branching". Again "increased" means increased relative to a control plant of the same type and age.

The term "increased flower branching" means at least one of: an increase in the number of stalks bearing inflorescences, and an increase in the number of spikelets within an inflorescence.

Increased Seed Yield

In one embodiment the plant with "increased flower branching" also has "increased seed yield". Again "increased" means increased relative to a control plant of the same type and age.

A plant with "increased seed yield" produces more seed biomass than a control plant of the same type and age. This can be assessed by dry weight or wet weight. A plant with increased seed yield may produce more seeds, and/or larger seeds than a control plant. Preferably, the plant produced more seed than a control plant.

Control Plant

In one embodiment the control plant is a wild-type plant. In a further embodiment the control plant is a plant that does not express a PEAPOD gene. In a further embodiment the control plant is a non-transformed plant. In a further embodiment the control plant is a plant that has not been transformed with a PEAPOD polynucleotide. In a further embodiment the control plant is a plant that has not been transformed with a construct. In a further embodiment the control plant is a plant that has been transformed with a control construct. In one embodiment the construct is an empty vector construct.

Tissue Preferred Promoters

In certain embodiments, the PEAPOD protein encoding polynucleotides are expressed under the control of tissue preferred promoters. The term "preferred" with respect to tissue preferred promoters means that the promoter primarily drives expression in that tissue. Thus, for example, a leaf-preferred promoter drives a higher level of expression of an operably linked polynucleotide in leaf tissue than it does in other tissues or organs or the plant. Similarly a root-preferred promoter drives a higher level of expression of an operably linked polynucleotide in root tissue than it does in other tissues or organs or the plant.

Leaf-Preferred Promoters

A leaf-preferred promoter drives a higher level of expression of an operably linked polynucleotide in leaf tissue than it does in other tissues or organs or the plant.

Leaf preferred promoters may include photosynthetic tissue preferred promoters and light regulated promoters.

Photosynthetic Tissue Preferred Promoters

Photosynthetic tissue preferred promoters include those that are preferentially expressed in photosynthetic tissues of the plants. Photosynthetic tissues of the plant include leaves, stems, shoots and above ground parts of the plant. Photosynthetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

Root Preferred Promoters

A root-preferred promoter drives a higher level of expression of an operably linked polynucleotide in root tissue than it does in other tissues or organs or the plant.

Root-preferred promoters may include non-photosynthetic tissue preferred promoters and light-repressed regulated promoters.

Non-Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

The term "preferentially expressed" with respect to a promoter being preferentially expressed in a certain tissue, means that the promoter is expressed at a higher level in that tissue than in other tissues of the plant.

The term "tissue specific" with respect to a promoter, means that the promoter is expressed substantially only in that tissue, and not other tissues of the plant.

In one embodiment the leaf-preferred promoter is a leaf-specific promoter.

In one embodiment the root-preferred promoter is a root-specific promoter.

The term "gene" as used herein means an endogenous genomic sequence which includes a coding sequence which encodes a polypeptide or protein. The coding sequence may be interrupted by one or more introns. A gene typically also includes a promoter sequence, 5' untranslated sequence, 3' untranslated sequence, and a terminator sequence. Genomic sequences that regulate expression of the protein may also be considered part of the gene.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide refers to a contiguous subsequence of larger a polynucleotide sequence. Preferably the fragment is at least 15 nucleotides preferably at least 16 nucleotides, more preferably at least 17 nucleotides, more preferably at least 18 nucleotides, more preferably at least 19 nucleotides, more preferably at least 20 nucleotides, more preferably at least 21 nucleotides, more preferably at least 22 nucleotides, more preferably at least 23 nucleotides, more preferably at least 24 nucleotides, more preferably at least 25 nucleotides, more preferably at least 26 nucleotides, more preferably at least 27 nucleotides, more preferably at least 28 nucleotides, more preferably at least 29 nucleotides, more preferably at least 30 nucleotides, more preferably at least 31 nucleotides, more preferably at least 32 nucleotides, more preferably at least 33 nucleotides, more preferably at least 34 nucleotides, more preferably at least 35 nucleotides, more preferably at least 36 nucleotides, more preferably at least 37 nucleotides, more preferably at least 38 nucleotides, more preferably at least 39 nucleotides, more preferably at least 40 nucleotides, more preferably at least 41 nucleotides, more preferably at least 42 nucleotides, more preferably at least 43 nucleotides, more preferably at least 44 nucleotides, more preferably at least 45 nucleotides, more preferably at least 46 nucleotides, more preferably at least 47 nucleotides, more preferably at least 48 nucleotides, more preferably at least 49 nucleotides, more preferably at least 50 nucleotides, more preferably at least 51 nucleotides, more preferably at least 52 nucleotides, more preferably at least 53 nucleotides, more preferably at least 54 nucleotides, more preferably at least 55 nucleotides, more preferably at least 56 nucleotides, more preferably at least 57 nucleotides, more preferably at least 58 nucleotides, more preferably at least 59 nucleotides, more preferably at least 60 nucleotides, more preferably at least 61 nucleotides, more preferably at least 62 nucleotides, more preferably at least 63 nucleotides, more preferably at least 64 nucleotides, more preferably at least 65 nucleotides, more preferably at least 66 nucleotides, more preferably at least 67 nucleotides, more preferably at least 68 nucleotides, more preferably at least 69 nucleotides, more preferably at least 70 nucleotides, more preferably at least 71 nucleotides, more preferably at least 72 nucleotides, more preferably at least 73 nucleotides, more preferably at least 74 nucleotides, more preferably at least 75 nucleotides, more preferably at least 76 nucleotides, more preferably at least 77 nucleotides, more preferably at least 78 nucleotides, more preferably at least 79 nucleotides, more preferably at least 80 nucleotides, more preferably at least 81 nucleotides, more preferably at least 82 nucleotides, more preferably at least 83 nucleotides, more preferably at least 84 nucleotides, more preferably at least 85 nucleotides, more preferably at least 86 nucleotides, more preferably at least 87 nucleotides, more preferably at least 88 nucleotides, more preferably at least 89 nucleotides, more preferably at least 90 nucleotides, more preferably at least 91 nucleotides, more preferably at least 92 nucleotides, more preferably at least 93 nucleotides, more preferably at least 94 nucleotides, more preferably at least 95 nucleotides, more preferably at least 96 nucleotides, more preferably at least 97 nucleotides, more preferably at least 98 nucleotides, more preferably at least 99 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides and most preferably at least 500 nucleotides of contiguous nucleotides of a polynucleotide disclosed. A fragment of a polynucleotide sequence can be used in antisense, RNA interference (RNAi), gene silencing, triple helix or ribozyme technology, or as a primer, a probe, included in a microarray, or used in polynucleotide-based selection methods of the invention.

In one embodiment the fragment encodes a polypeptide that performs, or is capable of performing, the same function as the polypeptide encoded by the larger polynucleotide that the fragment is part of.

The term "primer" refers to a short polynucleotide, usually having a free 3'OH group that is, or can be, hybridized to a template and used for priming polymerization of a polynucleotide complementary to the target.

The term "probe" refers to a short polynucleotide that is, or can be, used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide refers to a contiguous subsequence of larger a polypeptide. Preferably the fragment is at least 5, more preferably at least 10, more preferably at least 20, more preferably at least 30, more preferably at least 40, more preferably at least 50, more preferably at least 100, more preferably at least 120, more preferably at least 150, more preferably at least 200, more preferably at least 250, more preferably at least 300, more preferably at least 300, more preferably at least 400 amino acids in length.

In one embodiment the fragment performs, or is capable of performing, the same function as the polypeptide that the fragment is part of.

Preferably the fragment performs a function that is required for the biological activity and/or provides three dimensional structure of the polypeptide.

The term "isolated" as applied to the polynucleotide or polypeptide sequences disclosed herein is used to refer to sequences that are removed from their natural cellular environment. In one embodiment the sequence is separated from its flanking sequences as found in nature. An isolated molecule may be obtained by any method or combination of methods including biochemical, recombinant, and synthetic techniques.

The term "recombinant" refers to a polynucleotide sequence that is synthetically produced or is removed from sequences that surround it in its natural context. The recombinant sequence may be recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides and polynucleotides disclosed herein possess biological activities that are the same or similar to those of the disclosed polypeptides or polypeptides. The term "variant" with reference to polypeptides and polynucleotides encompasses all forms of polypeptides and polynucleotides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp<dot>ncbi<dot>nih<dot>gov/blast/). In one embodiment the default parameters of bl2seq are utilized. In a further embodiment the default parameters of bl2seq are utilized, except that filtering of low complexity parts should be turned off.

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from www<dot>hgmp<dot>mrc<dot>ac<dot>uk/Software/EMBOSS/. The European Bioinformatics Institute server also provides the facility to perform EMBOSS-needle global alignments between two sequences on line at www <dot>ebi<dot>ac<dot>uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot> ncbi<dot> nih<dot>gov/blast/).

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp<dot>ncbi<dot>nih<dot>gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp<dot>ncbi<dot>nih<dot>gov/blast/). In one embodiment the default parameters of bl2seq are utilized. In a further except the default parameters of bl2seq are utilized, except that filtering of low complexity parts should be turned off.

Polypeptide sequence identity may also be calculated over the entire length of the overlap between a candidate and subject polynucleotide sequences using global sequence alignment programs. EMBOSS-needle (available at www<dot>ebi<dot>ac<dot>uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

A variant polypeptide includes a polypeptide wherein the amino acid sequence differs from a polypeptide herein by one or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine.

Non-conservative substitutions will entail exchanging a member of one of these classes for a member of another class.

Analysis of evolved biological sequences has shown that not all sequence changes are equally likely, reflecting at least in part the differences in conservative versus non-conservative substitutions at a biological level. For example, certain amino acid substitutions may occur frequently, whereas others are very rare. Evolutionary changes or substitutions in amino acid residues can be modelled by a scoring matrix also referred to as a substitution matrix. Such matrices are used in bioinformatics analysis to identify relationships between sequences, one example being the BLOSUM62 matrix shown below (Table 1).

TABLE 1

The BLOSUM62 matrix containing all possible substitution scores [Henikoff and Henikoff, 1992].

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -2 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |

TABLE 1-continued

The BLOSUM62 matrix containing all possible substitution scores
[Henikoff and Henikoff, 1992].

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4 |

The BLOSUM62 matrix shown is used to generate a score for each aligned amino acid pair found at the intersection of the corresponding column and row. For example, the substitution score from a glutamic acid residue (E) to an aspartic acid residue (D) is 2. The diagonal show scores for amino acids which have not changed. Most substitutions changes have a negative score. The matrix contains only whole numbers.

Determination of an appropriate scoring matrix to produce the best alignment for a given set of sequences is believed to be within the skill of in the art. The BLOSUM62 matrix in Table 1 is also used as the default matrix in BLAST searches, although not limited thereto.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs Constructs, Vectors and Components Thereof The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
 a) a promoter functional in the host cell into which the construct will be transformed,
 b) the polynucleotide to be expressed, and
 c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR.

These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

A "transgene" is a polynucleotide that is introduced into an organism by transformation. The transgene may be derived from the same species or from a different species as the species of the organism into which the transgene is introduced. The transgene may also be synthetic and not found in nature in any species.

A "transgenic plant" refers to a plant which contains new genetic material as a result of genetic manipulation or transformation. The new genetic material may be derived from a plant of the same species as the resulting transgenic plant or from a different species, or may be synthetic.

Preferably the "transgenic" is different from any plant found in nature due the presence of the transgene.

An "inverted repeat" is a sequence that is repeated, where the second half of the repeat is in the complementary strand, e.g.:

```
(5')GATCTA...TAGATC(3')  (SEQ ID NO: 139)

(3')CTAGAT...ATCTAG(5')  (SEQ ID NO: 140).
```

Read-through transcription will produce a transcript that undergoes complementary base-pairing to form a hairpin structure provided that there is a 3-5 bp spacer between the repeated regions. The spacer can be any polynucleotide sequence but is typically at least 3 base pairs in length.

Host Cells

Host cells may be derived from, for example, bacterial, fungal, insect, mammalian or plant organisms.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp<dot>ncbi<dot>nih<dot>gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbg<dot>fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www<dot>expasy<dot>org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in genetic constructs may be functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene Silencing

Transformation strategies may be designed to reduce expression of a polynucleotide/polypeptide in a plant cell, tissue, organ or at a particular developmental stage which/when it is normally expressed. Such strategies are known as gene silencing strategies.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'          3'CTAGAT 5'
(coding strand)      (antisense strand)

3'CUAGAU 5' mRNA     5'GAUCUCG 3' antisense RNA
```

Genetic constructs designed for gene silencing may also include an inverted repeat. An 'inverted repeat' is a sequence that is repeated where the second half of the repeat is in the complementary strand, e.g.,

```
5'-GATCTA...TAGATC-3' (SEQ ID NO: 141)

3'-CTAGAT...ATCTAG-5' (SEQ ID NO: 142).
```

The transcript formed may undergo complementary base pairing to form a hairpin structure. Usually a spacer of at least 3-5 bp between the repeated region is required to allow hairpin formation. Constructs including such invented repeat sequences may be used in RNA interference (RNAi) and therefore can be referred to as RNAi constructs.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, of the corresponding gene.

Other gene silencing strategies include dominant negative approaches and the use of ribozyme constructs (McIntyre, 1996, Transgenic Res, 5, 257).

Pre-transcriptional silencing may be brought about through mutation of the gene itself or its regulatory elements. Such mutations may include point mutations, frame-shifts, insertions, deletions and substitutions.

Transformation Protocols

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); cereals (U.S. Pat. No. 6,074,877); pear (Matsuda et al., 2005, Plant Cell Rep. 24(1):45-51); Prunus (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), Rubus (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412) and *Actinidia eriantha* (Wang et al., 2006, Plant Cell Rep. 25, 5: 425-31), silver birch (Keinonen-Mettala et al., 1998, Plant Cell Rep. 17: 356-361.) and aspen (Nilsson O, et al., 1992, Transgenic Research. 1: 209-220). Transformation of other species is also contemplated by the invention. Suitable methods and protocols are available in the scientific literature.

Several further methods known in the art may be employed to alter expression of activity of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

The terms "to alter expression of" and "altered expression" of a polynucleotide or polypeptide of the invention, or used in the methods of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

Methods of Selecting Plants

Methods are also provided for selecting plants with increased leaf or root biomass. Such methods involve testing of plants for altered for the expression of at least one PEAPOD polynucleotide or polypeptide, including those as defined or disclosed herein. Such methods may be applied at a young age or early developmental stage when the increased leaf or root biomass characteristics may not necessarily be easily measurable.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with increased leaf or root biomass. The polynucleotides of the invention, or disclosed herein, may be used as probes in hybridization experiments, or as primers in PCR based experiments, designed to identify such plants.

Alternatively antibodies may be raised against PEAPOD polypeptides as described or disclosed herein Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of such polypeptides. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with increased leaf or root biomass are useful in conventional breeding programs designed to produce varieties with such altered characteristics.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

Control of Plant Growth and Development by Gibberellins (GA), Brassinosteroids (BR) And Other Plant Hormones Gibberellins (GA) and Brassinosteroids (BR) are two classes of plant hormones; between them they are involved in many aspects of plant morphogenesis and growth; including: seed germination, cell elongation, vascular development, see size, leaf erectness, flowering, leaf and fruit senescence (Mathew et al 2009, NZJAR 52, 213-225; Hou et al 2010, Developmental Cell 19, 884-894; Jiang and Lin 2013, Plant Signaling and Behaviour 8:10, e25928).

Given their roles in plant development the ability to manipulate either the levels of GA and BR or their downstream targets is highly desirable in terms of improving both yield and quality in many plant species. Indeed there are some commercial examples where exogenous applications of either hormone are used to improve agronomic value.

GA can be applied to ryegrass pasture to stimulate out-of-season growth as well as promote flowering (Mathew et al 2009, NZJAR 52, 213-225), it can also be used to counteract the adverse effects of cooler temperatures on sugarcane (a tropical C4 grass). GAs are also used to enlarge fruit size of seedless grapes and cherries, to promote fruit set in apple and pear and to delay rind-aging in particular citrus crops (Sun 2011, Current Biology 21, R338-R345). Similarly, BR preparations are recommended for improving crop yield and quality of tomato, potato, cucumber, pepper and barley, rice, maize, wheat, cotton, and tobacco (Prusakova et al 1999, Agrarian Russia, 41-44; Khripach et al 2000 Annals of Botany 86, 441-447; Anjum et al 2011 J. Agronomy Crop Sci. 197, 177-185; Vardhini 2012 J. Phytology 4, 1-3). However, the low adoption of commercially applied brassinosteroids may reflect the cost and the fact that plants do not efficiently absorb steroids when they are applied exogenously. In addition, the need to strictly control timing and concentration of exogenous supplied GA and BR limits their applications.

For the most part the GA and BR biosynthesis and catabolic pathways in angiosperms have been characterized and include negative regulators and downstream transcription factor targets. Upon binding GA or BR to their respective receptor a complex signal pathway ensues and in both cases a central point of regulation involves the ubiquitin-proteasome pathway altering the level of the negative regulator DELLA (in the case of GA) and the transcriptional regulator BZR1 (in the case of BR).

The removal of DELLA proteins results in the removal of growth repression and promotion of GA-responsive growth and development. Conversely the detection of BR leads to the accumulation of unphosphorylated BZR1 protein in the nucleus. Dephosphorylation of BZR1 prevents its degradation by the proteasome and instead allows the binding of BZR1 with other DNA binding transcription factors and interacts with transcriptional cofactors. This leads to the regulation of thousands of genes involved in growth and other cellular processes, including the inhibition of expression of BR biosynthetic genes (He et al 2005, Science 307, 1634-1638; Guo et al 2013, Current Opinion Plant Biol. 16, 545-553).

There are a number of endogenous signals and environmental cues that influence the GA-GID1-DELLA regulatory module in which DELLA integrates different signalling activities by direct protein-protein interaction with multiple key regulatory proteins from other pathways. As such DELLA proteins are master growth repressors that control plant growth and development by integrating internal signals from other hormone pathways (auxin, abscisic acid, jasmonic acid and ethylene), and external biotic (pathogen) and abiotic (light conditions, cold and salt stresses) cues (Sun 2011, Current Biology 21, R338-R345). Drought is one of the most important environmental constraints limiting plant growth and agricultural productivity. Unsurprisingly, there is a positive correlation between improved drought tolerance with a more extensive root system including deeper roots and more lateral roots both of which enable soil exploration and below-ground resources acquisition (Yu et al 2008, Plant Cell 20, 1134-1151; Werner et al 2010, Plant Cell 22, 3905-3920). Thus it follows that a common agricultural target is the optimization of root system architecture in order to help overcome yield limitations in crop plants caused by water or nutrient shortages. However, of all the abiotic stresses that curtail crop productivity, drought is the most devastating one and the most recalcitrant to breeder's efforts. Classic breeding approaches are difficult because the trait is governed by many genes and is difficult to score (Werner et al 2010, Plant Cell 22, 3905-3920). While marker-assisted selection (MAS), quantitative trait loci (QTL) and other genomic approaches are being widely used to assist breeding efforts to produce drought-resilient cultivars (Tuberosa and Salvi, 2006, Trends in Plant Science, 11:405-412) the system is limited to the variation present in the screening population.

Interestingly, rice has only one DELLA protein (SLR1), Maize has two (d8 and d9) (Lawit et al 2010, Plant Cell Physiol 51, 1854-1868) while *Arabidopsis* has five (GA1, RGA, RGL1, RGL2 and RGL3) (Achard and Genschik 2009, J. Exp. Bot. 60, 1085-1092). Furthermore, in a recent phylogenetic analysis it Chen et al 2013 found five out of the six grass species they analysed had only a single DELLA while 14 out of the 18 dicot species had two or more DELLA proteins. In contrast, there are 6 members of the BZR family in rice, 10 in maize (www<dot>Grassius<dot>org) and 6 in *Arabidopsis* (Wang et al 2002, Developmental Cell 2, 505-513).

The growth and development of plants relies on numerous connections between signalling pathways that provides the high developmental plasticity demanded by their sessile life habit (Gallego-Bartolome et al 2012, PNAS 109, 13446-13451).

Thus rather than each hormone-signalling pathway existing as an insulated module current evidence indicates that there is a high degree of interaction between different pathways and that a given hormone frequently modulates the output triggered by the rest. By example, it has recently been shown that the cross talk between the GA and BR signalling pathways involves direct interaction between DELLAs and BZR1/BES1 whereby DELLA proteins not only affect the protein stability but also inhibit the transcriptional activity of BZR1 (Li and He 2013, Plant Signaling and Behaviour 8:7, e24686 and references therein). Thus the promotion of cell elongation by GA is partly through the removal of the DELLA-mediated inhibition of BZR1.

It has recently been demonstrated that plant growth and development can be modified through direct manipulation of the master growth regulators DELLA (Lawit, Kundu, Rao and Tomes, 2007, Isolated polynucleotide molecules corresponding to mutant and wild-type alleles of the maize D9 gene and methods of use, WO 2007124312 A2) and BZR1 (Chory and Wang, 2005, Genes involved in brassinosteroid hormone action on plants, U.S. Pat. No. 6,921,848 B2).

Steroid hormones play an essential role in the coordination of a wide range of developmental and physiological processes in both plants and animals (Thummel and Chory 2002, Genes Dev. 16, 3113-3129). In plants the steroid hormone brassinosteroid (BR) has extensive effects on growth, development and responses to both biotic and abiotic stresses (Zhu et al 2013, Development 140, 1615-1620; Clouse 2011, Plant Cell 23, 1219-1230). In contrast to animal steroid hormone signalling, which functions through nuclear receptors, in plants BRs bind to the extracellular domain of the cell surface receptor kinase BRASSINOSTEROID INSENSITIVE 1 (BRI1) and activate an intracellular signal transduction cascade that regulates gene expression (Clouse 2011, Plant Cell 23, 1219-1230; Kinoshita et al 2005, Nature 433, 167-171). There are multiple steps involving activation and inactivation of intermediates leading to the phosphorylation of two transcription factors, Brassinazole Resistant 1 (BZR1) and BZR2 (also known as BES1). Thus the signal transduction BZR transcription factors are the target components converting signalling into BR responsive gene expression.

There is an emerging pattern in plant hormone signalling where the target transcription factors activated by hormones are also negatively regulated by specific repressor complexes. For example, in the jasmonic acid (JA), auxin, abscisic acid (ABA) and strigolactone (SL) signalling pathways the target transcription factors are negatively regulated by repressor complexes utilising TOPLESS (TPL) as a common co-repressor recruited by a hormone pathway specific repressor (Pauwels et al 2010, Nature 464, 788-791). In the JA transduction pathway the JASMONATE ZIM DOMAIN (JAZ) family of transcriptional repressors both interact with the target JA-responsive transcriptional activator MYC2 and recruit TPL, either directly or via the adaptor protein Novel Interactor of JAZ (NINJA) (Pauwels et al 2010, Nature 464, 788-791).

Accordingly, the ability to regulate the GA and BR pathways to influence many different agricultural traits of interest is of considerable value to commercial agriculture.
The Applicant's Invention As discussed above, the present invention relates to a method for increasing at least one of leaves and root biomass in Poaceae plants by ectopic expression of PEAPOD.

Without wishing to be bound by theory, the applicants have shown that: PEAPOD (PPD) appears to be involved in the modulation of both the GA and BR pathways either through direct or indirect interaction with the master growth regulators DELLA and BZR.

Analysis of the primary amino add structure of PPD proteins indicates the presence of a highly conserved novel plant specific domain present only these proteins. There are homologues of PPD in a wide range of eudicot, conifers and some monocot plants (palms, banana, orchids, duckweed) but not Poaceae (grasses).

The PPD genes of *Arabidopsis* encode proteins that are members of the plant-specific TIFY family, named after the core TIF[F/Y]XG motif found within a domain known as ZIM (Vanholme et al 2007, Trends Plant Sci. 12, 239-244). The two *Arabidopsis* PPD proteins, PPD1 and PPD2, are included in the same class II TIFY group as twelve well characterised JAZ proteins that act as repressors of jasmonate responses. However, the PPD proteins and the one other non-JAZ protein in the group do not appear to be involved in responses to jasmonate hormone signalling (Pauwels et al 2010, Nature 464, 788-791).

Again, without wishing to be bound by theory, the applicants propose that the increases in leaf and root biomass, according to the invention, are mediated by a new mechanism for regulating both the GA and BR pathways in the Poaceae family using the PPD gene. Examples 3 and 4 below support this proposal, This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which are described as follows:

FIG. 1A shows the synteny map of flanking genes around the PPD loci in various dicotyledonous and monocotyledonous plants and the absence of PPD genes in the same location in the Poaceae.

FIG. 1B shows the presence of numerous repeats in the rice chromosome where synteny predicts PPD should have been.

FIG. 2 shows the 46 amino acid residues comprising the PEAPOD region from a range of plant species, identical residues are shown by an asterisk.

FIG. 3 shows the internal 27 amino acid residues within the PEAPOD region from a range of plant species, identical residues are shown by an asterisk.

FIG. 4 shows the 6 amino acid residues of the TIFY domain on PEAPOD proteins from a range of plant species, identical residues are shown by an asterisk.

EXAMPLES

Figure 5:
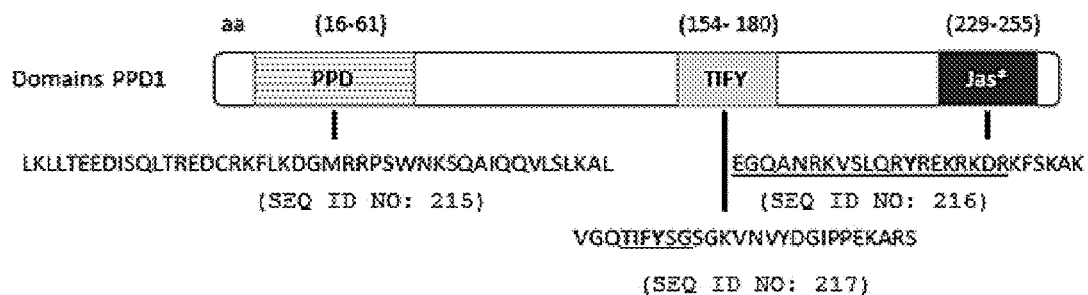
FIG. 5 shows a schematic representation of the PPD protein and the approximate location of conserved PPD, TIFY and Jas* regions

The invention will now be illustrated with reference to the following non-limiting examples.

Example 1: Characterisation of PEAPOD Genes Multiple Plant Species

To identify PPD gene orthologues in other plant species the conserved PPD region (46 amino acids) from the *Arabidopsis* PPD1 gene (SEQ ID NO: 27) was used for searches of public plant gene sequence databases using the search programmes TBLASTN and BLASTP (Altschul et al 1990). PEAPOD sequences were identified from a diverse range of plant species including the mosses, conifers, all orders of dicotyledonous examined and some of the monocotyledonous orders, including: palms, bananas, orchids and duckweed. The same search method indicated that PEAPOD sequences are not found in the grasses. Extensive syntany comparisons showed that in the poace genomes analysed (*Brachypodium distachyon, Oryza sativa* and *Zea mays*) the region expected to contain PPD genes has been disrupted (FIG. 1A) and now contains numerous repeats (FIG. 1B). Representative PEAPOD protein sequences are shown in SEQ ID NO: 1-26 and nucleic acid sequences are shown in SEQ ID NO:80-104 respectively.

The 46 amino acid PEAPOD region from *Arabidopsis thaliana* PPD1 is shown in SEQ ID NO:27. This region from polypeptides SEQ ID NO: 1—was aligned by vector NTI (VNTI) as shown in FIG. 2.

SEQ ID NO:28 shows the consensus for this 46 amino acid PPD region. SEQ ID NO:29 shows the same consensus region but shows which amino acids can be present at each of the variable positions.

A 27 amino acid subsequence from within the 46 amino acid PEAPOD region from *Arabidopsis thaliana* PPD1 is shown in SEQ ID NO:30.

Alignment of this 27 amino acid subsequence for reach of the same sequences as in FIG. 2, is shown in FIG. 3.

SEQ ID NO:31 shows the consensus for this 27 amino acid PPD region. SEQ ID NO:32 shows the same consensus region but shows which amino acids can be present at each of the variable positions.

In each of the PPD peptide sequences of SEQ ID NO: 1-26 there is also a conserved TIFY motif which is located after the 46 amino acid PPD region. The number of amino acid residues separating the C-terminus of the PPD region and the N-terminus of the TIFY motif depends on the source of the PPD; for example the number varies between 46 to 140 amino acids for SEQ ID NO:1-26.

SEQ ID NO: 33 shows the *Arabidopsis* PPD1 sequence over the TIFY motif. The alignment of the TIFY motif (as described by Vanholme et al 2007, Trends Plant Sci. 12, 239-244) from SEQ ID NO:1-26 is shown in FIG. 4.

SEQ ID NO:34 shows the consensus for this 6 amino acid TIFY motif. SEQ ID NO:35 shows the same consensus region but shows which amino acids can be present at each of the variable positions.

Completely conserved residues in the PPD and TIFY domains are highlighted with asterisks in FIGS. 2-4.

The applicants assert that these regions and motifs described above are found in all PEAPOD proteins identified and are diagnostic for such PEAPOD proteins

Example 2: Demonstrating PEAPOD Functionality of PEAPOD Sequences from Multiple Plant Species The functionality of any PEAPOD sequence can be confirmed by complementation of the *Arabidopsis* Δppd mutant leaf phenotype. Complementation of the *Arabidopsis* Δppd mutant leaf phenotype was first used to identify the *Arabidopsis* PPD gene (White 2006). This was seen by a restoration of the wild type flattened leaf phenotype and normal rosette shape as opposed to the domed leaf and the twisting of the rosette to a "propeller" phenotype.

PEAPOD sequences, such as those of SEQ IN NO: 1-26 (including: palm, conifer, moss, orchid and other dicot species) or any other PEAPOD sequence to be tested can be transformed into the *Arabidopsis* Δppd mutant by methods well known to those skilled in the art. An example of such a method is described below.

Cloning and Gene Constructs

Generation of CaMV35s::*Arabidopsis thaliana* PPD1 Construct for Over Expression of *Arabidopsis* PPD1 in the *Arabidopsis* Δppd Mutant An expression construct was synthesised to enable the over expression of *Arabidopsis thaliana* PPD1 under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:105 and SEQ ID NO:111 respectively.

Generation of CaMV35s::*Trifolium repens* PPD Construct for Over Expression of *Trifolium repens* PPD1 in the *Arabidopsis* Δppd Mutant An expression construct was synthesised to enable the over expression of *Trifolium repens* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:106 and SEQ ID NO:112 respectively.

Generation of CaMV35s::*Amborella trichopoda* PPD Construct for Over Expression of *Amborella trichopoda* PPD in the *Arabidopsis* Δppd Mutant An expression construct was synthesised to enable the over expression of *Amborella trichopoda* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997), Nucleic Acid Research 15, 6643-6653, optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:107 and SEQ ID NO:113 respectively.

Generation of CaMV35s::*Musa acuminate* PPD Construct for Over Expression of *Musa acuminate* PPD in the *Arabidopsis* Δppd Mutant An expression construct was synthesised to enable the over expression of *Musa acuminate* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:108 and SEQ ID NO:114 respectively.

Generation of CaMV35s::*Picea sitchensis* PPD1 Construct for Over Expression of *Picea sitchensis* PPD in the *Arabidopsis* Δppd Mutant An expression construct was synthesised to enable the over expression of *Picea sitchensis* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:109 and SEQ ID NO:115 respectively.

Generation of CaMV35s::*Selaginella moellendorffii* PPD1 Construct for Over Expression of *Selaginella moellendorffii* PPD in the *Arabidopsis* Δppd Mutant An expression construct was synthesised to enable the over expression of *Selaginella moellendorffii* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:110 and SEQ ID NO:116 respectively.

Plant Materials and Growth Conditions

*Arabidopsis thaliana* (L.) Heynh ecotype Ler can be used as wild-type (WT). The Δppd loss of function deletion mutant (with PPD1 and PPD2 deleted) is as previously described in White 2006, PNAS 103, 13238-13243.

Plants are grown in a temperature-controlled glasshouse at a continuous 21° C. or in a controlled environment cabinet at 23° C. in 16-h light_8-h dark cycles.

Transformation of *Arabidopsis*

Constructs above can be transformed into *Arabidopsis* by the floral dip infiltration method (Clough and Bent, 1998, Plant J 16, 735-43). The Δppd line is transformed to express the PPD polypeptides by standard techniques. Transgenic plants are confirmed by standard PCR analysis techniques with a combination of transgene-specific and T-DNA primers.

Complementation of the Δppd line to produce a wild-type leaf and rosette phenotype in T1 seedlings (the off-spring of the infiltrated plant) confirms PEAPOD functionality of the introduced gene, which can be shown in photographs.

This approach can be use to confirm the PEAPOD functionality of any gene which the applicant asserts, demonstrates it suitability of use in the present invention.

Figure 13:
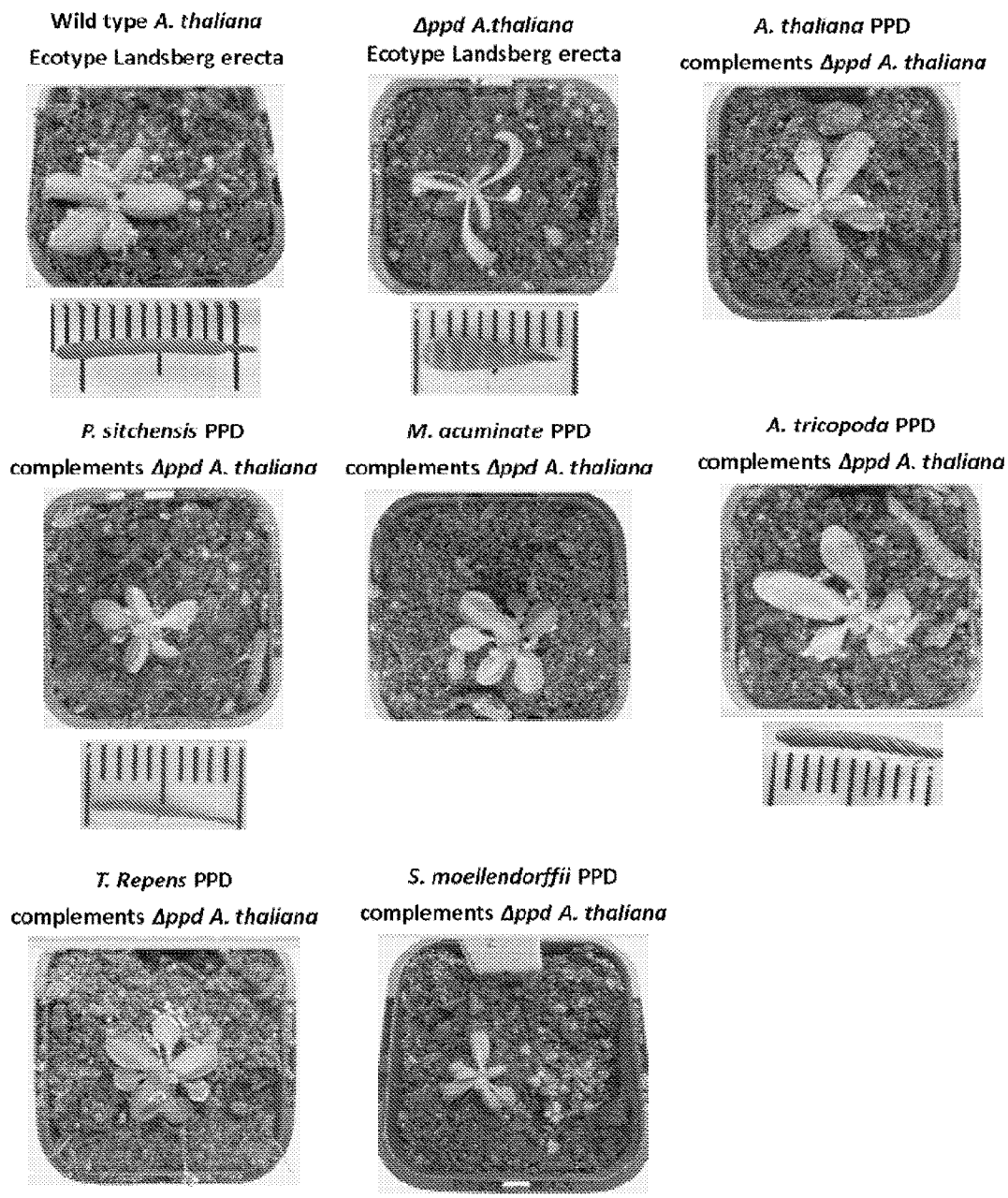
FIG. 13 shows that the PEAPOD proteins from *Arabidopsis thaliana; Picea sitchensis, Amborella trichopoda, Musa acuminate, Trifolium repens* and *Selaginella moellendorffii* are functionally equivalent. An optimized PEAPOD coding sequence from each was used to complement the PEAPOD deletion mutant Δppd *Arabidopsis thaliana* (ecotype Landsberg erecta). Seedling images were taken at an equivalent developmental stage.

The PEAPOD proteins from *Arabidopsis thaliana; Picea sitchensis, Amborella trichopoda, Musa acuminate,* and *Selaginella moellendorffii* were shown to be functionally equivalent by the complementation of the PEAPOD deletion mutant Δppd *Arabidopsis thaliana* ecotype Landsberg erecta (FIG. 13).

Example 3: PEAPOD May be Involved in Regulating the Brassinosteroid Signalling Pathway The applicants used yeast two hybrid (Y2H) assays Bi-molecular fluorescence (BiFC) to investigate the interactions between PPD, NINJA, TPL and BZR1.

Cloning and Constructs

The constructs for Y2H and BiFC assays were generated as follows. *Arabidopsis* DNA sequences encoding the open reading frames for; At4g14713 (PPD1) and truncation and deletion derivatives of PPD1: PPD1; PPD1Δppd (N-terminal truncation of sequences encoding aa 1-61), PPD1Δtify, (internal deletion of sequences encoding aa 154-186), PPD1Δjas*(C-terminal truncation of sequences encoding aa 229-313) (FIG. 5), At4g28910 (NINJA), At1g15750 (TPL), At1g75080 (BZR1), a synthetic PUAS-35S promoter, and sequences encoding GAL4DBD and c-myc fusion proteins were synthesised and sequence verified by GeneArt. Most sequences were supplied as clones in pENTR221 ready for Gateway cloning into yeast and plant expression vectors. The exception, a promoter sequence for in planta transcription activation assays, incorporating 5' Xho1 and 3' Nco1 restriction enzyme sites, was supplied cloned in pMA-RQ. Plasmids for the transient LUC reporter assay: A synthetic promoter with 5×UAS GAL4 DNA binding sites upstream of a −105 bp CaMV35S promoter was cloned into the XhoI-NcoI sites within a dual luciferase construct pNWA62, which contains an intron-containing Firefly Luciferase gene (LUC) and 35Spro::*Renilla* Luciferase (REN) as an internal standard, to construct pAML7. For the over expression of GAL4DBD fusion proteins DNA sequences encoding a GAL4 DNA-binding domain (GAL4DBD aa 1-147) and N-terminal GAL4DBD fusions (using a linker encoding GGGGS) with 2× the VP16 activator domain (GAL4DBD-VP16) or PPD1 (GAL4DBD-PPD1), were cloned using Gateway technology into pRSh1 (Winichayakul et al 2008) to construct vectors pRSh1-GAL4DBD, pRSh1-GAL4DBD-VP16, and pRSh1-GAL4DBD-PPD1 for expression of the fusion proteins in planta.

Plasmids for Yeast Two-Hybrid Analysis

Full length coding sequences of BZR1, NINJA, TPL, and PPD1, together with truncation or deletion derivatives of PPD1 (PPD1Δppd, PPD1Δtify, and PPD1Δjas*), were Gateway sub-cloned into pDEST32 (N-terminal GAL4DBD) or pDEST22 (N-terminal GAL4AD), to construct pDEST32-PPD1, pDEST32-PPD1Δppd, pDEST32-PPD1Δtify, pDEST32-PPD1Δjas*, pDEST32-TPL, as bait vectors and pDEST22-PPD1, pDEST22-BZR1, and pDEST22-NINJA as prey vectors. When expressed these constructs produced proteins listed in sequences 53-69; including: DNA binding domain (DBD), activation domain (AD), PPD1 fused to DBD (PPD1-DBD), PPD1 fused to AD (PPD1-AD), PPD1 with no TIFY domain fused to AD (PPD1-tify-AD), PPD1 with no jas domain fused to AD (PPD1-jas*-AD), TOPLESS (TPL), TPL fused to DBD (TPL-DBD), NINJA, NINJA fused to AD (NINJA-AD), BZR1 fused to AD (BZR1-AD), PPD1 minus the ppd domain fused to DBD (PPD1-Δppd-DBD), PPD1 minus the TIFY domain fused to DBD (PPD1-tify-DBD), PPD1 minus the jas domain fused to DBD (PPD1-jas*-DBD).

Plasmids for Bimolecular Fluorescence Complementation

The binary BiFC-Gateway YFP vectors pDEST-VYNE (R)$^{GW}$ (Venus aa 1-173) and pDEST-VYCE(R)$^{GW}$ (Venus aa 156-239) with N-terminal fusions, were used to construct the following vectors; pDESTnYFP-BZR1, pDESTnYFP-NINJA, pDESTnYFP-PPD1, pDESTcYFP-BZR1, pDEST-cYFP-PPD1, pDESTcYFP-PPD1Δppd, pDESTcYFP-PPD1Δtify and pDESTcYFP-PPD1Δjas*. For transient in planta expression of proteins interacting with PPD1 or BZR, NINJA and TPL were Gateway® sub-cloned into pRSh1, to construct pRSh1-NINJA and pRSh1-TPL. Plasmids for co-immunoprecipitation: A synthesised DNA construct encoding PPD1 with a 3×c-myc C-terminal fusion was sub-cloned into pRSh1 to produce pRSh1-PPD1-3×c-myc, while the NINJA cDNA sequence was sub-cloned into pB7FWG2,0 (Karimi et al 2002, Trends Plant Sci. 7, 193-195) to construct pB7FWG2-NINJA-GFP. When expressed these constructs produced proteins listed in sequences 60, 62, 70 71 72 73 74 75 76 77 78 79: including TOPLESS (TPL), NINJA, Bimolecular Fluorescence (BiFC) nYFP, BiFC cYFP, BiFC nYFP-NINJA, BiFC nYFP-BZR1, BiFC cYFP-PPD1, BiFC cYFP-NINJA, BiFC cYFP-BZR1, BiFC cYFP-PPD1-ppd, BiFC cYFP-PPD1-tify, BiFC cYFP-PPD1-jas*.

The ProQuest two-hybrid system (Invitrogen) was used to analyse interactions between PPD1, NINJA, TPL, and BZR1. Combinations of bait and prey constructs were used to co-transform yeast strain MaV203 (Invitrogen), with selection on synthetic dropout (SD) SD/-Leu/-Trp agar plates. Transformed strains were tested for interactions using 10 μl droplets of 1 in 10 and 1 in 100 dilutions on SD/-Leu/-Trp/-His plates with different concentrations of 3-aminotriazol (3-AT) (Sigma).

Transient BiFC experiments were performed using combinations of pDESTnYFP and pDESTcYFP plasmids, with or without plasmids for the expression of NINJA (pRSh1-NINJA) or TPL (pRSh1-TPL) and Agrobacterium-infiltration of Nicotiana benthamiana leaves. For infiltration Agrobacterium tumefaciens GV3101 strains containing the binary vectors were re-suspended from plates and prepared for transformation as described for the LUC assay. All YFP and expression strains were mixed in ratios of 1:1 (vol/vol) with the addition of strain P19 at ¹/₁₀th volume. Five leaf discs were sampled from each infiltrated leaf after 40 h. Two hours prior to sampling for microscopic fluorescence observations leaves were infiltrated with a 1 μg/ml DAPI solution to stain nuclei. YFP fluorescence and DAPI staining was detected using an Olympus Fluoview FV10i confocal laser scanning microscope. Each experiment was repeated twice.

Figure 6:
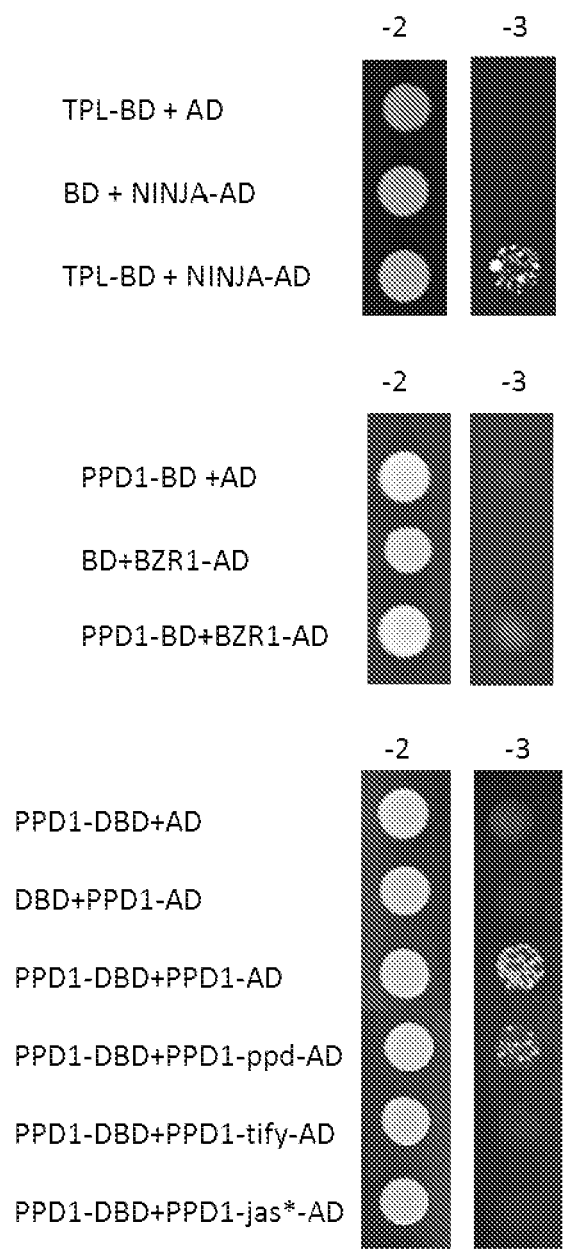
FIG. 6 shows the dimerization of PPD and the interaction between TPL and NINJA in Y2H assays.
Figure 7:
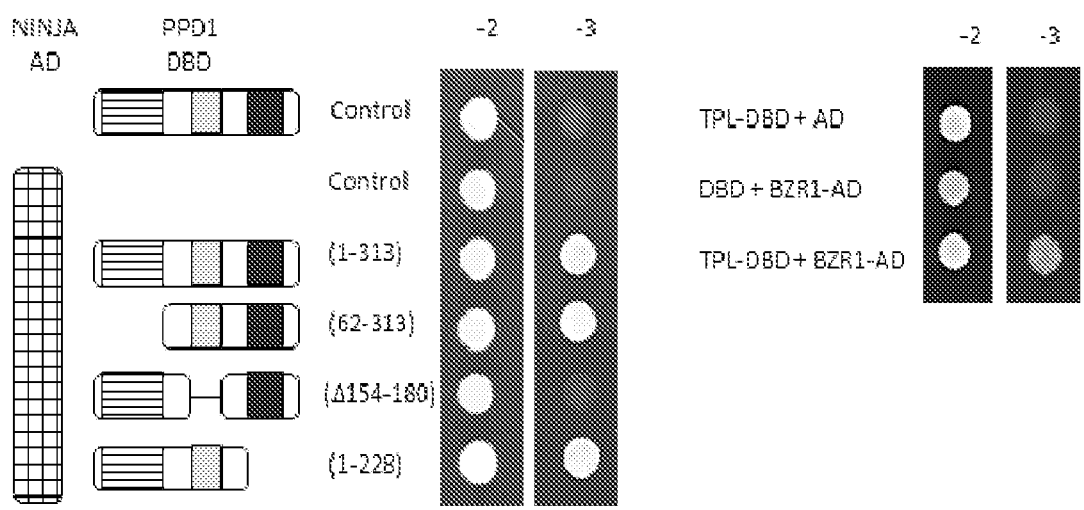
FIG. 7 shows the interaction between PPD and NINJA and the interaction between TPL and BZR1 in Y2H assays.
Figure 8:
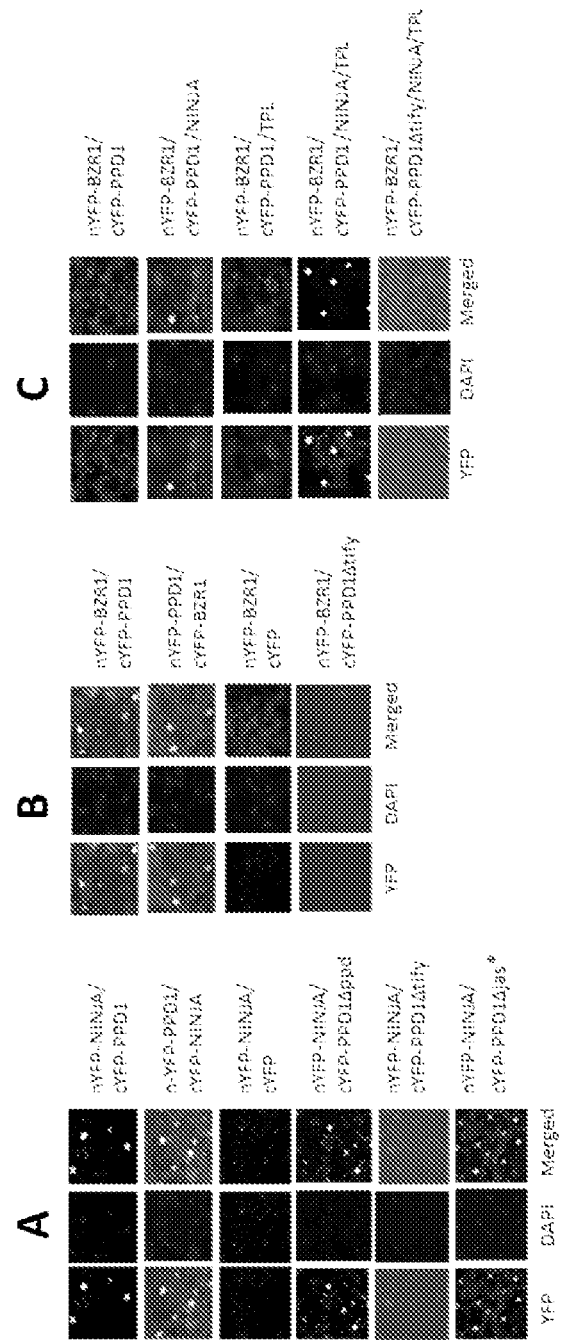
FIG. 8 shows the interaction between PPD, NINJA, TPL and BZR1 in young (A and B) and old (C) leaves using BiFC assays.

Y2H screening using PPD1 as a bait protein identified NINJA as a direct interactor with PPD1. Results from BiFC assays suggested PPD1 interacted with NINJA in plants, and that the TIFY motif was also essential for this interaction (FIG. 8). It is possible that NINJA functions as a bridge between TPL and PPD1. Using Y2H no direct interaction between PPD1 and BZR1 was observed (FIG. 6). However, recent tandem affinity purification (TAP) experiments have shown that TPL may interact with BZR1 (Wang et al 2013, Mol. Cell. Proteomics 12, 3653-3665), and here Y2H results confirmed that a direct interaction occurs (FIG. 7).

To determine the molecular function of the PPD proteins the interactions of PPD1, NINJA, TPL, and BZR1 were studied in planta. Bimolecular fluorescence (BiFC) was used to show that in the pavement cells of immature Nicotiana benthamiana leaves PPD1 appears to interact with BZR1 in the nucleus (FIG. 8A,B). The NINJA-binding TIFY motif in PPD1 was essential for this interaction. Moreover, no interaction was observed when nYFP-PPD1 and cYFP-BZR1 were co-expressed in fully expanded leaves (FIG. 8C). Interestingly, interaction between PPD1 and BZR1 was restored upon co-expression of NINJA but not TPL alone, suggesting the lack of interaction in the mature leaf was due to a limitation of endogenous NINJA. As for immature leaves, interaction between PPD1 and BZR1, even in the presence of NINJA and TPL co-expression, was not observed when the PPD1 NINJA-binding TIFY motif was deleted (FIG. 8C). These results suggest that PPD1, NINJA, TPL and BZR1 exist as a complex in plants and that NINJA is required to recruit PPD1 to interact via TPL with BZR1.

Figure 9:
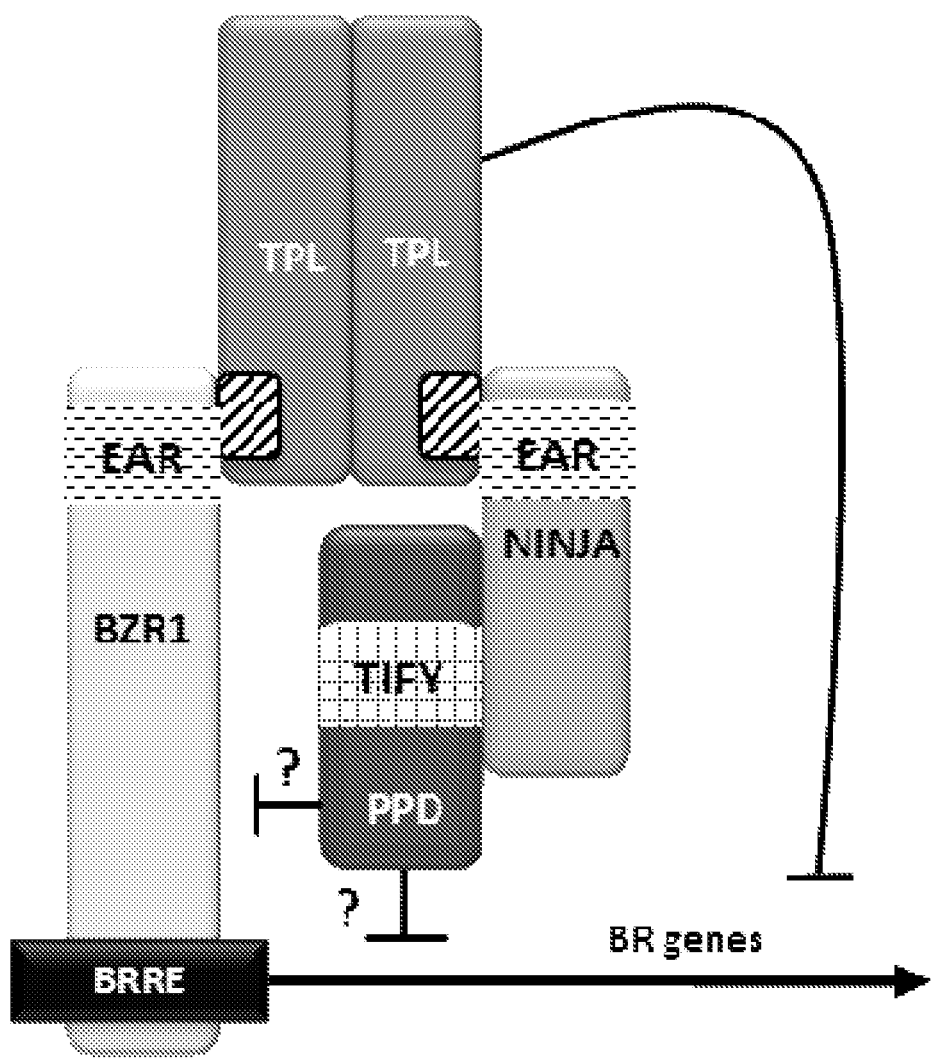
FIG. 9 shows a schematic representation of the PPD-NINJA-TPL-BZR1 complex.

PPD1 does not appear to directly interact with the target BZR1 transcription factor. Instead the results of PPD1 protein interaction experiments suggest a model in which the PPD proteins recruit TPL transcriptional co-repressors, using NINJA as an adaptor, and this PPD-NINJA-TPL complex interacts with the EAR motif of the BZR transcription factors (FIG. 9). Thus in this model the PEAPOD1 (PPD1) protein of Arabidopsis thaliana would act as a repressor of the BR signalling pathway and in combination with NINJA and TPL, negatively regulates BZR1.

Example 4: PEAPOD May be Involved in Regulating the Gibberellin Signalling Pathway Giberellic acid (GA) treatment is known to reduce levels of the DELLA proteins (including RGA1) which are GA repressors; to determine the relationship between PPD, DELLA and the GA signalling pathway the applicants performed a yeast two-hybrid (Y2H) analysis between PPD and DELLA (RGA1) and applied gibberellic acid (GA) hormone and GA biosynthesis inhibitor (paclobutrazol, PAC) to wild type, Δppd mutant, and the Δppd mutant PPD over expressor (PPD-OX).

The ProQuest two-hybrid system (Invitrogen) was used to analyse interactions between PPD1, and RGA1. Full length coding sequences of PPD1, together with truncation or deletion derivatives of PPD1 (PPD1Δppd, PPD1Δtify, and PPD1Δjas*) (FIG. 5), were Gateway sub-cloned into pDEST32 (N-terminal GAL4DBD) or pDEST22 (N-terminal GAL4AD). When translated these generated the following peptide sequences: 55, 65, 66, 67, 68, 7169, which are PPD1-DBD, RGA1, RGA1-AD, PPD1-ppd-DBD, PPD1-tify-DBD, PP1-jas*-DBD respectively.

Figure 10:
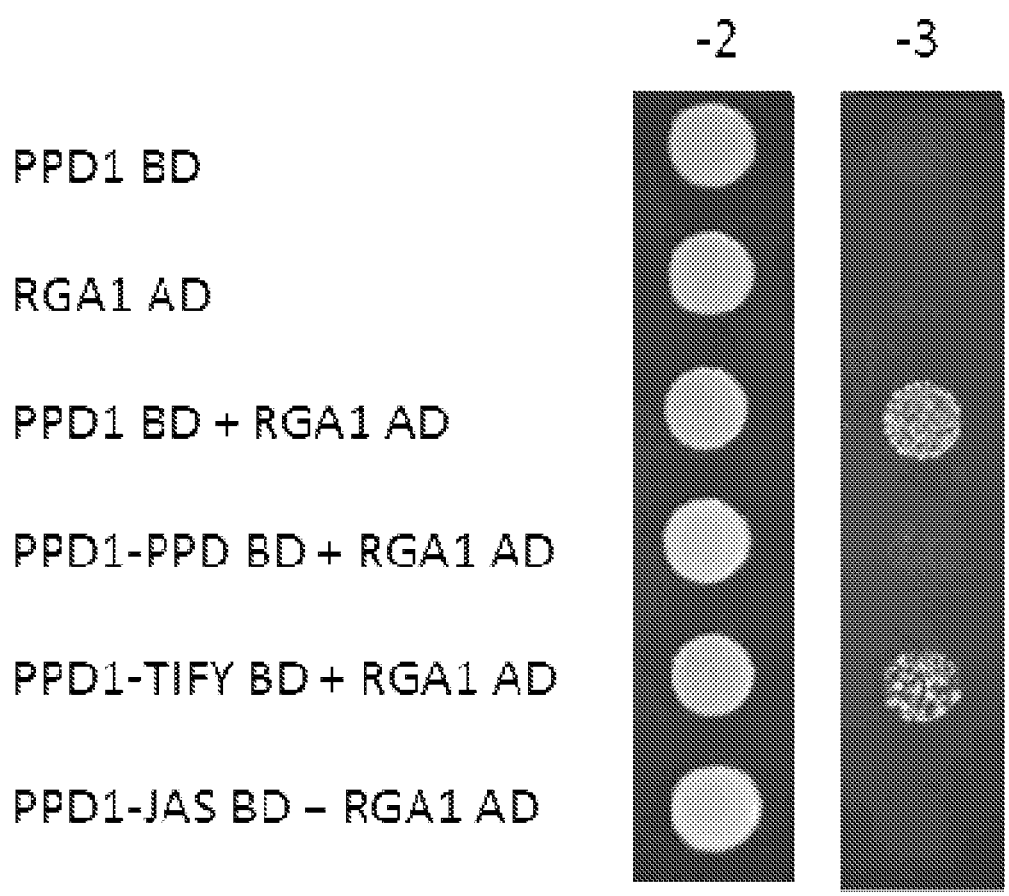
FIG. 10 shows the interaction between PPD and BZR1 in Y2H assays.

Combinations of bait and prey constructs were used to co-transform yeast strain MaV203 (Invitrogen), with selection on synthetic dropout (SD) SD/-Leu/-Trp agar plates. Transformed strains were tested for interactions using 10 μl droplets of 1 in 10 and 1 in 100 dilutions on SD/-Leu/-Trp/-His plates with different concentrations of 3-aminotriazol (3-AT) (Sigma). The PPD1-RGA1 interaction was tested with PPD1-DBD used as bait. Transformed yeast was spotted as a ten-fold dilution on control medium (−2) or selective medium (−3) with 15 mM 3AT. Controls were empty vectors, DBD, GAL4 DNA binding domain, AD, GAL4 activation domain (FIG. 5). The Y2H results suggest that PPD can directly bind to DELLA (FIG. 10).

Figure 11:
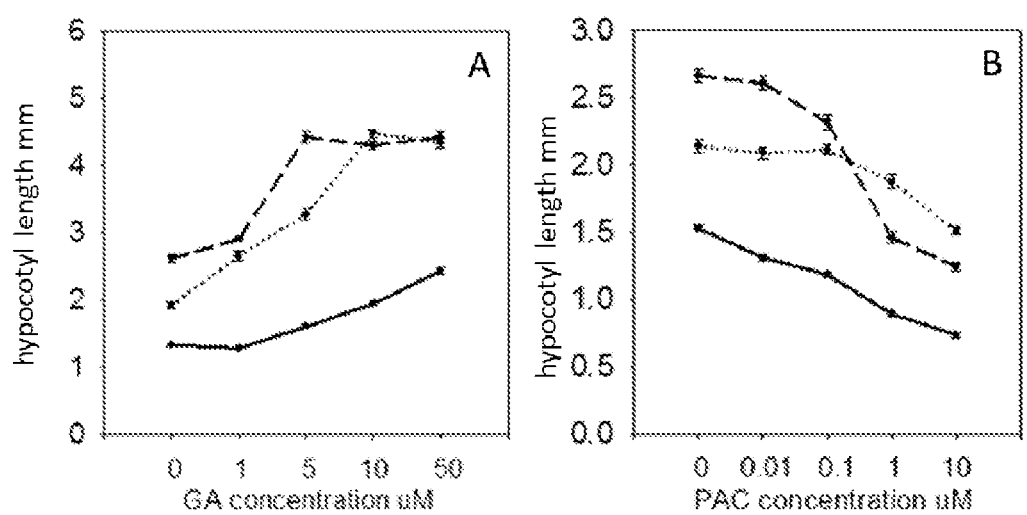
FIG. 11 shows the response of Wild Type, Δppd mutant, and PEAPOD overexpressor (PPD-OX) hypocotyl length to exogenous GA and PAC applications.

For exogenous applications of GA or PAC seeds were surface sterilised with 70% ethanol, 0.01% Triton X-100 for 10 min, followed by 100% ethanol for 5 min, air dried on sterile filter paper, and transferred to media plates containing half-strength MS salts, 1% sucrose and 0.8% agar. Plates were incubated for 5 days at 4° C. in the dark then transferred to 24° C. with a 14 h light/10 h dark daily cycle. Light was provided by fluorescent tubes (Philips TLD 58W/865) at an intensity of 100 µM $m^{-2}s^{-1}$. Wild-type (Col-0) Δppd mutant and transgenic PPD-OX seedlings were grown for five days on medium with different concentrations of GA (FIG. 11A) or PAC (FIG. 11B). GA (ACROS organics), and PAC (Sigma-Aldrich) were dissolved in ethanol and acetone respectively, filter sterilised and incorporated into media plates. Ethanol or acetone (0.5%) was used for mock treatments. Seedlings were grown at 24° C. under a 14 h light/10 h dark daily cycle for 5 days before hypocotyl lengths were analysed (n=35). Each treatment was repeated twice; error bars=standard error of the mean.

A reduction of DELLA leads to an increase in transcription of DELLA target genes promoting cell expansion and can be quantified by measuring hypocotyl elongation of seedlings growing on media containing varying levels of GA. The lowest concentration of GA (1 µM) did not promote elongation of the wild type (WT) hypocotyl whereas both the loss-of-function PPD mutant (Δppd) and the transgenic PPD over expressing (PPD-OX) seedlings showed increased hypocotyl elongation (FIG. 11A). At higher GA concentrations (5-50 µM) elongation of the WT hypocotyl occurred in a dose dependent manner. In comparison the Δppd and PPD-OX seedlings showed hypersensitive elongation up to 5 and 10 µM GA respectively where they both reached approximately the same length (FIG. 11A).

GA biosynthesis is inhibited by applications of exogenous paclobutrazol (PAC); this results in an increase in the DELLA repressor proteins and corresponding reduction in cell expansion. Wild type seedlings demonstrated a dose dependent decrease of hypocotyl elongation from 0 to 10 µM PAC (FIG. 11B). Once again the Δppd seedlings demonstrated a hyper sensitive response which was seen as a larger reduction in hypocotyl elongation over the same range of PAC applications. The PPD-OX seedlings however, were relatively insensitive until the PAC concentration was increased beyond 0.1 µM, after which they too showed a decrease in hypocotyl length (FIG. 11B).

The hypersensitive response to GA by the Δppd seedlings potentially reflects the combination of increased targeting of DELLA for degradation in the absence of transcription factor repression by PPD. Similarly, the addition of PAC in the Δppd background possibly leads to a greater reduction in hypocotyl elongation compared to WT because it is done in the absence of one of DELLAs natural antagonists—PPD, suggesting PPD and GA compete for binding to DELLA.

It can be predicted that the over expression of PPD would result in a higher level of antagonism of DELLA, as such the hypocotyl elongation of these plants ought to be hypersensitive to GA; indeed this is what we observed in the PPD-OX seedlings. In the reverse situation when the GA level was reduced (by the application of PAC) the PPD-OX seedlings were unresponsive until the PAC concentration was greater than 0.1 µM. This likely reflects the point at which there was a sufficient reduction in endogenous GA levels to see the influence of DELLA protein not antagonised by the over expressed PPD.

Example 5: Expression of PEAPOD in Monocotyledonous Plants

Constructs

Described below are several constructs for expressing PEAPOD sequences from various species, under the control of various promoters, for expression in monocotyledonous plants.

Generation of pRICE ACTIN::PPD Construct for (Constitutive) Expression of *Arabidopsis* PPD1

Two expression constructs were synthesised to enable the over expression of PPD1 under the Rice actin promoter in grasses, the nucleic acid coding sequence are shown in SEQ ID NO:40 and 117. The PPD ORF was optimised for expression in monocotyledonous plants; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>edu/cgi-bin/sp<dot>cgi).

The construct SEQ ID NO 40 (with and without the tail) was then placed between the rice actin promoter and NOS terminator by the GATEWAY® LR reaction, to create SEQ ID NO:41 and SEQ ID NO:47 which coded for SEQ ID NO:36 and SEQ ID NO:38 respectively. Similarly for the construct SEQ ID NO 117 with and without the tail which coded for SEQ ID NO: 105 and SEQ ID NO: 111 respectively.

Generation of pRICE ACTIN::PPD Construct for (Constitutive) Expression of *Trifolium repens* PPD An expression construct was synthesised to enable the over expression of *Trifolium repens* PPD under the Rice actin promoter in grasses, the nucleic acid coding sequence is shown in SEQ ID NO:118. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37 and addition of a double stop codon. The position of the intron was optimised for splice site prediction, performed by deepc2 (deepc2<dot>psi<dot>iastate<dot>edu/cgi-bin/sp<dot>cgi).

The construct (with and without the tail) was then placed between the rice actin promoter and NOS terminator by the GATEWAY® LR reaction, which coded for SEQ ID NO:106 and SEQ ID NO:112 respectively.

Generation of pRICE ACTIN::PPD Construct for (Constitutive) Expression of *Amborella trichopoda* PPD An expression construct was synthesised to enable the over expression of *Amborella trichopoda* PPD under the Rice actin promoter in grasses, the nucleic acid coding sequence is shown in SEQ ID NO:119. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>edu/cgi-bin/sp<dot>cgi).

The construct (with and without the tail) was then placed between the rice actin promoter and NOS terminator by the GATEWAY® LR reaction, which coded for SEQ ID NO:107 and SEQ ID NO:113 respectively.

Generation of pRICE ACTIN::PPD Construct for (Constitutive) Expression of *Musa acuminate* PPD An expression construct was synthesised to enable the over expression of *Musa acuminate* PPD under the Rice actin promoter in grasses, the nucleic acid coding sequence is shown in SEQ ID NO:120. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>edu/cgi-bin/sp<dot>cgi).

The construct (with and without the tail) was then placed between the rice actin promoter and NOS terminator by the GATEWAY® LR reaction, which coded for SEQ ID NO:108 and SEQ ID NO:114 respectively.

Generation of pRICE ACTIN::PPD Construct for (Constitutive) Expression of *Picea sitchensis* PPD An expression construct was synthesised to enable the over expression of *Picea sitchensis* PPD under the Rice actin promoter in grasses, the nucleic acid coding sequence is shown in SEQ ID NO:121. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>edu/cgi-bin/sp<dot>cgi).

The construct (with and without the tail) was then placed between the rice actin promoter and NOS terminator by the GATEWAY® LR reaction, which coded for SEQ ID NO:109 and SEQ ID NO:130 respectively.

Generation of pRICE ACTIN::PPD Construct for (Constitutive) Expression of *Selaginella moellendorffii* PPD An expression construct was synthesised to enable the over expression of *Selaginella moellendorffii* PPD under the Rice actin promoter in grasses, the nucleic acid coding sequence is shown in SEQ ID NO:122. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>eduicgi-bin/sp<dot>cgi).

The construct (with and without the tail) was then placed between the rice actin promoter and NOS terminator by the GATEWAY® LR reaction, which coded for SEQ ID NO:110 and SEQ ID NO:116 respectively.

Generation of pRICE CAB::PPD Construct for (Photosynthetic Tissue-Preferred/Light-Regulated) Expression of *Arabidopsis* PPD1

Two expression constructs were synthesised to enable the over expression of PPD1 under the pRICE CAB promoter in grasses, the nucleic acid coding sequences are shown in SEQ ID NO:40 and SEQ ID NO:117. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>eduicgi-bin/sp<dot>cgi).

The construct SEQ ID NO:40 (with and without the tail) was then placed between the rice CAB promoter and NOS terminator by the GATEWAY® LR reaction, to create SEQ ID NO:45 and SEQ ID NO:51 which coded for SEQ ID NO:36 and SEQ ID NO:38 respectively.

Similarly for the construct SEQ ID NO 117 with and without the tail which coded for SEQ ID NO: 105 and SEQ ID NO: 111 respectively.

Generation of pRICE Rubisco::PPD Construct for (Photosynthetic Tissue-Preferred/Light-Regulated) Expression of *Arabidopsis* PPD1

Two expression constructs were synthesised to enable the over expression of PPD1 under the pRICE Rubisco promoter in grasses, the nucleic acid coding sequences are shown in SEQ ID NO:40 and SEQ ID NO:117. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot>iastate<dot>eduicgi-bin/sp<dot>cgi).

The construct SEQ ID NO:40 (with and without the tail) was then placed between the rice Rubisco promoter and NOS terminator by the GATEWAY® LR reaction, to create SEQ ID NO:46 and SEQ ID NO:52 which coded for SEQ ID NO:36 and SEQ ID NO:38 respectively.

Similarly, for the construct SEQ ID NO 117 with and without the tail which coded for SEQ ID NO: 105 and SEQ ID NO: 111 respectively.

Generation of pTobRB7 Δ1.3::PPD Construct for (Root-Preferred) Expression of *Arabidopsis* PPD1

Two expression constructs were synthesised to enable the over expression of PPD1 under the pTobRB7 Δ1.3 promoter (Yamamoto et al 1991 Plant Cell, 3:371-382) in grasses, the nucleic acid coding sequences are shown in SEQ ID NO:40 and SEQ ID NO:117. The PPD ORF was optimised for expression in rice; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 deepc2<dot>psi <dot>iastate <dot>eduicgi-bin/sp<dot>cgi).

The construct SEQ ID NO:40 (with and without the tail) was then placed between the pTobRB7 Δ1.3 promoter and NOS terminator by the GATEWAY® LR reaction, to create SEQ ID NO:42 and SEQ ID NO:48 which coded for SEQ ID NO:36 and SEQ ID NO:38 respectively.

Similarly, for the construct SEQ ID NO 117 with and without the tail which coded for SEQ ID NO: 105 and SEQ ID NO: 111 respectively.

Generation of pTobRB7 Δ0.6::PPD Construct for (Root-Preferred) Expression of *Arabidopsis* PPD1

Two expression constructs were synthesised to enable the over expression of PPD1 under the pTobRB7 Δ0.6 promoter (Yamamoto et al 1991 Plant Cell, 3:371-382) in grasses, the nucleic acid coding sequence are shown in SEQ ID NO:40 and SEQ ID NO:117. The PPD ORF was optimised for expression in monocolyledonous plants; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by deepc2 (deepc2<dot>psi<dot> iastate<dot>edu/cgi-bin/sp<dot>cgi).

The construct SEQ ID NO:40 (with and without the tail) was then placed between the pTobRB7 Δ0.6 promoter and NOS terminator by the GATEWAY® LR reaction, to create SEQ ID NO:43 and SEQ ID NO:49 which coded for SEQ ID NO:36 and SEQ ID NO:38 respectively.

Similarly, for the construct SEQ ID NO 117 with and without the tail which coded for SEQ ID NO: 105 and SEQ ID NO: 111 respectively.

Generation of pAtWRKY6::PPD Construct for (Root-Preferred) Expression of *Arabidopsis* PPD1

Two expression constructs were synthesised to enable the over expression of PPD1 under the pAtWRKY6 promoter (Robatzek and Somssich 2001) in grasses, the nucleic acid coding sequences are shown in SEQ ID NO:40 and SEQ ID NO:117. The PPD ORF was optimised for expression in monocolyledonous plants; this included a modified Joshi sequence (Joshi 1997, Nucleic Acid Research 15, 6643-6653), optimisation of condons, removal of mRNA instability sequences, removal of polyA signal sequences, removal of cryptic splice sites, inclusion of the third intron from *Lolium perenne* DGAT1 (SEQ ID NO:39), addition of a BamHI removable C-terminal V5 epitope and His tag tail (encoding SEQ ID NO:36) and addition of a double stop codon. The position of the intron was optimised for splice site prediction, performed by deepc2 (deepc2<dot>psi<dot> iastate<dot>edu/cgi-bin/sp<dot>cgi).

The construct SEQ ID NO:40 (with and without the tail) was then placed between the pAtWRKY6 promoter and NOS terminator by the GATEWAY® LR reaction, to create SEQ ID NO:44 and SEQ ID NO:50 which coded for SEQ ID NO:36 and SEQ ID NO:38 respectively.

Similarly, for the construct SEQ ID NO 117 with and without the tail which coded for SEQ ID NO: 105 and SEQ ID NO: 111 respectively.

Transformation of Ryegrass

Ryegrass plants over-expressing the Peapod construct were generated by microprojectile bombardment using a method adapted from Altpeter et al. 2000 (Molecular Breeding 6: 519-528).

Calli for transformation were induced from immature inflorescences up to 7 mm. Floral tillers were harvested, surface sterilised in a sodium hypochlorite solution (4% available chlorine), dissected, then cultured in the dark at 25° C. for four to six weeks prior to transformation on a basal medium of Murashige and Skoog (MS) macro, micronutrients and vitamins (1962 Physiol Plant. 15: 473-497) supplemented with 30 g/L maltose, 5 mg/L 2,4-D, pH adjusted to 5.8 and solidified with 6 g/L agarose.

Plasmids were prepared using the Invitrogen Pure Link Hi Pure Plasmid Maxiprep Kit with the concentration adjusted to 1 μg/μL. The plasmid pAcH1, which contains an expression cassette comprising a chimeric hygromycin phosphotransferase (HPH) gene (Bilang et al. 1991 Gene 100: 247-250) expressed from the rice actin promoter with the first intron and terminated from the nos 3' polyadenylation signal, was used for selection. Plasmids containing PPD expression cassettes were mixed in a 1:1 molar ratio with pAcH1.

Plasmid DNA's were coated onto M17 tungsten particles (1.4 μM diameter mean distribution) using the method of Sanford et al. 1993 (Meth. Enzymol. 217: 483-509.) and transformed into target tissues using a DuPont PDS-1000/He Biolistic Particle Delivery System. Up to 6 hours before transformation the callus was sub-cultured onto the callus initiation media containing 64 g/L mannitol. Following transformation (approximately 16 hours) transformed calli were then transferred to a mannitol-free MS basal medium supplemented with 2 mg/L 2,4-D. After 2 days calli were transferred to the same medium containing 200 mg/L hygromycin and cultured in the dark for 4 weeks for the selection of transgenic events. Regeneration of whole plants from somatic embryos occurred under lights on a MS basal medium supplemented with 0.2 mg/L Kinetin, 30 g/L, sucrose, and 50 mg/L hygromycin, adjusted to pH 5.8 and solidified with 8 g/L phytoagar. Transformed plants were transferred to a contained greenhouse environment for analysis.

PCR Analysis of Transformants

PCR analysis was performed to confirm stable integration of the HPH and PPD transgenes into the genome for plants recovered from transformation experiments. Genomic DNA was extracted from approximately 50 mg of in vitro grown leaves using the Genomic DNA Mini Kit (Geneaid). Primer pairs specific to the HPH gene (hpt-1, 5'-GCTGGGG-CGTCGGTTTCCACTATCCG-3' (SEQ ID NO:131); hpt-2, 5'-CGCATAACAGCGGTCATTGACTGGAGC-3') (SEQ ID NO:132); and nos3' polyadenylation signal (nos3'-1f, 5'-CTGTTGCCGGTCTTGCGATG-3'-SEQ ID NO:133; nos3'-1r, 5'-GTCACATAGATGACACCGCG-3'-SEQ ID NO:134) were used to produce amplification products of 375 bp and 202 bp respectively. Control reactions comprising plasmid DNA template, non-transformed plant DNA or water only were also included. The protocol for PCR reactions consisted of: an initial denaturation of 94° C. for 5 minutes, 30 cycles of 95° C. 30 s, 55° C. 15 s, 72° C. 1 min, and an extension of 72° C. for 10 min. Amplification products were resolved on 1.0% agarose gels by gel electrophoresis in TAE buffer and visualized with a Bio-Rad Gel Doc imaging system.

Southern Blot Analysis of Grass Transformants

Southern blot hybridization was used to estimate the number of transgene copies per line. Genomic DNA was extracted from leaf material of greenhouse grown plants for Southern blot hybridization using the method of Doyle J and Doyle J 1990 (Focus, 12:13-15). DNA (20 µg) was digested and separated on a 0.8% agarose gel and transferred onto a nylon membrane (Roche) using capillary transfer with 0.4N NaOH. Genomic DNAs were digested with XbaI or HindIII when probing for the HPH and PPD transgenes respectively. Probes were prepared using the DIG PCR synthesis kit. Primer pairs specific to the HPH gene (rgh1, 5'-CTCGT-GCTTTCAGCTTCGATGTAG-3' [SEQ ID NO:135]; rgh5, 5'-GCTGGGGCGTCGGTTTCCACTATCGG-3' [SEQ ID NO:136]) and PPD (GrPPD1F, 5'-CACAGGATGGAT-TCTCCAAGG-3' [SEQ ID NO:137]; GrPPD1R, 5'-TAAGGTCCACGGAGAGGTTC-3' [SEQ ID NO:138]) were used to produce amplification products of 906 bp and 586 bp for probes respectively. Prehybridization (1 hour) and hybridization (12 hours) were performed at 45° C. using standard buffers (Roche). Detection was achieved using a non-radioactive method according to the manufacturer's protocol with CDP-Star as the chemiluminescent substrate. Light signals were detected using a Bio-Rad ChemiDoc MP System and software.

Generation of Polyclonal Antibodies Against PPD1 Protein and Immunoblotting

Custom made anti-PPD1 affinity-purified rabbit polyclonal antibodies were produced by GenScript using a full length *Arabidopsis thaliana* PPD1 protein. At a 1:5000 dilution the antibodies were capable of detecting less than 10 ng of purified PPD protein by immunoblot. Plant tissue was frozen in liquid nitrogen and ground to a fine powder. The frozen tissue powder was added to extraction buffer containing 50 mM Tris pH 7.5, 150 mM NaCl, 1 mM EDTA, 10% (vol/vol) glycerol, 5 mM DTT, 1% (vol/vol) complete protease inhibitor cocktail (Sigma), and 1% (vol/vol) Triton X-100 at a ratio of 1.0/1.5 (wt/vol), homogenised until thawed and then centrifuged for 12 min at 16,300 g and 4° C. Total soluble protein in the supernatant was quantified by Bradford assay (Coomassie Plus, Thermo Scientific), adjusted to give equivalent total protein concentrations per sample (typically between 10-40 µg), denatured in 1×Nu-PAGE LDS sample buffer (Invitrogen) and run in a 4-12% Bis-Tris SDS/PAGE gel (Novex). Following blotting to PVDF membrane using an iBlot apparatus (Invitrogen) protein detection was with a 1:5,000 dilution of the 1° anti-PPD1 polyclonal antibodies, followed by a 1:5,000 dilution of 2° anti-rabbit goat HRP antibodies (Sigma), application of Western Bright ECL reagent (Advansta), and image capture using a ChemiDoc™ instrument (BioRad).

Leaf Biomass Analysis of Grass Transformants

Figure 12A:
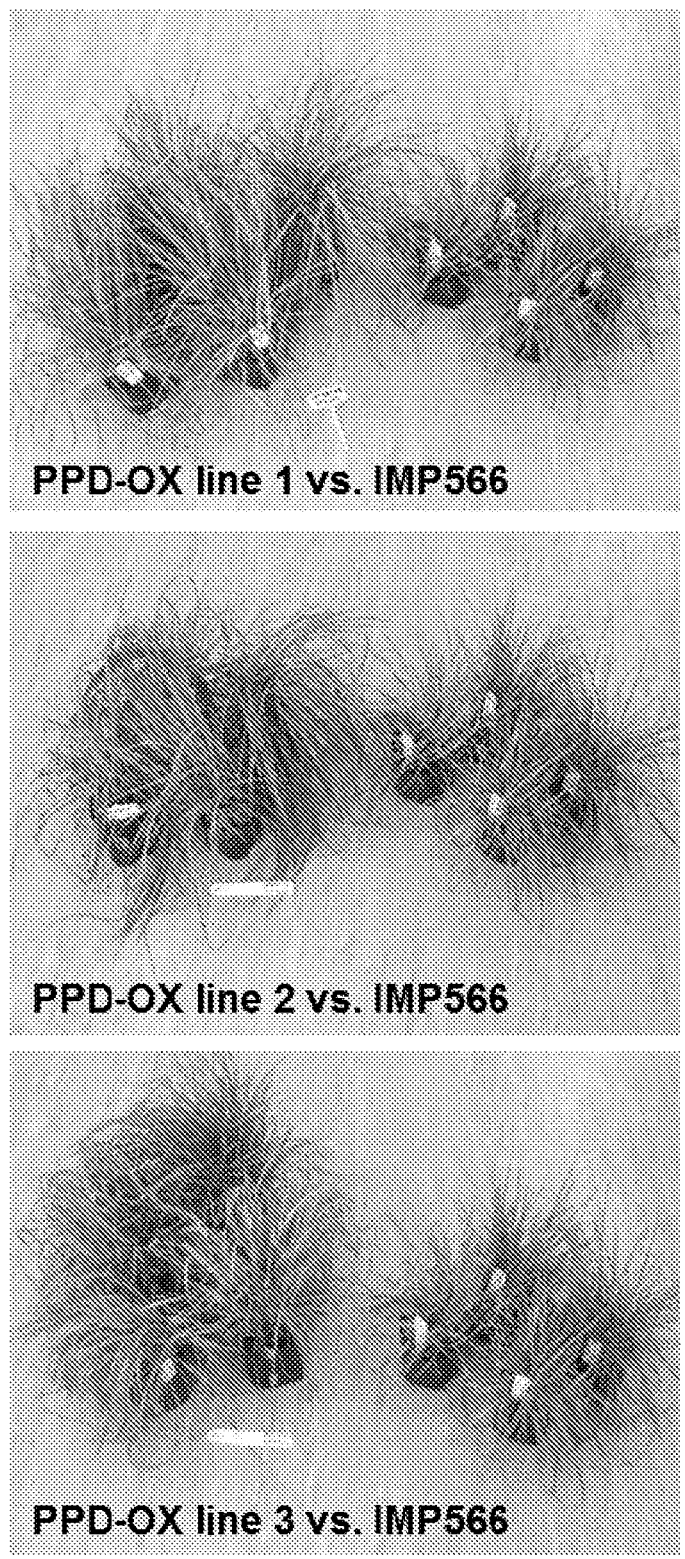
FIGS. 12A and 12B show the increase in shoot and root growth of ryegrass plants over expressing PEAPOD from *Arabidopsis thaliana* or PEAPOD from *Ambroella trichopoda* compared to the wild type and vector control.

An equal number (typically 4-10) of tillers were taken from WT and ryegrass plants transformed with *Arabidopsis* PPD under one of two green tissue promoters. Tillers were planted into plastic grow bags containing potting mix and pruned to be of equal height. Plants were grown for approximately 6 weeks in the glasshouse; the increase in leaf biomass/growth/length/branching of ryegrass plants transformed with *Arabidopsis* PPD under a green tissue promoter compared to WT plants could be seen by observing the leaf growth (FIG. 12A). The increase in leaf/shoot biomass can be quantified removing the attached above ground portion (leaves and shoots) and drying them at 65° C. for 48 hr then weighing the dry weights.

An equal number (typically 4-10) of tillers were taken from WT and ryegrass plants transformed with *Arabidopsis* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Arabidopsis* PPD under a constitutive promoter compared to WT plants could be seen by observing the leaf growth (FIG. 12A). The increase in leaf/shoot biomass was quantified removing the attached above ground portion (leaves and shoots) and drying them at 65° C. for 48 hr then weighing the dry weights (Table 2).

TABLE 2

|  | Wt ryegrass | Vector control | Constit promoter:: Arabidopsis PPD line 1 | Constit promoter:: Arabidopsis PPD line 2 | Constit promoter:: Arabidopsis PPD line 3 | Constit promoter:: Arabidopsis PPD line 4 |
| --- | --- | --- | --- | --- | --- | --- |
| Av tiller number (n = 12) | 43.5 | 28.4 | 131.7 | 117.1 | 104.3 | 136.0 |
| SE | 3.5 | 8.9 | 15.2 | 8.8 | 11.4 | 12.3 |
| Av shoot weight (g) (n = 12) | 0.6789 | 0.2854 | 2.5113 | 1.9946 | 1.8395 | 2.0015 |
| SE | 0.1118 | 0.1064 | 0.2026 | 0.2799 | 0.2248 | 0.2133 |

An equal number (typically 4-10) of tillers were taken from WT and ryegrass plants transformed with *Trifolium repens* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Trifolium repens* PPD under a constitutive promoter compared to WT plants could be seen by observing the leaf growth (FIG. 12A). The increase in leaf/shoot biomass can be quantified removing the attached above ground portion (leaves and shoots) and drying them at 65° C. for 48 hr then weighing the dry weights.

An equal number (typically 4-10) of tillers were taken from WT and ryegrass plants transformed with *Amborella trichopoda* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Amborella trichopoda* PPD under a constitutive promoter compared to WT plants could be seen by observing the leaf growth (FIG. 12A).

The increase in leaf/shoot biomass can be quantified removing the attached above ground portion (leaves and shoots) and drying them at 65° C. for 48 hr then weighing the dry weights.

An equal number (typically 4-10) of tillers were taken from WT and ryegrass plants transformed with *Musa acuminate* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Musa acuminate* PPD under a constitutive promoter compared to WT plants could be seen by observing the leaf growth (FIG. 12A). The increase in leaf/shoot biomass can be quantified removing the attached above ground portion (leaves and shoots) and drying them at 65° C. for 48 hr then weighing the dry weights.

An equal number (typically 4-10) of tillers were taken from WT and ryegrass plants transformed with *Picea sitchensis* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Picea sitchensis* PPD under a constitutive promoter compared to WT plants could be seen by observing the leaf growth (FIG. 12A). The increase in leaf/shoot biomass can be quantified removing the attached above ground portion (leaves and shoots) and drying them at 65° C. for 48 hr then weighing the dry weights.

An equal number (typically 4-10) of tillers were taken from WT and ryegrass plants transformed with *Selaginella moellendorffii* PPD under a constitutive promoter. Tillers were planted into plastic grow bags containing potting mix and pruned to be of equal height. Plants were grown for approximately 6 weeks in the glasshouse; the increase in leaf biomass/growth/length/branching of ryegrass plants transformed with *Selaginella moellendorffii* PPD under a constitutive promoter compared to WT plants could be seen by observing the leaf growth (FIG. 12A). The increase in leaf/shoot biomass can be quantified removing the attached above ground portion (leaves and shoots) and drying them at 65° C. for 48 hr then weighing the dry weights.

Root Biomass Analysis of Grass Transformants

Figure 12B:
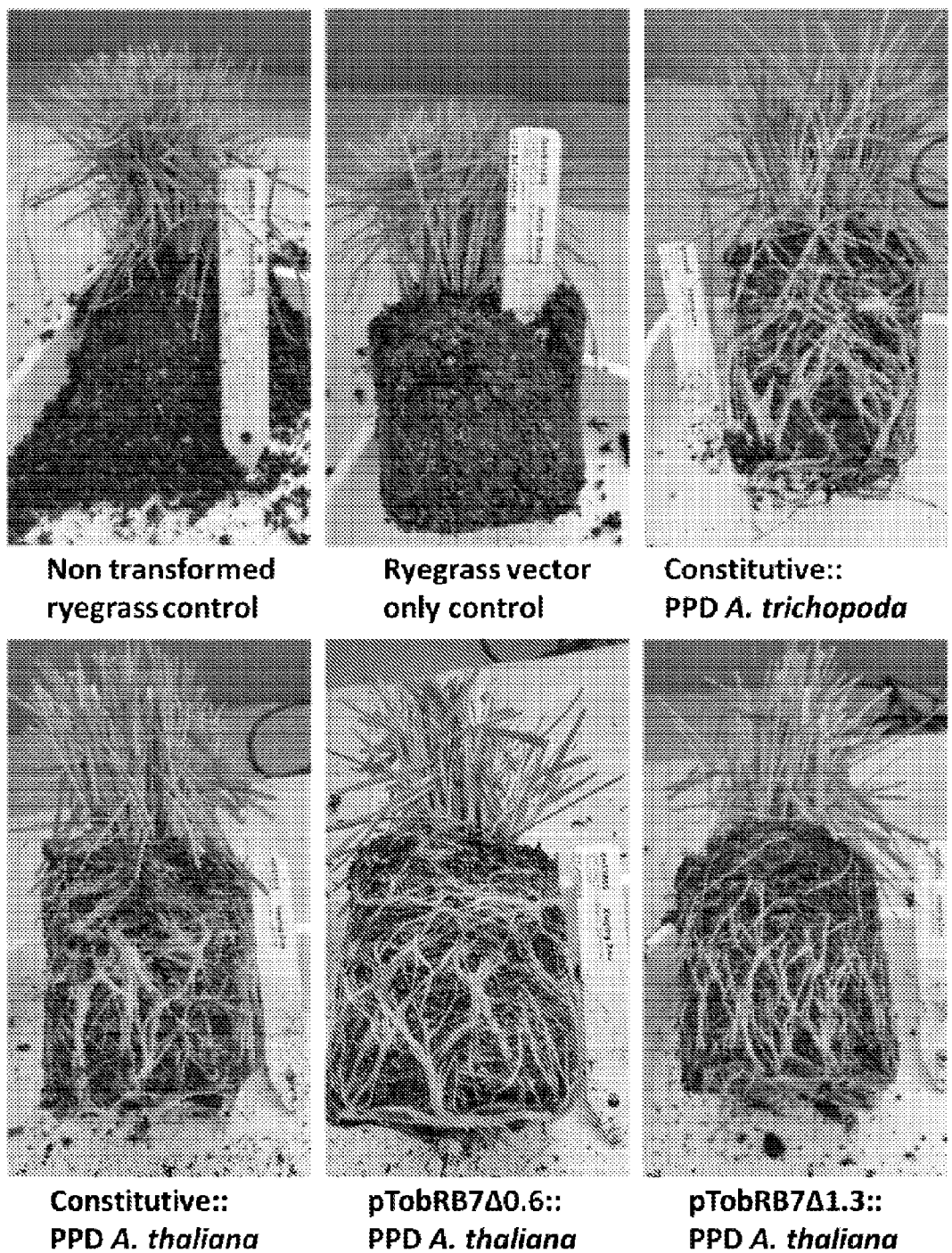

An equal number (typically 4-10) of tillers were taken from WT and ryegrass plants transformed with *Arabidopsis* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *Arabidopsis* PPD under a root promoter compared to WT plants could be seen by observing the root growth beyond the grow bag (FIG. 12B). The increase in root biomass was quantified removing the attached above ground portion (leaves and shoots) and drying the roots at 65° C. for 48 hr then weighing the dry weights (Tables 3 and 4)

TABLE 3

|  | Wt ryegrass | Vector control | pTobRB7Δ0.6:: Arabidopsis PPD line 1 | pTobRB7Δ0.6:: Arabidopsis PPD line 2 | pTobRB7Δ0.6:: Arabidopsis PPD line 3 |
| --- | --- | --- | --- | --- | --- |
| Av root weight (9) (n = 12) | 0.0733 | 0.0387 | 0.2338 | 0.3686 | 0.3704 |
| SE | 0.0138 | 0.0125 | 0.0357 | 0.0356 | 0.0611 |

TABLE 4

|  | Wt ryegrass | Vector control | pTobRB7Δ1.3:: Arabidopsis PPD line 1 | pTobRB7Δ1.3:: Arabidopsis PPD line 2 | pTobRB7Δ1.3:: Arabidopsis PPD line 3 | pTobRB7Δ1.3:: Arabidopsis PPD line 4 |
| --- | --- | --- | --- | --- | --- | --- |
| Av root weight (g) (n = 12) | 0.0733 | 0.0387 | 0.3227 | 0.2338 | 0.2720 | 0.4014 |
| SE | 0.0138 | 0.0125 | 0.0556 | 0.0191 | 0.0581 | 0.0445 |

An equal number (typically 4-10) of tillers were taken from WT and ryegrass plants transformed with *Arabidopsis* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Arabidopsis* PPD under a constitutive promoter compared to WT plants could be seen by observing the root growth beyond the grow bag (FIG. 12B). The increase in root biomass was quantified removing the attached above ground portion (leaves and shoots) and drying the roots at 65° C. for 48 hr then weighing the dry weights (Table 5).

TABLE 5

|  | Wt ryegrass | Vector control | Constit promoter:: Arabidopsis PPD line 1 | Constit promoter:: Arabidopsis PPD line 2 | Constit promoter:: Arabidopsis PPD line 3 | Constit promoter:: Arabidopsis PPD line 4 |
|---|---|---|---|---|---|---|
| Av root weight (g) (n = 12) | 0.0733 | 0.0387 | 0.4506 | 0.5657 | 0.3077 | 0.3503 |
| SE | 0.0138 | 0.0125 | 0.0428 | 0.0625 | 0.0426 | 0.0638 |

An equal number (typically 4-10) of tillers were taken from WT and ryegrass plants transformed with *Trifolium repens* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Trifolium repens* PPD under a constitutive promoter compared to WT plants could be seen by observing the root growth beyond the grow bag. The increase in root biomass can be quantified removing the attached above ground portion (leaves and shoots) and drying the roots at 65° C. for 48 hr then weighing the dry weights.

An equal number (typically 4-10) of tillers were taken from WT and ryegrass plants transformed with *Amborella trichopoda* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Amborella trichopoda* PPD under a constitutive promoter compared to WT plants could be seen by observing the root growth beyond the grow bag (FIG. 12B). The increase in root biomass can be quantified removing the attached above ground portion (leaves and shoots) and drying the roots at 65° C. for 48 hr then weighing the dry weights.

An equal number (typically 4-10) of tillers were taken from WT and ryegrass plants transformed with *Musa acuminate* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Musa acuminate* PPD under a constitutive promoter compared to WT plants could be seen by observing the root growth beyond the grow bag. The increase in root biomass can be quantified removing the attached above ground portion (leaves and shoots) and drying the roots at 65° C. for 48 hr then weighing the dry weights.

An equal number (typically 4-10) of tillers were taken from WT and ryegrass plants transformed with *Picea sitchensis* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Picea sitchensis* PPD under a constitutive promoter compared to WT plants could be seen by observing the root growth beyond the grow bag. The increase in root biomass can be quantified removing the attached above ground portion (leaves and shoots) and drying the roots at 65° C. for 48 hr then weighing the dry weights.

An equal number (typically 4-10) of tillers were taken from WT and ryegrass plants transformed with *Selaginella moellendorffii* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Selaginella moellendorffii* PPD under a constitutive promoter compared to WT plants could be seen by observing the root growth beyond the grow bag. The increase in root biomass can be quantified removing the attached above ground portion (leaves and shoots) and drying the roots at 65° C. for 48 hr then weighing the dry weights.

Drought Tolerance Analysis of Grass Transformants

An equal number (typically 4-10) of tillers were taken from WT and ryegrass plants transformed with *Arabidopsis* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *T. repens* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *M. acuminate* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *A. trichopoda* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with P. sitchensis PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with S. moellendorffii PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with Arabidopsis PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

Flower Branching Analysis of Grass Transformants

An equal number (typically 4-10) of tillers were taken from WT and ryegrass plants transformed with Arabidopsis PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

An equal number (typically 4-10) of tillers were taken from WT and ryegrass plants transformed with T. repens PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

An equal number (typically 4-10) of tillers were taken from WT and ryegrass plants transformed with M. acuminate PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

An equal number (typically 4-10) of tillers were taken from WT and ryegrass plants transformed with A. trichopoda PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

An equal number (typically 4-10) of tillers were taken from WT and ryegrass plants transformed with P. sitchensis PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

An equal number (typically 4-10) of tillers were taken from WT and ryegrass plants transformed with S. moellendorffii PPD under a constitutive promoter. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number (stalks bearing inflorescences and/or an increase in the number of spikelets within an inflorescence) of flowering branches of the PPD over expressing plants and compared to the WT plants.

An equal number (typically 4-10) of tillers were taken from WT and ryegrass plants transformed with Arabidopsis PPD under one of three root promoters. Tillers were planted in large pots containing potting mix and soil. Plants were allowed to establish in the glasshouse before being induced to flower by growing at 6° C. in short days (8 hour photoperiod) for 10 weeks to vernalise followed by transfer to the greenhouse for floral development, long days (16+ hour photoperiod) at 20-25° C. The increase in floral branching can be quantified by counting the number of flowering branches (stalks bearing inflorescences and/or an increase in the number of spikelets within an inflorescence) of the PPD over expressing plants and compared to the WT plants.

REFERENCES

Achard, P. Genschik P. (2009). Releasing the brakes of plant growth: how Gas shutdown DELLA proteins. J. Exp. Bot., 60:1985-1092.

Altschul, S. F., Gish, W., Miller, W., Myers, E. W., Lipman, D. J. (1990). Basic local alignment search tool. J. Mol. Biol. 215:403-410.

Anjum, S A., Wang, L C., Farooq, M., Hussain, M., Zou, C M. (2011) Brassinolide application improves the drought tolerance in maize through modulation of enzymatic antioxidants and leaf gas exchange. J. Agronomy and Crop Sci. 197:177-185.

Chory and Wang, 2005, Genes involved in brassinosteroid hormone action in plants, U.S. Pat. No. 6,921,848 B2

Clouse, S. D. Brassinosteroid signal transduction: from receptor kinase activation to transcriptional networks regulating plant development. Plant Cell 23, 1219-1230 (2011).

Clough S. J. and Bent A. F. (1998) Floral dip: a simplified method for *Agrobacterium*-mediated transformation of *Arabidopsis thaliana*. Plant J. 16: 735-743.

Clouse, S. D. & Sasse, J. M. BRASSINOSTEROIDS: Essential regulators of plant growth and development. Annu. Rev. Plant Physiol. Plant Mol. Biol. 16, 427-451 (1998).

Gallego-Bartolome, J., Minguet, E G., Grau-Enguix, F., Abbas, M., Locascio, A., Thomas, S G., Alabadi, D., Blazquez, M A. (2012). Molecular mechanism for the interaction between gibberellin and brassionosteroid signalling pathways in *Arabidopsis*. PNAS, 109:13446-13451.

Garcia, M. E., Lynch, T., Peeters, J., Snowden, C. & Finkelstein, R. A small plant-specific protein family of ABI five binding proteins (AFPs) regulates stress response in germinating *Arabidopsis* seeds and seedlings. Plant Mol. Biol. 67, 643-658 (2008). Guo, H., Li, L., Aluru, M., Sluru, S., Yin, Y. (2013). Mechanisms and networks for brassinosteroid regulated gene expression. Current Opinion in Plant Biology 16:545-553.

He, J-X., Gendron, J M., Sun, Y., Gampaia, S L., Gendron, N., Sun, C Q., Wang, Z-Y. (2005). BZR1 is a transcriptional repressor with dual roles in brassinosteroid homeostasis and growth responses. Science 307:1634-1638.

Hothorn, M., Belkhadir, Y., Dreux, M., Dabi, T., Noel, J. P., Wilson, I. A. & Chory, J. Structural basis of steroid hormone perception by the receptor kinase BRI1. Nature 474, 467-471 (2011).

Hou, X., Lee L Y C, Xia, K., Yan, Y., Yu H. (2010). DELLAs modulate jasmonate signalling via competitive binding to JAZs. Devel. Cell 19:884-894.

Jiang, W-B., Lin, W-H. (2013). Brassinosteroid functions in *Arabidopsis* seed development. Plant Signaling & Behavior 8:10, e25928; October 2013.

Jiang, L., Liu, X., Xiong, G., Liu, H., Chen, F., Wang, L., Meng, X., Liu, G., Yu, H., Yuan, Y., Yi, W., Zhao, L., Ma, H., He, Y., Wu, Z., Melcher, K., Qian, Q., Xu, H. E., Wang, Y. & Li, J. DWARF 53 acts as a repressor of strigolactone signalling in rice. Nature 504, 401-405 (2013).

Karimi, M., Inzé, D. & Depicker, A. Gateway vectors for *Agrobacterium*-mediated plant transformation. Trends Plant Sci. 7, 193-195 (2002)

Khripach, V., Zhabinskii, V., Groot, A D. (2000). Twenty years of brassinosteroids: Steroidal plant hormones warrant better crops for the XXI century. Ann. Bot., 86:441-447.

Kinoshita, T., Caño-Delgado, A., Seto, H., Hiranuma, S., Fujioka, S., Yoshida, S. & Chory, J. Binding of brassinosteroids to the extracellular domain of plant receptor kinase BRI1. Nature 433, 167-171 (2005).

Lawit, Kundu, Rao and Tomes, 2007, Isolated polynucleotide molecules corresponding to mutant and wild-type alleles of the maize D9 gene and methods of use, WO 2007124312 A2

Li, Q-F., He, J-X. (2013). Mechanisms of signalling crosstalk between brassinosteroids and gibberellins. Plant Signaling & Behavior 8:7,e24686; July 2013; © 2013 Landes Bioscience.

Mathew, C., Hofmann, W A., Osborne, M A. (2009). Pasture response to gibberellins: A review and recommendations. NZ. J. Agric. Res., 52:213-225.

Pauwels, L., Barbero, G. F., Geerink, J., Tilleman, S., Grunewald, W., Pérez, A. C., Chico, J. M., Bossche, R. V., Sewell, J., Gil, E., Garcia-Casado, G., Witters, E., Inzě, D., Long, J. A., Jaeger, G. D., Solano, R. & Goossens, A. NINJA connects the co-repressor TOPLESS to jasmonate signalling. Nature 464, 788-791 (2010).

Pérez, A. C., Durand, A. N., Bossche, R. V., De Clercq, R., Persiau, G., Van Wees, S. C. M., Pieterse, C. M. J., Gevaert, K., De Jaeger, G., Goossens, A. & Pauwels, L. The non-JAZ TIFY protein TIFY8 from *Arabidopsis thalianais* a transcriptional repressor. PLos ONE 9, e84891 (2014).

Prusakova, L D., Ezhov, M N., Salnikov, A I. (1999). The use of emistim, epibrassinolide and uniconazole to overcome quality difference of buckwheat grains. Agrarian Russia: 41-44.

Robatzek and Somssich (2001). The Plant Journal, 28: 123-133

She, J., Han, Z., Kim, T. W., Wang, J., Cheng, W., Chang, J., Shi, S., Wang, J., Yang, M., Wang, Z-Y. & Chai, J. Structural insight into brassinosteroid perception by BRI1. Nature 474, 472-476 (2011).

Sun, T-P. (2011). The molecular mechanism and evolution of the GA-GID1-DELLA signalling module in plants. Review. Current Biology, 21:R338-R345.

Szemenyei, H., Hannon, M. & Long, J. A. TOPLESS mediates auxin-dependent transcriptional repression during *Arabidopsis* embryogenesis. Science 319, 1384-1386 (2008).

Thummel, C. S. & Chory, J. Steroid signalling in plants and insects-common themes, different pathways. Genes Dev. 16, 3113-3129 (2002).

Vanholme, B., Grunewald, W., Bateman, A., Kohchi, T., Gheysen, G. (2007). The tify family previously known as ZIM. Trends in Plant Science, 12:239-244.

Vardhini, B V. (2012). Application of brassinolide mitigates saline stress of certain metabolites of sorghum grown in Karaikal. J. Phytology, 4:1-3.

Wang, Z-Y., Nakano T., Gendron, J., He, J., Chen, M., Vafeados, D., Yang, Y., Fujioka, S., Yoshida, S., Asami, T., Chory, J. (2002). Nuclear-localised BZR1 mediates brassinosteroid-induced growth and feedback suppression of brassinosteroid biosynthesis. Developmental Cell 2:505-513.

Wang, C-M., Shang, J-X., Chen, Q-X., Oses-Prieto, J. A., Bai, M-Y, Yang, Y., Yuan, M., Zhang, Y-L., Mu, C-C., Deng, Z., Wei C-Q., Burlingame, A. L., Wang, Z-Y. & Sun, Y. Identification of BZR1-interacting proteins as potential components of the brassinosteroid signalling pathway in *Arabidopsis* through tandem affinity purification. Mol. Cell. Proteomics 12, 3653-3665 (2013).

Winichayakul, S., Pernthaner, A., Scott, R., Vlaming, R. & Roberts, N. (2008) Head-to-tail fusions of camelid antibodies can be expressed in planta and bind in rumen fluid. Biotech. & Appl. Biochem. 53, 111-122.

White, D. (2006) PEAPOD regulates lamina size and curvature in *Arabidopsis. PNAS,* 103:13238-13243.

White, D. (2007). Novel plant genes and uses thereof, WO 2007105967A8. Yamamoto et al (1991). Characterization of cis-acting sequences regulating root-specific gene expression in tobacco. Plant Cell, 3:371-382

Zhu, J-Y., Sae-Seaw, J. & Wang, Z-Y. Brassinosteroid signalling. Development 140, 1615-1620 (2013).

SUMMARY OF SEQUENCES

| SEQ ID NO: | Sequence type | Species/Source | Reference |
|---|---|---|---|
| 1 | polypeptide | *Arabidopsis thaliana* | PEAPOD 1 protein |
| 2 | polypeptide | *Arabidopsis thaliana* | PEAPOD 2 protein |
| 3 | polypeptide | *Populus trichocarpa* | PEAPOD protein |
| 4 | polypeptide | *Picea abies* | PEAPOD protein |
| 5 | polypeptide | *Picea sitchensis* | PEAPOD protein |
| 6 | polypeptide | *Gossypium raimondii* | PEAPOD protein |
| 7 | polypeptide | *Aquilegia coerulea* | PEAPOD protein 1 |
| 8 | polypeptide | *Aquilegia coerulea* | PEAPOD protein 2 |
| 9 | polypeptide | *Medicago truncatula* | PEAPOD protein |
| 10 | polypeptide | *Solanum lycopersicum* | PEAPOD protein |
| 11 | polypeptide | *Trifolium repens* | PEAPOD protein |
| 12 | polypeptide | *Amborella trichopoda* | PEAPOD protein |
| 13 | polypeptide | *Selaginella moellendorffii* | PEAPOD protein 1 |
| 14 | polypeptide | *Selaginella moellendorffii* | PEAPOD protein 2 |
| 15 | polypeptide | *Nicotiana tabacum* | PEAPOD protein |
| 16 | polypeptide | *Solanum tuberosum* | PEAPOD protein |
| 17 | polypeptide | *Glycine max* | PEAPOD protein |
| 18 | polypeptide | *Citrus clementine* | PEAPOD protein |
| 19 | polypeptide | *Ricinus communus* | PEAPOD protein |
| 20 | polypeptide | *Vitis vinifera* | PEAPOD protein |
| 21 | polypeptide | *Morus notabilis* | PEAPOD protein |
| 22 | polypeptide | *Phoenix dactylifera* | PEAPOD protein |
| 23 | polypeptide | *Theobroma cacao* | PEAPOD protein |
| 24 | polypeptide | *Spirodela polyrhiza* | PEAPOD protein |
| 25 | polypeptide | *Musa species* | PEAPOD protein |
| 26 | polypeptide | *Phalaenopsis aphrodite* | PEAPOD protein |
| 27 | polypeptide | Artificial | internal 46 amino acid Arabidopsis PPD1 region |
| 28 | polypeptide | Artificial | internal 46 amino acid consensus motif 1, identical residues |
| 29 | polypeptide | Artificial | internal 46 amino acid consensus motif 2, variable residues |
| 30 | polypeptide | Artificial | internal 27 amino acid Arabidopsis PPD1 region |
| 31 | polypeptide | Artificial | internal 27 amino acid consensus motif 1, identical residues |
| 32 | polypeptide | Artificial | internal 27 amino acid consensus motif 2, variable residues |
| 33 | polypeptide | Artificial | 6 amino acid TIFY motif from Arabidopsis PPD1 |
| 34 | polypeptide | Artificial | 6 amino acid TIFY consensus motif 1, identical residues |
| 35 | polypeptide | Artificial | 6 amino acid TIFY consensus motif 1, variable residues |
| 36 | polypeptide | Artificial | PPD1 V5-HIS tail peptide sequence |
| 37 | polypeptide | Artificial | Linker and V5-His tail peptide sequence |
| 38 | polypeptide | Artificial | PPD1 (no tail) peptide sequence |
| 39 | polynucleotide | Artificial | Lolium perenne DGAT1 intron 3 nucleic acid sequence |
| 40 | polynucleotide | Artificial | GENEART synthesised rice optimised PPD1 coding region (with intron) nucleic acid sequence for expression in grass under the rice actin/maize Ubi constitutive promoters; rice CAB green |

| SEQ ID NO: | Sequence type | Species/Source | Reference |
|---|---|---|---|
| | | | tissue promoter; the rice Rubisco green tissue promoter; the tobacco TobRB7 Δ1.3 root promoter; the tobacco TobRB7 Δ0.6 root promoter; and the Arabidopsis AtWRKY6 root promoter. |
| 41 | polynucleotide | Artificial | Rice actin promoter::attB1::rice optimised PPD-V5-His (INTRON)::attB2::terminator expression cassette nucleic acid sequence |
| 42 | polynucleotide | Artificial | TobRB7 Δ1.3 promoter::attB1::rice optimised PPD1-V5-His (INTRON)::attB2::nos terminator expression cassette nucleic acid sequence |
| 43 | polynucleotide | Artificial | TobRB7 Δ0.6 promoter::attB1::rice optimised PPD1-V5-His (INTRON)::attB2::nos terminator expression cassette nucleic acid sequence |
| 44 | polynucleotide | Artificial | AtWRKY6 promoter::attB1::rice optimised PPD1-V5-His (INTRON)::attB2::nos terminator expression cassette nucleic acid sequence |
| 45 | polynucleotide | Artificial | Rice CAB promoter::attB1::rice optimised PPD1-V5-His (INTRON)::attB2::nos terminator expression cassette nucleic acid sequence |
| 46 | polynucleotide | Artificial | Rice Rubisco promoter::attB1::rice optimised PPD1-V5-His (INTRON)::attB2::nos terminator expression cassette nucleic acid sequence |
| 47 | polynucleotide | Artificial | Rice actin promoter::attB1::rice optimised PPD1 (INTRON)::attB2::terminator expression cassette nucleic acid sequence |
| 48 | polynucleotide | Artificial | TobRB7 Δ1.3 promoter::attB1::rice optimised PPD1 (INTRON)::attB2::nos terminator expression cassette |
| 49 | polynucleotide | Artificial | TobRB7 TobRB7 Δ0.6 promoter::attB1::rice optimised PPD1 (INTRON)::attB2::nos terminator expression cassette |
| 50 | polynucleotide | Artificial | AtWRKY6 promoter::attB1::rice optimised PPD1 (INTRON)::attB2::nos terminator expression cassette. |
| 51 | polynucleotide | Artificial | Rice CAB promoter::attB1::rice optimised PPD1 |

| SEQ ID NO: | Sequence type | Species/Source | Reference |
|---|---|---|---|
| | | | (INTRON)::attB2::nos terminator expression cassette nucleic acid sequence |
| 52 | polynucleotide | Artificial | Rice Rubisco promoter::attB1::rice optimised PPD1 (INTRON)::attB2::nos terminator expression cassette nucleic acid sequence |
| 53 | polypeptide | Artificial | Yeast two Hybrid (Y2H) DNA binding domain (DBD) peptide sequence |
| 54 | polypeptide | Artificial | Y2H activation domain (AD) peptide sequence |
| 55 | polypeptide | Artificial | Y2H PPD1-DBD peptide sequence |
| 56 | polypeptide | Artificial | Y2H PPD1-AD peptide sequence |
| 57 | polypeptide | Artificial | Y2H PPD1-ppd-AD peptide sequence |
| 58 | polypeptide | Artificial | Y2H PPD1-tify-AD peptide sequence |
| 59 | polypeptide | Artificial | Y2H PPD1-jas*-AD peptide sequence |
| 60 | polypeptide | Artificial | TPL peptide sequence |
| 61 | polypeptide | Artificial | Y2H TPL-DBD peptide sequence |
| 62 | polypeptide | Artificial | NINJA peptide sequence |
| 63 | polypeptide | Artificial | Y2H NINJA-AD peptide sequence |
| 64 | polypeptide | Artificial | Y2H BZR1-AD peptide sequence |
| 65 | polypeptide | Artificial | Y2H RGA1 peptide sequence |
| 66 | polypeptide | Artificial | Y2H RGA1-AD peptide sequence |
| 67 | polypeptide | Artificial | Y2H PPD1-ppd-DBD peptide sequence |
| 68 | polypeptide | Artificial | Y2H PPD1-tify-DBD peptide sequence |
| 69 | polypeptide | Artificial | Y2H PPD1-jas*-DBD peptide sequence |
| 70 | polypeptide | Artificial | Bimolecular Fluorescence (BiFC) nYFP peptide sequence |
| 71 | polypeptide | Artificial | BiFC cYFP peptide sequence |
| 72 | polypeptide | Artificial | BiFC nYFP-NINJA peptide sequence |
| 73 | polypeptide | Artificial | BiFC nYFP-BZR1 peptide sequence |
| 74 | polypeptide | Artificial | BiFC cYFP-PPD1 peptide sequence |
| 75 | polypeptide | Artificial | BiFC cYFP-NINJA peptide sequence |
| 76 | polypeptide | Artificial | BiFC cYFP-BZR1 peptide sequence |
| 77 | polypeptide | Artificial | BiFC cYFP-PPD1-ppd peptide sequence |
| 78 | polypeptide | Artificial | BiFC cYFP-PPD1-tify peptide sequence |
| 79 | polypeptide | Artificial | BiFC cYFP-PPD1-jas* peptide sequence |
| 80 | polynucleotide | *Arabidopsis thaliana* | *Arabidopsis thaliana* PPD1 coding sequence |
| 81 | Polynucleotide | *Arabidopsis thaliana* | *Arabidopsis thaliana* PPD2 coding sequence |
| 82 | Polynucleotide | *Populus trichocarpa* | *Populus trichocarpa*, PPD coding sequence |
| 83 | Polynucleotide | *Picea abies* | *Picea abies*, PPD genomic sequence |
| 84 | Polynucleotide | *Gossypium raimondii* | *Gossypium raimondii*, PPD coding sequence |
| 85 | Polynucleotide | *Aquilegia coerulea* | *Aquilegia coerulea*, PPD coding sequence 1 |

-continued

| SEQ ID NO: | Sequence type | Species/Source | Reference |
|---|---|---|---|
| 86 | Polynucleotide | Aquilegia coerulea | Aquilegia coerulea, PPD coding sequence 2 |
| 87 | Polynucleotide | Medicago truncatula | Medicago truncatula, PPD coding sequence |
| 88 | Polynucleotide | Solanum lycopersicum | Solanum lycopersicum, PPD coding sequence |
| 89 | Polynucleotide | Trifolium repens | Trifolium repens, PPD coding sequence |
| 90 | Polynucleotide | Amborella trichopoda | Amborella trichopoda, PPD coding sequence |
| 91 | Polynucleotide | Selaginella moellendorffii | Selaginella moellendorffii, PPD coding sequence 1 |
| 92 | Polynucleotide | Selaginella moellendorffii | Selaginella moellendorffii, PPD coding sequence 2 |
| 93 | Polynucleotide | Nicotiana tabacum | Nicotiana tabacum, PPD coding sequence |
| 94 | Polynucleotide | Solanum tuberosum | Solanum tuberosum, PPD coding sequence |
| 95 | Polynucleotide | Glycine max | Glycine max, PPD coding sequence |
| 96 | Polynucleotide | Citrus clementine | Citrus clementine, PPD coding sequence |
| 97 | Polynucleotide | Ricinus communus | Ricinus communus, PPD coding sequence |
| 98 | Polynucleotide | Vitis vinifera | Vitis vinifera, PPD coding sequence |
| 99 | Polynucleotide | Morus notabilis | Morus notabilis, PPD coding sequence |
| 100 | Polynucleotide | Phoenix dactylifera | Phoenix dactylifera, PPD coding sequence |
| 101 | Polynucleotide | Theobroma cacao | Theobroma cacao, PPD coding sequence |
| 102 | Polynucleotide | Spirodela polyrhiza | Spirodela polyrhiza, PPD genomic sequence |
| 103 | Polynucleotide | Musa species | Musa species, PPD coding sequence |
| 104 | Polynucleotide | Phalaenopsis aphrodite | Phalaenopsis aphrodite, PPD coding sequence |
| 105 | Polypeptide | Artificial | Arabidopsis thaliana PPD1 + V5-His tag |
| 106 | Polypeptide | Artificial | Trifolium repens PPD + V5-His tag |
| 107 | Polypeptide | Artificial | Amborella trichopoda PPD + V5-His tag |
| 108 | Polypeptide | Artificial | Musa acuminate PPD + V5-His tag |
| 109 | Polypeptide | Artificial | Picea sitchensis PPD + V5-His tag |
| 110 | Polypeptide | Artificial | Selaginella moellendorffii PPD + V5-His tag |
| 111 | Polypeptide | Artificial | Arabidopsis thaliana PPD - no tag |
| 112 | Polypeptide | Artificial | Trifolium repens PPD - no tag |
| 113 | Polypeptide | Artificial | Amborella trichopoda PPD - no tag |
| 114 | Polypeptide | Artificial | Musa acuminate PPD - no tag |
| 115 | Polypeptide | Artificial | Picea abies PPD - no tag |
| 116 | Polypeptide | Artificial | Selaginella moellendorffii PPD - no tag |
| 117 | Polynucleotide | Artificial | Arabidopsis thaliana PPD - monocot optimised nucleic acid sequence |
| 118 | Polynucleotide | Artificial | Trifolium repens PPD - monocot optimised nucleic acid sequence |
| 119 | Polynucleotide | Artificial | Amborella trichopoda PPD - monocot optimised nucleic acid sequence |
| 120 | Polynucleotide | Artificial | Musa acuminate PPD - monocot optimised nucleic acid sequence |
| 121 | Polynucleotide | Artificial | Picea sitchensis PPD - monocot optimised nucleic acid sequence |

| SEQ ID NO: | Sequence type | Species/Source | Reference |
|---|---|---|---|
| 122 | Polynucleotide | Artificial | *Selaginella moellendorffii* PPD - monocot optimised nucleic acid sequence |
| 123 | Polynucleotide | Artificial | *Arabidopsis thaliana* PPD - dicot optimised nucleic acid sequence |
| 124 | Polynucleotide | Artificial | *Trifolium repens* PPD - dicot optimised nucleic acid sequence |
| 125 | Polynucleotide | Artificial | *Amborella trichopoda* PPD - dicot optimised nucleic acid sequence |
| 126 | Polynucleotide | Artificial | *Musa acuminate* PPD - dicot optimised nucleic acid sequence |
| 127 | Polynucleotide | Artificial | *Picea abies* PPD - dicot optimised nucleic acid sequence |
| 128 | Polynucleotide | Artificial | *Selaginella moellendorffii* PPD - dicot optimised nucleic acid sequence |
| 129 | Polynucleotide | Cauliflower mosaic virus | CaMV35s promoter sequence |
| 130 | Polypeptide | Artificial | *Picea sitchensis* PPD no tag |
| 131 | Polynucleotide | Artificial | Primer, hpt-1 |
| 132 | Polynucleotide | Artificial | Primer, hpt-2 |
| 133 | Polynucleotide | Artificial | Primer, nos3'-1f |
| 134 | Polynucleotide | Artificial | Primer, nos3'-1r |
| 135 | Polynucleotide | Artificial | Primer, rgh1 |
| 136 | Polynucleotide | Artificial | Primer, rgh5 |
| 137 | Polynucleotide | Artificial | Primer, GrPPD1F |
| 138 | Polynucleotide | Artificial | Primer, GrPPD1R |

The invention claimed is:

1. A method for at least one of:
   a) increasing at least one of root biomass and above-ground biomass and in a Poaceae plant, and
   b) producing a Poaceae plant with at least one of increased root biomass and increased above-ground biomass,
   the method comprising the step of expressing a PEAPOD protein in the Poaceae plant as a consequence of the plant, or its ancestor plant or plant cell, being transformed with a polynucleotide encoding the PEAPOD protein.

2. The method of claim 1 in which the plant is transgenic for a polynucleotide expressing the PEAPOD protein.

3. The method of claim 1 in which the Poaceae plant is transformed with a polynucleotide encoding the PEAPOD protein.

4. The method of claim 1 comprising the step of transforming the Poaceae plant, or transforming a Poaceae plant cell which is regenerated into the Poaceae plant, with a polynucleotide encoding the PEAPOD protein.

5. The method of claim 1 which includes the additional step of testing or assessing the plant for at least one of increased root biomass and increased above-ground biomass.

6. The method of claim 1 in which the PEAPOD protein is a polypeptide comprising the sequence of at least one of the sequences of SEQ ID NO: 28, 29, 31, 32, 34 and 35.

7. The method of claim 1 in which the PEAPOD protein is a polypeptide comprising a sequence with at least 70% identity to any one of SEQ ID NO: 1 to 26.

8. The method of claim 1 in which expression is increased by introducing a polynucleotide encoding the PEAPOD protein into the plant cell or plant.

9. The method of claim 8 in which the polynucleotide comprises a sequence with at least 70% identity to the coding sequence of any one of SEQ ID NO: 80 to 104.

10. The method of claim 8 in which the polynucleotide comprises a sequence with at least 70% identity to the sequence of any one of SEQ ID NO: 80 to 104.

11. The method of 8 in which the polynucleotide is introduced into the plant as part of an expression construct.

12. The method of claim 11 in which the expression construct comprises a promoter operatively linked to the polynucleotide.

13. The method of claim 12 in which the promoter is capable of driving, or drives, expression of the operatively linked polynucleotide constitutively in all tissues of the plant.

14. The method of claim 12 in which the promoter is a tissue-preferred promoter.

15. The method of claim 12 in which the promoter is capable of driving, or drives, expression of the operatively linked polynucleotide in the above-ground parts of the plant.

16. The method of claim 12 in which the promoter is capable of driving, or drives, expression of the operatively linked polynucleotide in the below ground tissues of the plant.

17. A Poaceae plant expressing a PEAPOD protein that has at least one of:
   a) increased root biomass, and
   b) increased above-ground biomass,
   as a result of expressing the PEAPOD protein as a consequence of the plant, or its ancestor plant or plant cell, having been transformed with a polynucleotide encoding the PEAPOD protein.

18. The Poaceae plant of claim 17 that is transgenic for a polynucleotide expressing the PEAPOD protein.

19. The Poaceae plant of claim 17 in which the polynucleotide is operatively linked polynucleotide to a tissue-preferred promoter.

20. The Poaceae plant of claim 19 in which the promoter is capable of driving, or drives, expression of the operatively linked polynucleotide in the above-ground parts of the plant.

21. The Poaceae plant of claim 19 in which the promoter is capable of driving, or drives, expression of the operatively linked polynucleotide in the below ground tissues of the plant.

22. A cell, part, propagule or progeny of the plant of 17 that is transgenic for the polynucleotide.

23. A cell, part, propagule or progeny of the plant of claim 19 that is transgenic for the polynucleotide and operatively linked promoter.

\* \* \* \* \*